United States Patent
Sun et al.

(10) Patent No.: US 9,334,256 B2
(45) Date of Patent: May 10, 2016

(54) AGENTS AND METHODS FOR TREATING ISCHEMIC AND OTHER DISEASES

(75) Inventors: Xiujun Sun, Toronto (CA); Michael Tymianski, Toronto (CA)

(73) Assignee: NoNO INC. (CA)

( * ) Notice: Subject to any disclaimer, the term of this patent is extended or adjusted under 35 U.S.C. 154(b) by 0 days.

(21) Appl. No.: 14/125,928

(22) PCT Filed: Jun. 15, 2012

(86) PCT No.: PCT/US2012/042826
§ 371 (c)(1),
(2), (4) Date: Apr. 7, 2014

(87) PCT Pub. No.: WO2012/174488
PCT Pub. Date: Dec. 20, 2012

(65) Prior Publication Data
US 2014/0221423 A1    Aug. 7, 2014

Related U.S. Application Data

(60) Provisional application No. 61/497,511, filed on Jun. 15, 2011.

(51) Int. Cl.
| | |
|---|---|
| *C07D 215/00* | (2006.01) |
| *C07D 311/00* | (2006.01) |
| *C07D 311/20* | (2006.01) |
| *C07D 333/70* | (2006.01) |
| *C07D 409/06* | (2006.01) |
| *C07D 409/12* | (2006.01) |
| *C07D 215/227* | (2006.01) |
| *C07D 311/58* | (2006.01) |

(52) U.S. Cl.
CPC .......... *C07D 311/20* (2013.01); *C07D 215/227* (2013.01); *C07D 311/58* (2013.01); *C07D 333/70* (2013.01); *C07D 409/06* (2013.01); *C07D 409/12* (2013.01)

(58) Field of Classification Search
CPC ......................... C07D 215/227; C07D 311/20
USPC ........................................ 546/157; 549/289
See application file for complete search history.

(56) References Cited

U.S. PATENT DOCUMENTS

| | | | |
|---|---|---|---|
| 5,968,959 A * | 10/1999 | Haikala et al. ............... | 514/345 |
| 6,774,103 B1 | 8/2004 | Pollesello et al. | |
| 2003/0220356 A1 | 11/2003 | Ibrahim et al. | |
| 2009/0004209 A1 | 1/2009 | Ruchelman et al. | |
| 2009/0042918 A1 | 2/2009 | Kearney et al. | |
| 2009/0264412 A1 | 10/2009 | Kampen et al. | |
| 2010/0004233 A1 | 1/2010 | Iikura et al. | |

FOREIGN PATENT DOCUMENTS

| | | | | |
|---|---|---|---|---|
| EP | 2521724 A2 | 11/2012 | | |
| WO | WO 01/07431 A2 | 2/2001 | | |
| WO | WO 07/144625 A1 | 12/2007 | | |
| WO | WO 2009031706 | * | 3/2009 | .......... C07D 311/16 |
| WO | WO 2011/072275 A2 | 6/2011 | | |
| WO | WO 2011/072275 A3 | 6/2011 | | |
| WO | WO 2012/174488 A2 | 12/2012 | | |

OTHER PUBLICATIONS

Kumar et al. Journal of the Indian Chemical Society (1964), 41(3), 200-2.*
Lopez-Alvarado et al. Synthesis (1998), (2), 186-194.*
Brandt et al. International Journal of Quantum Chemistry, Quantum Biology Symposium (1986), 13, 155-65.*
Kumar, Journal of the Indian Chemical Society (1964), 41(3), 200-2.*
Stadbauer et al., "Oxidative Hydroxylierung Von Heterocyclischen Beta-Dicarbonylberbindungen," Monatshefte Fur Chemie—Chemical Monthly, 116(8/09): 1005-1015, (1985).
Ahvale et at., "4-Cyano-6,7-Dimethoxycarbostyrils with Solvent- and pH-Independent Fluorescence Quantum Yields and Emission High Maxima," European Journal of Organic Chemistry, 2008(3), pp. 563-571, (2008).
EPO Application No. 12800164.1, Supplementary European Search Report and European Search Opinion mailed Oct. 13, 2014.
Fabian et al., "Substituent effects on absorption and fluorescence spectra of carbostyril," Journal of Molecular Structure, 477:209-220, (1999).
King et al., "93. Hydroxy-carbonyl compounds. Part IX. Benzopyrones related to phloretin," Journal of the Chemical Society (Resumed), pp. 403-405, (1934).
Kirkiacharian et al., "Structure-activity relationships of some 3-substituted-4-hydroxycoumarins as HIV-1 protease inhibitors", IL Farmaco, 57(9):703-708, (2002).
Rabaron et al., "Etude par RMN du 13C d'Hydroxy-4 Coumarines Substituees en 3. Analyse par Correlation des Effets de Substituants," Organic Magnetic Resonance, pp. 284-288, (1979). (p. 284, compounds 4 and 14).
Stadbauer et al., "Oxidative Hydroxylierung Von Heterocyclischen Beta-Dicarbonylberbindungen," Monatshefte Fur Chemie—Chemical Monthly, 116(8/09): 1005- 1015, (1985).
WIPO Application No. PCT/US2012/042826, PCT International Preliminary Report on Patentability issued Dec. 17, 2013.
WIPO Application No. PCT/US2012/042826, PCT International Search Report mailed Feb. 1, 2013.
WIPO Application No. PCT/US2012/042826, PCT Written Opinion of the International Searching Authority mailed Feb. 1, 2013.
Ziegler et al.,"Synthesen von Heterocyclen, 20. Mitt.: Eine Synthese von Di-und Trihydroxycumarinen," Monatshefte Fur Chemie—Chemical Monthly, 90(2):206-210, (1959). (Machine Translation p. 207, compound V; p. 210, example 8).

* cited by examiner

*Primary Examiner* — Nizal Chandrakumar
(74) *Attorney, Agent, or Firm* — Alston & Bird LLP

(57) ABSTRACT

This invention relates to compounds that modulate TRPM7 protein activity and use of the same for treatment or prophylaxis of ischemia, cancer, pain or glaucoma.

12 Claims, 51 Drawing Sheets

A
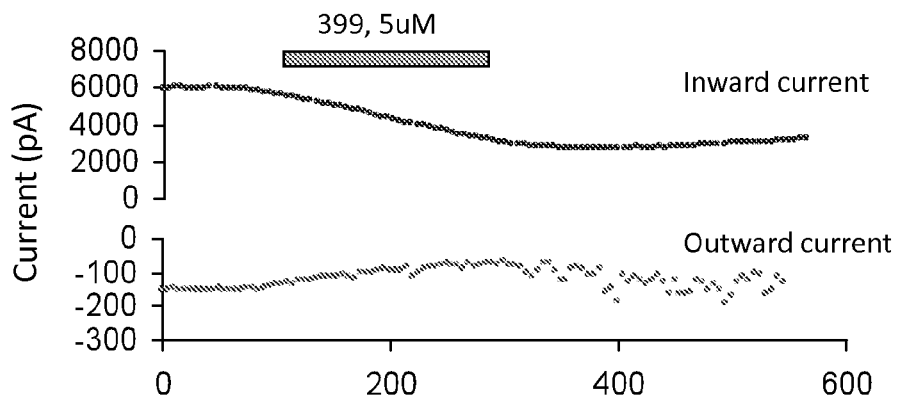
B
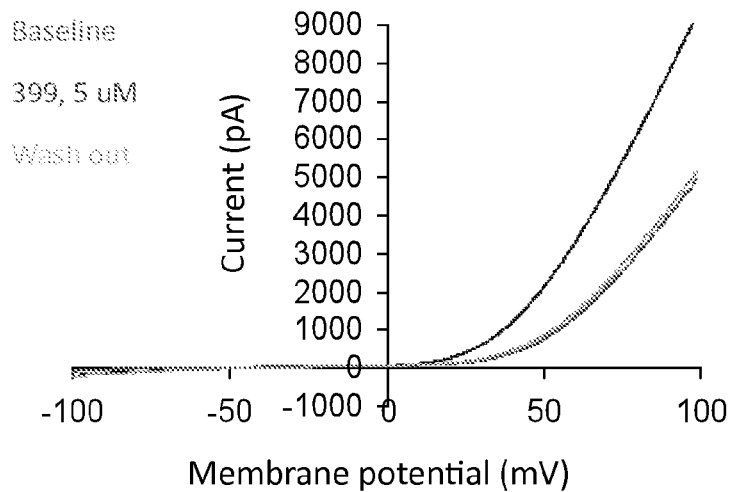
C
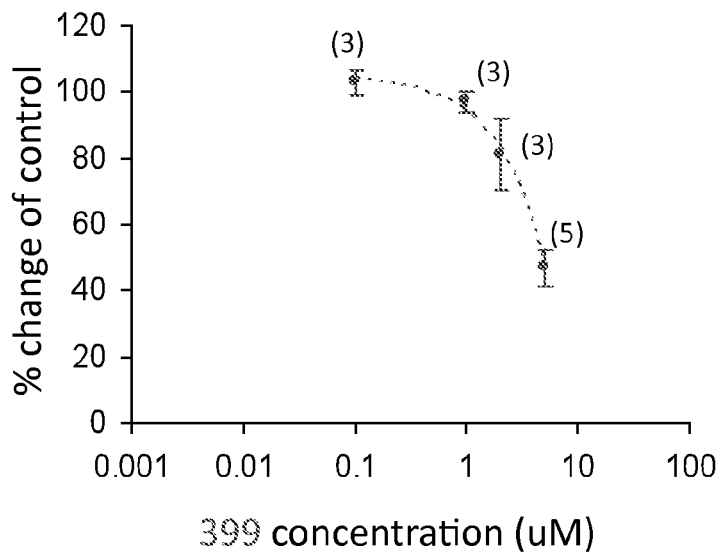
FIG. 2A-C

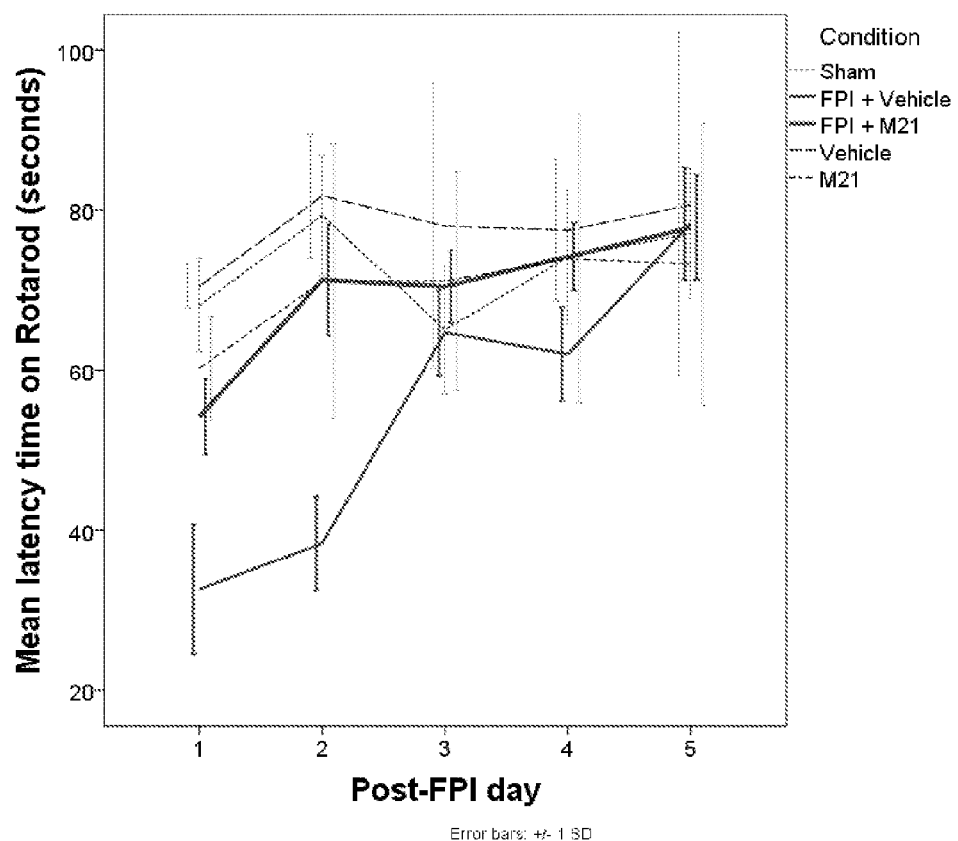
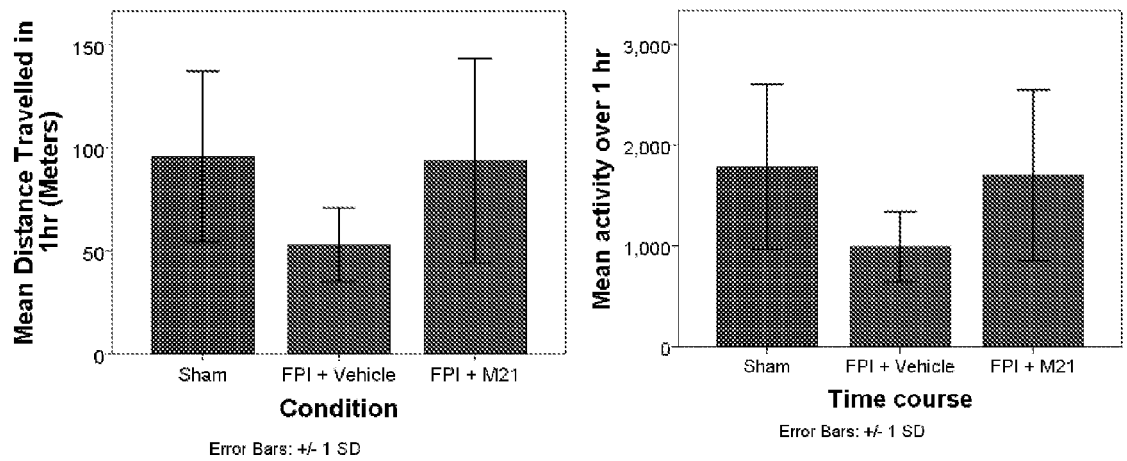
FIG. 4A-B

A
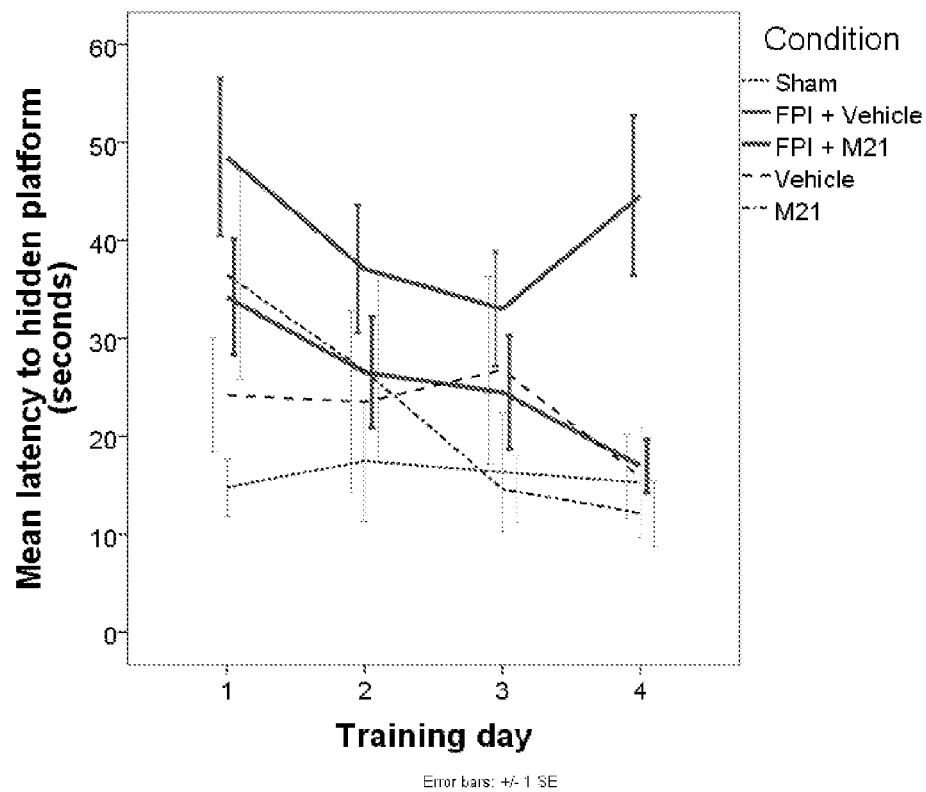
B
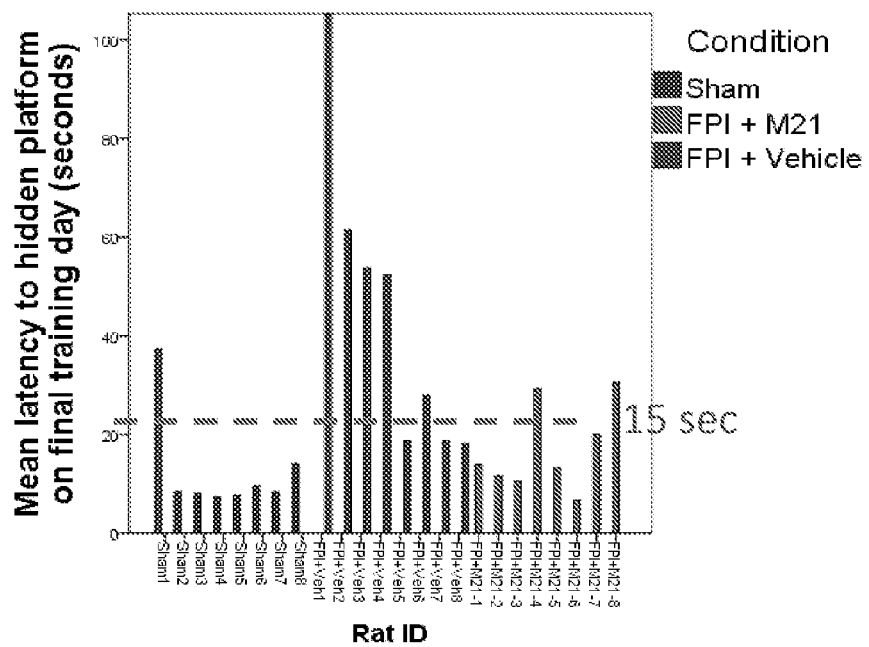
FIG. 5A-B

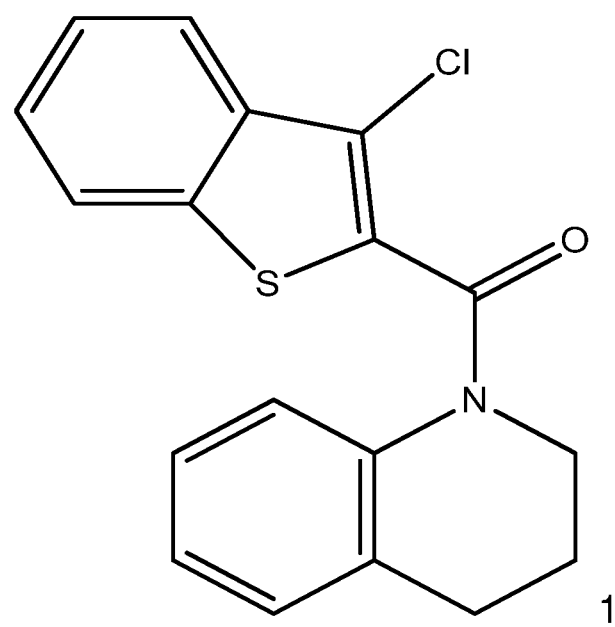
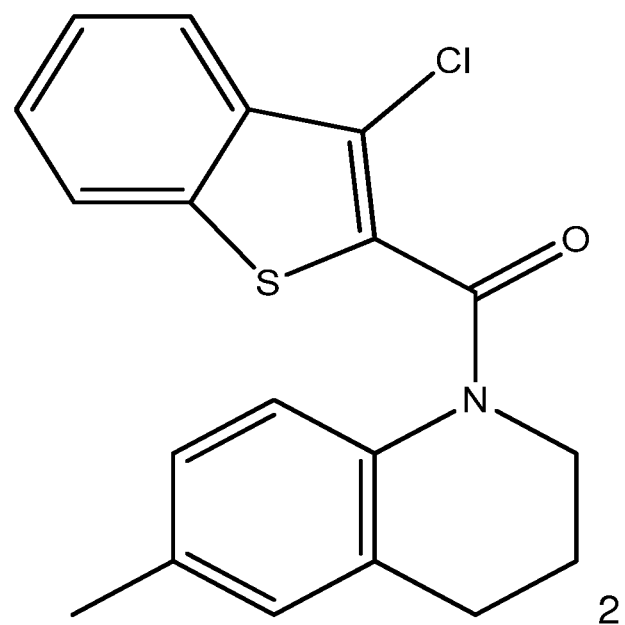
Fig. 7

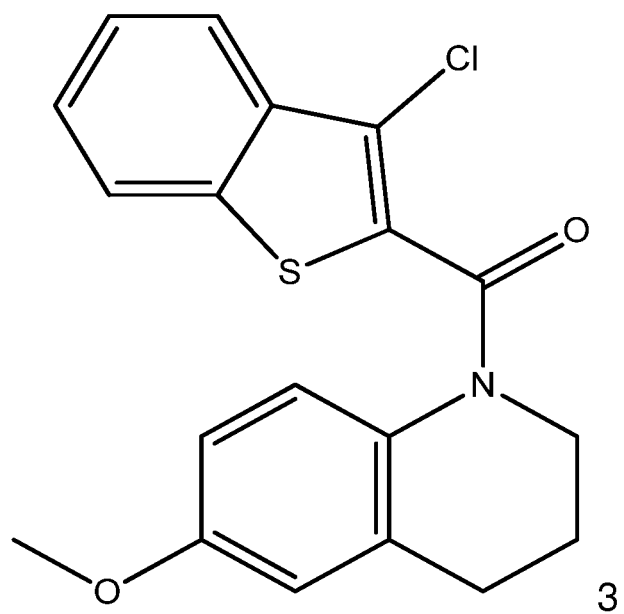
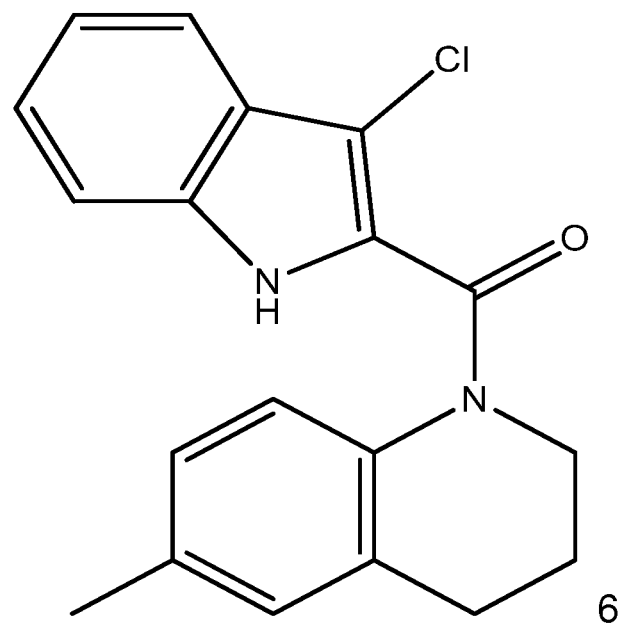
Fig. 8

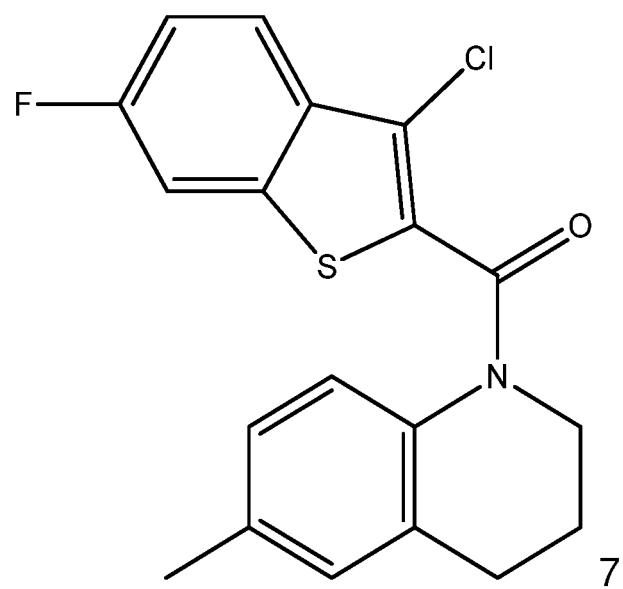
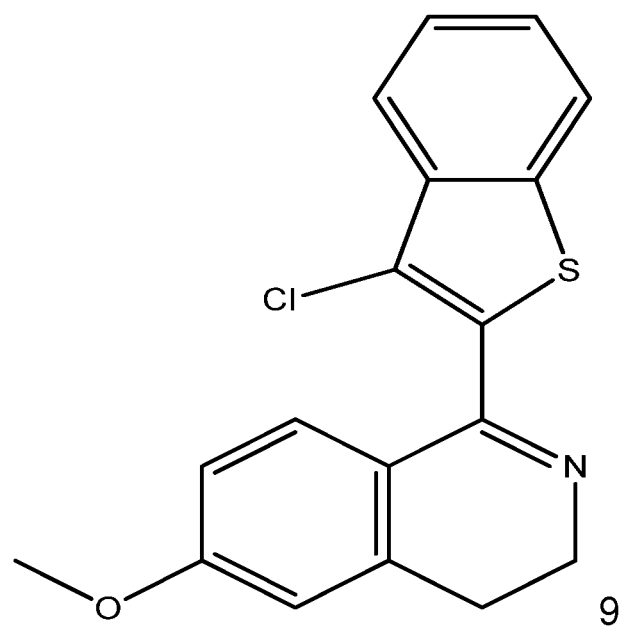
Fig. 9

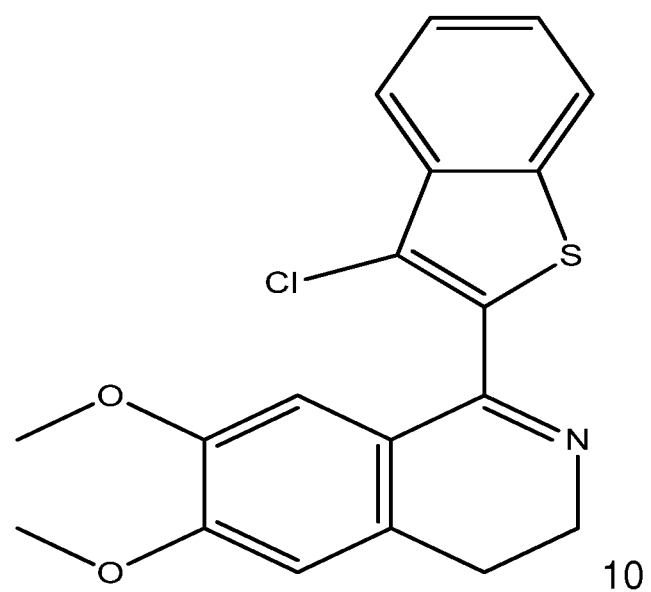
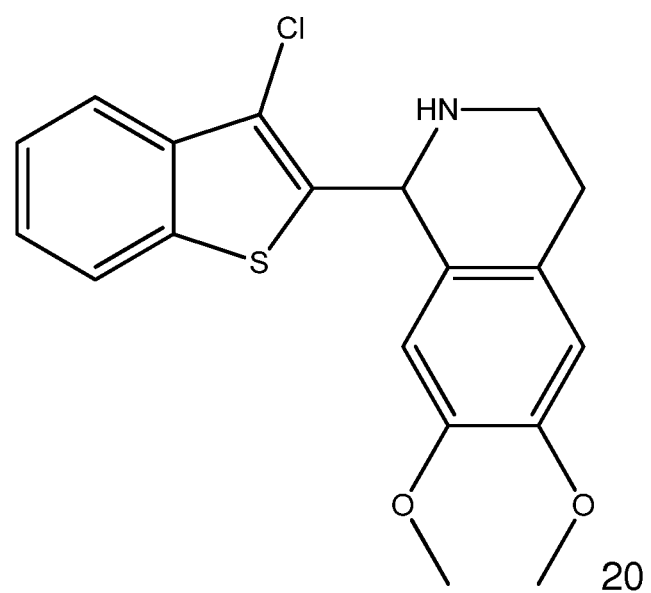
Fig. 10

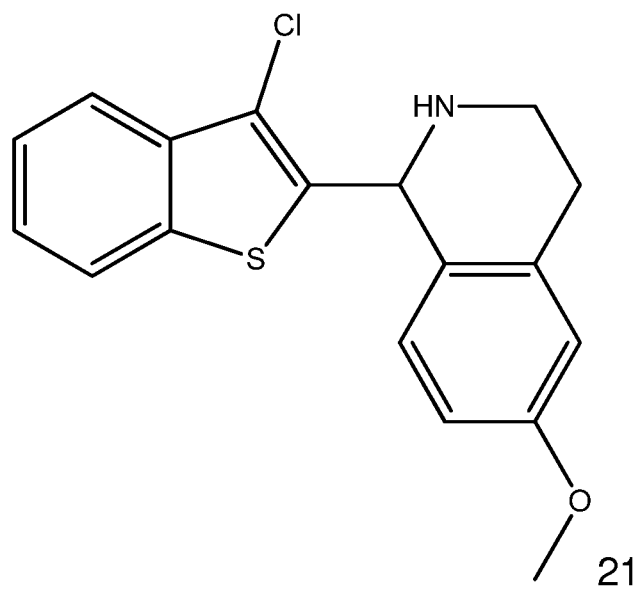
21
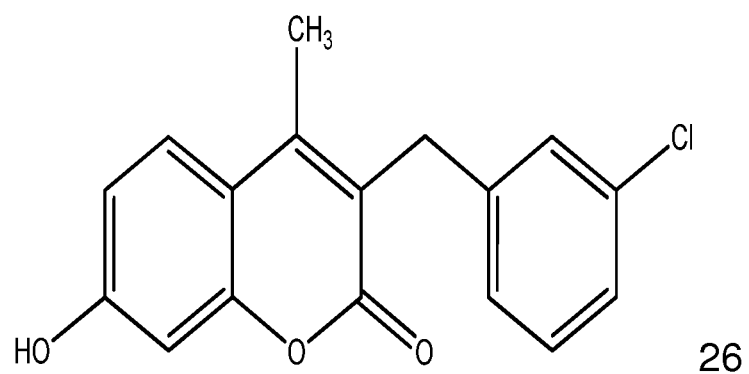
26
Fig. 11

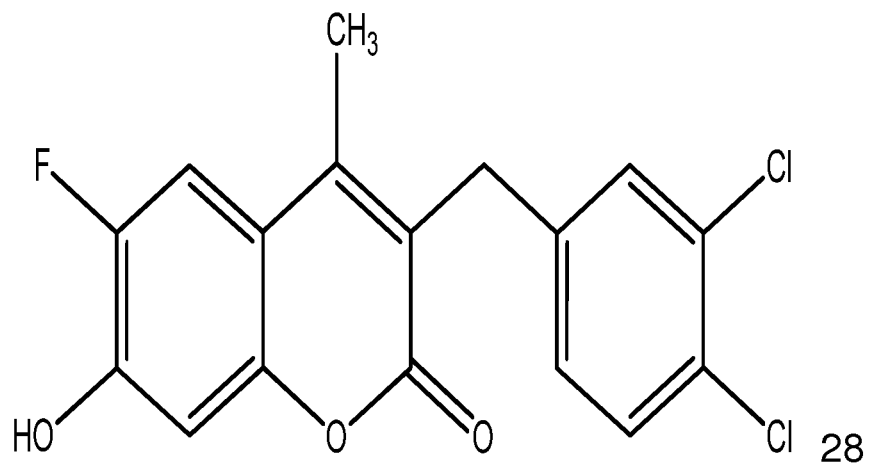
28
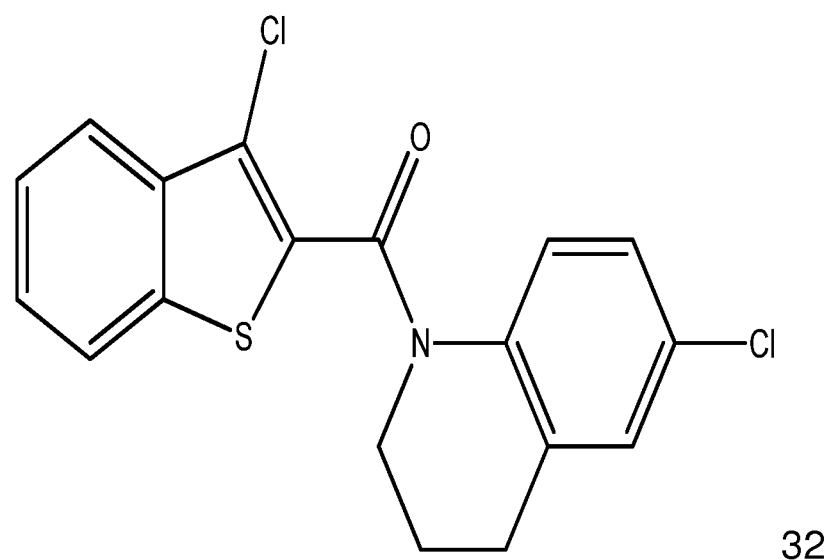
32
Fig. 12

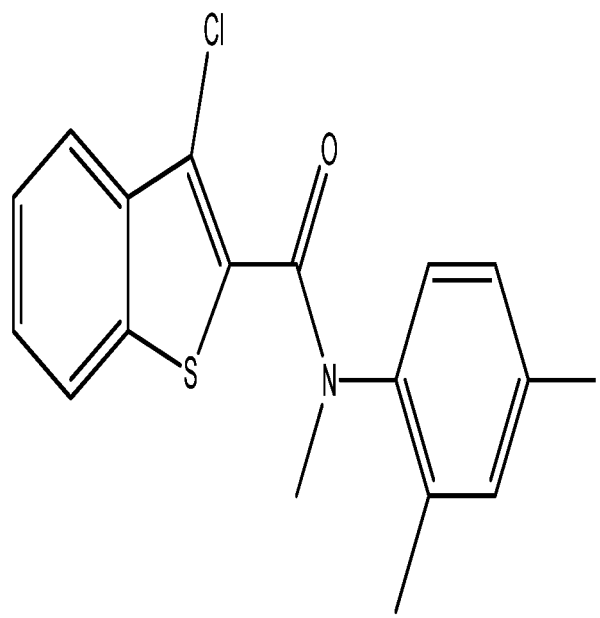
35
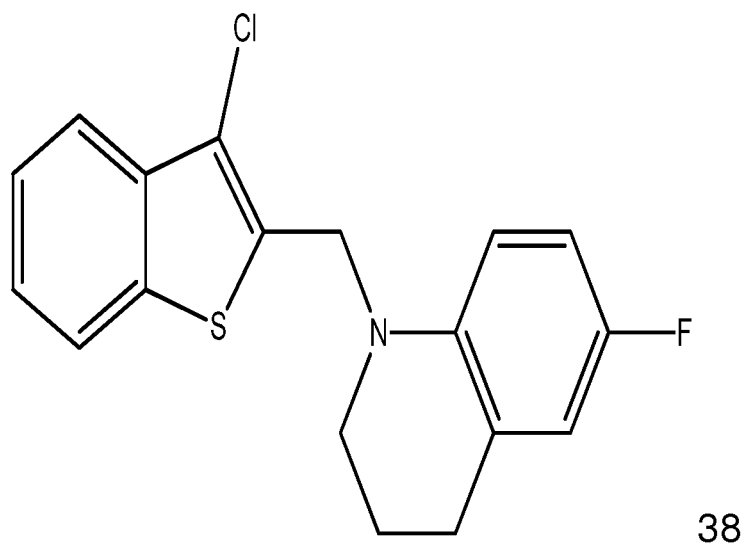
38
Fig. 13

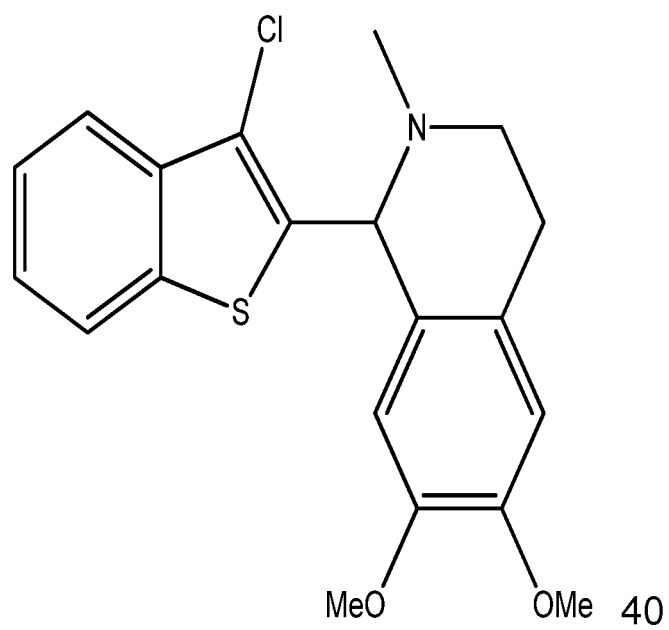
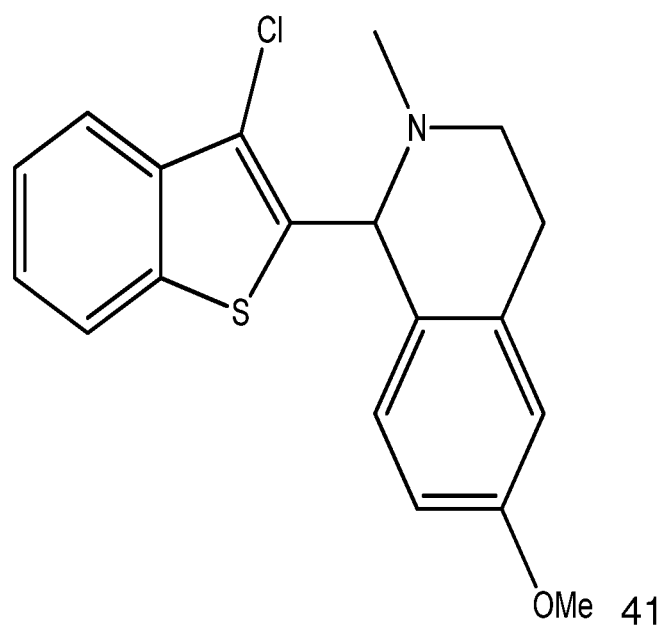
Fig. 14

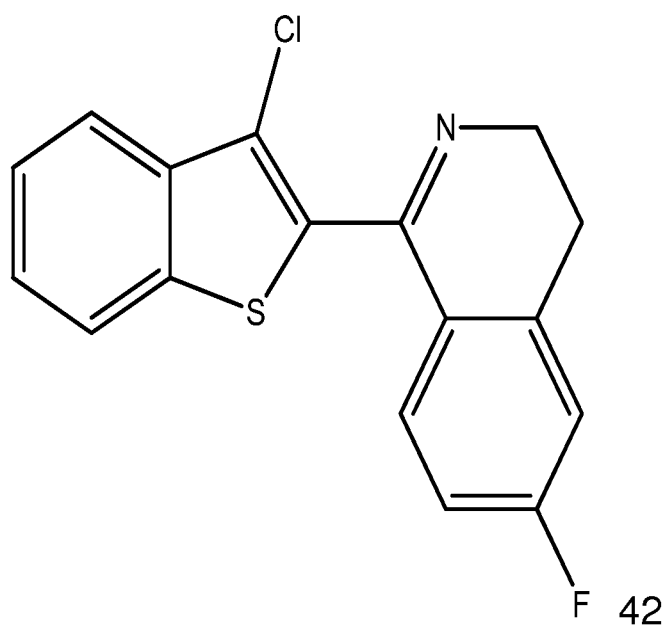
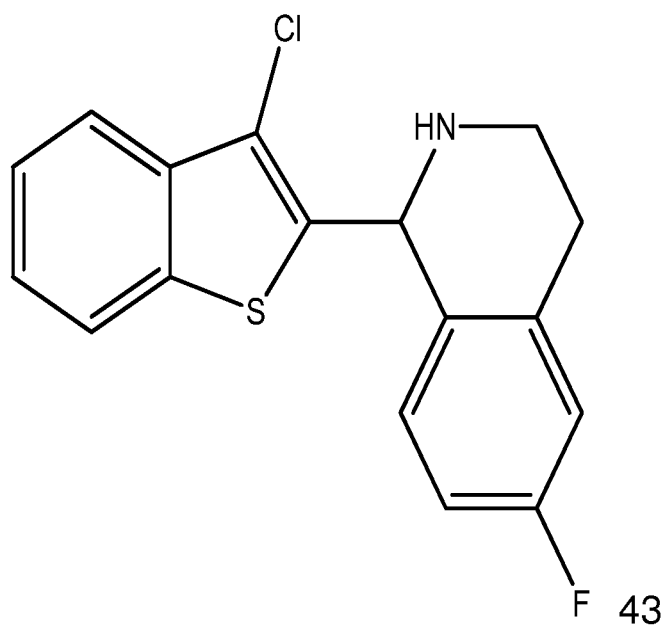
Fig. 15

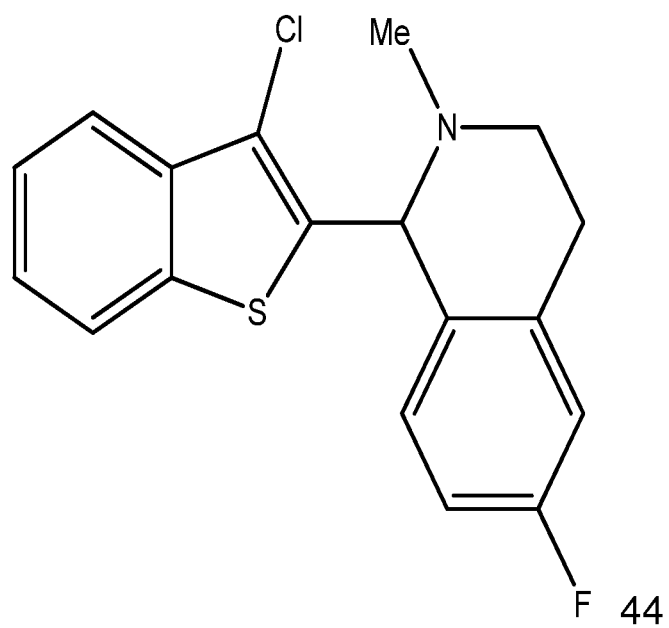
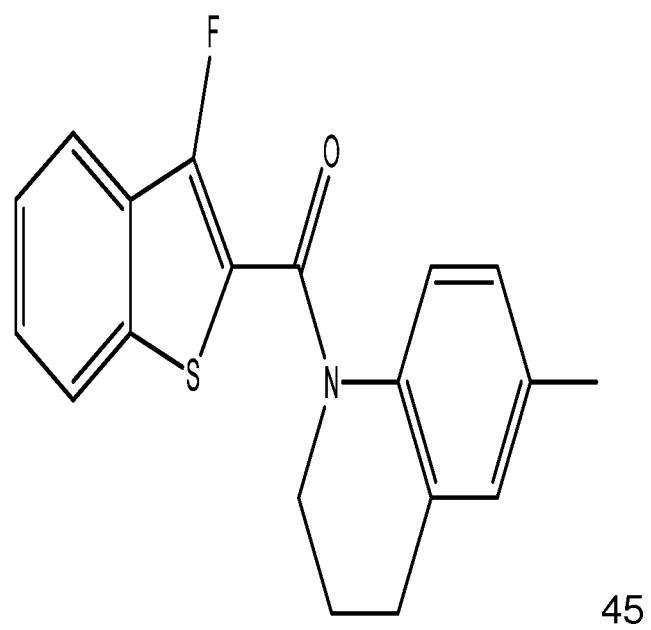
Fig. 16

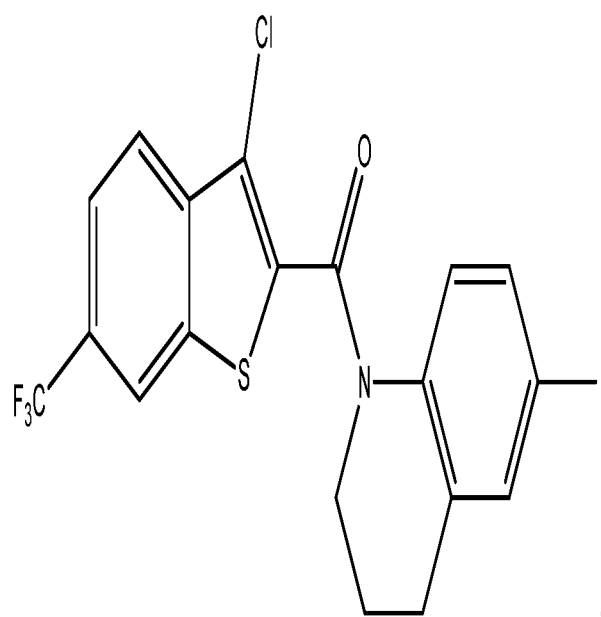
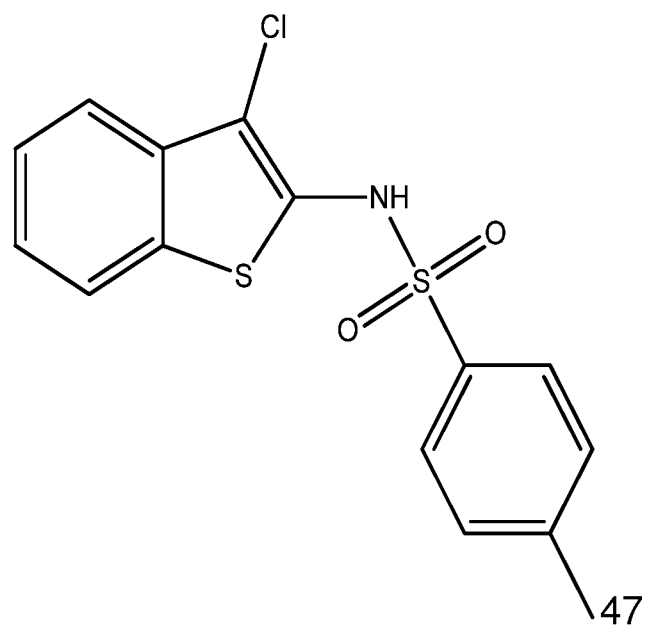
Fig. 17

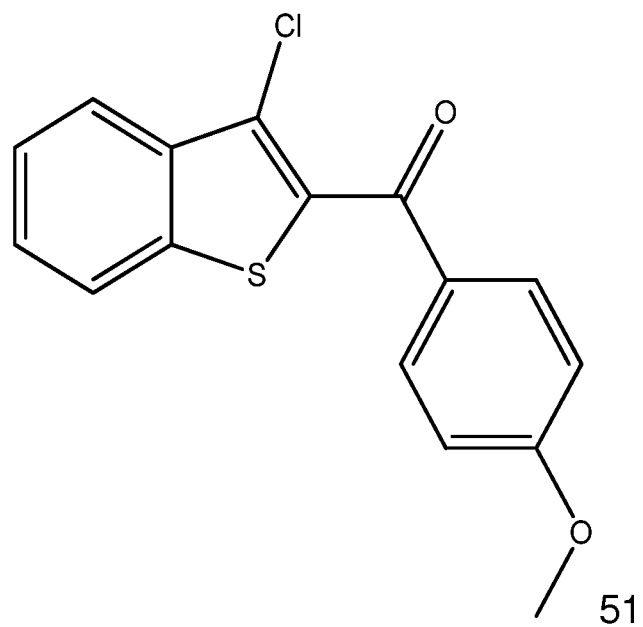
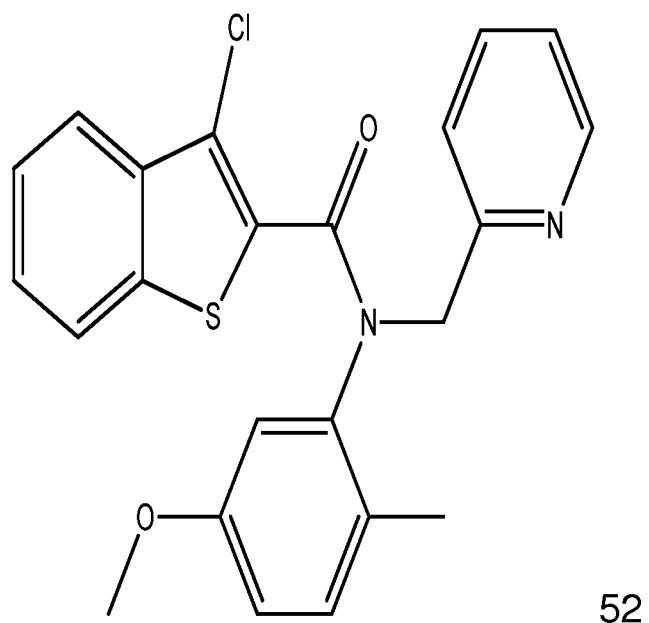
Fig. 18

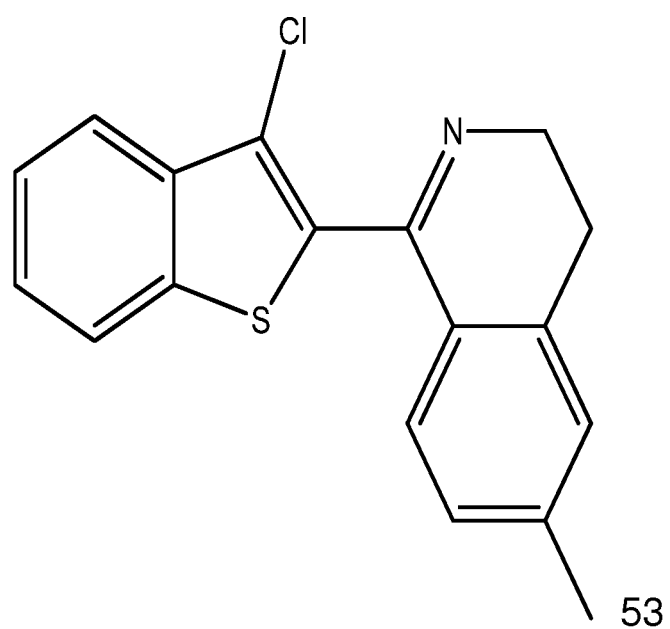
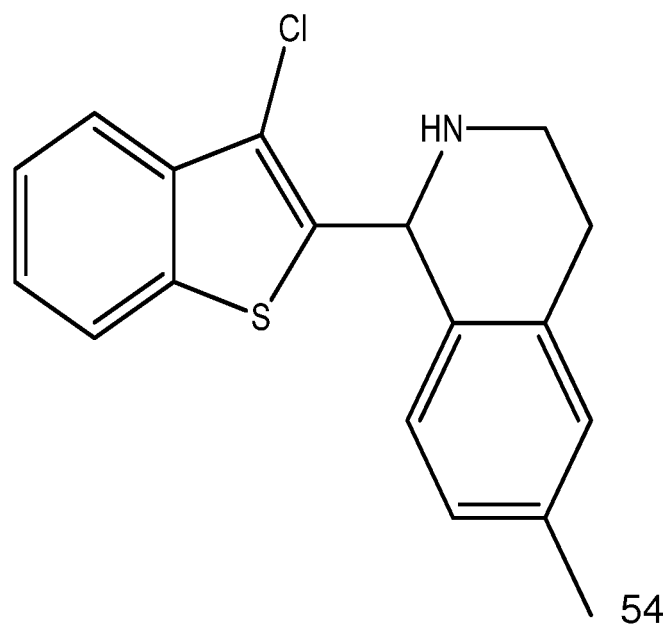
Fig. 19

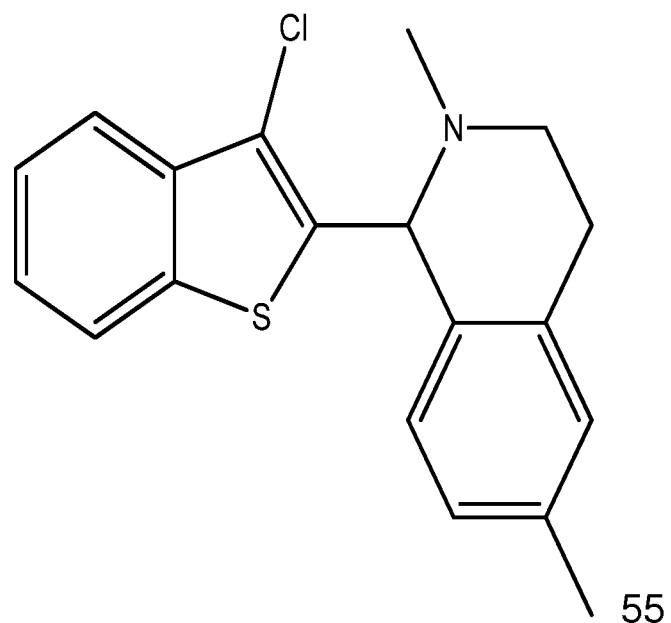
55
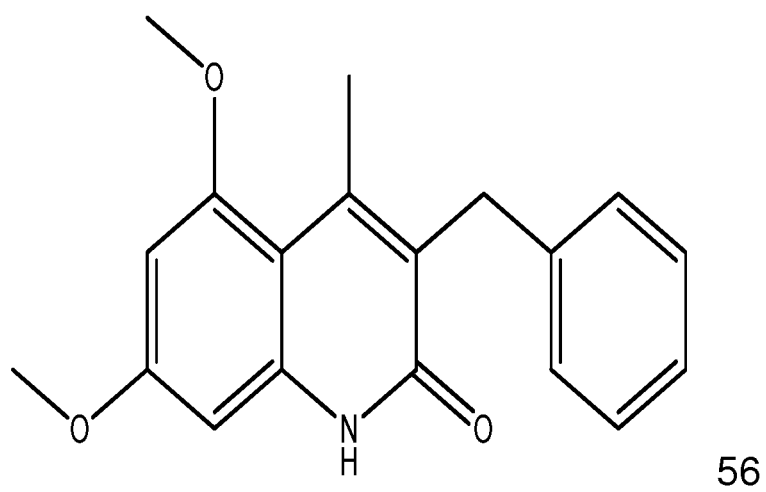
56
Fig. 20

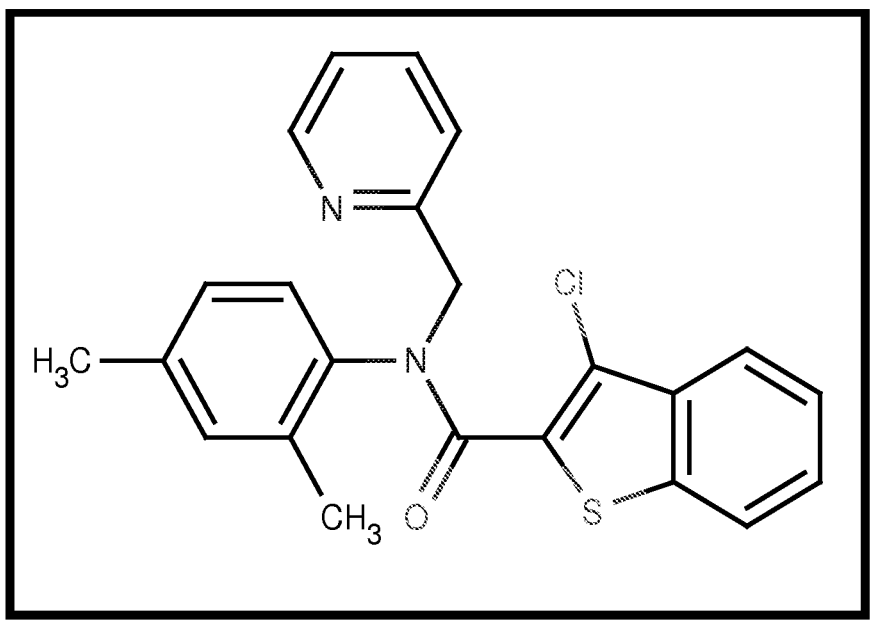
57
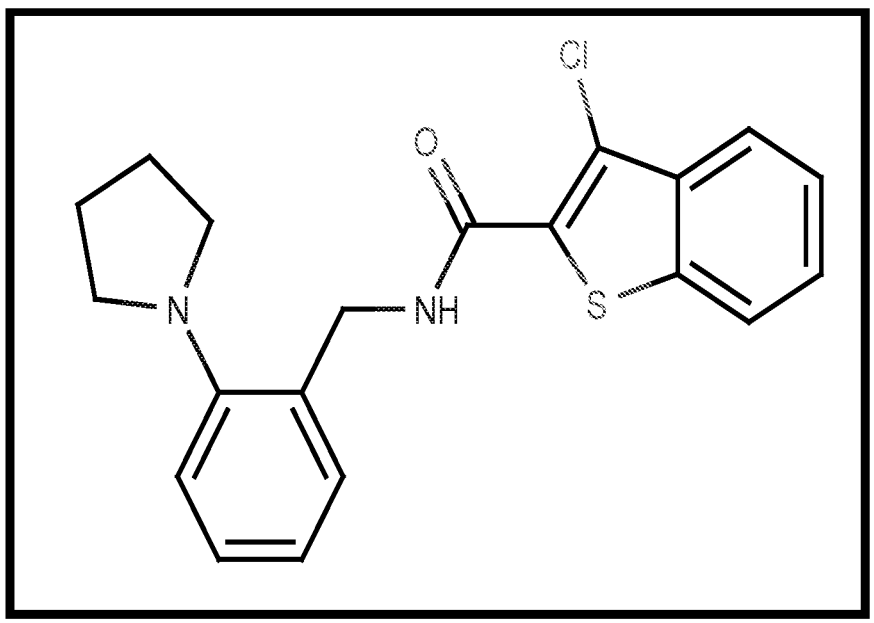
59
Fig. 21

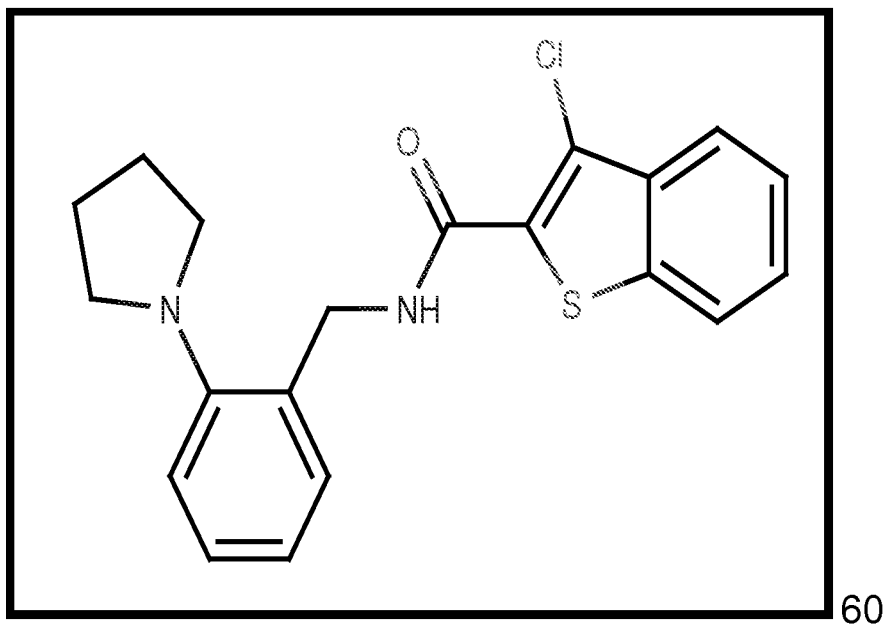
60
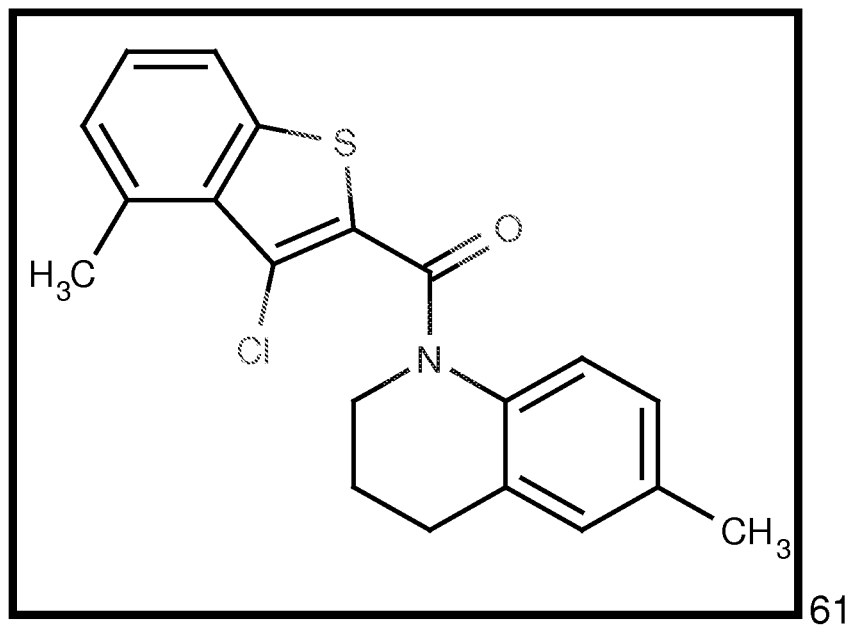
61
Fig. 22

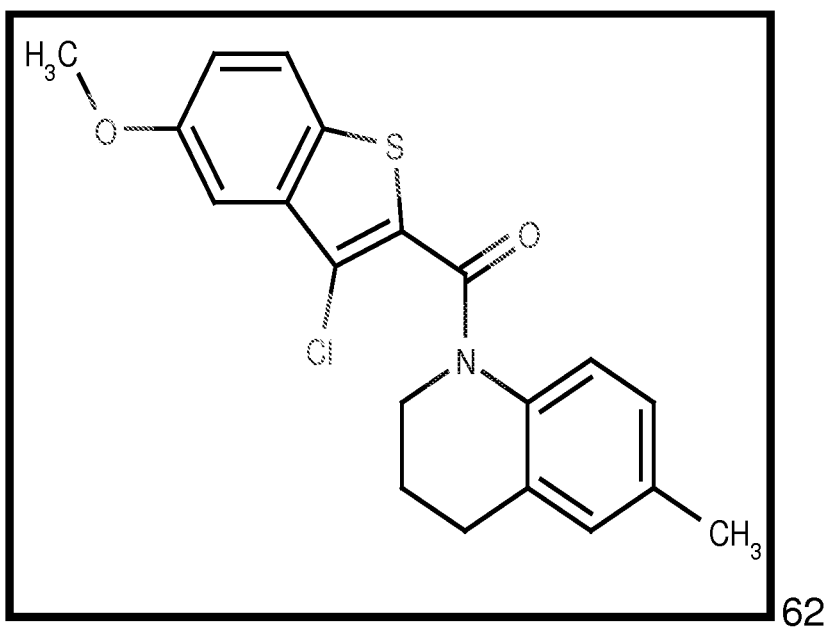
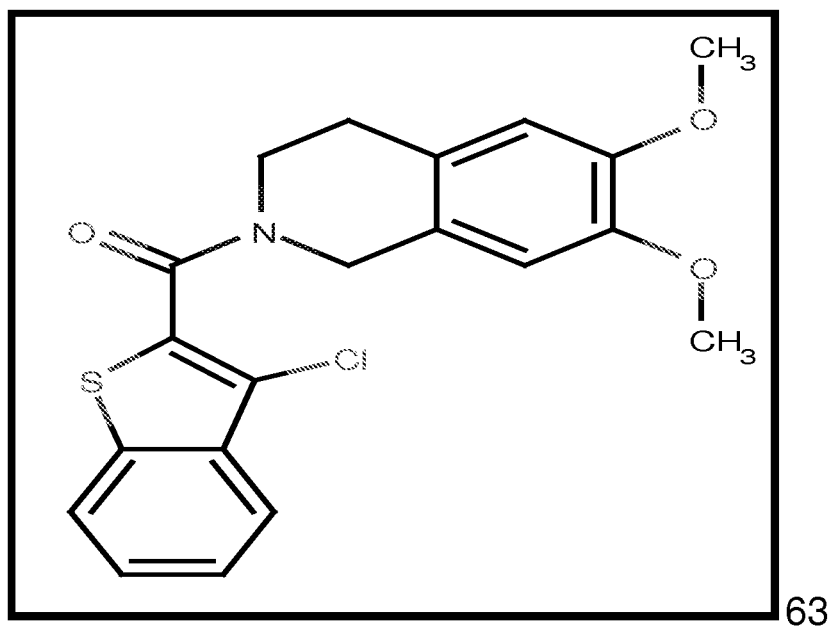
Fig. 23

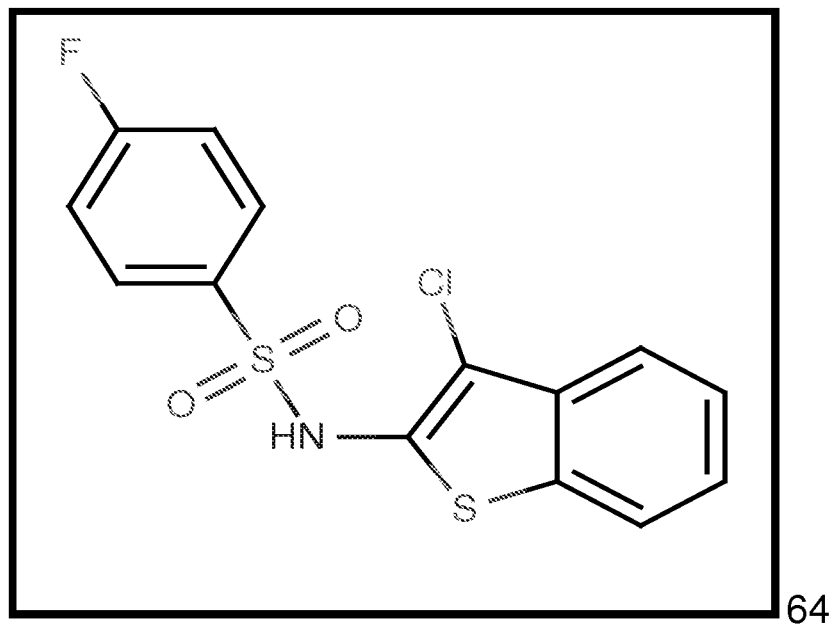
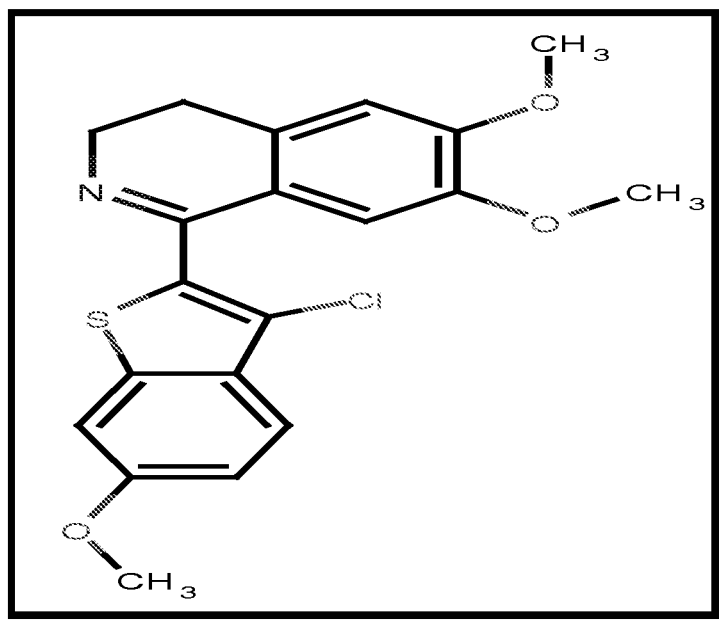
Fig. 24

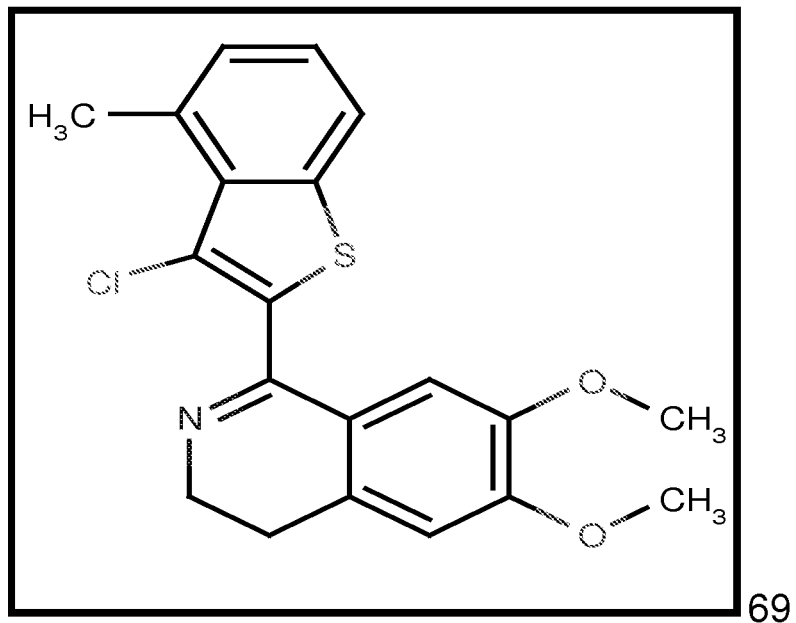
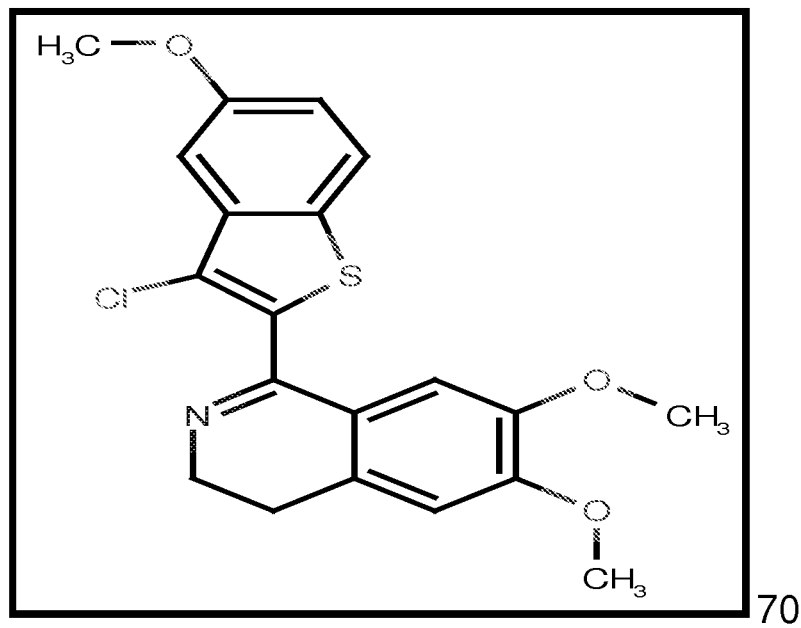
Fig. 25

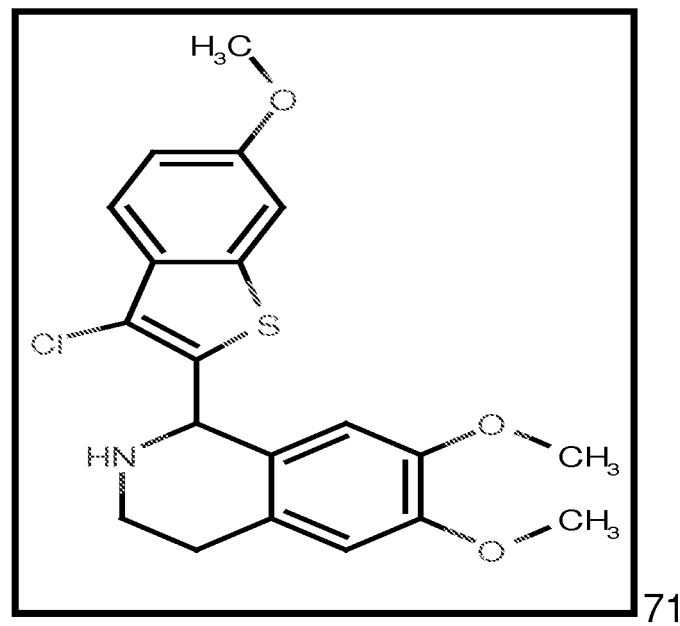
71
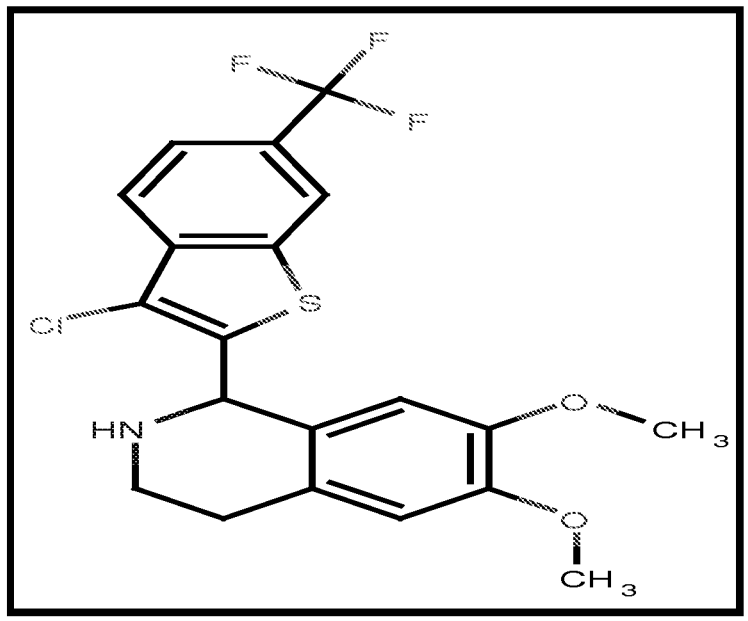
72
Fig. 26

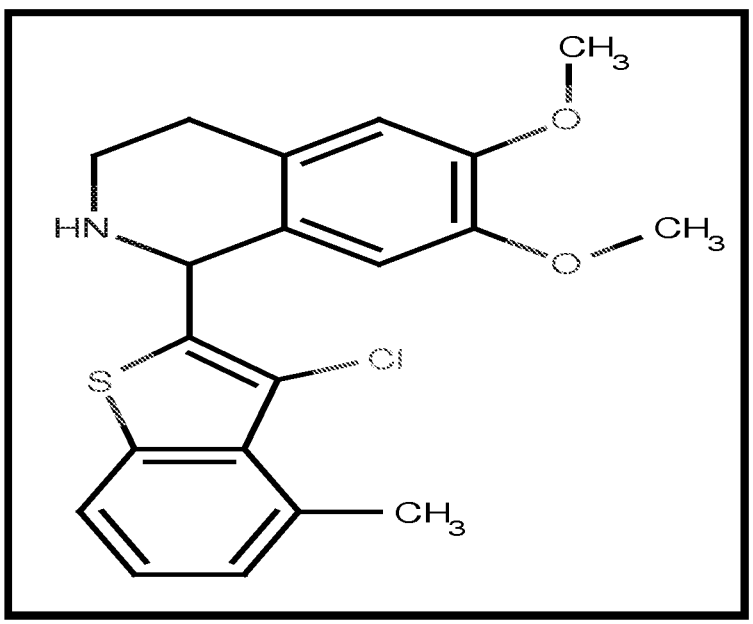
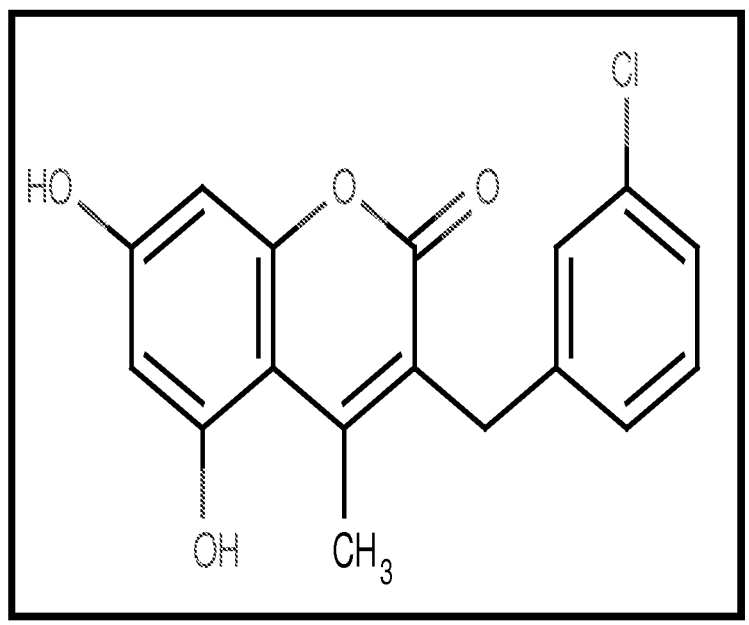
Fig. 27

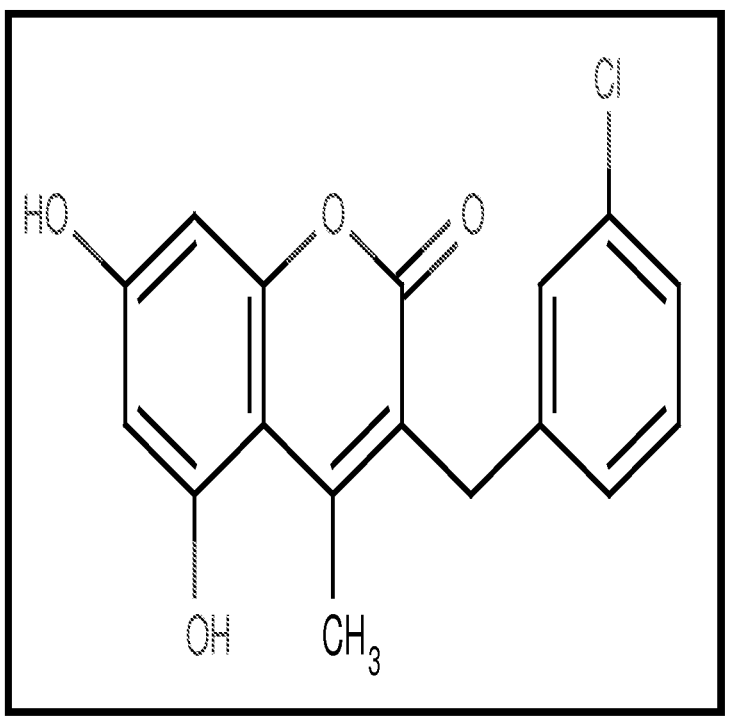
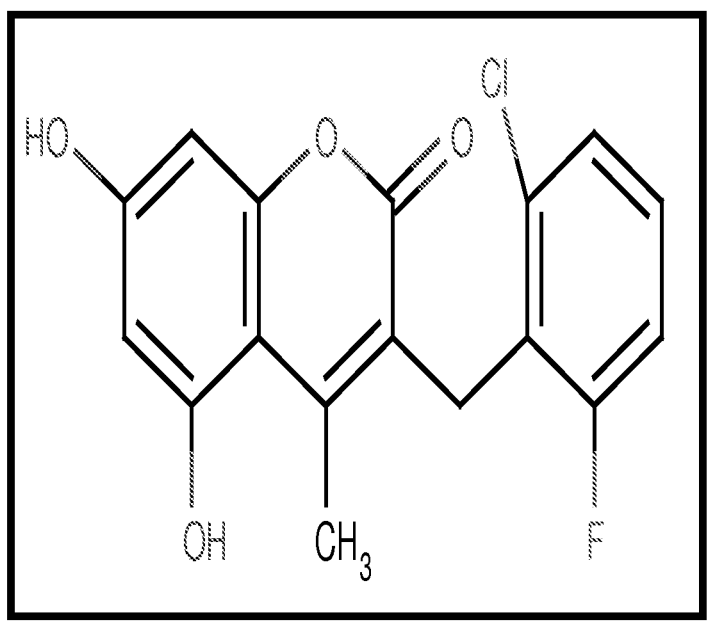
Fig. 28

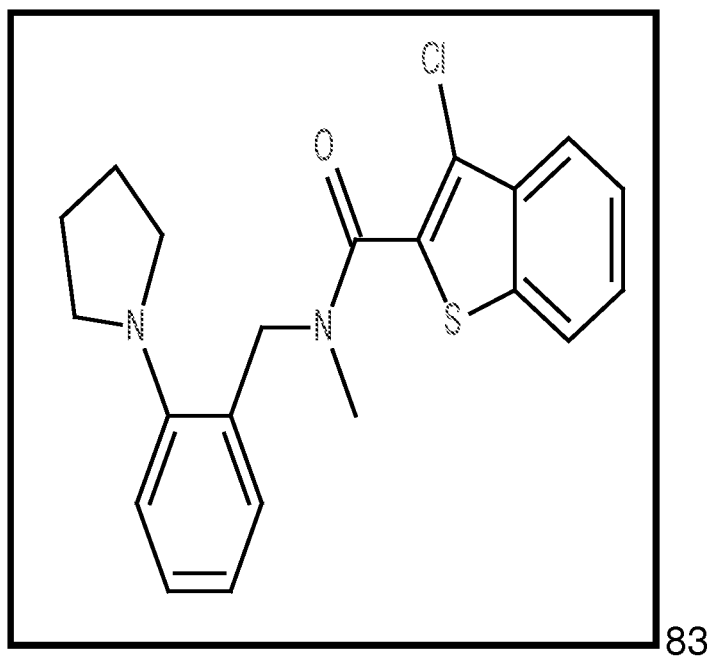
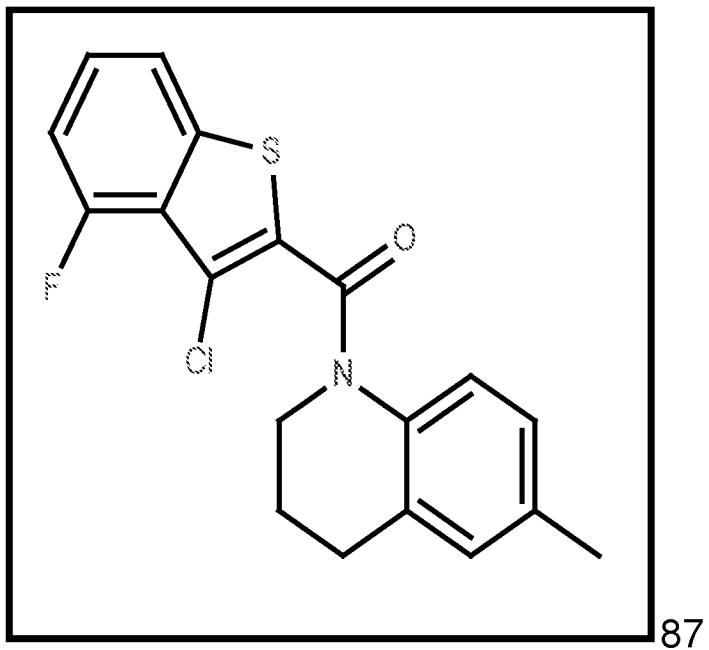
Fig. 29

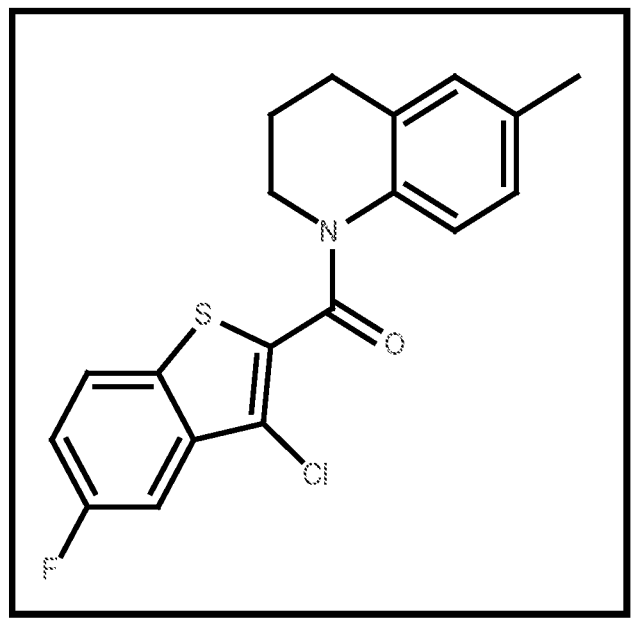
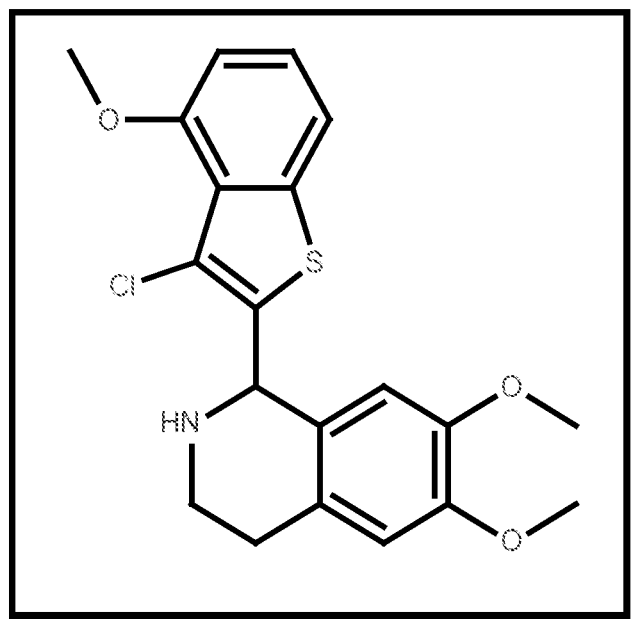
Fig. 30

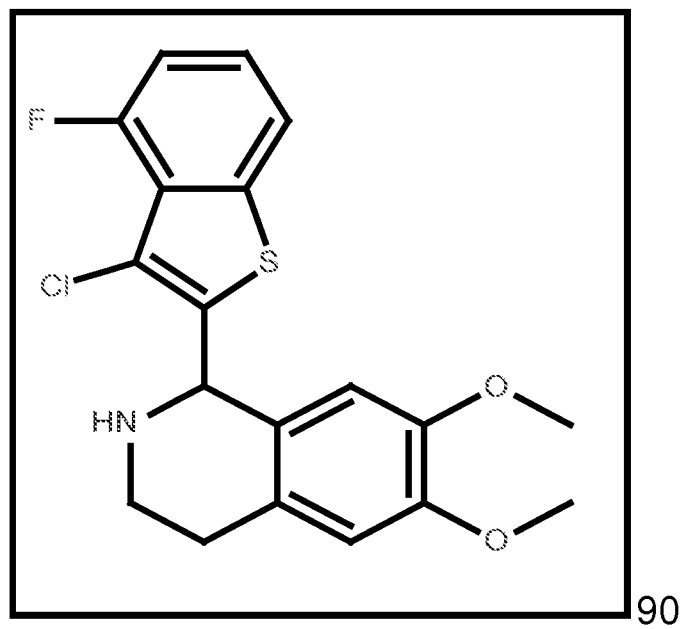
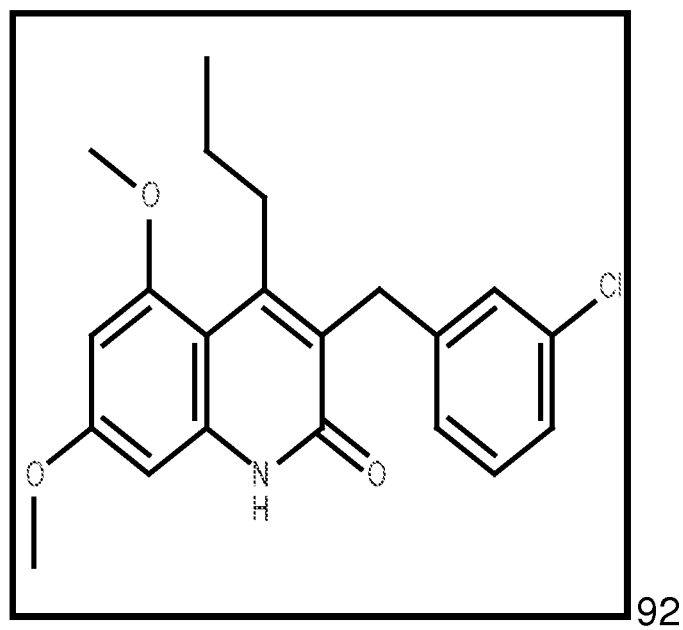
Fig. 31

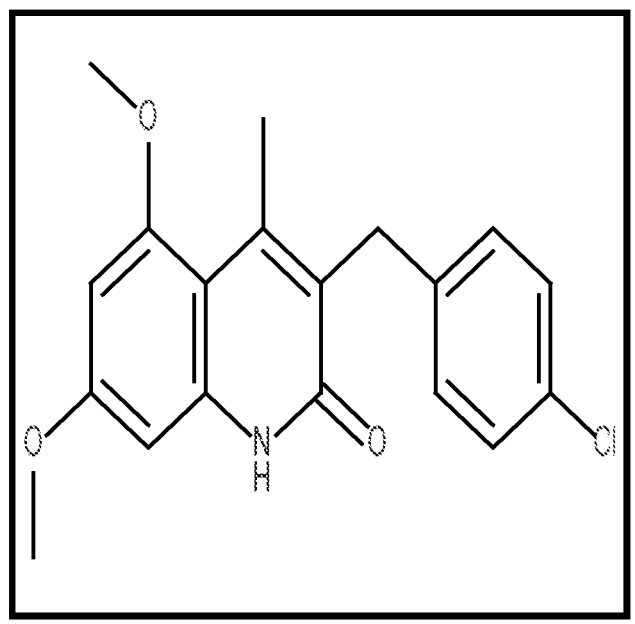
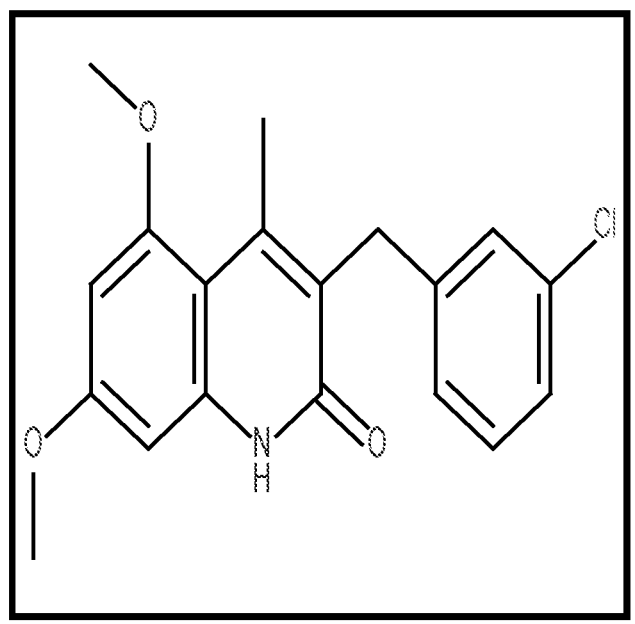
Fig. 32

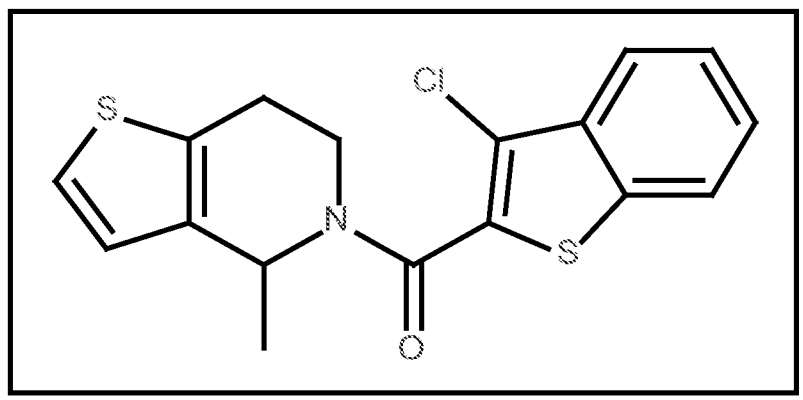
96
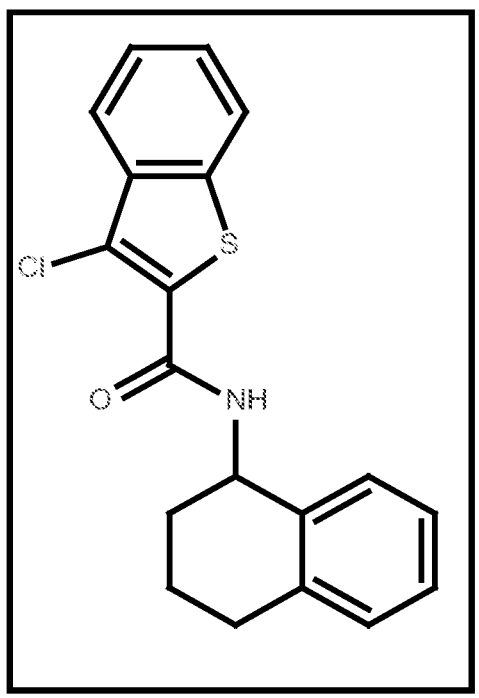
97
Fig. 33

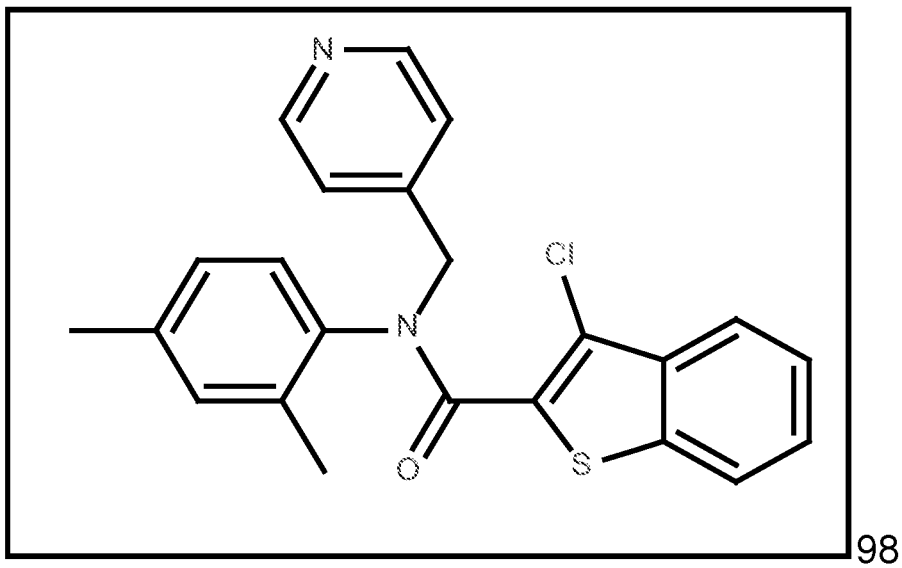
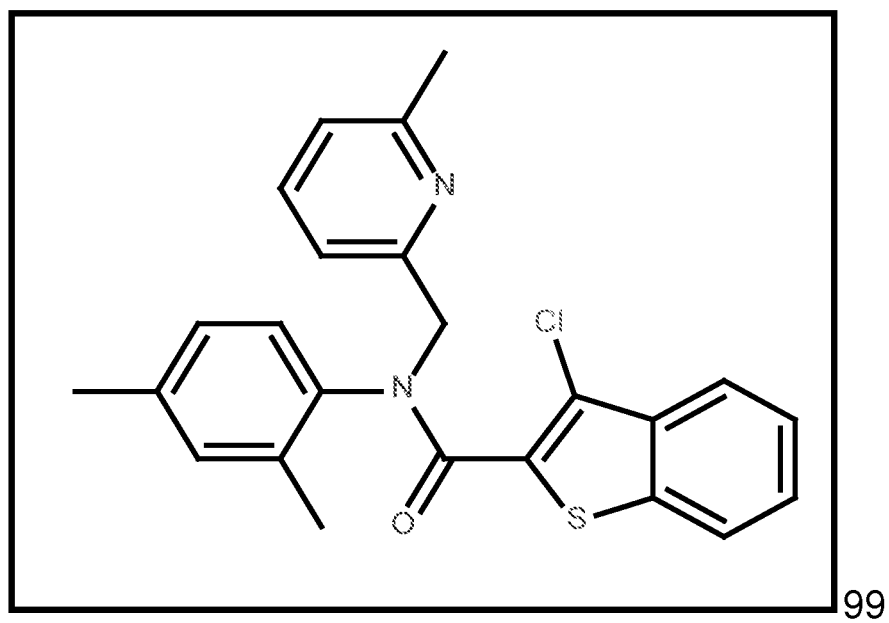
Fig. 34

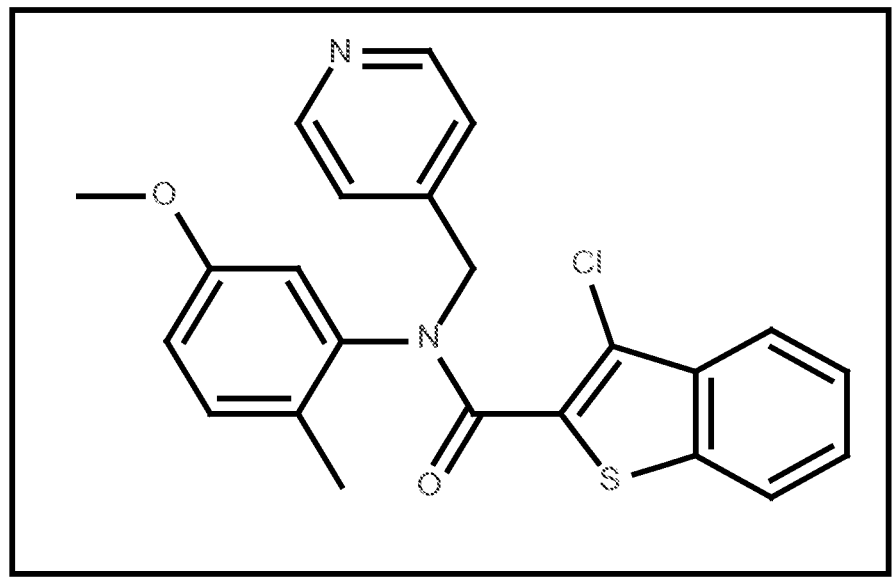
101
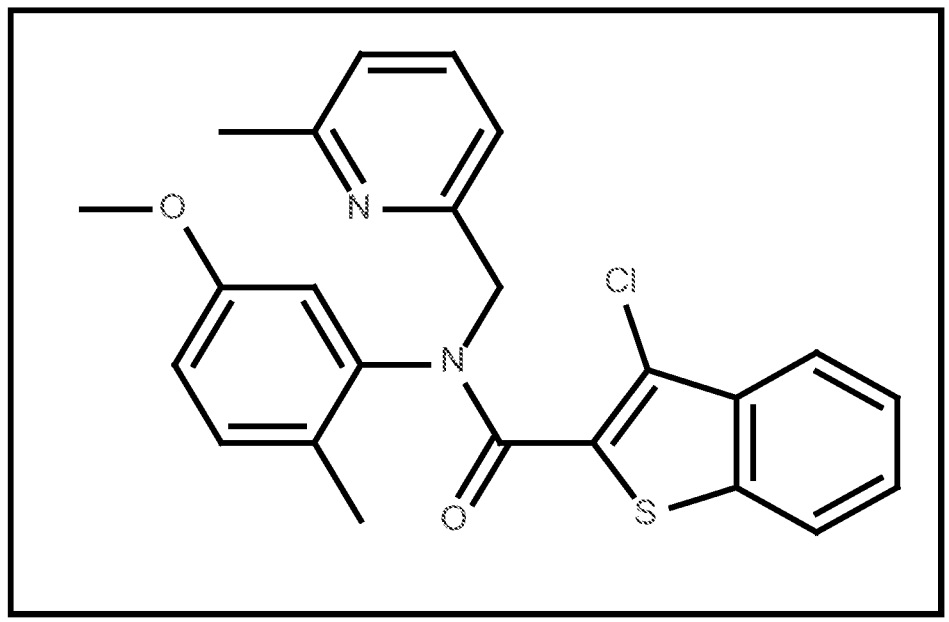
102
Fig. 35

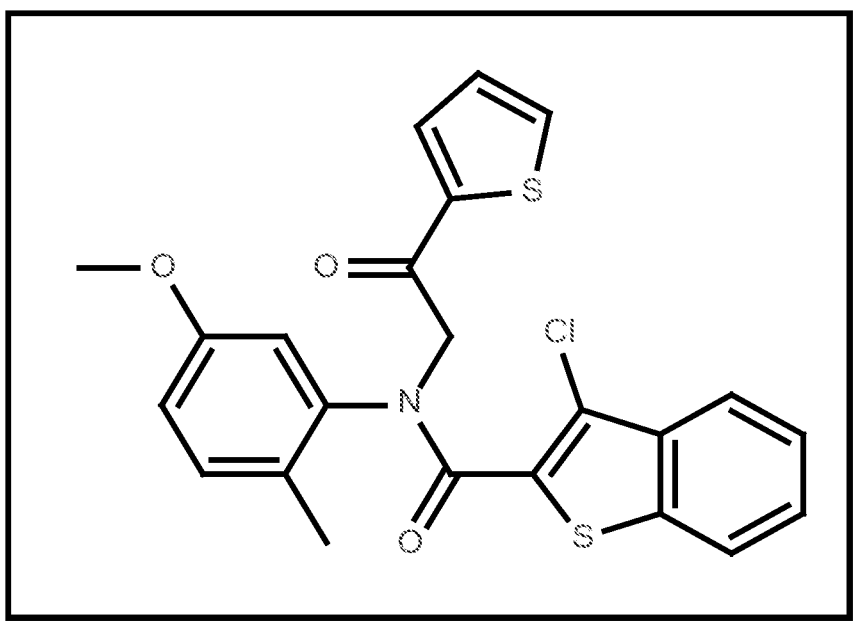
103
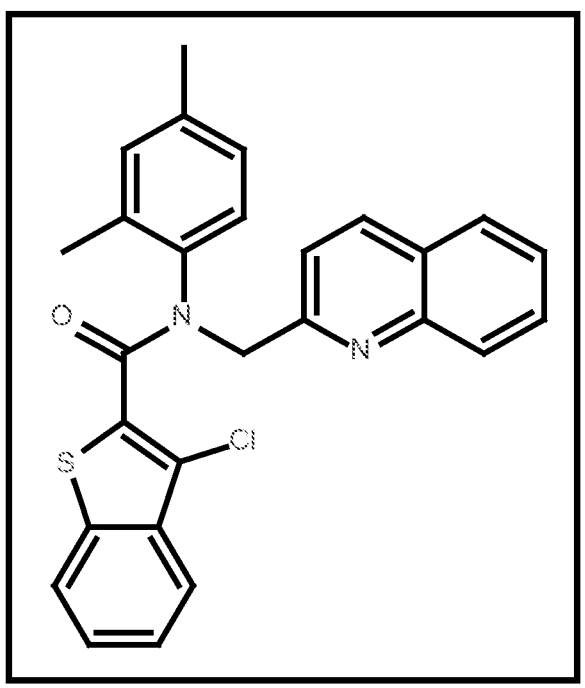
104
Fig. 36

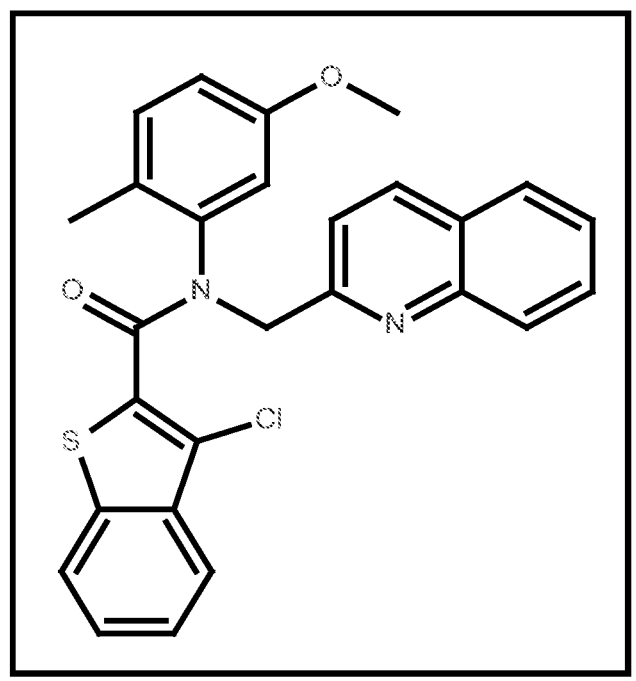
105
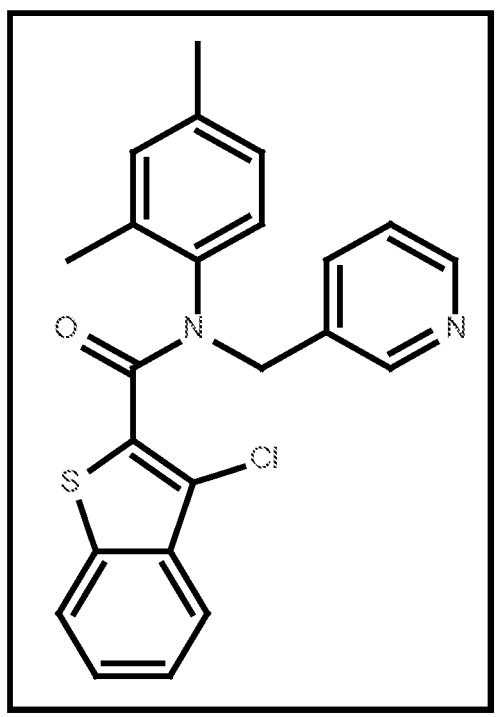
106
Fig. 37

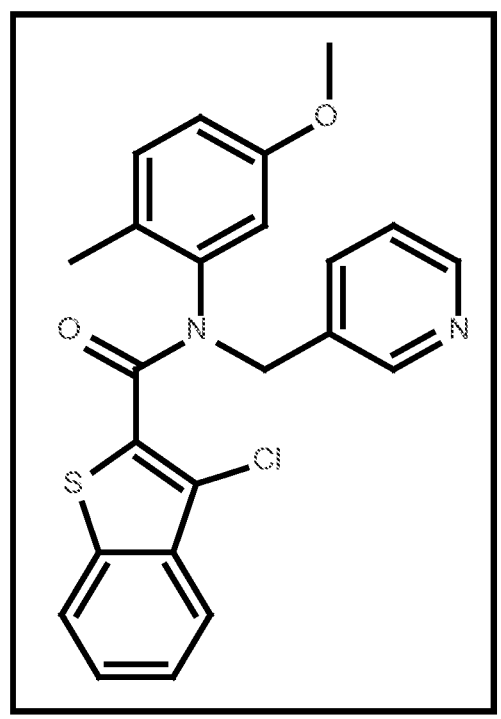
107
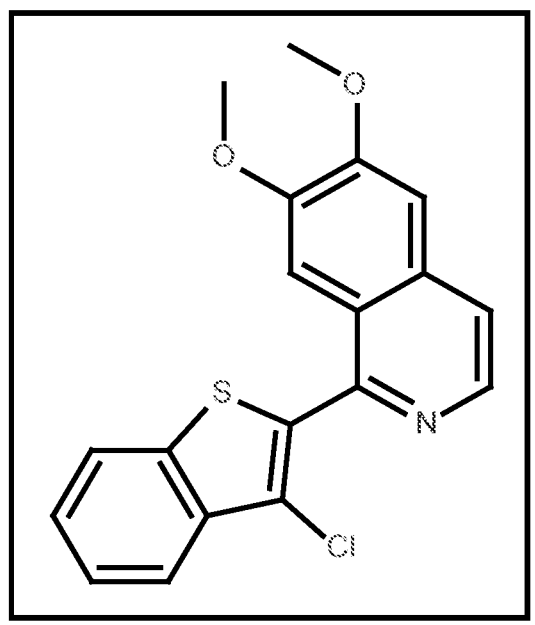
108
Fig. 38

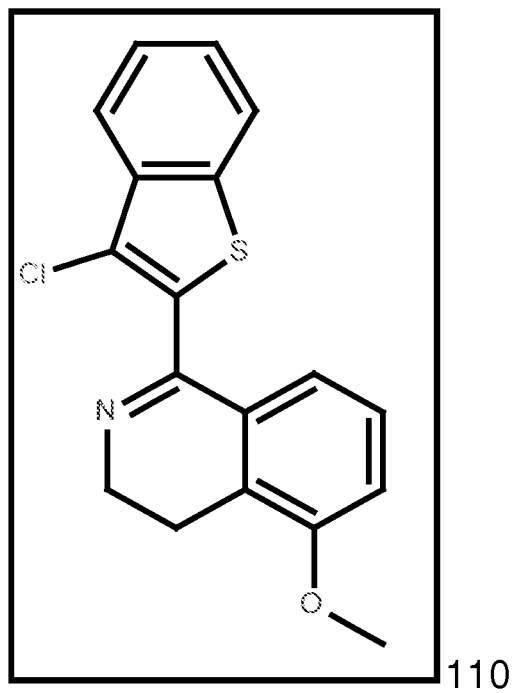
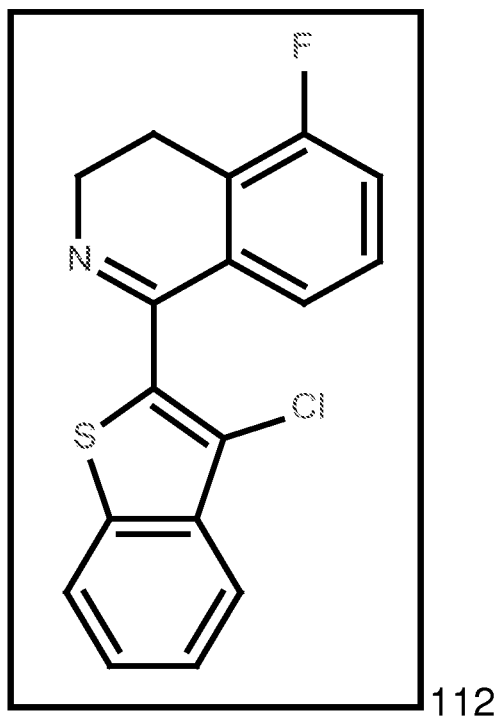
Fig. 39

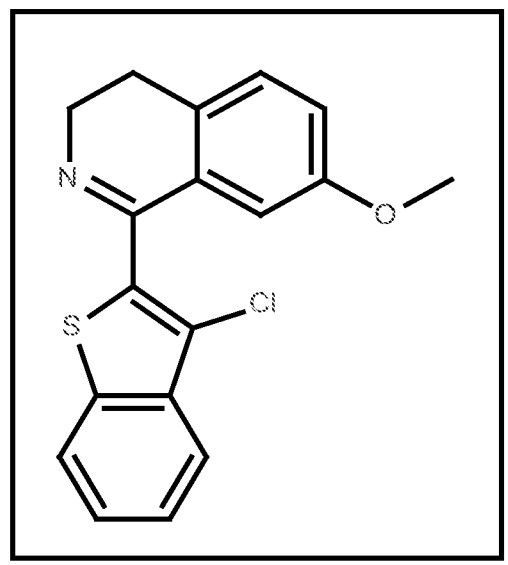
113
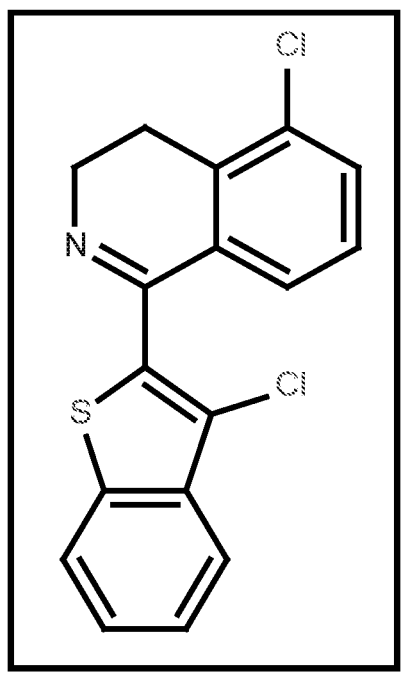
114
Fig. 40

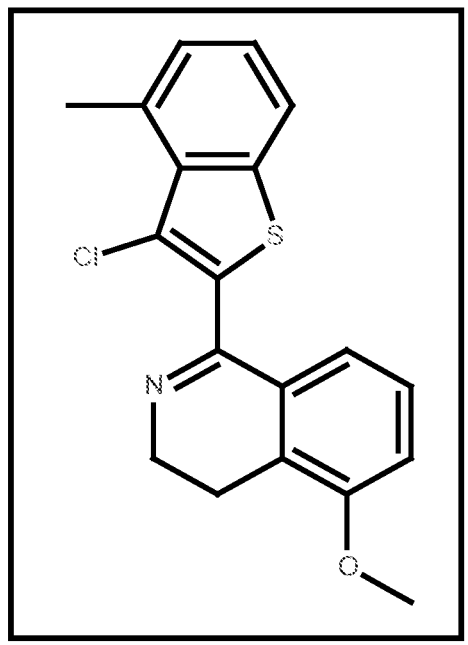
115
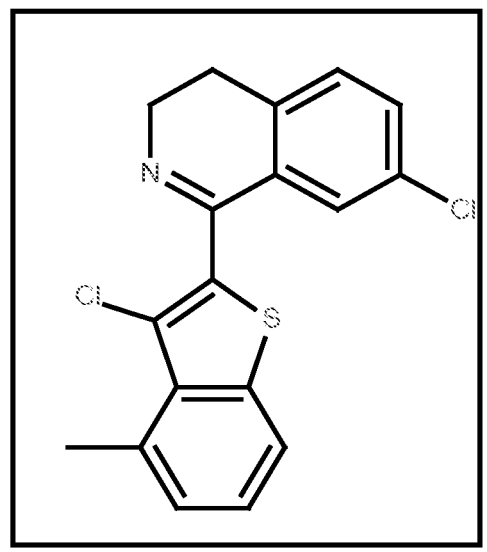
116
Fig. 41

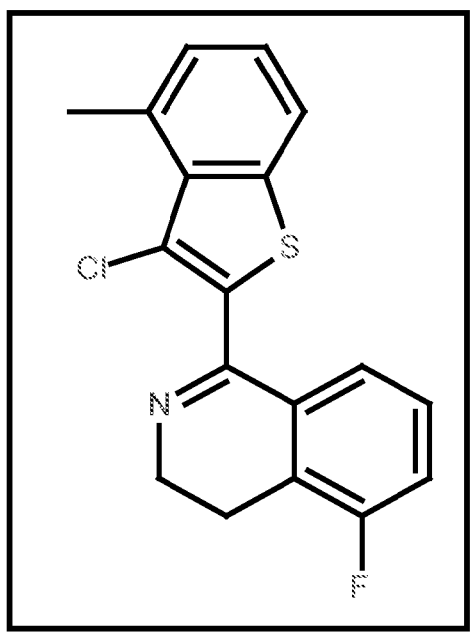
117
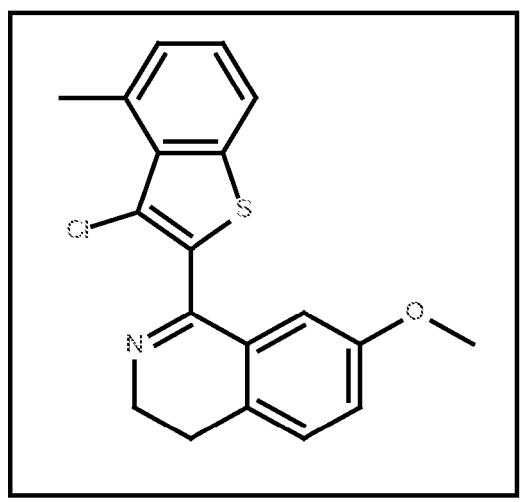
118
Fig. 42

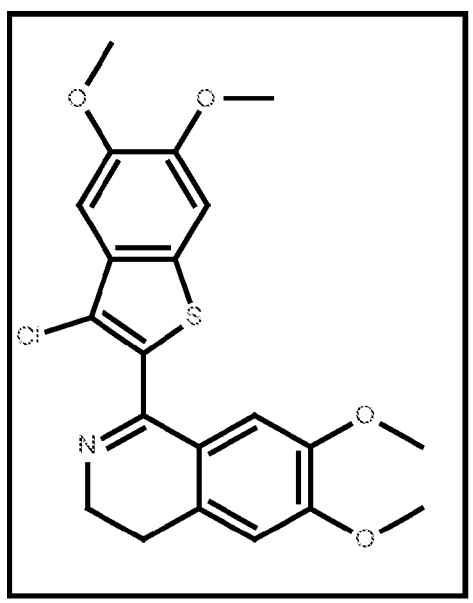
120
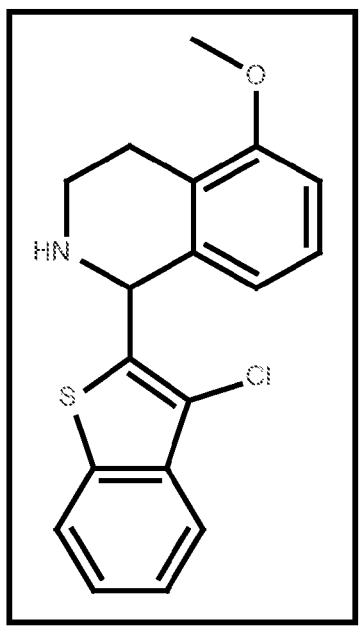
121
Fig. 43

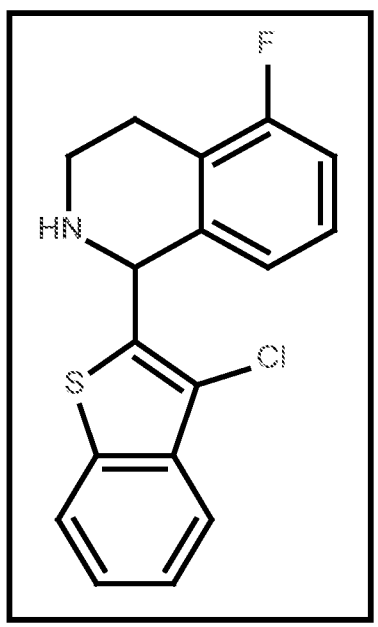
123
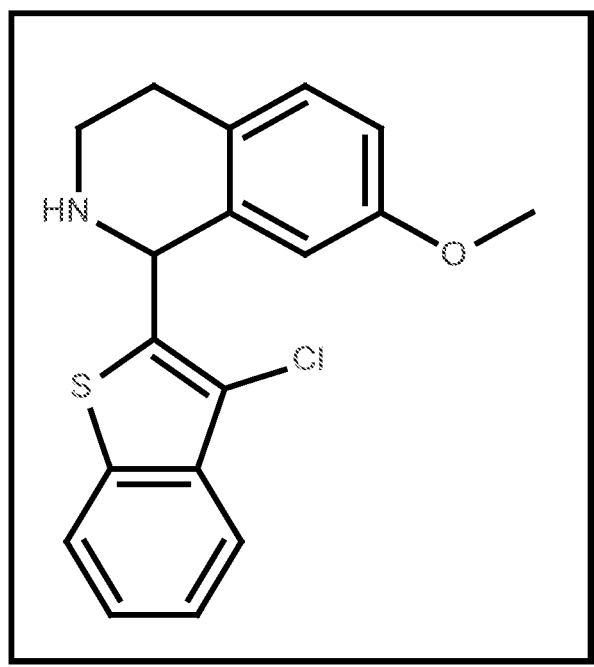
124
Fig. 44

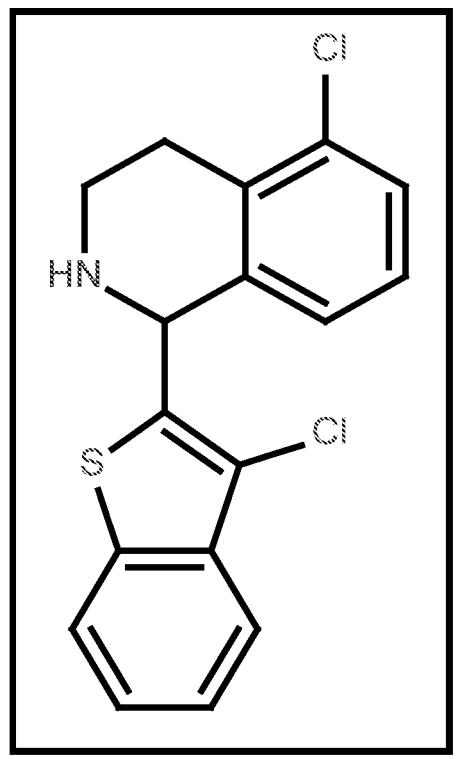
125
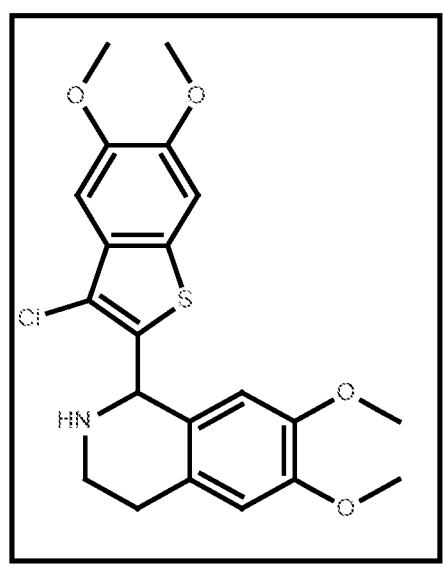
126
Fig. 45

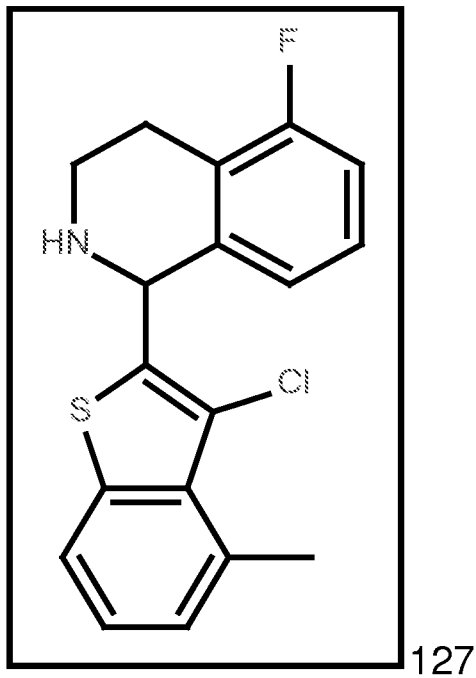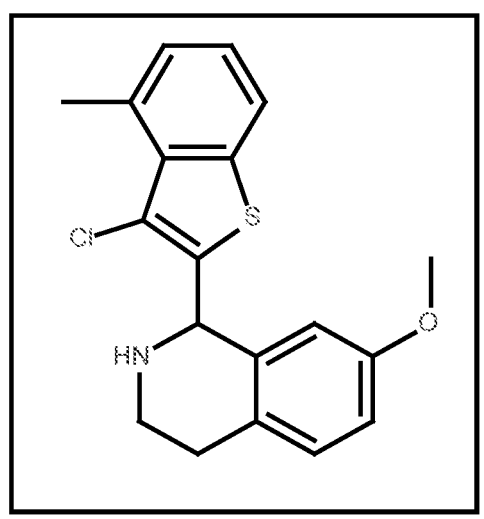
Fig. 46

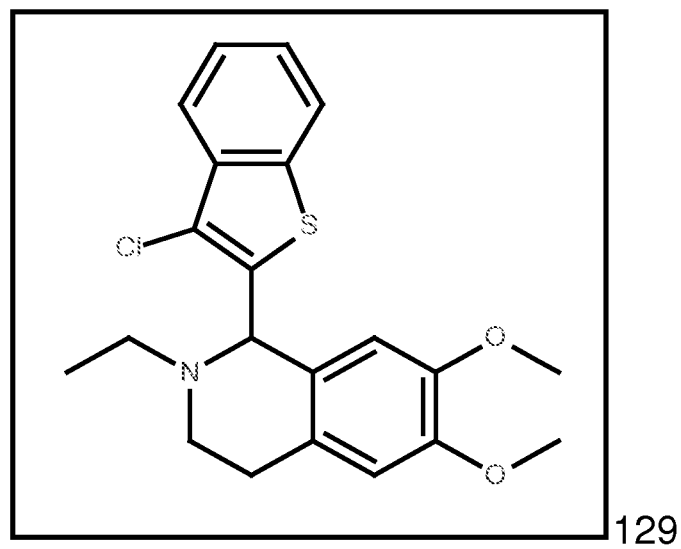
129
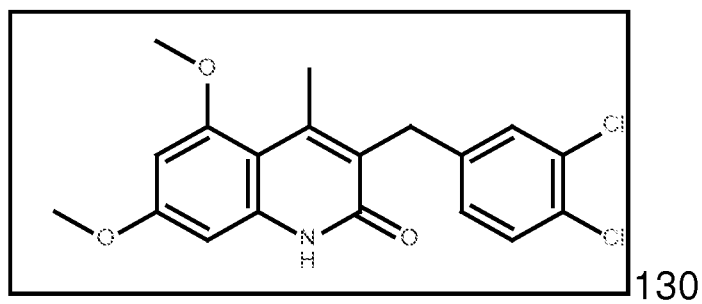
130
Fig. 47

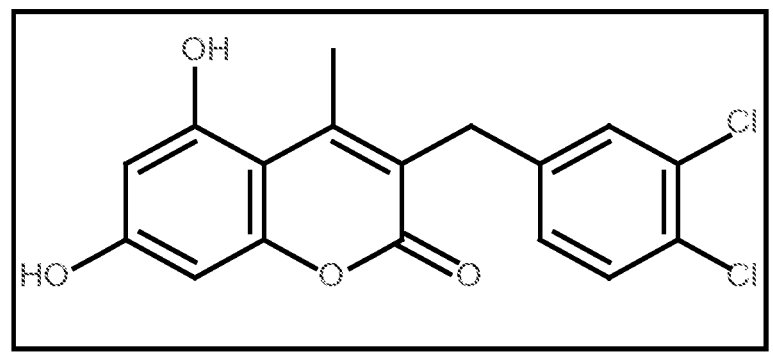
131
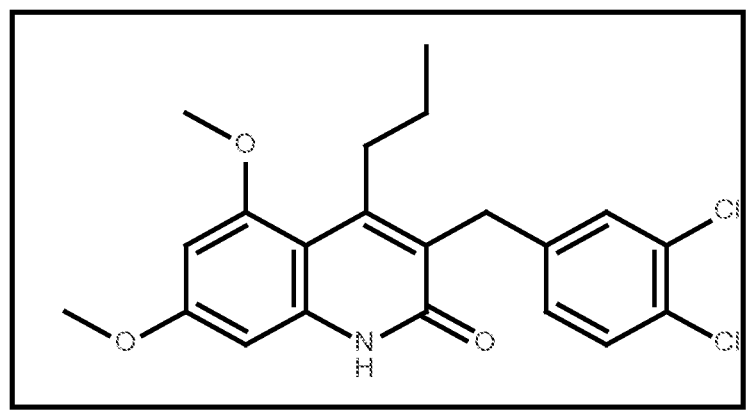
132
Fig. 48

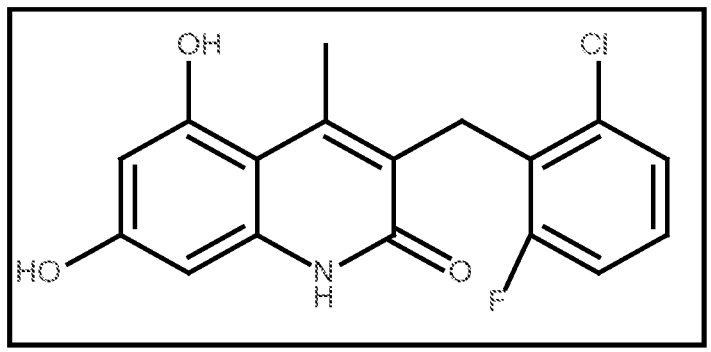
133
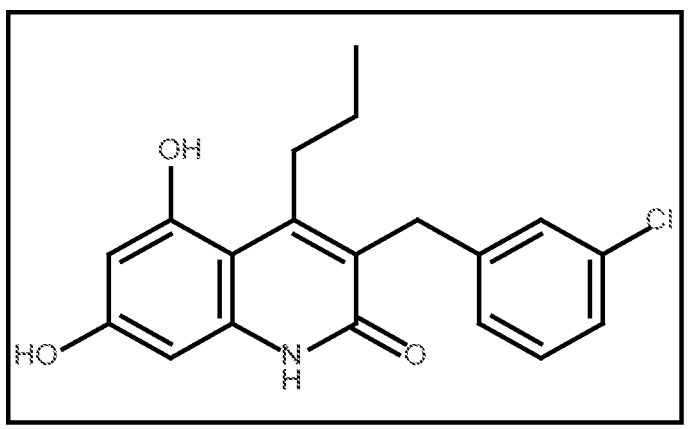
134
Fig. 49

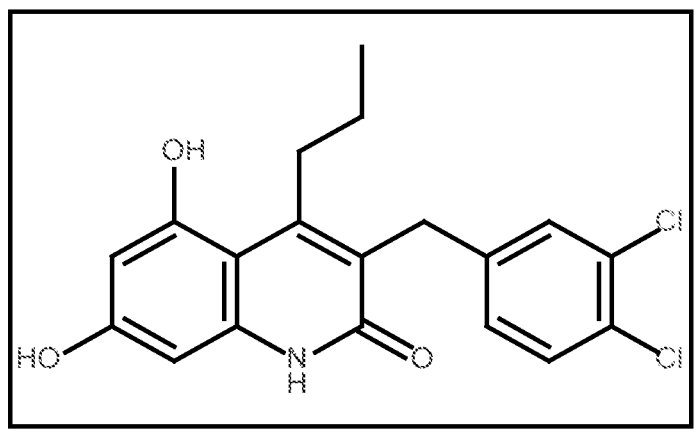
136
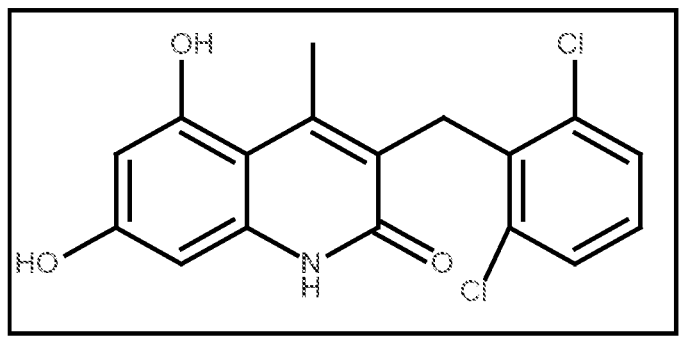
137
Fig. 50

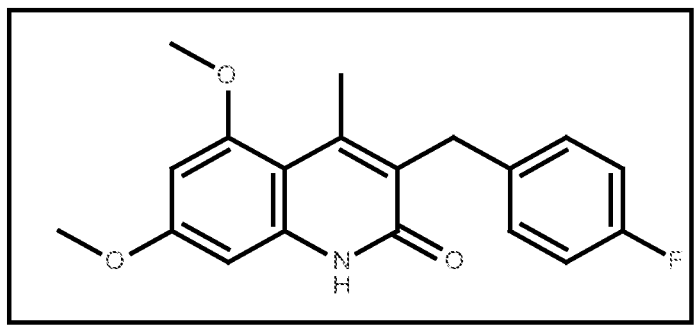
138
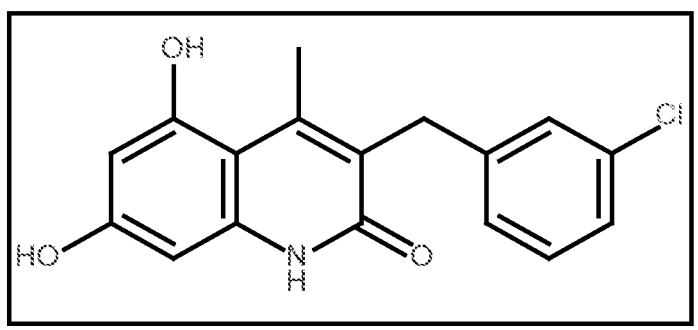
140
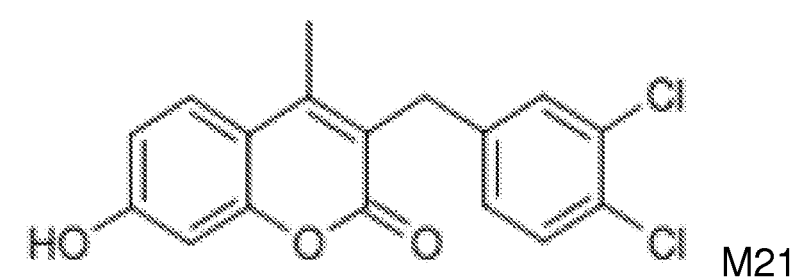
M21
Fig. 51

AGENTS AND METHODS FOR TREATING ISCHEMIC AND OTHER DISEASES

CROSS REFERENCE OF RELATED APPLICATION

This application is a U.S. National Stage of PCT/US2012/042826 filed Jun. 15, 2012, which claims priority to U.S. Provisional Application No. 61/4975,11, which is incorporated by reference in its entirety for all purposes.

BACKGROUND

The transient receptor potential channel TRPM7 is a member of the TRP superfamily of cation channels that comprises greater than 20 cation channels that play critical roles in varied processes within the body. TRP channels are integral membrane proteins in which the ion-conducting pores are formed by six membrane-spanning helical segments that are similar to those of voltage-gated potassium channels and cyclic nucleotide-gated channels. TRP channels are divided into three families based on their homology. The families are the short TRP channel family, the osm TRP family, and the long TRP family. Long TRP channels can be distinguished by their having particularly long extensions outside the channel segment. Long TRP channels are involved in critical control mechanisms regulating cell growth, differentiation and death ((Montell et al., 2002, Harteneck et al., 2000).

The TRPM7 channel belongs to the long TRP family. The human TRPM7 protein was first identified by Runnels et al (2001)) and was identified as a bifunctional protein with kinase and ion channel activities. In another study by Nadler et al. (2001), TRPM7 was identified as a Mg-ATP regulated cation channel required for cell viability. Runnels et al. (2002) reported that TRPM7 is a calcium-permeant ion channel. It was also reported that the kinase domain of TRPM7 directly associates with the C2 domain of phospholipase C (PLC) and that 4,5-biphophate ($PIP_2$), the substrate of PLC, is a key regulator of TRPM7. The TRPM7 channel produces pronounced outward currents at nonphysiological voltages ranging from +50 to +100 mV and small inward currents at negative potentials between −100 to −40 mV when expressed heterologously in mammalian cells (Jiang et al., 2005) The basal activity of TRPM7 was originally reported to be regulated by millimolar levels of intracellular mgATP and $Mg^{2+}$. It is now recognized that the TRPM7 channel is unlikely to be gated by ATP (it was the Mg2+ in the MgATP that, when depleted, caused the channel to open). TRPM7 is activated by depletion of intracellular $Mg^{2+}$, and is inhibited by high concentrations of $Mg^{2+}$ with an $IC_{50}$ of about 0.6 mM (Nadler et al., supra, Jiang et al., supra). The TRPM7 channel is also known as the CHAK, CHAK1, LTRPC7, FLJ20117 or TRPPLIK channel. The TRPM7 channel is also activated by a reduction in extracellular divalent cation levels, especially Mg2+ and Va2+. More recently, the TRPM7 channel has been shown to be involved in ischemic CNS injury and anoxic neuronal cell death (Aarts et al., 2003; Aarts and Tymianski, 2005a, Aarts and Tymianski, 2005b).

Excitotoxicity in brain ischemia triggers neuronal death and neurological disability, and yet these are not prevented by antiexcitotoxic therapy (AET) in humans. Aarts et al. (2003) have shown that in murine neurons subjected to prolonged oxygen glucose deprivation (OGD), AET unmasks a dominant death mechanism perpetuated by a Ca2+-permeable nonselective cation conductance (IOGD). IOGD was activated by reactive oxygen/nitrogen species (ROS), and permitted neuronal Ca2+ overload and further ROS production despite AET. IOGD currents corresponded to those evoked in HEK-293 cells expressing the nonselective cation conductance TRPM7. In cortical neurons, blocking IOGD or suppressing TRPM7 expression blocked TRPM7 currents, anoxic 45Ca2+ uptake, ROS production, and anoxic death. TRPM7 suppression eliminated the need for AET to rescue anoxic neurons and permitted the survival of neurons previously destined to die from prolonged anoxia. Thus, excitotoxicity may be is a subset of a greater overall anoxic cell death mechanism, in which TRPM7 channels play a key role.

Exposure to low Ca(2+) and/or Mg(2+) is tolerated by cardiac myocytes, astrocytes, and neurons, but restoration to normal divalent cation levels paradoxically causes Ca(2+) overload and cell death. This phenomenon has been called the "Ca(2+) paradox" of ischemia-reperfusion. The mechanism by which a decrease in extracellular Ca(2+) and Mg(2+) is "detected" and triggers subsequent cell death is unknown. Transient periods of brain ischemia are characterized by substantial decreases in extracellular Ca(2+) and Mg(2+) that mimic the initial condition of the Ca(2+) paradox. Wei et al. (2007) have shown that In CA1 hippocampal neurons, lowering extracellular divalents stimulates a nonselective cation current. They showed that this current resembles TRPM7 currents in several ways. Both (i) respond to transient decreases in extracellular divalents with inward currents and cell excitation, (ii) demonstrate outward rectification that depends on the presence of extracellular divalents, (iii) are inhibited by physiological concentrations of intracellular Mg(2+), (iv) are enhanced by intracellular phosphatidylinositol 4,5-bisphosphate (PIP(2)), and (v) can be inhibited by Galphaq-linked G protein-coupled receptors linked to phospholipase C beta1-induced hydrolysis of PIP(2). Furthermore, suppression of TRPM7 expression in hippocampal neurons strongly depressed the inward currents evoked by lowering extracellular divalents. Finally, they show that activation of TRPM7 channels by lowering divalents significantly contributes to cell death. Together, the results suggest that TRPM7 contributes to the mechanism by which hippocampal neurons "detect" reductions in extracellular divalents and provide a means by which TRPM7 contributes to neuronal death during transient brain ischemia.

The present application is related to 61/312,154 filed Mar. 9, 2010, 61/285,954 filed Dec. 11, 2009, and PCT/US2010/059976 (WO/2011/072275) filed Dec. 10, 2010, each of which is incorporated by reference in its entirety for all purposes.

BRIEF SUMMARY OF THE CLAIMED INVENTION

The invention provides pharmaceutical compositions comprising a compound according to Formula Ia or IIa, or any other compound or genera of compounds disclosed herein, or pharmaceutically acceptable salts of such compounds. Some compounds inhibit TRPM7-mediated cell death in mammalian cells by at least 50, 60, 70 or 80% relative to a control assay lacking the compound.

In some pharmaceutical composition the compound or pharmaceutically acceptable salt thereof is at least 95 or 99% w/w pure of contaminants from its production. Some compositions further comprise a carrier acceptable for human administration. Some compositions contain a unit dose of the compound or pharmaceutically acceptable salt thereof. Some pharmaceutical compositions are formulated for oral administration. Some such pharmaceutical compositions are formulated as a pill or capsule. Some pharmaceutical compositions are formulated for patenteral administration. Some such pharmaceutical compositions are packaged in a vial containing a unit dose of the agent. Any of these pharmaceutical compositions can be used in prophylaxis of treatment of disease.

The invention provides methods of treating or effecting prophylaxis of a damaging effect of ischemia in a patient, comprising administering to a patient having or at risk of ischemia an effective regime of a pharmaceutical composition, compound or a pharmaceutically acceptable salt thereof as specified above or herein. Optionally, the ischemia is cardiac, renal, retinal or CNS ischemia.

The invention provides methods of treating or effecting prophylaxis of cancer in a patient, comprising administering to a patient having a cancer or at risk of cancer an effective regime of a pharmaceutical composition, compound or a pharmaceutically acceptable salt thereof as specified above or herein. Optionally, the cancer is renal cancer, small lung cell cancer, non-small lung cell cancer, colon cancer, retinoblastoma, breast cancer, melanoma, adrenal carcinoma, cervical cancer, or osteosarcoma.

The invention provides methods of treating or effecting prophylaxis pain, glaucoma, or traumatic brain injury in a patient, comprising administering to a patient having or at risk of such condition an effective regime of a pharmaceutical composition, compound or a pharmaceutically acceptable salt thereof as specified above or herein.

The invention further provides a compound according to formula I, Ia or IIa, for example, M21, for treating traumatic injury to the CNS.

BRIEF DESCRIPTION OF THE DRAWINGS

FIGS. 2A, B: TRPM7 Inhibitor 399 effectively blocks TRPM7 currents). FIG. 2C shows the dose-response curve of 399 effects on TRPM7 like currents.

FIGS. 4A, B: Treatment of rats subjected to lateral Fluid Percussion Injury (FPI) with TRPM7 inhibitors mediates neuronal damage as measured by Rotarod performance.

FIGS. 5A, B: A: Treatment with TRPM7 inhibitors improves morris water maze learning and memory tasks following FPI. B: Individual performance of rats in each group

FIGS. 7-51 show the structures of compounds for which data are provided in Table X. The compound number in the figure corresponds to the first column of Table X.

DETAILED DESCRIPTION OF THE INVENTION

1. Introduction

Figure 1:
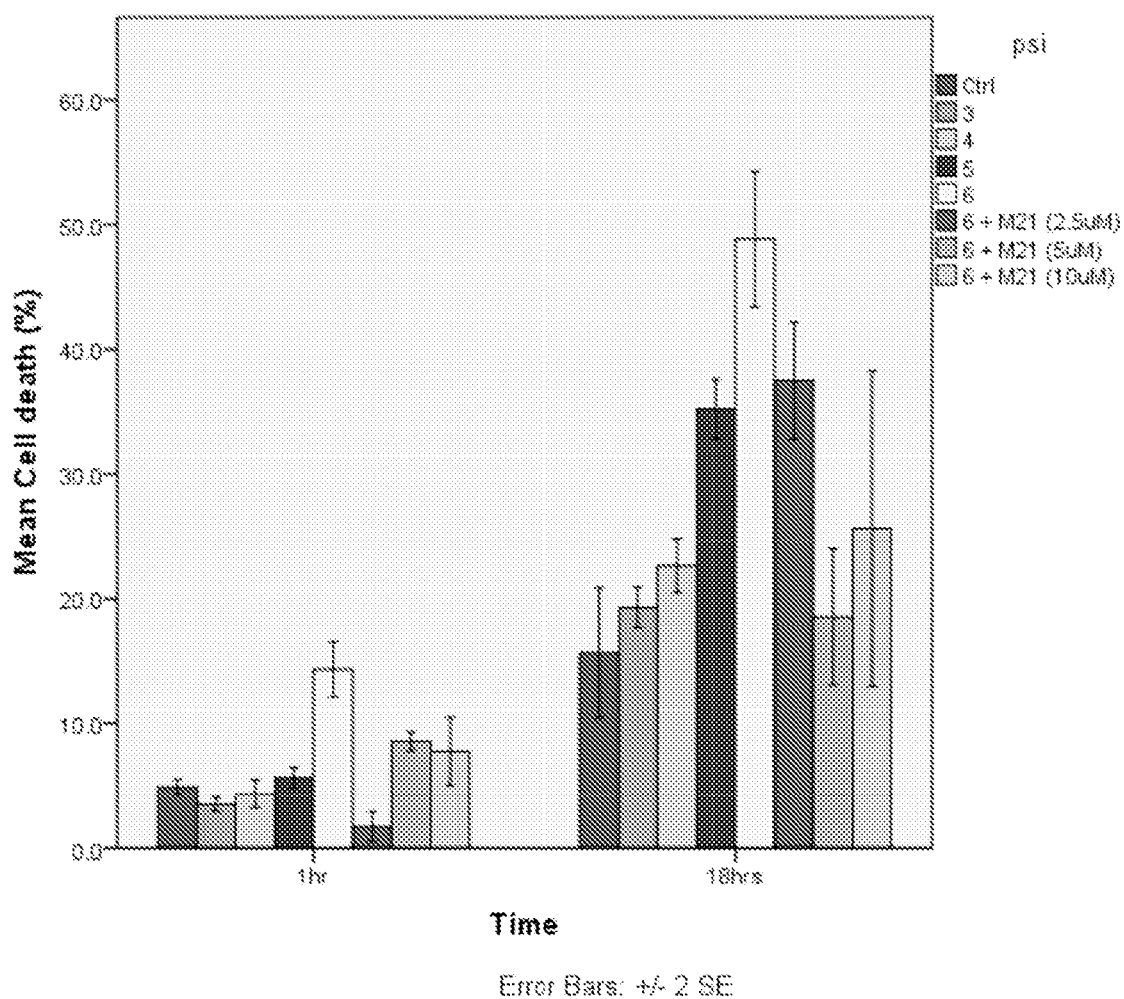
FIG. 1: TRPM7 inhibitor M21 is able to protect the brain from injuries sustained from concussive trauma.

The present invention provides, inter alia, modulators (sometimes referred to as compounds or agents) and methods of screening for other modulators (e.g., activators, inhibitors, stimulators, enhancers, agonists, and antagonists) of TRPM7 proteins. Such modulators can be used in the prophylactic or therapeutic treatment of ischemic and cytodegenerative diseases and conditions, including neurological diseases and conditions, such as stroke, traumatic brain injury, Alzheimer's disease, Parkinson's disease, Huntington's disease, dementia, epilepsy, spinocerebellar ataxia, spinal and bulbar muscular dystrophy, dentatorubropallidoluysian atrophy, brain injury, spinal cord injuries, prion-based diseases, and other traumatic, ischemic or neurodegenerative nervous system injuries. Such modulators can also be used in the prophylactic or therapeutic treatment of non-neurological diseases, including ischemic and degenerative disorders and conditions of other tissues, such as those of the CNS, brain, heart, liver, kidneys, muscles, retina, skin, intestines, pancreas, gall bladder, thyroid, thymus, spleen, bone, cartilage, joints, lungs, diaphragm, adrenal glands, salivary and lacrimal glands, blood vessels, and cells of endodermal, mesodermal and ectodermal origin. Such modulators can also be used in the prophylactic or therapeutic treatment of ocular disorders including macular degeneration, diabetic retinopathy, glaucoma, ischemic retinopathy. Such modulators can further be used in the prophylactic or therapeutic treatment of cancer and other proliferative disorders, including breast cancer, retinoblastoma, head and neck cancers, gastric cancer, adrenal cancer, cervical cancer, osteosarcoma, colon cancer, renal cancer, lung cancer including small or non-small cell lung cancer, melanoma, leukemia and lymphoma. The modulators can also be used to for prophylaxis or therapeutic treatment of pain. The modulators can also be used to preserve or enhance memory, in the prophylaxis or therapeutic treatment of hypertension, autoimmune disorders, arrhythmia, depressive disorders, stress disorders or immune disorders.

The use of cells, cell lines, primary neuronal cultures, whole tissue preparations and whole animals provides a means for assaying for modulators for TRPM7 activity that can then be tested in animal models of diseases, including animal models of diseases modulated by TRPM7 activity, including stroke.

Related methodology is described in US 20080119412 and Sun et al., Nat. Neurosci. 2009 October; 12(10): 1300-7, each incorporated by reference in its entirety for all purposes.

As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of +/−20% or +/−110%, more preferably +/−5%, even more preferably +/−1%, and still more preferably +/−0.1% from the specified value, as such variations are appropriate to perform the disclosed methods.

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991).

Unless otherwise indicated TRPM7 includes reference to human and/or murine TRPM7 proteins.

"Murine TRPM7 protein" refers to an amino acid sequence that has at least 80%, at least 90%, at least 95%, preferably at least 99% amino acid sequence identity, including at least 99.1%, 99.2%, 99.3%, 99.4%, 99.5%, 99.6%, 99.7%, 99.8%, or at least 99.9%, identity to an amino acid sequence encoded by a murine TRPM7 nucleic acid, e.g., a murine TRPM7 protein of Swiss-Prot Q923J1.

"Nucleic acid encoding murine TRPM7 protein" or "TRPM7 gene" or "TRPM7 nucleic acid" refers to a nucleic acid sequence that has at least 96% nucleic acid sequence identity, or at least 90%, 95%, 96.5%, 97%, 97.5%, 98%, 98.5%, 99%, 99.1%, 99.2%, 99.3%, 99.4%, 99.5%, 99.6%, 99.7%, 99.8%, or at least 99.9%, to a murine TRPM7 nucleic acid as shown in e.g., EMBL AY032951, their complements, or conservatively modified variants thereof.

A murine TRPM7 polynucleotide or polypeptide sequence can be naturally occurring or non-naturally occurring. It can be isolated from murine or synthetically constructed.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "functional effects" in the context of assays for testing compounds that affect a TRPM7 gene, TRPM7 protein or TRPM7-mediated cellular injury includes the determination of any parameter that is indirectly or directly under the influence of the TRPM7 gene or protein. It includes changes in ion flux and membrane potential, changes in ligand binding, changes in gene expression, changes in the fluorescence of ion indicator molecules, changes in cellular viability markers, changes in cellular integrity markers, changes in cellular metabolism markers, and changes in the quantity or function of ischemic tissue in a tissue preparation or in a whole animal. "Functional effects" also means all physiological and pathological effects such as increases or decreases in cell death following administration of a test compound.

By "determining the functional effect" refers to determining the functional effect of a compound on a physiological or pathological process mediated by TRPM7 gene or protein. Such functional effects can be measured by any known means, e.g., cell death assays, cell viability assays, ion-sensitive fluorescent probes, electrophysiological techniques, and animal models of disease, and the like.

"TRPM7 activity" refers to one or more of: TRPM7 gene function, TRPM7 protein expression, TRPM7 protein activity as measured by electrophysiological measurements of ion channel activity, TRPM7 protein activity as measured by fluorescent ion indicators, and TRPM7 protein activity as measured using assays of cell metabolism or cell death or cell survival.

The term "modulation" as used herein refers to both upregulation, (i.e., activation or stimulation) for example by agonizing, and downregulation (i.e., inhibition or suppression) for example by antagonizing, TRPM7 activity as measured using the assays described herein. An inhibitor or agonist may cause partial or complete modulation of binding.

"Inhibitors," "activators," and "modulators" (sometimes referred to simply as agents or compounds), of TRPM7 activity, TRPM7 genes and their gene products in cells also refer to inhibitory or activating molecules identified using assays for TRPM7 activity. Inhibitors are compounds that decrease, block, prevent, delay activation, inactivate, desensitize, or down regulate the TRPM7 activity. Activators are compounds that increase, open, activate, facilitate, enhance activation, sensitize or up regulate the TRPM7 activity. Such assays for inhibitors and activators include e.g., expressing TRPM7 in cells or cell membranes and then inferring the flux of ions through the use of fluorescent ion indicators, or through measuring cell survival or cell death, after contacting a cell expressing TRPM7 with a putative modulator of TRPM7 activity. To examine the extent of inhibition, samples or assays comprising a TRPM7 protein are treated with a potential activator or inhibitor and are compared to control samples without the activator inhibitor. Control samples (untreated with inhibitors) are assigned a relative TRPM7 activity value of 100%. Inhibition of TRPM7 is achieved when the TRPM7 activity value relative to the control is about 90% or less, optionally about 80% or less, 70% or less, 60% or less, 50% or less, 40% or less, 30% or less; or 25-0%. Activation of TRPM7 is achieved when the TRPM7 activity value relative to the control is about 110%, optionally 120%, 130%, 140%, 150% or more, 200-500% or more, 1000-3000% or more.

A "TRPM7 inhibitor," used interchangeably with "TRPM7 competitive inhibitor," (also sometimes referred to simply as a compound or agent), means that the subject compound reduces TRPM7 activity by at least 20%, e.g., at least 30%, at least 40%, at least 50%, at least 60%, at least 70%, at least 80%, at least 90%, at least 95%, up to about 99% or 100%, as compared to controls that do not include the test compound. In general, agents of interest are those which exhibit IC50 values in a particular assay in the range of about 1 mM or less. Compounds that exhibit lower IC50s, for example, have values in the range of about 250 µM, 100 µM, 50 µM, 25 µM, 10 µM, 5 µM, 2 µM, 1 µM, 500 nM, 250 nM, 100 nM, 50 nM, 25 nM, 10 nM, 5 nM, 1 nM, or even lower, and compounds with these attributes are presently preferred.

The term "analog" is used herein to refer to a small molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility in modulating a TRPM7 activity. Synthesis and screening of analogs, to identify variants of known compounds having improved traits (such as higher binding affinity, or higher selectivity of binding to a target and lower activity levels to non-target molecules) is an approach that is well known in pharmaceutical chemistry.

As used herein, "contacting" has its normal meaning and refers to bringing two or more agents into contact, e.g., by combining the two or more agents (e.g., two proteins, a protein and a small molecule, etc.). Contacting can occur in vitro, in situ or in vivo.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

"Recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A host cell is any cell suitable for expression of subject polypeptide-encoding nucleic acid. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293); HEK-293T cells; baby hamster kidney cells (BHK, ATCC CCL 10); chinese hamster ovary-cells (CHO); mouse sertoli cells (TM4); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells; NIH/3T3 cells (ATCC CRL-1658); and mouse L cells (ATCC CCL-1). Additional cell lines are available from the American Type Culture Collection, 10801 University Boulevard, Manassas, Va. 20110-2209.

"A monovalent cation indicator" refers to a molecule that is readily permeable to a cell membrane or otherwise amenable to transport into a cell e.g., via liposomes, etc., and upon entering a cell, exhibits a fluorescence signal, or other detectable signal, that is either enhanced or quenched upon contact with a monovalent cation. Examples of monovalent cation indicators useful in the invention are set out in Haugland, R. P. Handbook of Fluorescent Probes and Research Chemicals, 9th ed. Molecular Probes, Inc Eugene, Oreg., (2001).

"A divalent cation indicator" refers to a molecule that is readily permeable to a cell membrane or otherwise amenable to transport into a cell e.g., via liposomes, etc., and upon entering a cell, exhibits a fluorescence signal, or other detectable signal, that is either enhanced or quenched upon contact with a divalent cation.

"Specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions can require a binding moiety that is selected for its specificity for a particular target antigen. A variety of assay formats can be used to select ligands that are specifically reactive with a particular protein. For example, solid-phase ELISA immunoassays, immunoprecipitation, Biacore and Western blot are used to identify peptides that specifically react with the antigen. Typically a specific or selective reaction is at least twice background signal or noise and more typically more than 10 times background.

"Naturally-occurring" as applied to an object refers to the fact that an object can be found in nature. For example, a polypeptide or polynucleotide sequence that is present in an organism (including viruses) that can be isolated from a source in nature and which has not been intentionally modified in the laboratory is naturally-occurring.

The term "assessing" includes any form of measurement, and includes determining if an element is present or not. The terms "determining," "measuring," "evaluating," "assessing" and "assaying" are used interchangeably and may include quantitative and/or qualitative determinations. Assessing may be relative or absolute. "Assessing binding" includes, e.g., determining the amount of binding, the KD for binding affinity and/or determining whether binding has occurred (i.e., whether binding is present or absent).

The terms "treatment," "treating," "treat," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting or slowing its development or onset; and (c) relieving the disease, i.e., causing regression of the disease and/or relieving one or more disease symptoms. "Treatment" is also meant to encompass delivery of an agent to provide for a pharmacologic effect, even in the absence of a disease or condition.

"Subject," "individual," "host" and "patient" are used interchangeably herein, to refer to an animal, human or non-human, amenable to a treatment according to a method of the invention. Generally, the subject is a mammalian subject. Exemplary subjects include humans, domestic and non-domestic animals: e.g., non-human primates, mice, rats, cattle, sheep, goats, pigs, dogs, cats, and horses; with humans being of particular interest.

For any molecule described as containing one or more optional substituents only sterically practical and/or synthetically feasible compounds are meant to be included. Further, combinations of substituents and/or variables are permissible only if such combinations result in stable compounds.

"Optionally substituted" refers to all subsequent modifiers in a term, for example in the term "optionally substituted phenyl ($C_{1-6}$)alkyl," optional substitution may occur on both the alkyl portion and the phenyl portion of the molecule. Preferably, the alkyl groups herein can have one hydrogen on the alkyl backbone substituted with aromatic and heteroaromatice ring systems that are described herein, which themselves can be further optionally substituted. Another example is "optionally substituted $C_{5-7}$ aryl-($C_{1-6}$)alkyl can be a fluoro,chloro-benzyl group.

Another preferred alkyl is a "haloalkyl." Haloalkyl refers to any of the alkyl groups disclosed herein that is substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl. A haloalkyl can have other substitutions in addition to the halogen.

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected. Examples include fluoromethyl, hydroxypropyl, nitromethyl, aminoethyl or and the like, optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloro-pyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—CO$_2$H), optionally substituted carboalkoxy (that is, acyloxy or —OC(=O)R), optionally substituted carboxyalkyl (that is, esters or —CO$_2$)), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfanyl, optionally substituted alkylsulfonyl, thiol, oxo, carbamyl, optionally substituted acylamino, optionally substituted hydrazino, optionally substituted hydroxylamino, and optionally substituted sulfonamido.

An "alkyl" group refers to a saturated aliphatic hydrocarbon, including straight-chain, branched chain, and cyclic alkyl groups. Alkyl groups can comprise any combination of acyclic and cyclic subunits. Further, the term "alkyl" as used herein expressly includes saturated groups as well as unsaturated groups. Unsaturated groups contain one or more (e.g., one, two, or three), double bonds and/or triple bonds. The term "alkyl" includes substituted and unsubstituted alkyl groups. "Lower alkyl" is defined as having 1-7 carbons. Preferably, the alkyl group has 1 to 18 carbons and is straight-chain or branched. The term can include a saturated linear or branched-chain monovalent hydrocarbon radical of a specified number of carbon atoms, wherein the alkyl radical may be optionally substituted independently with one or more substituents described herein. Substituents can be chosen form any of the radicals, groups or moieties described herein. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl(n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), and the like. Thus, when an alkyl residue having a specific number of carbons is named, all geometric isomers having that number of carbons are intended to be encompassed; thus, for example, either "butyl" or "C$_4$ alkyl" is meant to include n-butyl, sec-butyl, isobutyl, t-butyl, isobutenyl and but-2-yne radicals; and for example, "propyl" includes n-propyl, propenyl, and isopropyl. The term "C$_1$-C$_6$ alkyl" encompasses alkyl groups of 1 to 6 carbons. Preferably, the carbon number is one to three in all embodiments.

The term "alkoxy" means a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length. The substitutions on alkoxy groups are similar to those on alkyl groups. Haloalkoxy groups are preferred optionally substituted alkoxy groups, for example, trifluormethoxy.

The term "alkylamine" by itself or as part of another group refers to an amino group which is substituted with one alkyl group as defined above.

The term "dialkylamine" by itself or as part of another group refers to an amino group which is substituted with two alkyl groups as defined above.

The term "halo" or "halogen" by itself or as part of another group refers to chlorine, bromine, fluorine or iodine, unless defined otherwise in specific uses in the text and/or claims.

The term "carbonyl" refers to a C double bonded to an O, wherein the C is further covalently bound.

The term "heterocycle" or "heterocyclic ring", as used herein except where noted, represents a stable 5- to 7-membered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful arc rings contain one nitrogen combined with one oxygen or sulfur, or two nitrogen heteroatoms. Examples of heterocyclyl radicals include, but are not limited to, azctidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl, most preferably piperazinyl and morpholinyl.

The term "aryl," "aromatic" and "heteroaromatic" refer to aromatic six- to fourteen-membered carbocyclic ring, for example, benzene, naphthalene, indane, tetralin, fluorene and the like. The "aryl" "aromatic" and "heteroaromatic" group may be substituted with substituents including lower alkyl, hydroxyl, halo, haloalkyl, nitro, cyano, alkoxy and lower alkylamino, and the like.

The term "heteroatom" is used herein to mean an oxygen atom ("0"), a sulfur atom ("S") or a nitrogen atom ("N"). When the heteroatom is nitrogen, it may form an NRR moiety, wherein each R is independently from one another hydrogen or a substitution.

The term "alkenyl" refers to linear or branched-chain hydrocarbon radical of two to six carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

An "alkenyl" group refers to an unsaturated hydrocarbon group containing at least one carbon-carbon double bond, including straight-chain, branched-chain, and cyclic groups. Preferably, the alkenyl group has 1 to 18 carbons. The alkenyl group may be substituted or unsubstituted. The term includes a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include ethynyl (—C≡CH), propynyl (propargyl, —CH$_2$C≡CH), and the like.

The terms "cyclic," "bicyclic" and "heterobycyclic" refer to a saturated or partially unsaturated ring having from 5 to 12 carbon atoms as a monocyclic ring or 7 to 12 carbon atoms as a bicyclic ring. Bicyclic rings having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Included in this definition are bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, biphenyl, benzoamidazoles, indole, coumarin, pyranopyrole, benzothiophene, indazole, indenyl, indanyl, 1,2-dihydronapthalene, 1,2,3,4-tetrahydronapthyl, and the like. Aryl groups are optionally substituted independently with one or more substituents described herein.

An "Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like.

An "alkynyl" group refers to an unsaturated hydrocarbon group containing at least one carbon-carbon triple bond, including straight-chain, branched chain, and cyclic groups. Preferably, the alkynyl group has 1 to 18 carbons. The alkynyl group may be substituted or unsubstituted.

As used herein, the term "acute insult to the central nervous system" includes short-term events that pose a substantial threat of neuronal damage mediated by glutamate excitotoxicity, or caused by trauma, inflammation TRPM7 channels, TRPM2 or other channels as well as, longer-term propagation of stroke-induced ischemic damage mediated e.g. by inflammation Ischemic events may also involve inadequate blood flow, such as a stroke or cardiac arrest, hypoxic events (involving inadequate oxygen supply, such as drowning, suffocation, or carbon monoxide poisoning), trauma to the brain or spinal cord (in the form of mechanical or similar injury), certain types of food poisoning which involve an excitotoxic poison such as domoic acid, and seizure-mediated neuronal degeneration, which includes certain types of severe epileptic seizures. It can also include trauma that occurs to another part of the body, if that trauma leads to sufficient blood loss to jeopardize blood flow to the brain (for example, as might occur following a shooting, stabbing, or automobile accident).

"Cardiovascular ischemia" which is used interchangeably with "myocardial ischemia" or cardiac or heart ischemia is intended to mean acute and chronic damage in the circulatory system with cell death resulting, e.g., from hypoxia, e.g., heart attack, suffocation, carbon monoxide poisoning, trauma, pulmonary dysfunction and the like; decreased blood flow, e.g., from occlusion, atherosclerosis, diabetic microvascular insufficiency and the like; dysregulation of nitric oxide; dysfunction of the endothelium or vascular smooth muscle; and the like.

2. Assays for Modulators of Murine TRPM7 Production or TRPM7 Activity

TRPM7 has been identified as a Mg2+ and Ca2+-regulated and calcium-permeant ion channel required for cell viability. As an ion channel, TRPM7 conducts calcium, Mg2+ and monovalent cations to depolarize cells and increase intracellular calcium. TRPM7 currents are activated at low intracellular Mg levels or low extracellular levels of divalent cations and are blocked by a number of divalent and polyvalent cations, including magnesium, zinc, spermine, 2-aminophenoxyborate, Mn(III) tetrakis (4-benzoic acid) porphyrin chloride, and lanthanum (Harteneck, Arch Pharmacol 2005 371"307-314). Both $Mg^{2+}$ and $Zn^2$ permeate TRPM7 channels and block the monovalent cation flow through them (Kozak et al., Biophys. 2003 84:2293-2305). The TRPM7 channel produces pronounced outward currents at nonphysiological voltages ranging from +50 to +100 mV and small inward currents at negative potentials between −100 to −40 mV when expressed heterologously in mammalian cells (Jiang et al, J. Gen. Physiol. 2005 126(2), 137-150) TRPM7 has also been shown to be modulated by Src-family kinases (Jiang et al., J. Biol. Chem. 2003 278:42867-42876), phosphatidylinositol 4,5-biphosphate (PIP.sub.2) (Runnels et al., Nat Cell Biol 2002 4:329-336), and its own .alpha.-kinase domain (Takezawa et al., PNAS USA 2004 101:6009-6014). Heterologously expressed TRPM7 channels, e.g., TPRM7 channels expressed in HEK-293 cells, exhibit currents with a high $Ca^{2+}$ permeability, an outwardly rectifying I-V curve, enhancement by low $Ca^{2+}$ concentration and a block of current by the polyvalent cation gadolinium. Overexpression of TRPM7 channels has been shown to be lethal to HEK-293 cells. The lethality can be prevented by increasing extracellular $Mg^{2+}$ to restore $Mg.^{2+}$ homeostasis (Aarts et al., Cell 2003 115:863-877).

The present invention provides, inter alia, cell based systems that can be used to identify modulators, for example, inhibitors or activators of TRPM7 production or TRPM7 activity. The amount or activity of a TRPM7 channel can be assessed using a variety of assays, including measuring current, measuring membrane potential, measuring ion flux, measuring ligand binding, measuring second messengers and transcription levels or physiological effects such as cell survival.

Modulators of the TRPM7 channels can be tested using biologically active TRPM7, either recombinant or naturally occurring. Murine TRPM7 can be isolated, co-expressed or expressed in a cell, or expressed in a membrane derived from a cell. Samples or assays that are treated with a potential TRPM7 channel inhibitor or activator can be compared to control samples without the test compound, to examine the extent of modulation. Control samples (untreated with activators or inhibitors) are assigned a relative TRPM7 activity value of 100%. Inhibition of channels comprising TRPM7 is achieved when the ion channel activity value relative to the control is, for example, about 90%, preferably about 50%, more preferably about 25%. Activation of channels comprising TRPM7 is achieved when the ion channel activity value relative to the control is 110%, more preferably 150%, more preferable 200% higher.

Changes in ion flux can be assessed by determining changes in polarization (i.e., electrical potential) of the cell membrane expressing the TRPM7 channel. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Runnels et al. Science 2001 291:1043-1047, Jiang et al, J. Gen. Physiol. 2005 126 (2), 137-150). Whole cell currents are conveniently determined using the standard methodology (see, e.g., Hamil et al., PFlugers. Archiv. 1981, 391:85). Other known assays include: radiolabeled rubidium flux assays and fluorescence assays using ion-sensitive dyes, voltage-sensitive dyes (see, e.g., Vestergarrd-Bogind et al., J. Membrane Biol. 1988, 88:67-75; Daniel et al., J. Pharmacol. Meth. 1991, 25:185-193; Holevinsky et al., J Membrane Biology 1994, 137:59-70). Generally, the compounds to be tested are present in the range from about 1 µM to about 100 mM.

The present invention provides, inter alia, methods of identifying molecules that bind TRPM7, methods of identifying molecules that modulate TRPM7 ion channel activity, and/or methods of identifying molecules that alter expression of TRPM7 within a cell. These molecules are candidate bioactive agents that can be useful for treating conditions or diseases regulated by TRPM7 activity. Such modulators can be used in the therapeutic or prophylactic treatment of any of the diseases and disorders described herein including ischemic injuries as described herein, as well as neurodegenerative conditions, including neurological diseases and conditions, such as stroke, traumatic brain injury, Alzheimer's disease, Parkinson's disease, Huntington's disease, dementia, epilepsy, spinocerebellar ataxia, spinal and bulbar muscular dystrophy, dentatorubropallidoluysian atrophy, brain injury, spinal cord injury, and other traumatic nervous system injuries. Such modulators can also be used in the therapeutic treatment of non-neurological diseases, including ischemic disorders and conditions of other tissues, such as ischemia of the heart, liver, kidneys, muscles, retina, skin, intestines, pancreas, gall bladder, thyroid, thymus, spleen, bone, cartilage, joints, lungs, diaphragm, adrenal glands, salivary and lacrimal glands, blood vessels, and cells of endothelial, mesanchymal and neural origin. In a preferred embodiment, these methods can be used to identify drug candidates that inhibit murine TRPM7 activity.

The present invention provides methods of screening for a candidate bioactive agent capable of reducing TRPM7-mediated cellular injury. In some embodiments, the candidate bioactive agent binds to a particular domain of the TRPM7 protein, such as, the C-terminal kinase domain. In other embodiments, the candidate bioactive agent acts on a downstream signaling pathway that is associated and/or activated by TRPM7 activity, and that mediate the injurious consequences of TRPM7 activity on the cell.

In one embodiment for binding assays, either TRPM7 or a candidate bioactive agent is labeled. The label can be any detectable label, such as those described herein. The label provides a means of detecting the binding of the candidate agent to TRPM7. In some binding assays, TRPM7 is immobilized or covalently attached to a surface and contacted with a labeled candidate bioactive agent. In other assays, a library of candidate bioactive agents are immobilized to a surface or covalently attached to a surface, e.g., biochip and contacted with a labeled TRPM7.

The present invention provides methods for blocking or reducing murine TRPM7 gene expression as well as methods for screening for a candidate bioactive agent capable of blocking or reducing TRPM7 gene expression and thus, TRPM7 activity. Expression of TRPM7 can be specifically suppressed by methods such as RNA interference (RNAi) (Science, 288: 1370-1372 (2000)). Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. In RNA interference methods, post-transcriptional gene silencing is brought about by a sequence-specific RNA degradation process which results in the rapid degradation of transcripts of sequence-related genes. Small nucleic acid molecules, such as short interfering nucleic acid (siNA), short interfering RNA (siRNA), double-stranded RNA (dsRNA), micro-RNA (mRNA), and short hairpin RNA (shRNA) molecules can all be used to modulate the expression of TRPM7 genes. Small nucleic acid molecules capable of suppressing TRPM7 through RNA interference can be prepared by methods known in the art. See, for example, US Publication No. 2005/0124567 and Aarts et al., Cell 2003 115:863-877.

Accordingly, the present invention provides molecules capable of modulating e.g., blocking or reducing murine TRPM7 activity, as well as methods of screening for a candidate bioactive agent capable of modulating murine TRPM7 activity, such as anti-sense RNAs and DNAs, ribozymes, and other small nucleic acid molecules such as those described herein. All of these agents can be used as therapeutic agents for blocking the expression of certain TRPM7 genes in vivo. In some embodiments, they can be used to prevent TRPM7 gene transcription into mRNAs, to inhibit translation of TRPM7 mRNAs into proteins, and to block activities of pre-existing TRPM7 proteins. Standard immunoassays, such as western blotting, ELISA, and the like, can be performed to confirm that the candidate bioactive agent has an effect on TRPM7 gene expression. Alternatively, TRPM7 expression can be determined by RT-PCR. Methods of performing RT-PCR are known in the art and are thus, not described herein. The effect of these molecules on TRPM7 channel activity can be assessed using a variety of assays described herein, including measuring current, measuring membrane potential, measuring ion flux, and measuring cell survival.

In some embodiments, the present invention provides methods for identifying molecules that modulate the divalent or monovalent cationic permeability of the TRPM7 channel.

Modulation of the monovalent cationic permeability of the TRPM7 channel can, for example, be determined by measuring the inward and outward currents in whole cell patch clamp assays or single-channel membrane patch assays in the presence and absence of the candidate bioactive agent. In an alternative embodiment, the modulation of monovalent cation activity can be monitored as a function of cation currents and/or membrane-potential of a cell comprising a TRPM7 channel. For example, the modulation of membrane potential can be detected with the use of a membrane potential-sensitive probe, such as bis-(1,3-dibutylbarbituric acid)trimethine oxonol (DiBAC4(3)) (Handbook of Fluorescent Probes and Research Chemicals, 9th ed. Molecular Probes). The use of a fluorescent membrane potential-sensitive probe allows rapid detection of change in membrane potential by monitoring change in fluorescence with the use of such methods as fluorescence microscopy, flow cytometry and fluorescence spectroscopy, including use of high through-put screening methods utilizing fluorescence detection (Alvarez-Barrientos, et al., "Applications of Flow Cytometry to Clinical Microbiology", Clinical Microbiology Reviews, 13(2): 167-195, (2000)).

Modulation of the monovalent cationic permeability of the TRPM7 channel by a candidate agent can be determined by contacting a cell that expresses TRPM7 with a monovalent cation and a monovalent cation indicator that reacts with the monovalent cation to generate a signal. The intracellular levels of the monovalent cation can be measured by detecting the indicator signal in the presence and absence of a candidate bioactive agent. Additionally, the intracellular monovalent cation levels in cells that express TRPM7 with cells that do not express TRPM7 can be compared in the presence and absence of a candidate bioactive agent.

The monovalent cation indicator can be, for example, a sodium or potassium indicator. Examples of sodium indicators include SBFI, CoroNa Green, CoroNa Red, and Sodium Green (Handbook of Fluorescent Probes and Research Chemicals, 9th ed. Molecular Probes). Examples of potassium indicators include PBFI (Handbook of Fluorescent Probes and Research Chemicals, 9th ed. Molecular Probes).

The present invention provides methods for identifying molecules that modulate the divalent cationic permeability of the TRPM7 channel. The TRPM7 channel is permeable to the divalent cations, zinc, nickel, barium, cobalt, magnesium, manganese, strontium, cadmium, and calcium (Harteneck, Arch Pharmacol 2005 371:307-314). Modulation of the divalent cationic permeability of the TRPM7 channel can, for example, be determined by measuring the inward and outward currents in whole cell patch clamp assays or single-channel membrane patch assays in the presence and absence of the candidate bioactive agent. In an alternative embodiment, the modulation of divalent cation activity can be monitored as a function of cation currents and/or membrane-potential of a cell comprising a TRPM7 channel.

Modulation of the divalent cationic permeability of the TRPM7 channel by a candidate agent can be determined by contacting a cell that expresses TRPM7 with a divalent cation and a divalent cation indicator that reacts with the divalent cation to generate a signal. The intracellular levels of the divalent cation can be measured by detecting the indicator signal in the presence and absence of a candidate bioactive agent. Additionally, the intracellular divalent cation levels in cells that express TRPM7 with cells that do not express TRPM7 can be compared in the presence and absence of a candidate bioactive agent.

The divalent cation indicator can be, for example, a fluorescent magnesium indicator. Examples of magnesium indicators include furaptra or Magfura (commercially available from Molecular Probes™, Invitrogen Detection Technologies).

Many forms of neurodegenerative disease are attributed to calcium ions. Excessive $Ca^{2+}$ influx or release from intracellular stores can elevate $Ca^{2+}$ loads to levels that exceed the capacity of $Ca^{2+}$-regulator mechanisms (Aarts et al., Cell 2003 115:863-877). The methods of the present invention include methods of detecting $Ca^{2+}$ flux through TRPM7 channels. The levels of intracellular $Ca^{2+}$ levels are detectable, for example, using indicators specific for $Ca^{2+}$. Indicators that are specific for $Ca^{2+}$ include, but are not limited to, fura-2, indo-1, rhod-2, fura-4F, fura-5F, fura-6F and fura-FF, fluo-3, fluo-4, Oregon Green 488 BAPTA, Calcium Green, X-rhod-1 and fura-red (Handbook of Fluorescent Probes and Research Chemicals, 9th ed. Molecular Probes). $Ca^{2+}$ loading can be determined by measuring $Ca^{2+}$ accumulation in the cells. See, for example, Sather et al., J. Neurochem, 1998 71, 2349-2364 and Aarts et al., Cell 2003 115:863-877.

Both the levels of monovalent and divalent cations into the cell can be measured either separately or simultaneously. For example, a $Ca^{2+}$ specific indicator can be used to detect levels of $Ca^{2+}$ and a monovalent cation specific indicator can be used to detect levels of monovalent cation. In some embodiments, the $Ca^{2+}$ indicator and the monovalent cation specific indicator are chosen such that the signals from the indicators are capable of being detected simultaneously. For example, in some embodiments, both indicators have a fluorescent signal but the excitation and/or emission spectra of both indicators are distinct such that the signal from each indicator can be detected at the same time.

Both the levels of divalent or monovalent cations and the change in membrane potential can be measured simultaneously. In this embodiment a $Ca^{2+}$ specific indicator can be used to detect levels of $Ca^{2+}$ and a membrane potential sensitive probe can be used to detect changes in the membrane potential. The $Ca^{2+}$ indicator and the membrane potential sensitive probe can be chosen such that the signals from the indictors and probes are capable of being detected simultaneously. For example, in some embodiments, both the indicator and probe have a fluorescent signal but the excitation and/or emission spectra of both indicators are distinct such that the signal from each indicator can be detected at the same time.

Before modulation of the TRPM7 channel is measured, TRPM7 is preferably activated. RPM7 channels are activated by millimolar levels of MgATP levels (Nadler et al., Nature 2001 411:590-595). TRPM7 can be activated by altering extracellular divalent cation concentrations prior to measuring the modulation of TRPM7 activity by a candidate modulating agent. Preferably, extracellular $Ca^{2+}$ concentration, extracellular $Mg^{2+}$ concentration, or both are altered. More preferably, such alteration comprise the lowering of extracellular $Mg^{2+}$ concentration by at least at least 10%, at least 20%, at least 30% at least 40% at least 50%, at least 60%, at least 70%, at least 80%, at least 90%, at least 95%, preferably at least 99%. Also preferably, such alteration comprise the lowering of extracellular $Ca^{2+}$ concentration by at least at least 10%, at least 20%, at least 30% at least 40% at least 50%, at least 60%, at least 70%, at least 80%, at least 90%, at least 95%, preferably at least 99%. Also preferably, such alteration comprise the simultaneous lowering of the extracellular $Ca^{2+}$ and $Mg^{2+}$ concentration to the extents described herein.

The TRPM7 activity can be measured in intact cells, e.g., HEK-293 cells, that are transformed with a vector comprising nucleic acid encoding TRPM7 and an inducible promoter operably linked thereto. After inducement of the promoter, the TRPM7 polypeptides are produced and form a TRPM7 channel. Endogenous levels of TRPM7 activity can be measured prior to inducement and then compared to the levels of TRM7 activity measured subsequent to inducement. In one embodiment, fluorescent molecules can be used to detect intracellular monovalent and divalent cation levels.

In certain embodiments, the candidate bioactive agents can, for example, open TRPM7 channels in a variety of cells such as cells of the nervous systems of vertebrates. In a preferred embodiment, the candidate bioactive agents close, e.g., inhibit, TRPM7 channels in a variety of cells such as cells of the nervous system. Preferred candidate bioactive agents close or inhibit TRPM7 channels. The closing or inhibition of the TRPM7 channels can, for example, prevent or significantly decrease neuronal cell death following ischemic injury.

In yet other embodiments, the candidate bioactive agents can, for example, increase the expression of TRPM7 channels in a variety of cells such as cells of the nervous systems of vertebrates. In a preferred embodiment, the candidate bioactive agents reduce, e.g., inhibit, the expression of TRPM7 channels in a variety of cells such as cells of the nervous system. Preferred candidate bioactive agents inhibit the expression of TRPM7 channels. The inhibition of expression of TRPM7 channels can, for example, prevent or significantly decrease neuronal cell death following ischemic injury.

In yet other certain embodiments, the candidate bioactive agents can, for example, potentiate the activity of downstream signaling pathways that depend on TRPM7 channel activity in a variety of cells such as cells of the nervous systems of vertebrates. In a preferred embodiment, the candidate bioactive agents inhibit the activity of downstream signaling pathways that depend on TRPM7 channel activity in a variety of cells such as cells of the nervous system. Preferred candidate bioactive agents inhibit the activity of downstream signaling pathways that depend on TRPM7 channel activity. The inhibition of downstream signaling pathways that depend on TRPM7 channel activity can, for example, prevent or significantly decrease neuronal cell death following ischemic injury.

The present provides methods for identifying candidate bioactive agents that modulate expression levels of TRPM7 within cells. Candidate agents can be used that wholly or partially suppress or enhance the expression of TRPM7 within cells, thereby altering the cellular phenotype. Examples of these candidate agents include naturally occurring or synthetic small molecules, antisense cDNAs and DNAs, regulatory binding proteins and/or nucleic acids, as well as any of the other candidate bioactive agents herein described that modulate transcription or translation of nucleic acids encoding TRPM7.

A particularly useful assay for use in the present invention measures the effect that a compound of interest has on cells expressing TRPM7 that have been exposed to conditions that activate TRPM7 channels as described herein. For example, such cells may be exposed to conditions of low extracellular Mg2+, low extracellular Ca2+ or both (Wei et al., 2007). By measuring cell survival or cell death after the activation of TRPM7 channels and comparing the amount of cell survival in a control cell sample versus the amount of cell survival in a cell sample treated with a test compound, it can be determined whether the test compound is a modulator of TRPM7 activity and of TRPM7-mediated cellular injury. Assays for measuring cell survival are known in the art and include, for example, assays for measuring lactate dehydrogenase which is released from dying cells and assays for measuring ATP in living cells. A preferred candidate bioactive agent rescue cells that have undergone TRPM7 channel activation. If desired, further tests can be performed to confirm that the compound had an effect on TRPM7 gene expression or biological activity of the protein. Standard immunoassays can be used, such as western blotting, ELISA and the like. For measurement of mRNA, amplification, e.g., using PCR, LCR, or hybridization assays, e.g., northern hybridization, RNase protection, dot blotting, are preferred. The level of protein or mRNA can be detected, for example, using directly or indirectly labeled detection agents, e.g., fluorescently or radioactively labeled nucleic acids, radioactively or enzymatically labeled antibodies, and the like, as described herein. After a compound is determined to have an effect on murine TRPM7 activity or/and gene or protein expression or/and cell survival, the compound can be used in an animal model, in particular a murine model, for ischemic injury, including, for example, stroke.

Another useful assay for use in the present invention measures the effect that a compound of interest has on cells expressing TRPM7 that have been denied oxygen and glucose. By measuring cell survival or cell death after the denial of oxygen and glucose and comparing the amount of cell survival in a control cell sample versus the amount of cell survival in a cell sample treated with a test compound, it can be determined whether the test compound is a modulator of TRPM7 activity and of ischemic death. Assays for measuring cell survival are known in the art and include, for example, assays for measuring lactate dehydrogenase which is released from dying cells and assays for measuring ATP in living cells. A preferred candidate bioactive agent rescue cells that have been denied oxygen and glucose. If desired, further tests can be performed to confirm that the compound had an effect on TRPM7 gene expression or biological activity of the protein as described herein.

In certain embodiments of the assays described herein are conducted in cells in which TRPM7 expression is inducible. The effects of a compound of interest has on the cells expressing TRPM7 is compared between the effect measured when the compound of interest is contacted with the cells prior to the induction of TRPM7 expression, preferably at a time ranging from 0 to 3 days prior to induction of TRPM7 expression, with the effects that the same compound of interest has on the cells expressing TRPM7 when the compound of interest is applied at or after the activation of TRPM7, preferably at a time ranging from 0 to 36 hours after the activation of TRPM7.

In some preferred embodiments of the current invention, the TRPM7 used in these assays has at least 99% identity to the amino acid sequence as set forth in Swiss-Prot Q923J1 [mouse], Q925B3 [rat], or Q96QT4 [human].

The various screening methods described vary in length of time needed to perform and information generated. For screening large numbers of agents (e.g., greater than 10,000) methods can be combined with a primary highthroughput screen performed on random compounds, and a secondary screen performed on agents showing a positive result in the first screen. A useful primary screen is to measure the effect of an agent on cell death/survival of cells expressing TRPM7 (either naturally or recombinantly). Typically TRPM7 is activated before performing the assay by decreasing the concentration of bivalent ion (e.g., Ca or Mg) in the culture media. The concentration can be changed by changing the culture media or simply by dilution. In the absence of an agent, a significant portion of cells die. However, some agents have a protective function against cell death. This protective function can be assessed from any measure of cell death or survival. Because cell death and survival are reciprocal events, a measurement of one effectively serves as a measure of the other. Some agents identified by the assay inhibit cell death or in other words promote cell survival. Other agents have the opposite effect of promoting cell death or inhibiting cell survival. Other agents have no effect in such an assay. Such effects are typically demonstrated relative to a control assay in which the agent being tested is not present. Agents identified by the primary screen are inhibitors or activators of TRPM7-mediated cell death. However, the agents need not act directly to inhibit expression or functional activity of TRPM7. For example, some agents may upstream or downstream in a molecular pathway by which TRPM7 mediated cells death occurs.

A secondary assay can be performed on agents found to inhibit or promote TRPM7-mediated cell death in the primary assay. The secondary assay measure an effect on ion currents through a TRPM7 ion channel as described in the examples. An ability to inhibit or promote such ion currents demonstrates the agent has a specific effect on TRPM7 activity, which may be directly on the channel although could also be indirect via upstream activation.

Additional tertiary assays can be performed on agents found to inhibit or promote ion currents in a TRPM7 channel can be further tested for pharmacological activity in treatment or prophylaxis of disease in cellular or animal models of disease, including any of the diseases described herein. Such models include cellular and animal models of ischemia, including stroke. Agents having positive activity in disease models (e.g., which reduce infarct size or reduce cognitive deficit), cancer, pain or glaucoma can be carried forward into clinical trials and then used as pharmaceuticals in indications, such as those described herein.

Additional assays can be performed in combination with the primary, second and tertiary assays described above. For example, following the primary assay, it can be useful to perform a dose response analysis on agents showing positive results from the primary assay. Existence of a dose response provides a safeguard against false positives as well as allowing more accurate comparison of potency of different agents and selection of which agents to carry forward to the secondary assay.

Other assays that can be performed include determining whether an agent binds to a TRPM7 protein, optionally in competition, with a compound known to inhibit TRPM7 or inhibits expression of a TRPM7 protein. Such assays can performed before or after the primary screen described above and are useful in selecting from a larger pool, agents that act specifically on TRPM7 or its expression.

A. Candidate Bioactive Agents

The term "modulator", "candidate substance", "candidate bioactive agent", "drug candidate", "agent," "compound" or grammatical equivalents as used herein describes any molecule, e.g., protein, oligopeptide, small organic molecule, polysaccharide, polynucleotide or oligonucleotide (e.g., antisense, siRNA), to be tested for bioactive agents that are capable of directly or indirectly altering the activity of a target gene, protein, or cell. Accordingly, the term "candidate bioactive agent" as used herein describes any molecule that binds to TRPM7, modulates the activity of a TRPM7 ion channel, alters the expression of TRPM7 within cells, or reduces the damaging effects of TRPM7 channel activation on cells by inhibiting TRPM7-dependent downstream pathways. Candidate agents may be bioactive agents that are known or suspected to bind to ion channel proteins or known to modulate the activity of ion channel proteins, or alter the expression of ion channel proteins within cells. Candidate agents can also be mimics of bioactive agents that are known or suspected to bind to ion channel proteins or known to modulate the activity of ion channel proteins, or alter the expression of ion channel proteins within cells. In a particularly preferred method, the candidate agents induce a response, or maintain such a response as indicated, for example, reduction of neuronal cell death following ischemic injury.

Candidate agents encompass numerous chemical classes, though typically they are organic molecules. Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

B. Combinatorial Chemical Libraries

The invention provides methods for identifying/screening for modulators (e.g., inhibitors, activators) of murine TRPM7 activity. In practicing the screening methods of the invention, a candidate compound is provided. Combinatorial chemical libraries are one means to assist in the generation of new chemical compound leads for, e.g., compounds that inhibit a murine TRPM7 activity. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks results in the theoretical synthesis of 100 million tetrameric compounds or 10 billion pentameric compounds. (See, e.g., Gallop et al., J. Med. Chem. 1994, 37: 1233-1250). Preparation and screening of combinatorial chemical libraries are well known to those of skill in the art, (see, e.g., U.S. Pat. Nos. 6,004,617; 5,985,356). Such combinatorial chemical libraries include, but are not limited to, peptide libraries. (see, e.g., U.S. Pat. No. 5,010,175; Furka, Int. J. Pept. Prot. Res. 1991, 37: 487-493; Houghton et al., Nature 1991, 354: 84-88). Other chemistries for generating chemical diversity libraries include, but are not limited to: peptoids (see, e.g., WO 91/19735), encoded peptides (see, e.g., WO 93/20242), random bio-oligomers (see, e.g., WO 92/00091), benzodiazepines (see, e.g., U.S. Pat. No. 5,288,514), diversomers such as hydantoins, benzodiazepines and dipeptides (see, e.g., Hobbs, Proc. Nat. Acad. Sci. USA 1993, 90: 6909-6913), vinylogous polypeptides (see, e.g., Hagihara, J. Amer. Chem. Soc. 1992, 114: 6568), non-peptidal peptidomimetics with a Beta-D-Glucose scaffolding (see, e.g., Hirschmann, J. Amer. Chem. Soc. 1992, 114: 9217-9218), analogous organic syntheses of small compound libraries (see, e.g., Chen, J. Amer. Chem. Soc. 1994, 116: 2661), oligocarbamates (see, e.g., Cho, Science 1993, 261:1303), and/or peptidyl phosphonates (see, e.g., Campbell, J. Org. Chem. 1994, 59: 658). See also (Gordon, J. Med. Chem. 1994, 37: 1385); for nucleic acid libraries, peptide nucleic acid libraries, (see, e.g., U.S. Pat. No. 5,539,083); for antibody libraries, (see, e.g., Vaughn, Nature Biotechnology 1996, 14: 309-314); for carbohydrate libraries, (see, e.g., Liang et al., Science 1996, 274: 1520-1522, U.S. Pat. No. 5,593,853); for small organic molecule libraries, (see, e.g., for isoprenoids U.S. Pat. No. 5,569,588); for thiazolidinones and metathiazanones, (U.S. Pat. No. 5,549,974); for pyrrolidines, (U.S. Pat. No. 5,525,735) and U.S. Pat. No. 5,519,134; for morpholino compounds, (U.S. Pat. No. 5,506,337); for benzodiazepines (U.S. Pat. No. 5,288,514).

Devices for the preparation of combinatorial libraries are commercially available (see, e.g., U.S. Pat. Nos. 6,045,755; 5,792,431; 357 MPS, 390 MPS), (Advanced Chem Tech, Louisville Ky., Symphony, Rainin, Woburn, Mass., 433A Applied Biosystems, Foster City, Calif., 9050 Plus, Millipore, Bedford, Mass.). A number of robotic systems have also been developed for solution phase chemistries. These systems include automated workstations, e.g., like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) that mimic the manual synthetic operations performed by a chemist. Any of the above devices are suitable for use with the present invention. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., and the like).

The compounds tested as modulators of murine TRPM7 genes or gene products can be any small organic molecule, or a biological entity, such as a protein, e.g., an antibody or peptide, a sugar, a nucleic acid, e.g., an antisense oligonucleotide or RNAi, or a ribozyme, or a lipid. Alternatively, modulators can be genetically altered versions of a murine TRPM7 protein. Typically, test compounds are small organic molecules (molecular weight no more than 1000 and usually no more than 500 Da), peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays that are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one embodiment, high throughput screening methods involve providing a combinatorial small organic molecule or peptide library containing a large number of potential therapeutic compounds (potential modulator or ligand compounds). Such "combinatorial chemical libraries" or "ligand libraries" (as described above) are then screened in one or more assays, as described herein, to identify those library members (particular chemical species or subclasses) that display a desired characteristic activity. The compounds thus identified can serve as conventional "lead compounds" or can themselves be used as potential or actual therapeutics.

C. Solid State and Soluble High Throughput Assays

In certain embodiments, the invention provide soluble assays using molecules such as a domain such as ligand binding domain, an active site, and the like; a domain that is covalently linked to a heterologous protein to create a chimeric molecule; murine TRPM7; a cell or tissue expressing murine TRPM7, either naturally occurring or recombinant. In another embodiment, the invention provides solid phase based in vitro assays in a high throughput format, where the domain, chimeric molecule, murine TRPM7, or cell or tissue expressing murine TRPM7 is attached to a solid phase substrate.

In exemplary high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-1500 different compounds. It is possible to assay several different plates per day; assay screens for up to about 6,000-20,000 different compounds is possible using the integrated systems of the invention.

The molecule of interest can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, and the like) Antibodies to molecules with natural binders such as biotin are also widely available and appropriate tag binders; see, SIGMA Immunochemicals 1998 catalogue SIGMA, St. Louis Mo.

Similarly any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott et al., The Adhesion Molecule Facts Book I, 1993. Similarly, toxins and venoms, viral epitopes, hormones (e.g., opiates, steroids, and the like), intracellular receptors (e.g. that mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders can be fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. (See, e.g., Merrifield, J. Am. Chem. Soc. 1963 85: 2149-2154 (describing solid phase synthesis of, e.g., peptides); Geysen et al., J. Immun. Meth. 1987 102: 259-274 (describing synthesis of solid phase components on pins); Frank et al., Tetrahedron 1988, 44: 6031-6040, (describing synthesis of various peptide sequences on cellulose disks); Fodor et al., Science, 1991, 251: 767-777; Sheldon et al., Clinical Chemistry 1993, 39: 718-719; and Kozal et al., Nature Medicine 1996, 7: 753-759 (all describing arrays of biopolymers fixed to solid substrates). Non-chemical approaches for fixing tag binders to substrates include other common methods, such as heat, cross-linking by UV radiation, and the like.

D. Computer-Based Assays

Compounds that modulate murine TRPM7 activity can also be determined by computer assisted drug design, in which a computer system is used to generate a three-dimensional structure of murine TRPM7 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering murine TRPM7 amino acid sequences of at least 10 amino acid residues or corresponding nucleic acid sequences encoding a murine TRPM7 polypeptide into the computer system. The amino acid sequence of the polypeptide or the nucleic acid encoding the polypeptide is selected from the group consisting of the sequences provided herein, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art. The three-dimensional structural model of the protein can be saved to a computer readable form and be used for further analysis (e.g., identifying potential ligand binding regions of the protein and screening for mutations, alleles and interspecies homologs of the gene).

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the murine TRPM7 protein to identify ligands that bind to murine TRPM7. Binding affinity between the protein and ligands is determined using energy terms to determine which ligands have an enhanced probability of binding to the protein. The software can then also be used to modify the structure of a candidate ligand in order to modify (e.g., enhance or diminish) its affinity to the protein. Thus, each candidate ligand may be used as a "lead compound" for the generation of other candidate ligands by the computer system. The results, such as three-dimensional structures for potential ligands and binding affinity of ligands, can also be saved to a computer readable form and can be used for further analysis (e.g., generating a three dimensional model of mutated proteins having an altered binding affinity for a ligand, or generating a list of additional candidate ligands for chemical synthesis).

3. Preferred Compounds of the Invention

The invention provides several genera and examples of compounds. The compounds can be provided as they are as a pharmaceutically acceptable salt or as pharmaceutical composition. Functional properties of compounds include any or all of specific binding to TRPM7, inhibiting TRPM7-mediated cell death, inhibiting TRPM7 currents, inhibiting damaging effects of ischemia (e.g., cell death) in any of the tissues disclosed herein, traumatic injury to the CNS as demonstrated in any of the assays of the Examples (among others), inhibiting proliferation, toxicity or metastasis of cancers of any of the types disclosed herein, as demonstrated by any of the assays in the Examples (among others), inhibiting pain, and/or inhibiting damaging effects of glaucoma (e.g., cell death). Preferred compounds exhibit any or all of the properties of TRPM7 inhibitors or candidate bioactive molecules described herein. For example, a preferred compound inhibits TRPM7-mediated cell death in a mammalian cell by at least 30, 40, 50, 60, 70 or 80%. The TRPM7 used in such assays can be human (Swiss prot Q96QT4), mouse or other mammalian origin. Likewise, cellular or animal systems used to demonstrate functional properties can be human, mouse or other mammalian. Because the primary therapeutic use of the compounds is usually in treating humans, it is preferred that binding and other functional effects occur on materials of human origin.

Some compounds are of Formula I:

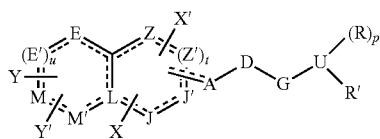

wherein

------ is a single or double bond,

Z, Z', J, J', E, E', L, M and M' are each independently S, O, N or C, wherein N or C in each instance can be further covalently bound to X, X', Y or Y', X and X' are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, or is O, which taken together with a C to which it is attached forms a carbonyl, Y and Y' are each independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, $C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, or is O, which taken together with a C to which it is attached forms a carbonyl, A is $NR^a$, $SO_2$, $(CR^1R^2)_x$ or $—(CR^1{=}CR^7)_{-x}$, wherein x is an integer from zero to four, D is carbonyl, sulfoxide, O, S or $(CR^3R^4)_y$, wherein y is an integer from zero to four, G is $NR^b$, $SO_2$, $(CR^5R^6)_Z$ or $—(CR^5{=}CR^6)_{-z}$, wherein z is an integer from zero to four, U is C—$(R^7)_q$ or N, wherein C—$R^7$ can be taken together to form a carbonyl when p is zero, or $R^7$ is as described below, p is one or zero, q is one or zero, t is one or zero, u is one or zero, R is selected from the group consisting of hydrogen, optionally substituted $C_1$-$C_6$ alkyl, optionally substituted phenyl ($C_1$-$C_6$) alkyl, and optionally substituted 5- to 10-member cyclic, heterocyclic, bicyclic or heterobicyclic ring, wherein said ring may be aromatic or heteroaromatic, R' is selected from the group consisting of optionally substituted $C_1$-$C_6$ alkyl, optionally substituted phenyl ($C_1$-$C_6$) alkyl, and optionally substituted 5- to 10-member cyclic, heterocyclic, bicyclic or heterobicyclic ring, wherein said ring may be aromatic or heteroaromatic, or R and R' taken together with U to form an optionally substituted 5- to 10-member cyclic, bicyclic, heterocyclic or heterobicyclic ring, wherein said ring may be aromatic or heteroaromatic, and $R^1$, $R^2$, $R^3$, $R^4$, $R^5$, $R^6$, $R^7$, $R^a$ and $R^b$ are each independently selected from the group consisting of hydrogen, optionally substituted $C_1$-$C_6$ alkyl, $C_1$-$C_6$ alkenyl, $C_1$-$C_6$ alkynyl, optionally substituted phenyl ($C_1$-$C_6$) alkyl, optionally substituted 5- to 10-member cyclic, heterocyclic, bicyclic or heterobicyclic ring, wherein said ring may be aromatic or heteroaromatic.

Examples of such compounds include M4, M5, M6, M9, M17, M21, M29 (FIGS. 11-16) and C04, C06, C10, C07, C08, C13, C15, D03, D11, D19, E07, E09, G17, G18, H06, H16, H21, I04, I14, I08, I10, I20, J08, K06, K16, C07, C11, C20, D09, D19, E18, F18, G11, G16, H19, and H20 (Table 3 of WO/2011/072275).

Some such compounds are of Formula II

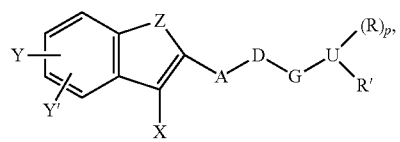

wherein

Z is S, O, N—H or C—H,

X is halogen,

Y and Y' are each independently selected from the group consisting of hydrogen, hydroxyl, optionally substituted saturated or unsaturated $C_1$-$C_6$ alkyl, $C_1$-$C_6$ alkenyl, $C_1$-$C_6$ alkynyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, or is O, which taken together with a C to which it is attached forms a carbonyl, A is $NR^a$ or $(CR^1R^2)_x$, wherein x is an integer from zero to four, D is carbonyl or $(CR^3R^4)_y$, wherein y is an integer from zero to four, G is $NR^b$ or $(CR^5R^6)_z$, wherein z is an integer from zero to four, U is C—$(R^7)q$ or N, wherein C—$R^7$ taken together are carbonyl and p is zero, or $R^7$ is as described below, p is one or zero, q is one or zero, R is hydrogen, optionally substituted $C_1$-$C_6$ alkyl, $C_1$-$C_6$ alkenyl, $C_1$-$C_6$ alkynyl, optionally substituted phenyl ($C_1$-$C_6$) alkyl, or an optionally substituted 5- to 10-member cyclic, heterocyclic, bicyclic or heterobicyclic ring, wherein said ring may be aromatic or heteroaromatic, R' is selected from the group consisting of optionally substituted $C_1$-$C_6$ alkyl, optionally substituted phenyl ($C_1$-$C_6$) alkyl, $C_1$-$C_6$ alkenyl, $C_1$-$C_6$ alkynyl, optionally substituted 5- to 10-member cyclic, heterocyclic, bicyclic or heterobicyclic ring, wherein said ring may be aromatic or heteroaromatic, or R and R' are taken together with U to form an optionally substituted 5- to 10-member cyclic, bicyclic, heterocyclic or heterobicyclic ring, wherein said ring may be aromatic or heteroaromatic, and $R^1$, $R^2$, $R^3$, $R^4$, $R^5$, $R^6$, $R^7$, $R^a$ and $R^b$ are each independently selected from the group consisting of substituted $C_1$-$C_6$ alkyl, $C_1$-$C_6$ alkenyl, $C_1$-$C_6$ alkynyl, optionally substituted phenyl ($C_1$-$C_6$) alkyl, optionally substituted 5- to 10-member cyclic, heterocyclic, bicyclic or heterobicyclic ring, wherein said ring may be aromatic or heteroaromatic.

Some such compounds have a structure wherein R, R' and U are taken together to form a ring selected from the group consisting of

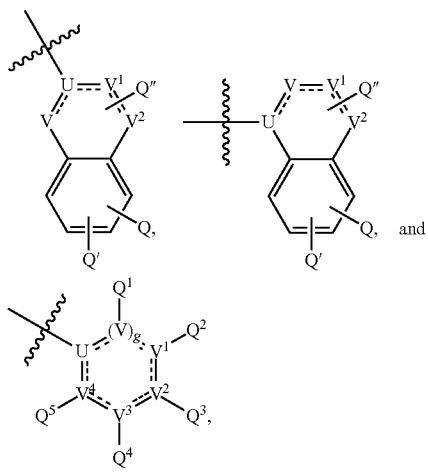

wherein V, V$^1$, V$^2$, V$^3$ and V$^4$ in each instance are independently selected from the group consisting of N, C and O, wherein N or C can be further covalently bound to Q″, Q$^1$, Q$^2$, Q$^3$, Q$^4$ and Q$^5$, g is zero, one or two and Q, Q', Q″, Q$^1$, Q$^2$, Q$^3$, Q$^4$ and Q$^5$ are each independently selected from the group consisting of hydrogen, hydroxyl, optionally substituted C$_1$-C$_6$ alkyl, C$_1$-C$_6$ alkenyl, C$_1$-C$_6$ alkynyl, optionally substituted phenyl (C$_1$-C$_6$) alkyl, C$_1$-C$_6$ alkoxy, amino, C$_1$-C$_6$ alkylamino, di-(C$_1$-C$_6$) alkylamino, halogen, thiol, cyano, nitro, and optionally substituted 5- to 7-member cyclic, heterocyclic, bicyclic or heterobicyclic ring, wherein said ring may be aromatic or heteroaromatic, optionally substituted C$_5$-C$_7$ aryl- or heteroaryl-thiamide, optionally substituted C$_5$-C$_7$ aryl- or heteroaryl-carboxy, optionally substituted C$_5$-C$_7$ aryl- or heteroaryl-(C$_1$-C$_6$) alkyl, or is O, which taken together with a C to which it is attached forms a carbonyl.

In some such compounds, the ring has the following structure

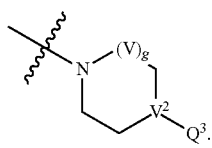

In some such compounds, Z in Formula II is S, and/or X is chlorine and/or Y and Y' are each hydrogen and/or D is carbonyl, x is zero and y is zero. In some such compounds, Q and Q' are each independently selected from the group consisting of hydrogen, hydroxyl, optionally substituted C$_1$-C$_6$ alkyl, optionally substituted phenyl (C$_1$-C$_6$) alkyl, C$_1$-C$_6$ alkoxy, amino, C$_1$-C$_6$ alkylamino, di-(C$_1$-C$_6$) alkylamino and halogen. For example, Q can be hydrogen, methoxy, ethoxy, propoxy, methyl, ethyl or propyl and Q' can be methoxy, ethoxy, propoxy, methyl, ethyl or propyl.

Compounds C10, C07, C08 and D08 from Table 3 of WO/2011/072275 have the following structures.

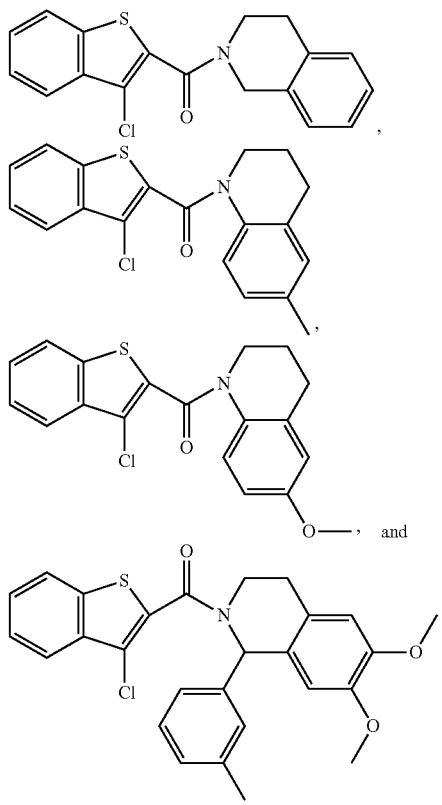

M6 and some related compounds can be represented by the compound of Formula III

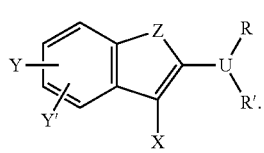

In some such compounds, Z is S, X is chlorine, Y and Y' are each hydrogen, and U is C—(R$^7$)$_q$. In some compounds R and R' are taken together with U to form an optionally substituted 5- to 10-member cyclic, bicyclic, heterocyclic or heterobicyclic ring, wherein said ring may be aromatic or heteroaromatic. M6 has the structure

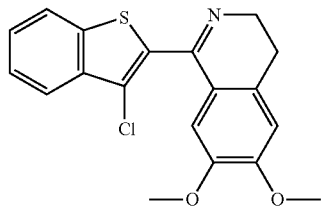

In some compounds of formula II, D is carbonyl, X is zero, Z is zero, and U is N. In some such compounds R is selected from the group consisting of hydrogen, optionally substituted C$_1$-C$_6$ alkyl, optionally substituted phenyl (C$_1$-C$_6$) alkyl, C$_1$-C$_6$ alkenyl, C$_1$-C$_6$ alkynyl, and optionally substituted 5- to 10-member cyclic, heterocyclic, bicyclic or heterobicyclic ring, wherein the ring may be aromatic or heteroaromatic, and R' is selected from the group consisting of optionally substituted $C_1$-$C_6$ alkyl, optionally substituted phenyl ($C_1$-$C_6$) alkyl, $C_1$-$C_6$ alkenyl, $C_3$-$C_6$ alkynyl, and optionally substituted 5- to 10-member cyclic, heterocyclic, bicyclic or heterobicyclic ring, wherein said ring may be aromatic or heteroaromatic. In some such compounds, R is hydrogen or $C_1$-$C_6$ alkyl, and R' is a substituted $C_1$-$C_6$ alkyl. Some exemplary compounds having such a structure are C15 and D03 from Table 3 of WO/2011/072275.

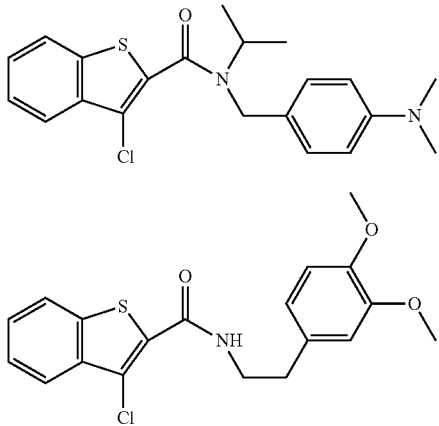

C15

D03

Some compounds of Formula I have a structure of Formula IV

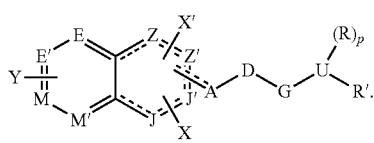

IV

In some such compounds, one of E, E', M and M' is C—Y, and the others are C—H. In some such compounds, Y is selected from the group consisting of hydrogen, hydroxyl, and optionally substituted, saturated or unsaturated $C_1$-$C_6$ alkyl, $C_1$-$C_6$ alkoxy and $C_1$-$C_6$ alkoxycarbonyl, or is O, which taken together with a C to which it is attached forms a carbonyl, and X and X' are each independently selected from the group consisting of hydrogen, hydroxyl, and optionally substituted, saturated or unsaturated $C_1$-$C_6$ alkyl, $C_1$-$C_6$ alkoxy and $C_1$-$C_6$ alkoxycarbonyl, or is O, which taken together with a C to which it is attached forms a carbonyl. M21 and related compounds are a preferred example of this formula and can be represented by Formula V

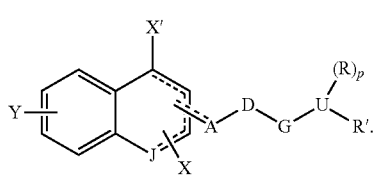

V

In some such compounds of Formula V, Y is hydrogen, hydroxyl, $C_1$-$C_6$ alkoxy, $C_1$-$C_6$ alkyl, amino, $C_1$-$C_6$ alkylamino, di-($C_1$-$C_6$) alkylamino or halogen,
X' is hydrogen, hydroxyl, $C_1$-$C_6$ alkoxy, $C_1$-$C_6$ alkyl, amino, $C_1$-$C_6$ alkylamino, di-($C_1$-$C_6$) alkylamino or halogen, or is O, which taken together with a C to which it is attached forms a carbonyl, X is hydrogen, hydroxyl, $C_1$-$C_6$ alkoxy, $C_1$-$C_6$ alkyl, amino, $C_1$-$C_6$ alkylamino, di-($C_1$-$C_6$) alkylamino or halogen, or is O, which taken together with a C to which it is attached forms a carbonyl, J is C—H, $CH_2$ or 0. In some such compounds, A is $(CR^1R^2)_x$ or $—(CR^1=CR^2)_{-x}$, wherein x is an integer from zero to one D is $(CR^3R^4)_y$, wherein y is zero, G is $(CR^5R^6)_z$, wherein z is zero. In some such compounds, R and R' are taken together with U to form an optionally substituted 5- to 10-member cyclic, bicyclic, heterocyclic or heterobicyclic ring, wherein said ring may be aromatic or heteroaromatic. Some such compounds are of Formula VI

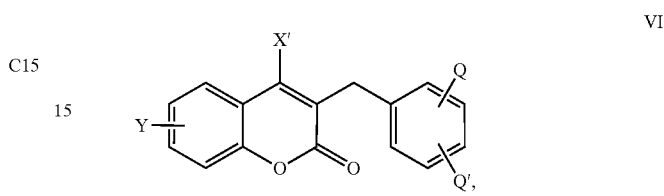

VI wherein
X' is hydrogen, hydroxyl, $C_1$-$C_6$ alkoxy or $C_1$-$C_6$ alkyl,
Y is hydrogen, hydroxyl, $C_1$-$C_6$ alkoxy or $C_1$-$C_6$ alkyl, and
Q and Q' are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic.

A preferred example of such compounds is M21 having the structure

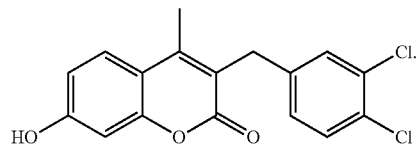 [SMILES: Cc1c(Cc2ccc(Cl)c(Cl)c2)c(=O)oc2cc(O)ccc12]

Other preferred examples of such compounds have the Formula VII or VIII

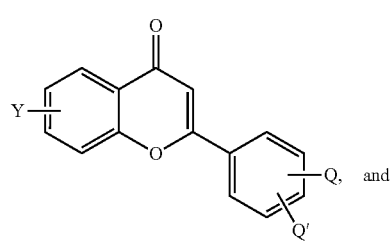

VII

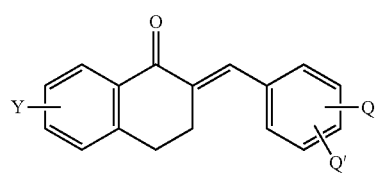

VIII wherein
Y is hydrogen, hydroxyl, $C_1$-$C_6$ alkoxy or $C_1$-$C_6$ alkyl, and
Q and Q' are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, cyano ($C_1$-$C_6$)alkyl, nitro, optionally substituted 5- to 7-member cyclic, heterocyclic, bicyclic or heterobicyclic ring, wherein said ring may be aromatic or heteroaromatic, optionally substituted $C_5$-$C_7$ aryl- or heteroaryl-thiamide, optionally substituted $C_5$-$C_7$ aryl- or heteroaryl-carboxy, optionally substituted $C_5$-$C_{10}$ aryl-S—, optionally substituted phenyl-SO$_2$—, optionally substituted phenyl-NH(CO)—, and optionally substituted $C_5$-$C_7$ aryl-($C_1$-$C_6$) alkyl or heteroaryl-($C_1$-$C_6$) alkyl, or is O, which taken together with a C to which it is attached forms a carbonyl.

In some such compounds Q and Q' are each independently selected from the group consisting of hydrogen, hydroxyl, optionally substituted $C_1$-$C_6$ alkyl, $C_1$-$C_6$ alkenyl, $C_1$-$C_6$ alkynyl, optionally substituted phenyl ($C_1$-$C_6$) alkyl, $C_1$-$C_6$ alkoxy, amino, $C_1$-$C_6$ alkylamino, di-($C_1$-$C_6$) alkylamino, halogen, thiol, cyano, nitro, and optionally substituted 5- to 7-member cyclic, heterocyclic, bicyclic or heterobicyclic ring, wherein said ring may be aromatic or heteroaromatic Two exemplary such compounds are I20 and E09 as shown in Table 3 of WO/2011/072275.

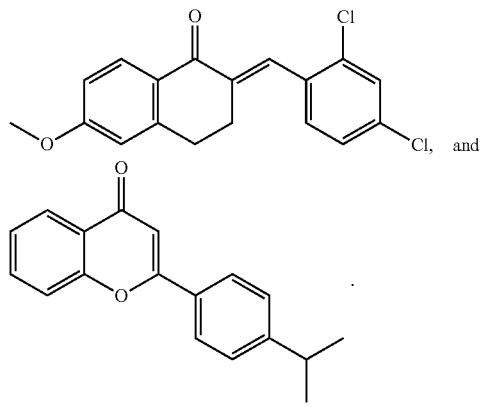

M5 is effective in inhibiting proliferation of various cancer cell lines providing evidence of utility of M5 and related compounds in treatment or prophylaxis of cancer, particularly, retinoblastoma, breast cancer, melanoma, adrenal carcinoma and cervical cancer. M5 is also effective in increasing survival after anoxia in neurons, hepatocytes, cardiomyoctes, and retina providing evidence of utility of M5 and related compounds in treatment and prophylaxis of ischemia, particularly of the CNS, brain, liver, heart and retina.

M6 is also effective in inhibiting proliferation of various cancer cell lines providing evidence of utility of M6 and related compounds in treatment or prophylaxis of cancer, particularly of retinoblastoma, breast cancer, melanoma, adrenal carcinoma, cervical cancer, osteosarcoma, lung cancer, non-small cell lung cancer, colon cancer, and renal cancer. M6 is also effective in increasing survival after anoxia in neurons and cardiomyocytes providing evidence of utility of M6 and related compounds in treatment or prophylaxis of ischemia, particularly for the heart, CNS and brain.

M21 is effective in inhibiting proliferation of a retinoblastoma cell line providing evidence of utility of M21 and related compounds in treatment or prophylaxis of cancer, particularly retinoblastoma. M21 is broadly effective in increasing survival after anoxia in various tissues providing evidence of utility of M21 and related compounds in treatment or prophylaxis of ischemia particularly of the CNS, brain, liver, heart and retina. M21 is also effective in reducing damaging effects of traumatic injury to the CNS. M21 and related compounds are also effective for treatment or prophylaxis of pain or glaucoma.

Example 5 describes screening additional compounds having structures related to M5, M6 or M21. Many of these compounds were also active in protecting against cell death in a propidium iodide assay. Some were more potent that the lead compound from which they were derived (i.e., M5, M6, or M21). Analysis of the common features of compounds showing improved or inferior potency to M5, M6 or M21 allows further definition of classes of compounds having related structures and similar function to M5, M6 or M21 respectively.

Useful compounds are of Formula (Ia), M5 and M-6 related compounds:

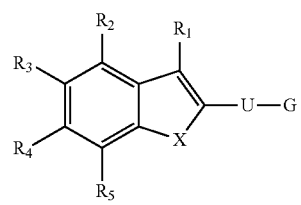

Ia wherein
X is N—H or S;
$R_1$ is halogen or $C_1$-$C_6$ alkoxy;
$R_2$, $R_3$, $R_4$ and $R_5$ are, in each instance, independently selected from the group consisting of hydrogen, hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, halo ($C_1$-$C_6$)alkyl, thiol, cyano, cyano($C_1$-$C_6$)alkyl and nitro,
U is

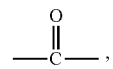

—(CH$_2$)$_y$—, wherein y is an integer from zero to 4 or —NHSO$_2$—;
G is selected from the group consisting of
  i. NR$_6$R$_7$, where R$_6$ and R$_7$ are each independently hydrogen, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, halo ($C_1$-$C_6$)alkyl, cyano($C_1$-$C_6$)alkyl, an optionally substituted $C_{10}$ bicyclic ring system, and optionally substituted aryl ($C_1$-$C_6$)alkyl or heteroaryl ($C_1$-$C_6$) alkyl;
  ii. a bicyclic ring having the structure G$_a$ or G$_b$:

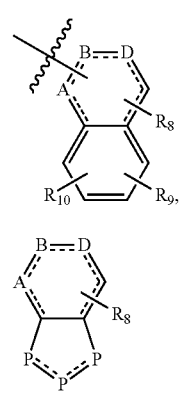

wherein,
one of P is S, the other two are C—R$_8$ and C—R$_9$,
A, B and D are selected from the group consisting of N, NR$_{11}$; —C—H and —C—R$_8$, wherein R$_{11}$, if present, is hydrogen, $C_1$-$C_6$ alkyl, ($C_1$-$C_6$) alkylcarbonyl, R$_8$ is hydrogen, and $R_9$ and $R_{10}$, are in each instance, independently selected from the group consisting of hydrogen, halogen, optionally substituted, saturated or unsaturated $C_1$-$C_6$ alkyl, $C_1$-$C_6$ alkoxy or halo ($C_1$-$C_6$)alkyl, $R_8$, $R_9$ and $R_{10}$ are each independently selected from the group consisting of hydrogen, $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, halo ($C_1$-$C_6$)alkyl, thiol, cyano, cyano($C_1$-$C_6$)alkyl and nitro, wherein, one of A, B and D is N and is the point of attachment to U, and the others of A, B and D are —C—H or —C—$R_8$, or one of A, B and D is C and is the point of attachment to U, and one of the others of A, B and D is $NR_{11}$, and one is —C—H or —C—$R_8$, and iii. a mono- or di-substituted phenyl ring substituted with hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, halo ($C_1$-$C_6$)alkyl, thiol, cyano, cyano($C_1$-$C_6$)alkyl or nitro;

optionally provided that the compound of Formula Ia is not:

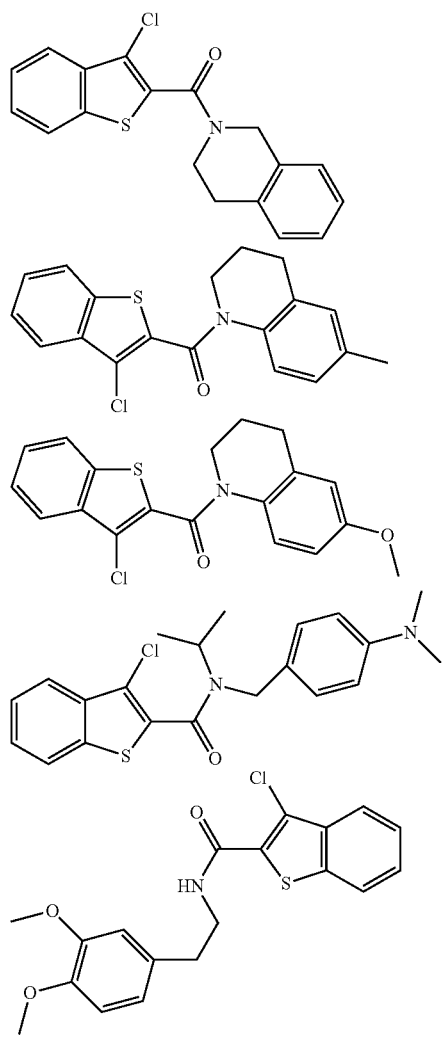

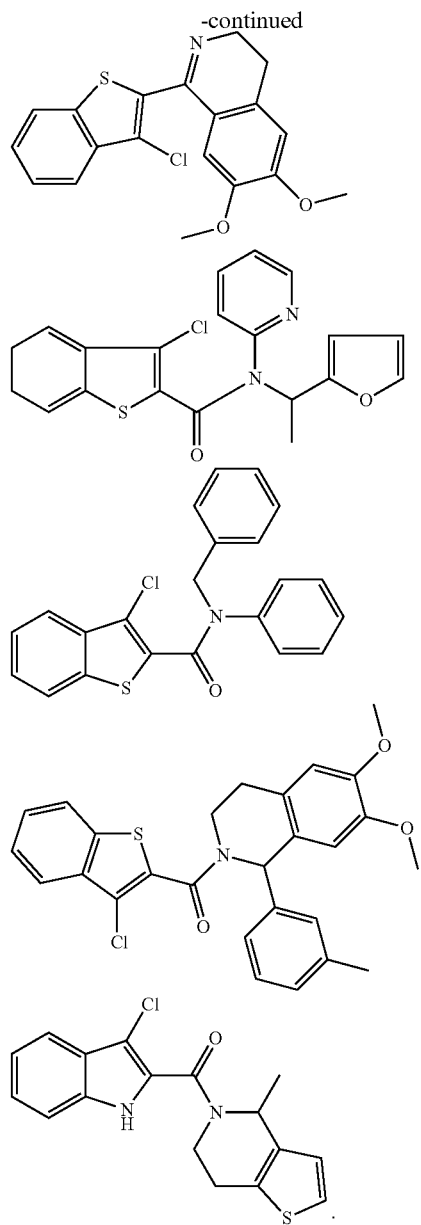

Useful compounds of Formula Ia include those where X is S.

Useful compounds of Formula Ia include those where $R_1$ is preferably methyl. In some compounds, $R_1$ is more preferably fluorine or chlorine.

Useful compounds of Formula Ia include those where one or two of $R_2$, $R_3$, $R_4$ and $R_5$ is, in each instance, independently hydroxyl, optionally substituted, saturated or unsaturated $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, di-($C_1$-$C_6$) alkylamino, halogen, halo ($C_1$-$C_6$)alkyl, thiol, cyano, cyano ($C_1$-$C_6$)alkyl or nitro, and the others of $R_2$, $R_3$, $R_4$ and $R_5$ are each hydrogen.

Useful compounds of Formula Ia include those where one of $R_2$, $R_3$, $R_4$ and $R_5$ is, in each instance, independently hydroxyl, optionally substituted, saturated or unsaturated $C_1$-$C_6$ alkyl, $C_1$-$C_6$ alkoxy, halogen or halo ($C_1$-$C_6$)alkyl, and the others of $R_2$, $R_3$, $R_4$ and $R_5$ are each hydrogen.

In some compounds of Formula Ia, U is preferably —N(C=O)—. In some compounds of Formula Ia, U is more preferably

In some other compounds of Formula Ia, U is most preferably —(CH$_2$)$_y$—, wherein y is an integer from zero to 4.

In some compounds of Formula Ia, where U is

or U is —(CH$_2$)$_y$—, G is i or ii.

Useful compounds of Formula Ia include those where G is i.

Useful compounds of Formula Ia include those where R$_6$ is selected from the group consisting of hydrogen, optionally substituted, saturated or unsaturated C$_1$-C$_6$ alkyl, C$_1$-C$_6$ alkenyl, C$_1$-C$_6$ alkynyl, C$_1$-C$_6$ alkoxy, C$_1$-C$_6$ alkoxycarbonyl, halo (C$_1$-C$_6$)alkyl, cyano(C$_1$-C$_6$)alkyl and optionally substituted aryl (C$_1$-C$_6$)alkyl or heteroaryl (C$_1$-C$_6$)alkyl, and R$_7$ is selected from the group consisting of optionally substituted aryl, heteroaryl, aryl (C$_1$-C$_6$)alkyl or heteroaryl (C$_1$-C$_6$)alkyl.

Useful compounds of Formula Ia include those where R$_2$, R$_3$, R$_4$ and R$_5$ is, in each instance, independently hydrogen, hydroxyl, optionally substituted, saturated or unsaturated C$_1$-C$_6$ alkyl, C$_1$-C$_6$ alkoxy, halogen or halo (C$_1$-C$_6$)alkyl, and the others of R$_2$, R$_3$, R$_4$ and R$_5$ are each hydrogen.

Some specific compounds of Formula Ia have one of the following structures:

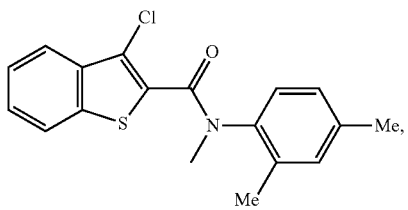

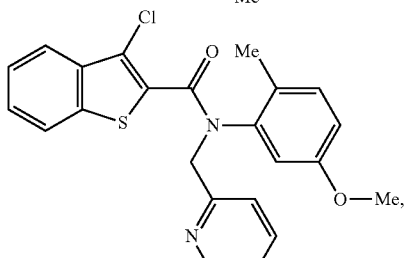

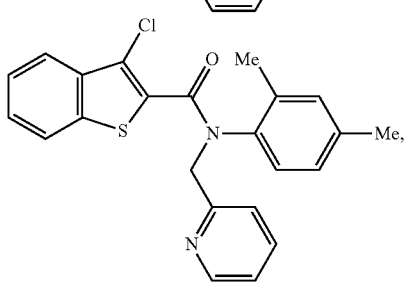

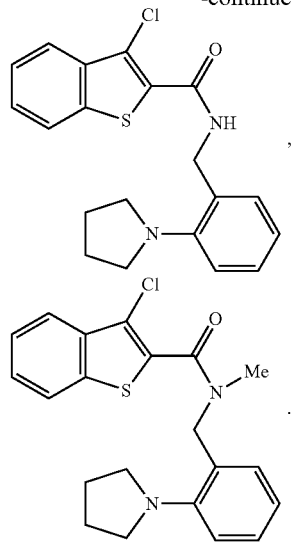

Useful compounds of Formula Ia include those where U is

or U is —(CH$_2$)$_y$—, and G is ii.

Useful compounds of Formula Ia include those where R$_8$ is hydrogen, optionally substituted, saturated or unsaturated C$_1$-C$_6$ alkyl, C$_1$-C$_6$ alkoxy or halo (C$_1$-C$_6$)alkyl. Preferably, R$_8$ is hydrogen, methyl, ethyl, propyl or butyl.

Useful compounds of Formula Ia include those where G is

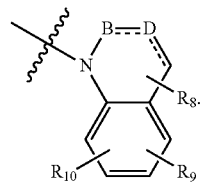

In some preferred compounds, G is

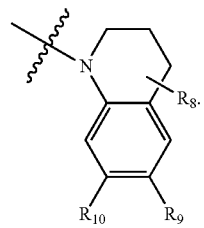

In this embodiment, R$_8$ is hydrogen, and R$_9$ and R$_{10}$, are in each instance, independently selected from the group consisting of hydrogen, halogen, optionally substituted, saturated or unsaturated C$_1$-C$_6$ alkyl, C$_1$-C$_6$ alkoxy or halo (C$_1$-C$_6$)alkyl. Preferably, R$_9$ is optionally substituted, saturated or unsaturated C$_1$-C$_6$ alkyl, halogen or C$_1$-C$_6$ alkoxy. More preferably, R$_9$ is methoxy. In some preferred compounds, R$_9$ is hydrogen or fluoro. Most preferably, R$_9$ is methyl or chloro.

Useful compounds of Formula Ia include those where one of $R_2$, $R_3$, $R_4$ and $R_5$ is, in each instance, independently hydrogen, hydroxyl, optionally substituted, saturated or unsaturated $C_1$-$C_6$ alkyl, $C_1$-$C_6$ alkoxy, halogen or halo ($C_1$-$C_6$)alkyl, and the others of $R_2$, $R_3$, $R_4$ and $R_5$ are each hydrogen. In some compounds, $R_2$, $R_3$, $R_4$ and $R_5$ is, in each instance, independently and preferably, fluoro or methyl, and the others of $R_2$, $R_3$, $R_4$ and $R_5$ are each hydrogen. In some compounds, $R_2$, $R_3$, $R_4$ and $R_5$ is, in each instance, independently and more preferably, hydrogen or trifluoromethyl, and the others of $R_2$, $R_3$, $R_4$ and $R_5$ are each hydrogen.

Some specific compounds of Formula Ia include:

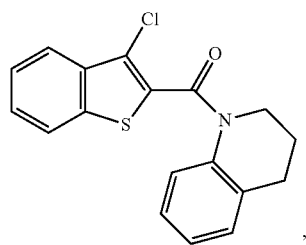
,
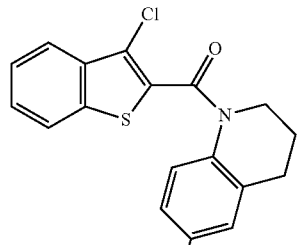
,
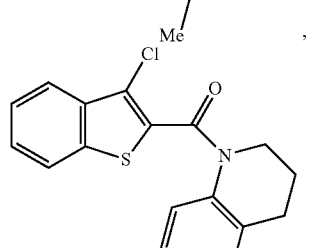
,
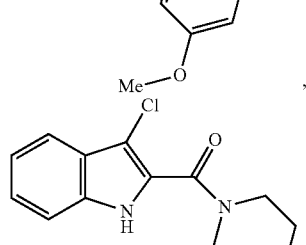
,
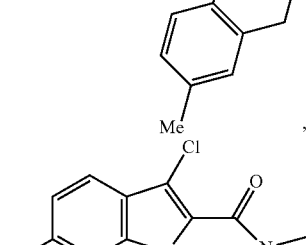
,
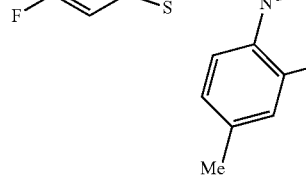
, -continued

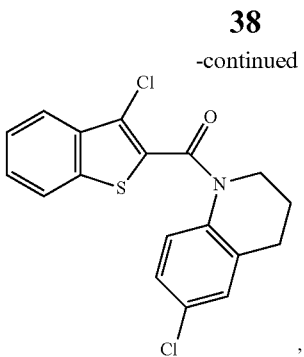
,
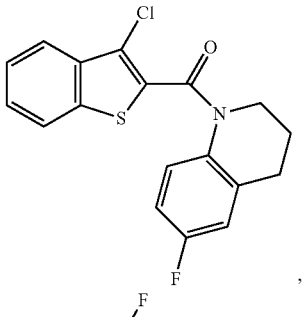
,
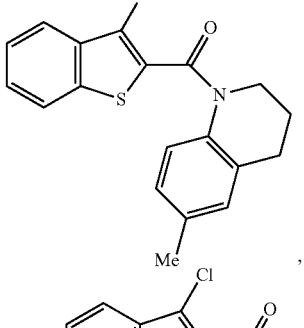
,
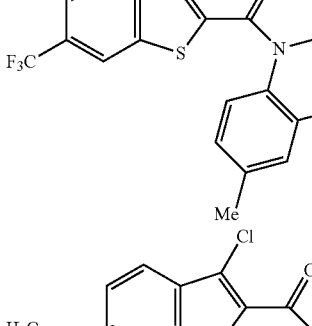
,
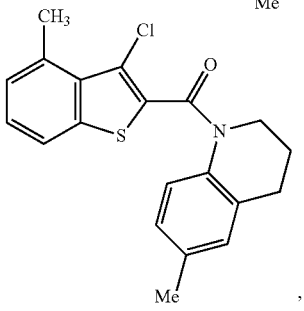
,

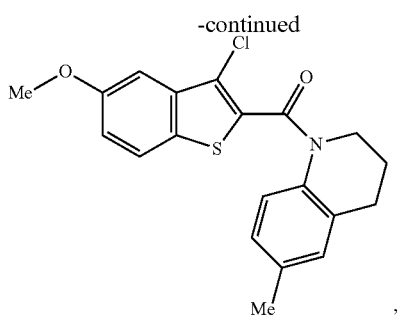
,

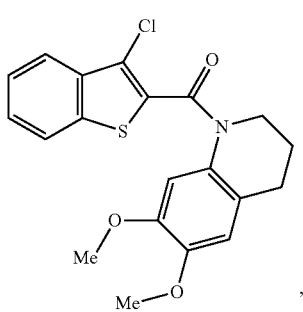
,

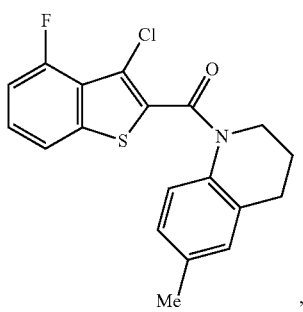
,

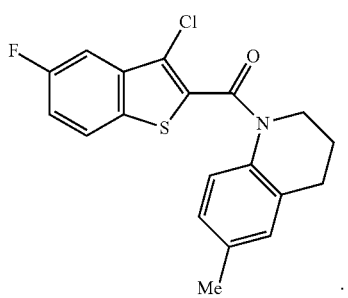
.

Useful compounds of Formula Ia include those where G is

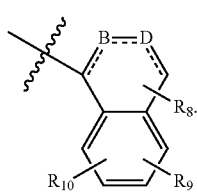

Preferably, in these compounds, B is NR$_{11}$. These compounds include those where G is

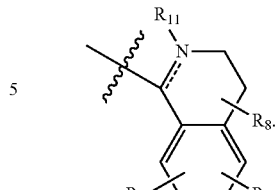

In such compounds, R$_{11}$, if present, is hydrogen, C$_1$-C$_6$ alkyl, methylcarbonyl or ethylcarbonyl, R$_8$ is hydrogen, and R$_9$ and R$_{10}$, are in each instance, independently selected from the group consisting of hydrogen, halogen, optionally substituted, saturated or unsaturated C$_1$-C$_6$ alkyl, C$_1$-C$_6$ alkoxy or halo (C$_1$-C$_6$)alkyl. Preferably, G is

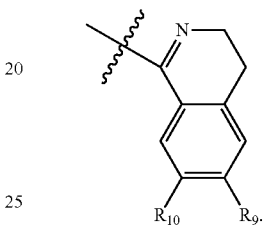

Useful compounds include those where R$_9$ is optionally substituted, saturated or unsaturated C$_1$-C$_6$ alkyl, halogen or C$_1$-C$_6$ alkoxy. Preferably, one of R$_2$, R$_3$, R$_4$ and R$_5$ is, in each instance, independently hydrogen, hydroxyl, optionally substituted, saturated or unsaturated C$_1$-C$_6$ alkyl, C$_1$-C$_6$ alkoxy, halogen or halo (C$_1$-C$_6$)alkyl, and the others of R$_2$, R$_3$, R$_4$ and R$_5$ are each hydrogen.

Some specific compounds of Formula Ia include:

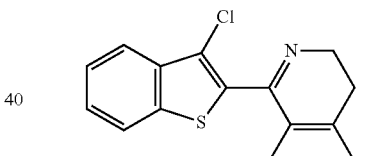

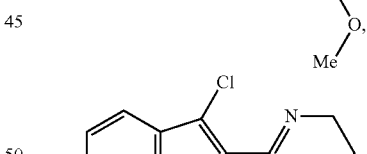

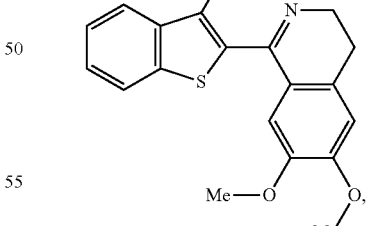
,

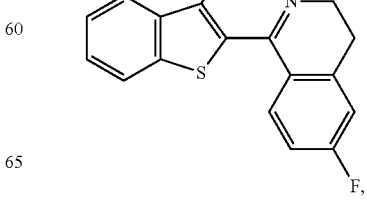
,

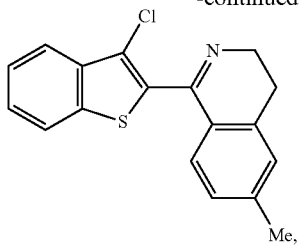

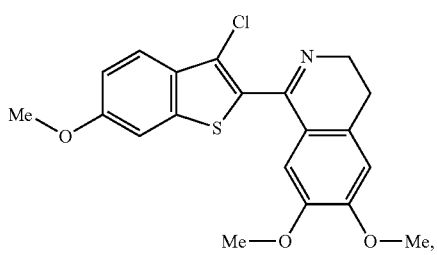

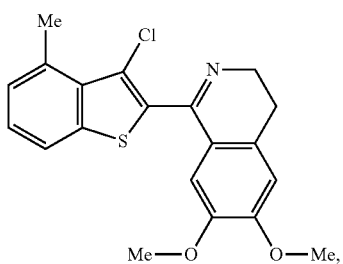

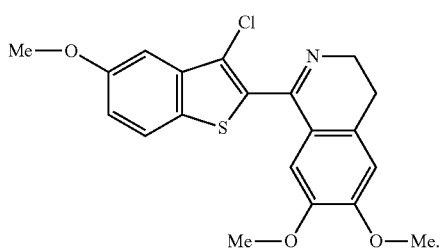 [SMILES: COc1ccc2sc(C3=NCCc4cc(OC)c(OC)cc43)c(Cl)c2c1]

Useful compounds of Formula Ia include those where G is

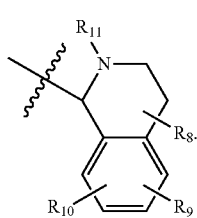

Useful compounds include those where $R_{11}$ is hydrogen, $C_1$-$C_6$ alkyl, methylcarbonyl or ethylcarbonyl. In these compounds, preferably $R_8$ is hydrogen, and $R_9$ and $R_{10}$, are in each instance, independently selected from the group consisting of hydrogen, halogen, optionally substituted, saturated or unsaturated $C_1$-$C_6$ alkyl, $C_1$-$C_6$ alkoxy or halo ($C_1$-$C_6$)alkyl. Preferably, G is

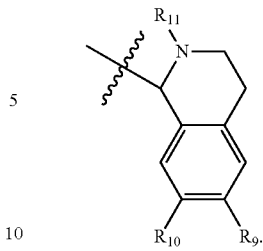

In preferred compounds, $R_9$ is optionally substituted, saturated or unsaturated $C_1$-$C_6$ alkyl, halogen or $C_1$-$C_6$ alkoxy. In these compounds, preferably one of $R_2$, $R_3$, $R_4$ and $R_5$ is, in each instance, independently hydrogen, hydroxyl, optionally substituted, saturated or unsaturated $C_1$-$C_6$ alkyl, $C_1$-$C_6$ alkoxy, halogen or halo ($C_1$-$C_6$)alkyl, and the others of $R_2$, $R_3$, $R_4$ and $R_5$ are each hydrogen.

Some specific compounds of Formula Ia include:

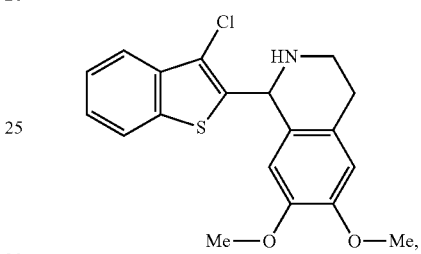

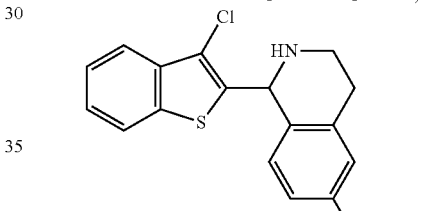

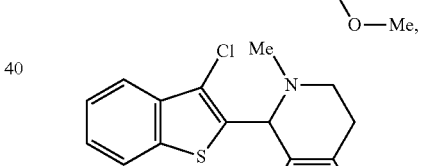

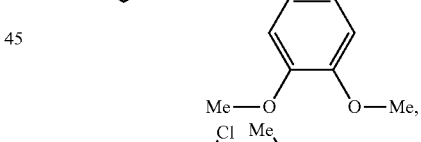

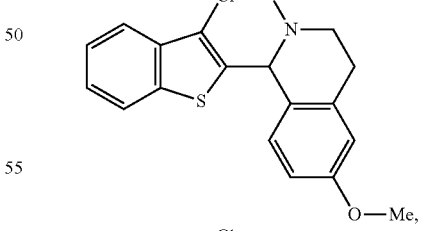

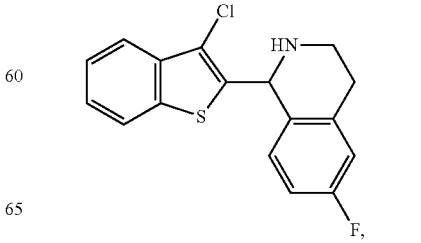

-continued

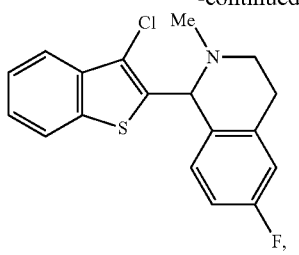

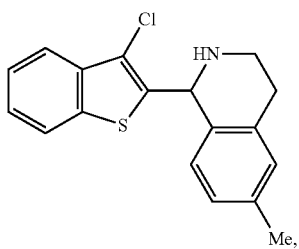

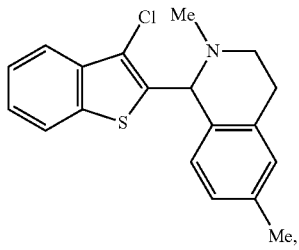

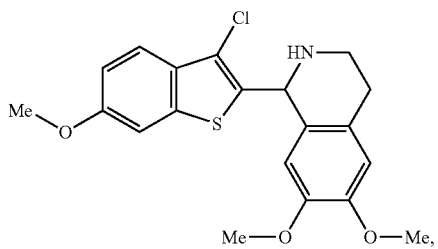

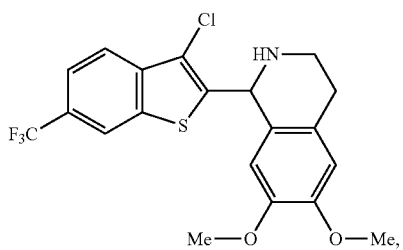

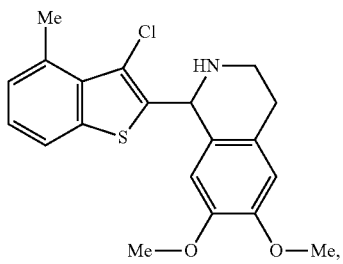

-continued

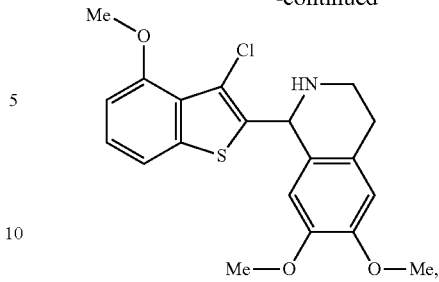

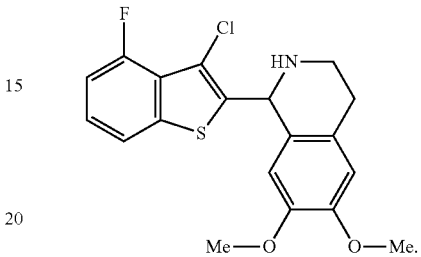

Useful compounds of Formula Ia include those where G is iii. In such compounds, G is

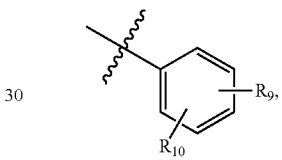

wherein, $R_9$ and $R_{10}$, are in each instance, independently selected from the group consisting of hydrogen, halogen, optionally substituted, saturated or unsaturated $C_1$-$C_6$ alkyl, $C_1$-$C_6$ alkoxy or halo ($C_1$-$C_6$)alkyl. Preferably, G is

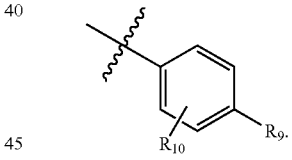

A specific compound of this embodiment has the following structure:

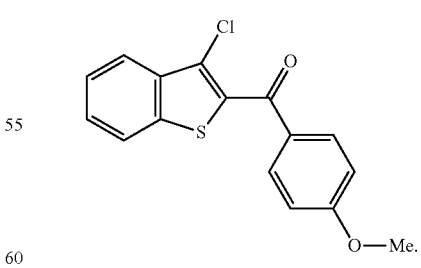

Useful compounds of Formula Ia include those where U is —(CH$_2$)$_y$—, wherein y is an integer from zero to 4, and preferably where y is zero or one.

Useful compounds of Formula Ia include those where U is —NHSO$_2$—. Preferably, in these compounds, G is iii. In such compounds, G is

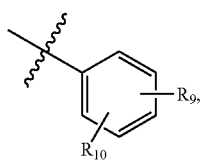

wherein, $R_9$ and $R_{10}$, are in each instance, independently selected from the group consisting of hydrogen, halogen, optionally substituted, saturated or unsaturated $C_1$-$C_6$ alkyl, $C_1$-$C_6$ alkoxy or halo ($C_1$-$C_6$)alkyl. Preferably, G is

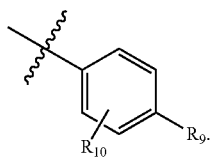

Some specific compounds of this embodiment have the following structures:

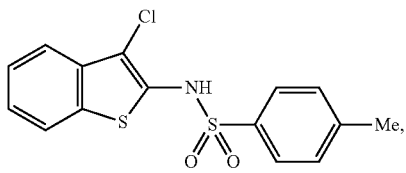

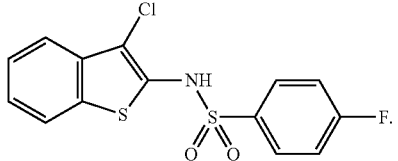

Useful compounds include those of Formula IIa (M21-related compounds) having the following structure:

IIa

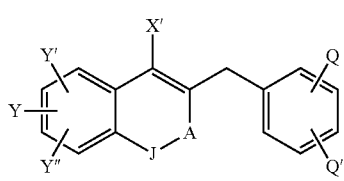

wherein,
Y is selected from the group consisting of hydroxyl, $C_1$-$C_6$ alkoxy, $C_1$-$C_6$ alkyl, amino, $C_1$-$C_6$ alkylamino, mono- or di-($C_1$-$C_6$) alkylamino, mono- or di-($C_1$-$C_6$) alkylaminoalkyl, thiol, cyano, cyano($C_1$-$C_6$)alkyl, nitro and halogen,
Y' and Y" are each independently selected from the group consisting of hydrogen, hydroxyl, $C_1$-$C_6$ alkoxy, $C_1$-$C_6$ alkyl, amino, $C_1$-$C_6$ alkylamino, mono- or di-($C_1$-$C_6$) alkylamino, mono- or di-($C_1$-$C_6$) alkylaminoalkyl, thiol, cyano, cyano($C_1$-$C_6$)alkyl, nitro and halogen,
X' is hydroxyl, $C_1$-$C_6$ alkoxy or $C_1$-$C_6$ alkyl,
Q and Q' are each independently selected from the group consisting of hydrogen, $C_1$-$C_6$ alkyl, $C_1$-$C_6$ alkenyl, $C_1$-$C_6$ alkynyl, $C_1$-$C_6$ alkoxy, $C_1$-$C_6$ alkoxycarbonyl, amino, $C_1$-$C_6$ alkylamino, mono- or di-($C_1$-$C_6$) alkylamino, mono- or di-($C_1$-$C_6$) alkylaminoalkyl, halogen, halo ($C_1$-$C_6$)alkyl, thiol, cyano, cyano($C_1$-$C_6$)alkyl and nitro, A is —C(CH$_3$)$_2$ or —C=O; preferably A is —C=O; and
J is O or NH;
optionally provided that the compound is not

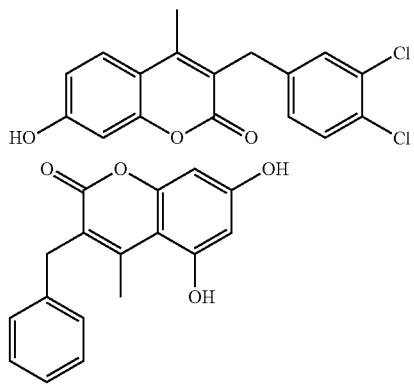

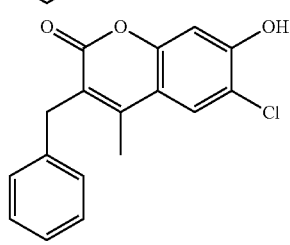

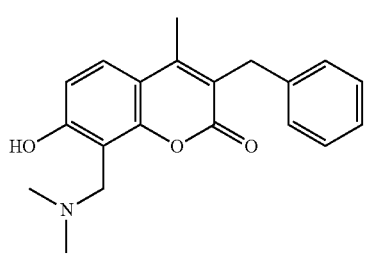

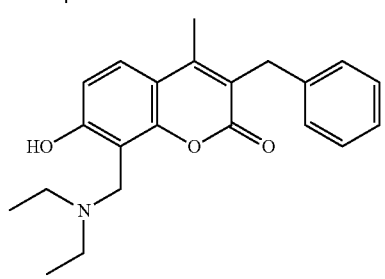

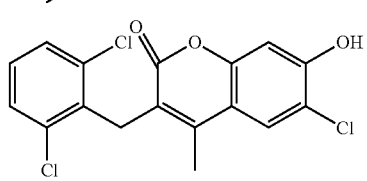

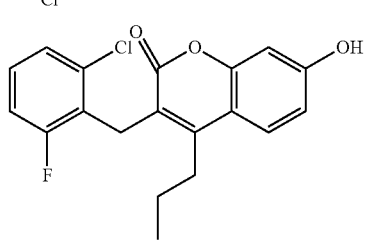

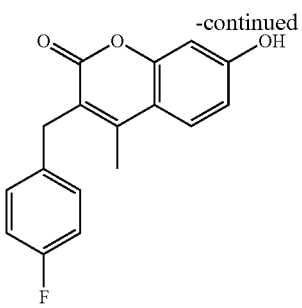

Useful compounds of Formula IIa include those where J is O.

Preferably, compounds of Formula IIa include those where X' is $C_1$-$C_6$ alkyl. More preferably, X' is pentyl, butyl, propyl, ethyl or methyl. Most preferably, X' is n-propyl.

Useful compounds of Formula IIa include those where Y and Y' are each independently selected from the group consisting of hydroxyl, $C_1$-$C_6$ alkoxy, $C_1$-$C_6$ alkyl, amino, $C_1$-$C_6$ alkylamino, mono- or di-($C_1$-$C_6$) alkylamino, mono- or di-($C_1$-$C_6$) alkylaminoalkyl and halogen. Preferably, Y and Y' are each independently selected from the group consisting of hydroxyl, $C_1$-$C_6$ alkoxy, mono- or di-($C_1$-$C_6$) alkylaminoalkyl and halogen. Also preferred are compounds where Y is chloro or fluoro, and Y' is other than hydrogen. Also preferred are compounds where Y is methoxy or ethoxy, and Y' is other than hydrogen. Also preferred are compounds where Y is hydroxy, and Y' is other than hydrogen. Also preferred are compounds where Y is mono- or di-($C_1$-$C_6$) alkylaminoalkyl, and Y' is other than hydrogen. Also preferred are compounds where Y is dimethylamino-($C_1$-$C_6$) alkyl. Also preferred are compounds where Y and Y' are each independently selected from the group consisting of hydroxyl, $C_1$-$C_6$ alkoxy, $C_1$-$C_6$ alkyl, amino, $C_1$-$C_6$ alkylamino, mono- or di-($C_1$-$C_6$) mono- or di-($C_1$-$C_6$) alkylaminoalkyl, thiol, cyano, cyano($C_1$-$C_6$) alkyl, nitro and halogen. Also preferred are compounds where Y" is hydrogen and Y' is selected from the group consisting of hydroxyl, $C_1$-$C_6$ alkoxy, $C_1$-$C_6$ alkyl, amino, $C_1$-$C_6$ alkylamino, mono- or di-($C_1$-$C_6$) alkylamino, mono- or di-($C_1$-$C_6$) alkylaminoalkyl, thiol, cyano, cyano($C_1$-$C_6$)alkyl, nitro and halogen.

The following structure shows the numbering scheme for certain compounds of Formula IIa.

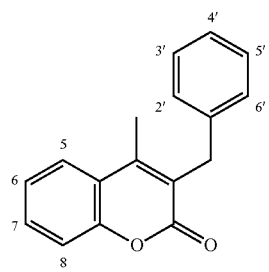 [SMILES: Cc1c(Cc2ccccc2)c(=O)oc2ccccc12]

Numbering Scheme for Quinolone Compounds of Formula IIa

In some compounds, Y and Y' are independently and preferably selected from the group hydrogen, hydroxyl, methyl, methoxy, chloro and fluoro. In some compounds, Y at the 5-position of Formula Ia, is preferably hydrogen. In some compounds, Y at the 5-position of Formula Ia is more preferably is hydroxyl. In some compounds, Y at the 6-position of Formula Ia is preferably methyl. In some compounds, Y at the 6-position of Formula Ia is more preferably hydrogen. In some compounds, Y at the 6-position of Formula Ia is even more preferably hydroxyl. In some compounds, Y at the 6-position of Formula Ia is most preferably fluorine or chlorine. In some compounds, Y at the 8-position of Formula Ia is preferably hydrogen, methyl, or hydroxyl. In some compounds, Y at the 8-position of Formula Ia is more preferably diethylaminomethylene. In some compounds, Y at the 8-position of Formula Ia is most preferably dimethylaminomethylene.

Useful compounds of Formula IIa include those where Q is selected from the group consisting of hydrogen, $C_1$-$C_6$ alkyl, $C_1$-$C_6$ alkoxy, amino, $C_1$-$C_6$ alkylamino, mono- or di-($C_1$-$C_6$) alkylamino, mono- or di-($C_1$-$C_6$) alkylaminoalkyl, halogen and halo ($C_1$-$C_6$)alkyl, and Q' is selected from the group consisting of $C_1$-$C_6$ alkyl, $C_1$-$C_6$ alkoxy, amino, $C_1$-$C_6$ alkylamino, mono- or di-($C_1$-$C_6$) alkylamino, mono- or di-($C_1$-$C_6$) alkylaminoalkyl, halogen and halo ($C_1$-$C_6$)alkyl. Preferably, Q is selected from the group consisting of hydrogen, $C_1$-$C_6$ alkoxy, halogen and halo ($C_1$-$C_6$)alkyl, and Q' is selected from the group consisting of hydrogen, $C_1$-$C_6$ alkoxy, halogen and halo ($C_1$-$C_6$)alkyl. In preferred compounds in this embodiment, the halogen in each instance is independently fluoro or chloro. Also preferred are compounds where Q is selected from the group consisting of hydrogen, chloro and fluoro, and Q' is selected from the group consisting of chloro and fluoro.

Useful compounds of Formula IIa include those where J is N—H.

In some preferred compounds Q, and Q' are selected from chloro and fluoro. In some compounds when Q' is hydrogen and when Q is chloro, 3',4'-dichloro is preferable. In some compounds when Q' is hydrogen and when Q is fluoro, chloro or hydrogen, 6'-fluoro, 2'-chloro, 2',6'-dichloro, hydrogen or 4'-chloro is more preferable. When Q' is hydrogen, and when Q is fluoro, 4'-fluoro is even more preferable. When Q' is hydrogen and when Q is chloro, 3'-chloro is most preferable.

Some specific compounds of Formula IIa have one of the following structures:

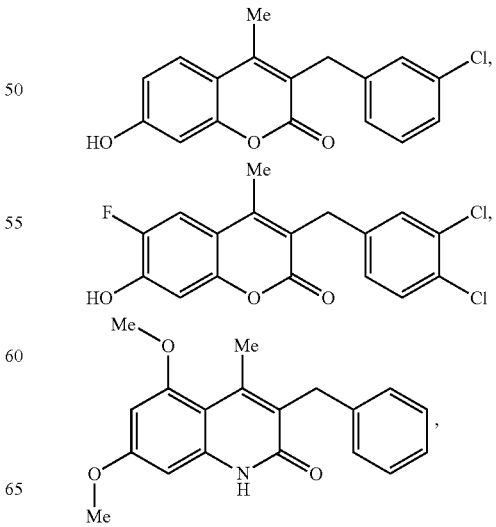

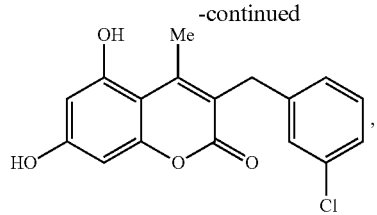

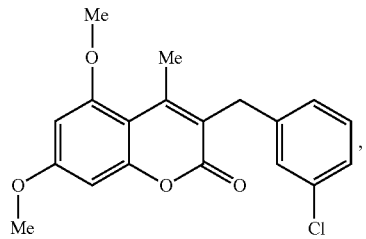

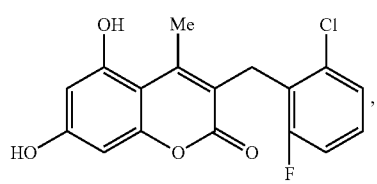

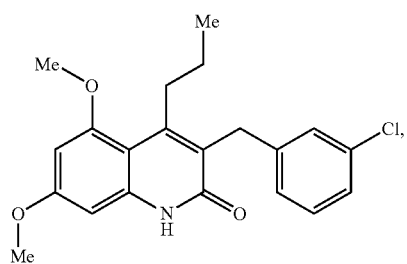

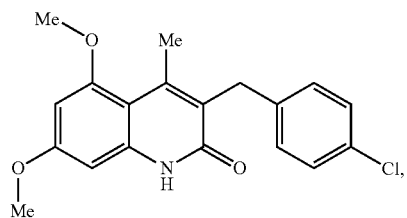

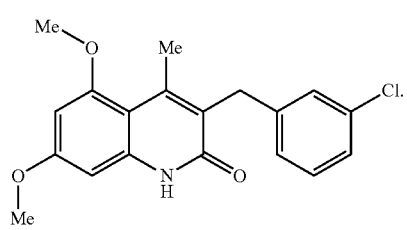

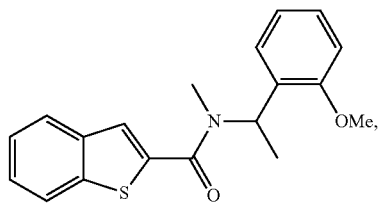

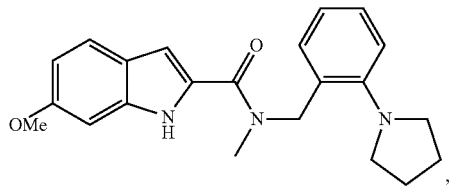

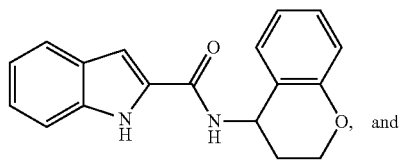

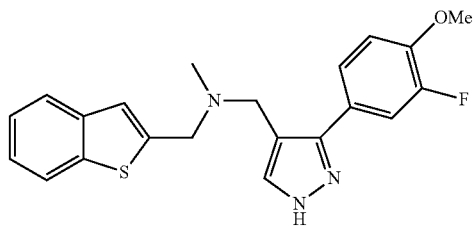

or a pharmaceutically acceptable salt of any of these compounds. Optionally, the compound of Formula Ia or IIa is not a compound disclosed by WO/2011/072275 or a pharmaceutically acceptable salt thereof. Optionally, the compound of Formula Ia or IIa is not M4

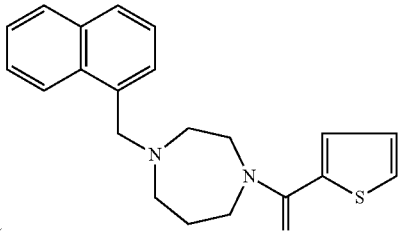

(        ), M5

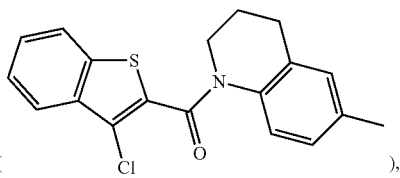

(        ), M6

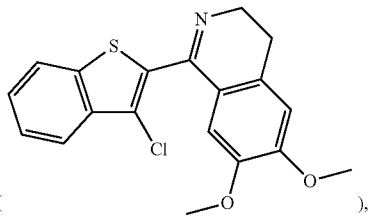

(        ),

Formula Ia and IIa compounds are described throughout the specification. Compounds specifically not encompassed or described by Formula Ia or IIa are also shown elsewhere in this specification including the claims. Optionally, the compound of Formula Ia or IIa is not a compound disclosed in Table 2 or Table 3 or FIGS. 1-82 of WO/2011/072275 or Table Y of the present specification (e.g., M9 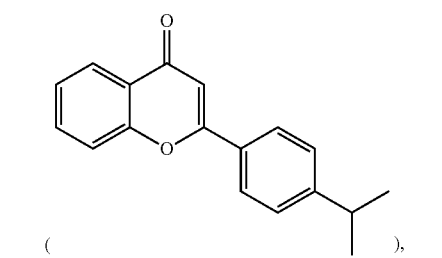,
M17 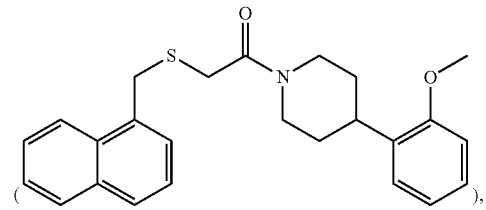,
M19 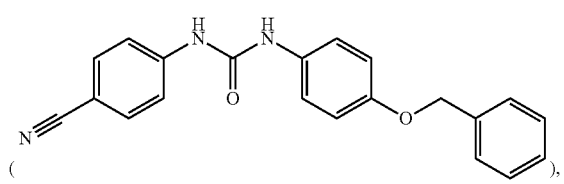,
M21 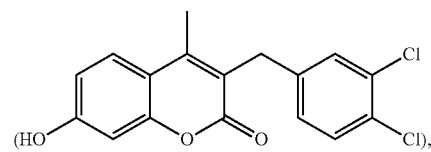,
M29 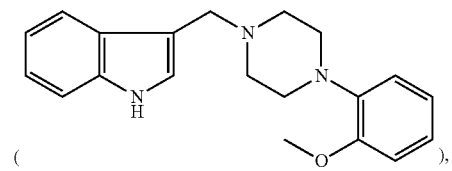,
C04 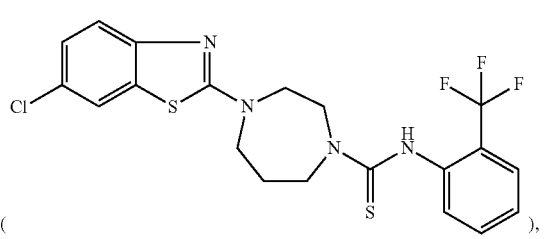,
C05 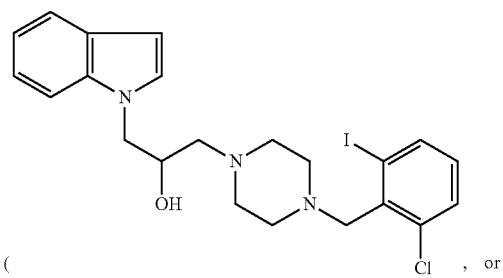, or
C06 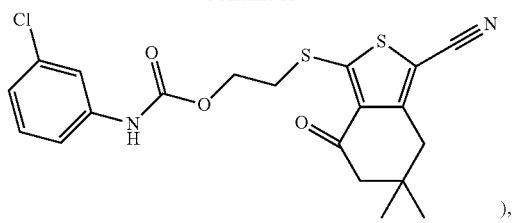,
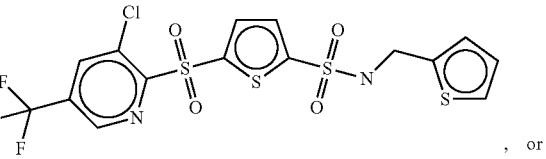, or
C10 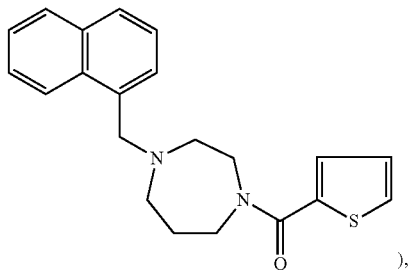,
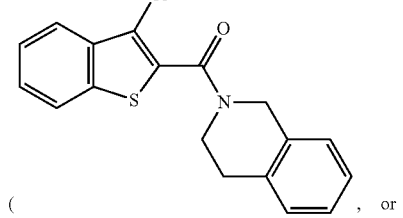,
C07 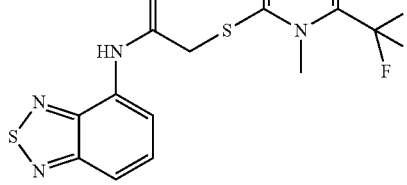,
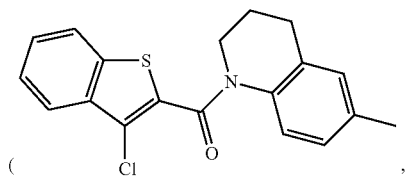,
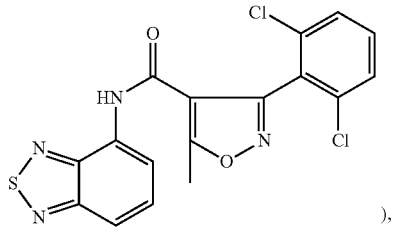, -continued
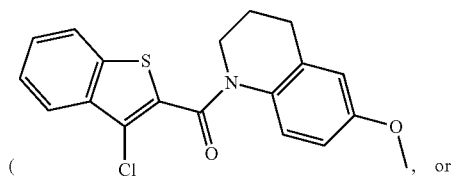
(  ), or
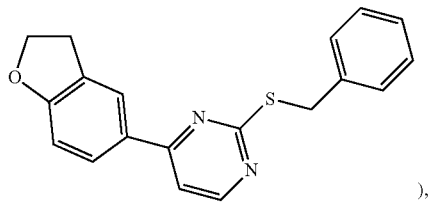
(  ),
C13
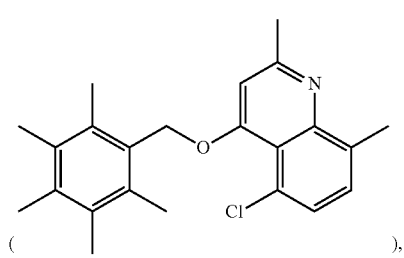
(  ),
C15
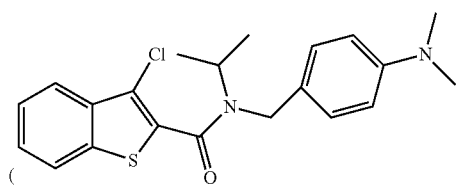
(  ), or
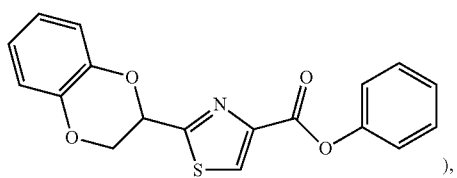
(  ),
D03
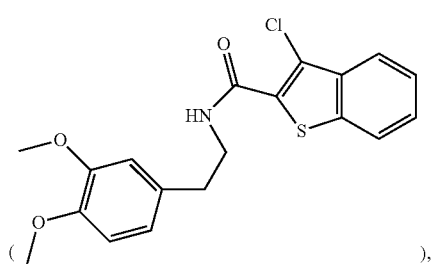
(  ),
D11
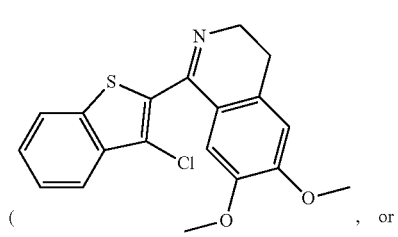
(  ), or
-continued
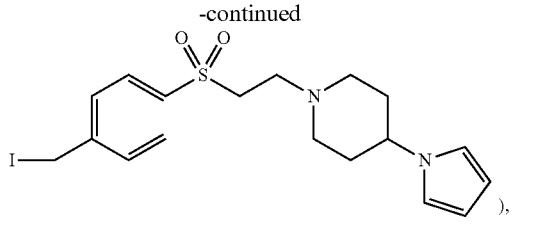
(  ),
D19
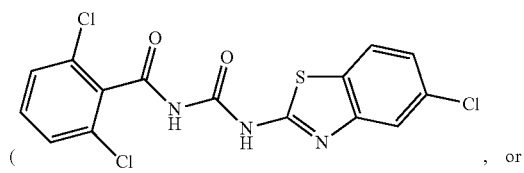
(  ), or
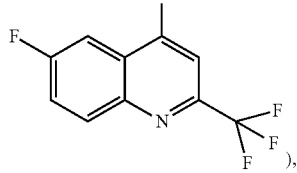
(  ),
E07
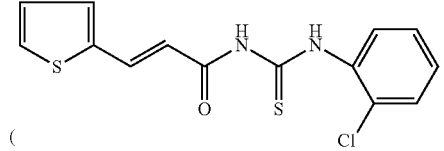
(  ), or
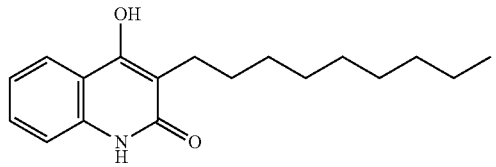
(  ),
E09
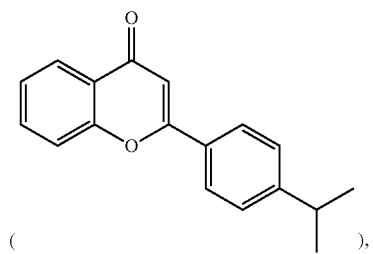
(  ),
G17
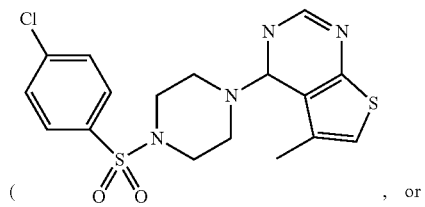
(  ), or
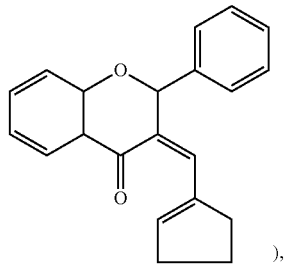
(  ),

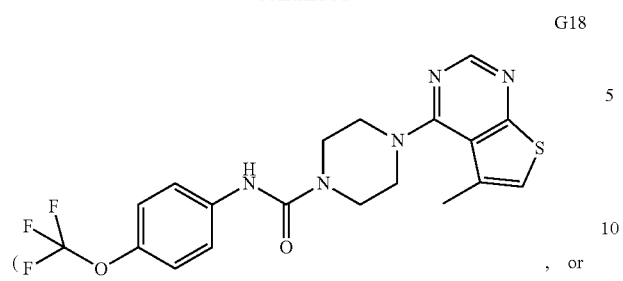
G18
, or
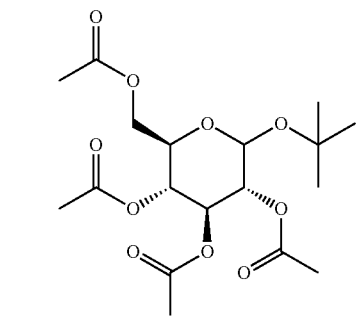
),
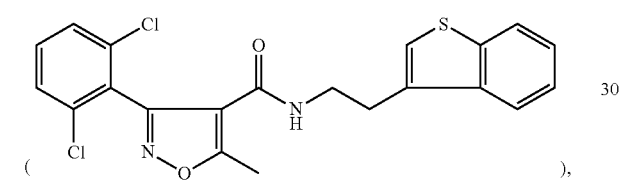
H06
),
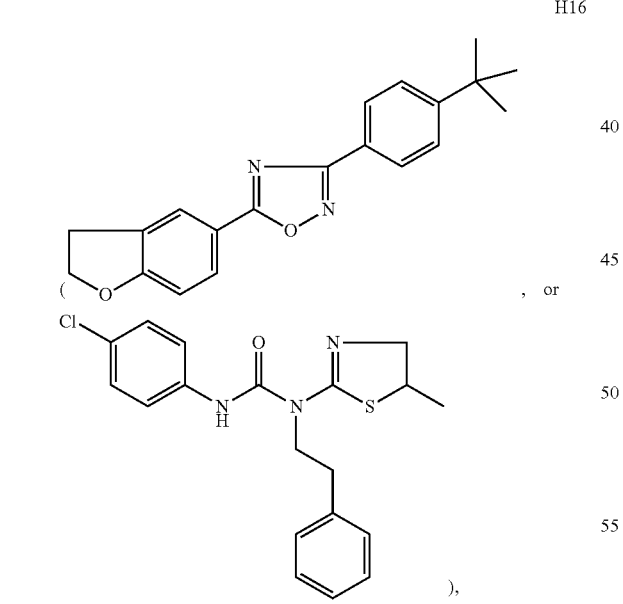
H16
, or
),
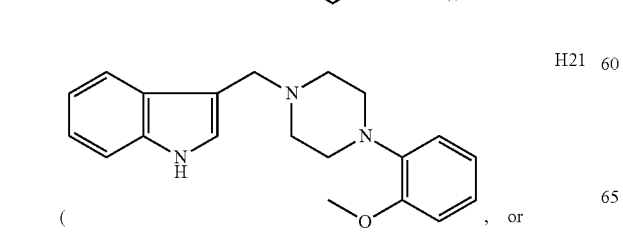
H21
, or
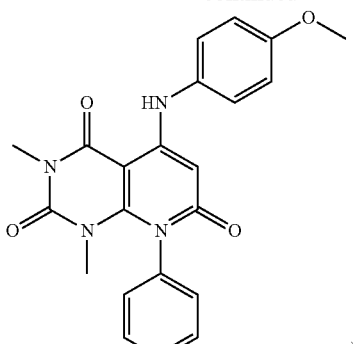
),
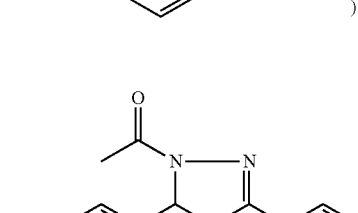
I04
, or
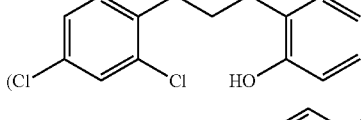
),
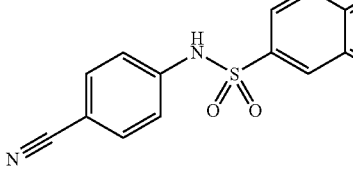
I14
),
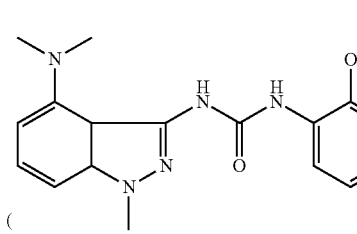
I08
, or
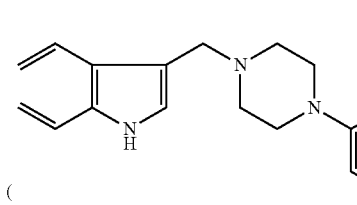
),
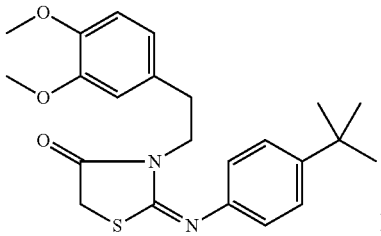
I10
),

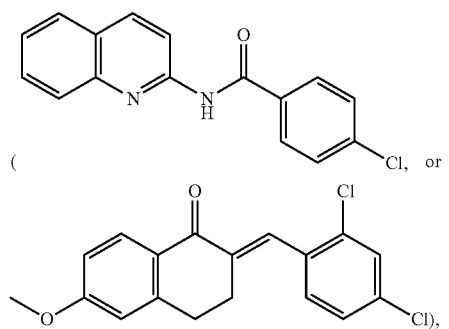
(   , or
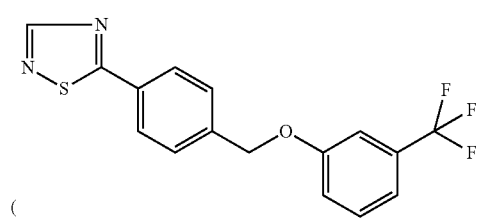
,
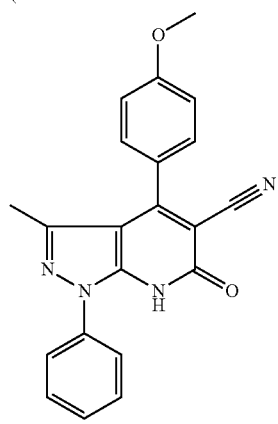
),
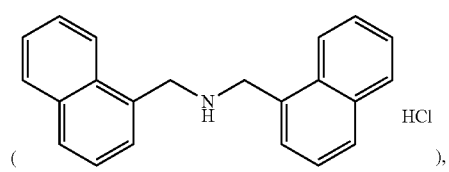
(   HCl   ),
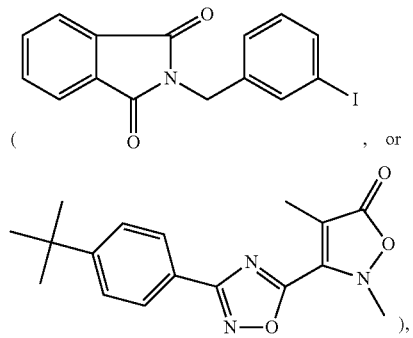
(   , or
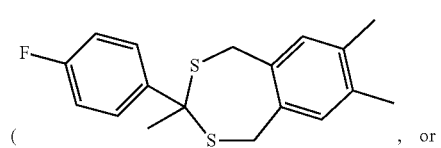
(   , or
I20
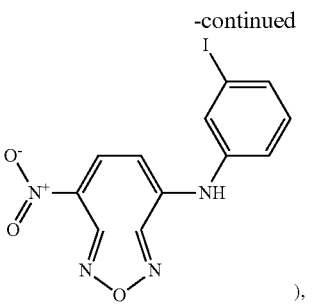
),
C20
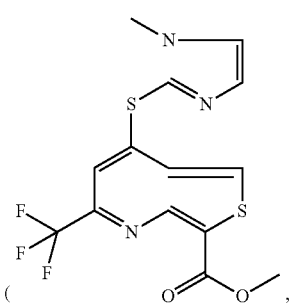
(   ,
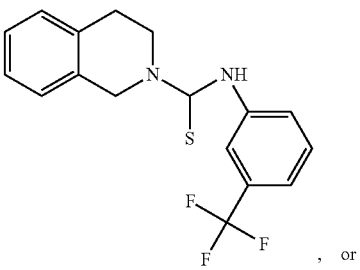
, or
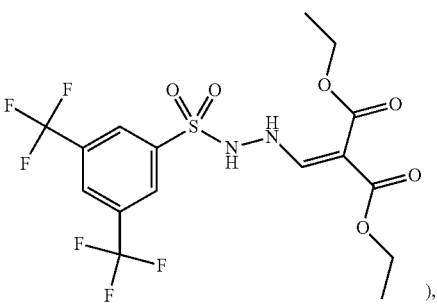
),
D09
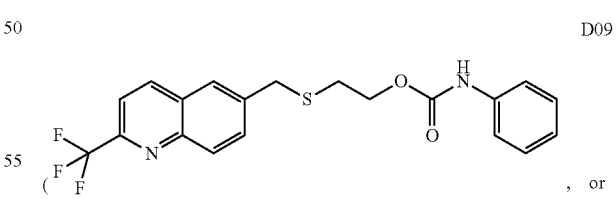
(   , or
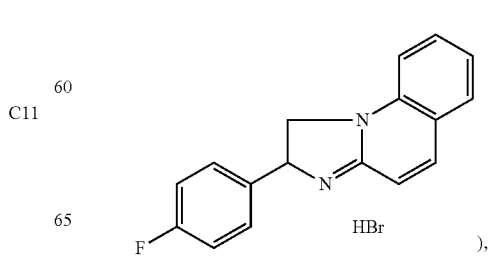
HBr   ),
J08
K06
K16
C11

E18

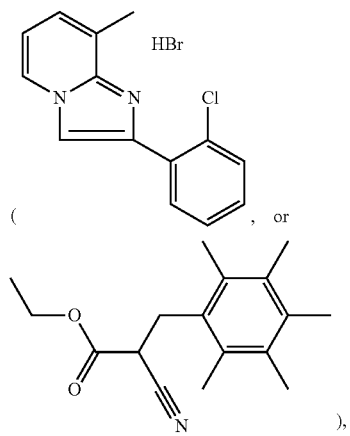

(  , or

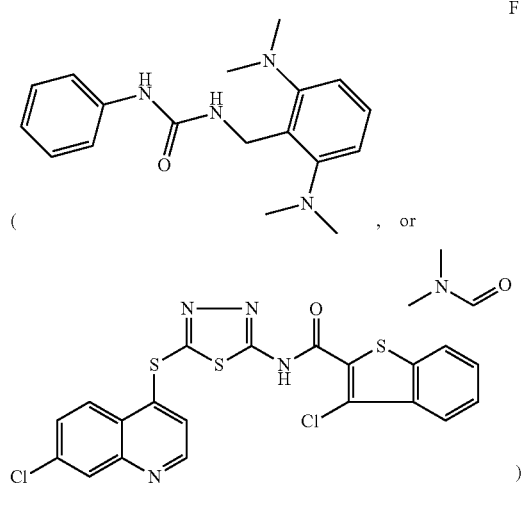

),

F18

),

G11

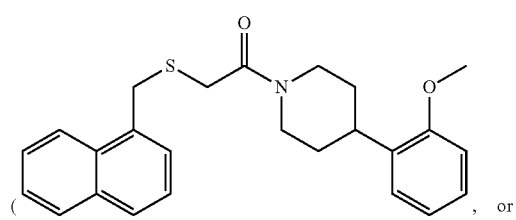

, or

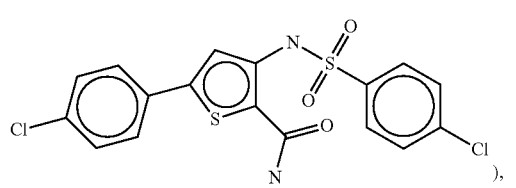

),

G16

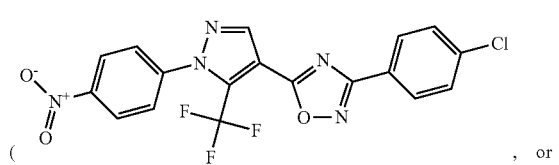

, or

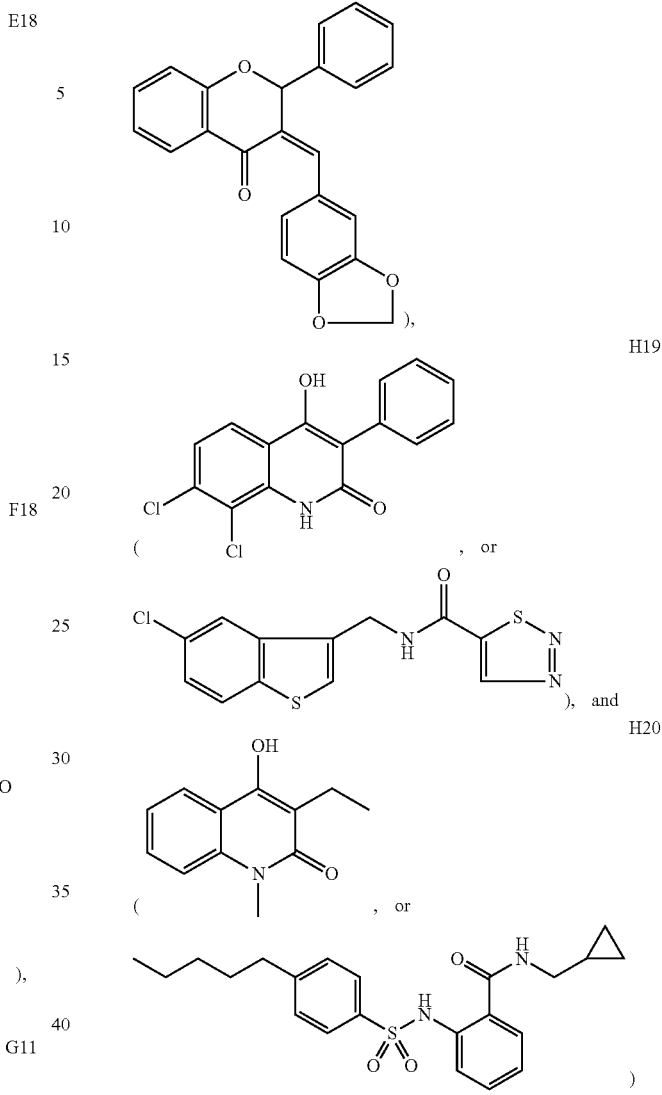

or a pharmaceutically acceptable salt thereof.

4. Pharmaceutical Compositions and Regimes

The agents and compositions of the invention are useful for in treatment or prophylaxis of a variety of diseases and manufacture of a medicament for such purposes as described below and elsewhere herein, particularly neurological diseases, and especially diseases mediated in part by ischemia. The agents and compositions are also effective for treatment or prophylaxis of cancer and pain. The method are useful in treating subjects in which sign(s) and/or symptom(s) of disease are already present or in prophylaxis of subjects without known symptom(s) of disease but at enhanced risk of developing symptoms by virtue of one or more risk factors associated with the disease. Risk factors can be for example, genetic, biochemical or environment. Risk factors can also occur because the subject is about to undergo an event that carriers a known predisposition to development of disease (e.g., cardiac or brain surgery predisposes to development of ischemia).

Disease amenable to treatment prophylaxis include ischemic and cytodegenerative diseases and conditions, including neurological diseases and conditions, such as stroke, traumatic brain injury, Alzheimer's disease, Parkinson's disease, Huntington's disease, dementia, epilepsy, spinocerebellar ataxia, spinal and bulbar muscular dystrophy, dentatorubropallidoluysian atrophy, brain injury, spinal cord injury, and other traumatic, ischemic or neurodegenerative nervous system injuries, or pain. Other non-neurological diseases, including ischemic and degenerative disorders and other conditions of other tissues, such as those of the heart, liver, kidneys, muscles, retina, skin, intestines, pancreas, gall bladder, thyroid, thymus, spleen, bone, cartilage, joints, lungs, diaphragm, adrenal glands, salivary, lacrimal glands, blood vessels and cells of endodermal, mesodermal and ectodermal origin. As shown in Example 5, TRPM7 shows detectable expression by Western blot or RT-PCR in all cell types and tissues tested. Other disease and conditions are optical disorders, such as glaucoma, diabetic retinopathy, and macular degeneration. Other diseases amenable to treatment include cancer and other proliferative disorders including solid tumors and hematological malignancies. Some such cancers and proliferative disorders show detectable levels of TRPM7 measured at either the protein (e.g., as described in the present examples) or mRNA level. Some such cancers and proliferative disorders show elevated levels of TRPM7 relative to noncancerous tissue of the same type, preferably from the same patient. Optionally, a level of TRPM7 in a cancer is measured before performing treatment. Some examples of cancers treatable by the disclosed compounds include breast cancer, adrenal carcinoma, cervical cancer, osteosarcoma, lung cancer (small cell and nonsmall cell), colon cancer, f cancer, retinoblastoma, head and neck cancers, gastric cancer, melanoma, ovarian cancer, endometrial cancer, prostate cancer, pancreatic cancer, esophageal cancer, hepatocellular carcinoma (liver cancer), mesothelioma, sarcomas, and brain tumors (e.g., gliomas, such as glioblastomas), leukemia and lymphoma. Other disease amenable to treatment include autoimmune disorders and under undesired immune response, arrhythmia, depressive disorders, stress disorders, bone formation (using activators of TRPM7). Evidence supporting a role of TRPM7 in various types of cancer is provided by Guilbert, Am. J. Cell. Phys. 257, C943-501 (2009) (breast cancer); Hanaro. J. Pharmacol. Sci. 95, 403-419 (2004) (retinoblastoma); Jian, Cancer Cell. Res. 67, 10929-10938 (2007) (head and neck cancer); Kim, Cancer Sci. 99, 2502-2509 (2008) (gastric cancer); McNeil, J. Invest. Derm. 127, 2020-2030 200) (melanoma); Salmi, Cell Metabolism 8, 84-93 (2008) (blood cancers). TRPM7 has also been implicated in hypertension (Trouyz, Am. J. Physiol. Heart Circ. Physiol. 294: H1103-H1118 (2008)), myocardial fibrosis and heart failure.

As used herein, the term "disease" includes pain. Thus, the agents described herein, e.g., TRPM7 modulators, can be used in treatment or prophylaxis of pain.

In its broadest usage, "pain" refers to an experiential phenomenon that is highly subjective to the individual experiencing it, and is influenced by the individual's mental state, including environment and cultural background. "Physical" pain can usually be linked to a stimulus perceivable to a third party that is causative of actual or potential tissue damage. In this sense, pain can be regarded as a "sensory and emotional experience associated with actual or potential tissue damage, or described in terms of such damage," according to the International Association for the Study of Pain (IASP). However, some instances of pain have no perceivable cause. For example, psychogenic pain, including exacerbation of a pre-existing physical pain by psychogenic factors or syndromes of a sometimes-persistent, perceived pain in persons with psychological disorders without any evidence of a perceivable cause of pain.

Pain includes nociceptive pain, neuropathic/neurogenic pain, breakthrough pain, allodynia, hyperalgesia, hyperesthesia, dysesthesia, paresthesia, hyperpathia, phantom limb pain, psychogenic pain, anesthesia dolorosa, neuralgia, neuritis. Other categorizations include malignant pain, anginal pain, and/or idiopathic pain, complex regional pain syndrome I, complex regional pain syndrome II. Types and symptoms of pain need not be mutually exclusive. These terms are intended as defined by the IASP.

Nociceptive pain is initiated by specialized sensory nociceptors in the peripheral nerves in response to noxious stimuli, encoding noxious stimuli into action potentials. Nociceptors, generally on A-δ and C fibers, are free nerve endings that terminate just below the skin, in tendons, joints, and in body organs. The dorsal root ganglion (DRG) neurons provide a site of communication between the periphery and the spinal cord. The signal is processed through the spinal cord to the brainstem and thalamic sites and finally to the cerebral cortex, where it usually (but not always) elicits a sensation of pain. Nociceptive pain can result from a wide variety of a chemical, thermal, biological (e.g., inflammatory) or mechanical events that have the potential to irritate or damage body tissue, which are generally above a certain minimal threshold of intensity required to cause nociceptive activity in nociceptors.

Neuropathic pain is generally the result of abnormal functioning in the peripheral or central nervous system, giving rise to peripheral or central neuropathic pain, respectively. Neuropathic pain is defined by the International Association for the Study of Pain as pain initiated or caused by a primary lesion or dysfunction in the nervous system. Neuropathic pain often involves actual damage to the nervous system, especially in chronic cases. Inflammatory nociceptive pain is generally a result of tissue damage and the resulting inflammatory process. Neuropathic pain can persist well after (e.g., months or years) beyond the apparent healing of any observable damage to tissues.

In cases of neuropathic pain, sensory processing from an affected region can become abnormal and innocuous stimuli (e.g., thermal, touch/pressure) that would normally not cause pain may do so (i.e., allodynia) or noxious stimuli may elicit exaggerated perceptions of pain (i.e., hyperalgesia) in response to a normally painful stimulus. In addition, sensations similar to electric tingling or shocks or "pins and needles" (i.e., paresthesias) and/or sensations having unpleasant qualities (i.e., dysesthesias) may be elicited by normal stimuli. Breakthrough pain is an aggravation of pre-existing chronic pain. Hyperpathia is a painful syndrome resulting from an abnormally painful reaction to a stimulus. The stimulus in most of the cases is repetitive with an increased pain threshold, which can be regarded as the least experience of pain which a patient can recognize as pain.

Examples of neuropathic pain include tactile allodynia (e.g., induced after nerve injury) neuralgia (e.g., post herpetic (or post-shingles) neuralgia, trigeminal neuralgia), reflex sympathetic dystrophy/causalgia (nerve trauma), components of cancer pain (e.g., pain due to the cancer itself or associated conditions such as inflammation, or due to treatment such as chemotherapy, surgery or radiotherapy), phantom limb pain, entrapment neuropathy (e.g., carpal tunnel syndrome), and neuropathies such as peripheral neuropathy (e.g., due to diabetes, HIV, chronic alcohol use, exposure to other toxins (including many chemotherapies), vitamin deficiencies, and a large variety of other medical conditions). Neuropathic pain includes pain induced by expression of pathological operation of the nervous system following nerve injury due to various causes, for example, surgical operation, wound, shingles, diabetic neuropathy, amputation of legs or arms, cancer, and the like. Medical conditions associated with neuropathic pain include traumatic nerve injury, stroke, multiple sclerosis, syringomyelia, spinal cord injury, and cancer.

A pain-causing stimulus often evokes an inflammatory response which itself can contribute to an experience of pain. In some conditions pain appears to be caused by a complex mixture of nociceptive and neuropathic factors. For example, chronic pain often comprises inflammatory nociceptive pain or neuropathic pain, or a mixture of both. An initial nervous system dysfunction or injury may trigger the neural release of inflammatory mediators and subsequent neuropathic inflammation. For example, migraine headaches can represent a mixture of neuropathic and nociceptive pain. Also, myofascial pain is probably secondary to nociceptive input from the muscles, but the abnormal muscle activity may be the result of neuropathic conditions.

The agents discussed herein can alleviate or prevent at least one symptom of pain. Symptoms of pain experienced by a patient may or may not be accompanied by signs of pain discernable to a clinician. Conversely, pain can be manifested by clinical signs without the patient being aware of symptoms.

Symptoms of pain can include a response to pain, e.g., in the form of a behavioral change. Exemplary responses to pain can include conscious avoidance of a painful stimulus, a protective response intended to protect the body or body parts from the painful stimulus, responses intended to minimize pain and promote healing, communication of pain, and physiological responses. Communicative responses can involve vocalizations of pain or modifications of facial expression or posture. Physiological responses are include responses mediated by the autonomic nervous system or endocrine system. e.g., enhanced release of adrenalin and noradrenalin, increased output of glucagon and/or hormones and/or corticosteroids. Physiological changes that can be monitored include locomotor effects such as twitching, convulsions, paralysis, dilated pupils, shivering, hyperesthesia and/or altered reflexes. Physiological cardiovascular responses to pain can include changes in blood pressure, alterations in pulse rate and quality, decreased peripheral circulation, cyanosis and congestion. Increased muscle tension (tone) is also symptomatic of pain. Changes in brain function in response to pain can be monitored by various techniques such as electroencephalography (EEG), frontal electromyography (FEMG) or positron emission tomography (PET).

Another symptom of pain can be referred pain, which is a perception of pain as being localized at a site adjacent to or at a distance from the actual site of the pain-causing stimulus. Often, referred pain arises when a nerve is compressed or damaged at or near its origin. In this circumstance, the sensation of pain is generally felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain is also felt in the region served by the compressed nerve (for example, the thigh, knee, or foot).

Nociceptive activity is a symptom of nociceptive pain. Nociceptive activity, even in the absence of consciously-perceived pain, may trigger withdrawal reflexes and a variety of autonomic responses such as pallor, diaphoresis, bradycardia, hypotension, lightheadedness, nausea and fainting.

One patient class amenable to treatments are patients undergoing a surgical procedure that involves or may involve a blood vessel supplying the brain, or otherwise on the brain or CNS. Some examples are patients undergoing cardiopulmonary bypass, carotid stenting, diagnostic angiography of the brain or coronary arteries of the aortic arch, vascular or endovascular surgical procedures and neurosurgical procedures. Patients with a brain aneurysm are particularly suitable. Such patients can be treated by a variety of surgical procedures including clipping the aneurysm to shut off blood, or performing endovascular surgery to block the aneurysm with small coils or introduce a stent into a blood vessel from which an aneurysm emerges, or inserting a microcatheter. Endovascular procedures are less invasive than clipping an aneurysm but the outcome still includes a high incidence of small infarctions.

The agents of the invention can be formulated and administered in the form of a pharmaceutical composition. An agent included in such a composition is typically substantially pure of contaminants (i.e., contaminants resulting from production of an agent including synthesis and/or purification). For example, an agent can be at least 75, 90, 95 or 99% w/w free of such contaminants. However, substantial freedom from contaminants does not preclude the agent being formulated with one or more pharmaceutically acceptable carriers, diluents as further described below.

Pharmaceutical compositions are manufactured under GMP conditions. Pharmaceutical compositions can be provided in unit dosage form (i.e., the dosage for a single administration). For example, a pill, capsule or the like can provide a single oral dose and a vial can provide a single dose for parenteral administration. Pharmaceutical compositions can be manufactured by means of conventional mixing, dissolving, granulating, dragee-making, levigating, emulsifying, encapsulating, entrapping or lyophilizing processes.

Pharmaceutical compositions can be formulated in conventional manner using one or more pharmaceutically acceptable carriers (including diluents, excipients or other auxiliaries) that facilitate processing, storage or administration of agents. Proper formulation is dependent on the route of administration chosen.

Administration can be parenteral, intravenous, oral, subcutaneous, intraarterial, intracranial, intrathecal, intraperitoneal, topical, intranasal or intramuscular.

Pharmaceutical compositions for parenteral administration are preferably sterile and substantially isotonic. For injection, agents can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents.

Alternatively agents can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, agents can be formulated with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the agents can also be formulated as a depot preparation. Such long acting formulations can be administered by implantation (for example subcutaneously or intramuscularly) or by intramuscular injection. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

Alternatively other pharmaceutical delivery systems can be employed. Liposomes and emulsions can be used to deliver agents. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the chimeric peptides for a few weeks up to over 100 days. Depending on the chemical nature and the biological stability of the therapeutic reagent, additional strategies for protein stabilization can be employed.

Agents can be formulated as free acids or bases or as pharmaceutically acceptable salts (see generally Berg et al., 66 J. PHARM. SCI. 1-19 (1977), and C. G. Wermuth and P. H. Stahl (eds.) "Pharmaceutical Salts: Properties, Selection, and Use" Verlag Helvetica Chimica Acta, 2002 [ISBN 3-906390-26-8]. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms. Pharmaceutically acceptable acid salts include hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include aluminum, calcium, lithium, magnesium, potassium, sodium, zinc, and diethanolamine salts The agents are used in a regime (i.e., dose, frequency, route of administration) effective to achieve the intended purpose (e.g., reduction of damage effect of ischemia). A therapeutically effective regime means a regime that reduces or at least inhibits further deterioration of at least one symptom or sign of disease in a population of patients (or animal models) treated with the agent relative to a control population of patients (or animal models) not treated with the agent. Signs and symptoms of disease include infarctions (in the case of ischemic diseases), delayed neuronal death, and cognitive deficits, e.g., in memory, in ischemic and other neurologic disease, and reduced proliferation, toxicity and/or metastasis for cancer. The regime is also considered therapeutically effective if an individual treated patient achieves an outcome more favorable than the mean outcome in a control population of comparable patients not treated by methods of the invention. In the context of stroke, a regime is also considered therapeutically effective if an individual treated patient shows a disability of two or less on the Rankin scale and 75 or more on the Barthel scale. A regime is also considered therapeutically effective if a population of treated patients shows a significantly improved (i.e., less disability) distribution of scores on a disability scale than a comparable untreated population, see Lees et at l., N Engl J Med 2006; 354:588-600. A prophylactically effective regime means a regime that delays the onset, reduces the frequency of onset, and/or reduces severity of at least one sign or symptom of disease in a population of patients (or animal models) treated with the agent relative to a control population of patients (or animal models) not treated with the agent. An effective regime refers to a regime that is effective therapeutically, prophylactically or both.

The amount of agent administered depends on the subject being treated, on the subject's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the present agents can provide therapeutic benefit without causing substantial toxicity. Toxicity of the chimeric peptides can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Chimeric peptides or peptidomimetics exhibiting high therapeutic indices are preferred (see, e.g., Fingl et al., 1975, In: The Pharmacological Basis of Therapeutics, Ch. 1, p. 1).

EXAMPLES

Example 1

An assay for detecting TRPM7-mediated Cellular Ion Flux and Cell Death mediated by Chemical Anoxia with NaCN.

Introduction

The TRPM7 channel provides a pathway for mono- and divalent cations into the cell, and is unique in that it contains a functional C-terminal α-kinase domain. Among the procedures known to activate TRPM7 channels, the TRPM7 channel has been shown to be activated by chemical anoxia using NaCN (Aarts et al., 2003). The induction of chemical anoxia in host cells such as recombinant HEK293 cells can be used to activate TRPM7. This activation is detectable with the use measurements of cellular calcium accumulation. This is achievable with the use of a fluorescent calcium indicator. Alternatively, this activation can also be measured using radiolabelled Ca2+ ($^{45}Ca^{2+}$) as described previously by Sattler et al. (Sattler et al., 1998) and Aarts et al. (Aarts et al., 2003).

Methods

Design of Specific TRPM7 Constructs

Flag-TRPM7/pBluescript II KS Construct

The TRPM7 construct was a Flag-TRPM7/pBluescript II KS construct (FIG. 27 of WO/2011/072275). The Flag-TRPM7 cDNA is comprised of the murine TRPM7 sequence (GenBank accession no. AY032591)) conjugated to a Flag epitope tag at its N-terminus, and was subcloned into the pBluescript vector from a Flag-TRPM7/pcDNA4/TO construct (Aarts et al., 2003). Restriction enzyme digest with EcoRI determined the direction of insert in the pBluescript vector. FIG. 27 of WO/2011/072275 illustrates that the banding pattern observed corresponded to a 3'→5' direction of insert (in bps): 3838, 3200, and 1592.

pTracer-CMV2 Constructs

For expression in a mammalian cell line, the TRPM7 sequence was subcloned into a modified pTracer-CMV2 vector (Promega, Madison Wis.) (FIG. 28 of WO/2011/072275). This vector had been modified such that the GFP cDNA of the original was replaced by enhanced GFP (eGFP) cDNA. The Flag-TRPM7/pTracer-CMV2 construct was generated by ligating the 5745 bp fragment of a SpeI/KpnI digest of Flag-TRPM7/pBluescript with the 6140 bp fragment of a KpnI/XbaI digest of pTracer, ensuring that the Flag tag is preserved through the subcloning and that the TRPM7 sequence is inserted into the pTracer vector in the correct orientation (5'→3') for expression. Selected transformants were screened by restriction enzyme digest with EcoRI, then with EcoRV, PmeI, and BamHI.

An additional pTracer construct was designed for use in calcium imaging experiments (FIG. 28 of WO/2011/072275). This construct does not contain the eGFP cDNA, as its excitation/emission spectrum ($\lambda$ excitation=488 nm, $\lambda$ emission=509 nm) overlaps with that of the calcium dye used (fluo-3; $\lambda$ excitation=506 nm, $\lambda$ emission=526 nm). The eGFP(−) construct was generated by digesting the Flag-TRPM7/pTracer or Flag-APDZ/pTracer constructs with NgoMIV to excise the eGFP gene and a portion of the preceding EF-1α promoter, and religating the larger 10060 bp fragment. The ligated product was used to transform Subcloning Efficiency™ DH5α cells (Invitrogen) and selected transformants screened with EcoRI, PmeI, and BamHI.

Cell Culture

HEK-293 tSA (HEK-293T) cells were cultured in Dulbecco's Modified Eagle Medium with L-glutamine and sodium pyruvate (DMEM; Gibco, Burlington, ON), supplemented with 10% fetal bovine serum (FBS; Gibco) and 1% antibiotic-antimycotic (Gibco) on polystyrene cell culture dishes (Sarstedt, Montreal, QC). Cells were maintained in a humidified incubator (Steri-Cycle® CO2 incubator, model 370; Thermo Electron Corp.) set at 37° C. and 5% CO2. Media was replaced routinely in 60 mm and 35 mm dishes with 5 mL and 2 mL respectively. When cells reached 75-90% confluency, as estimated under a light microscope (NIKON Diaphot-TMD; Nikon Canada, Mississauga, ON), they were passaged into new dishes by the following method: media from the confluent dish was aspirated, the dish washed once with phosphate buffered saline (PBS), replaced with trypsin-EDTA (0.05% solution; Gibco) and incubated at 37° C. until cells could be dissociated by gentle shaking. Pre-warmed DMEM (Gibco) was added to the dish, then drawn up and dispensed several times from a pipette (Sarstedt) using a Pipet Aid® (Drummond, Broomall, Pa.) to dissociate any remaining cell clumps. Cells were divided into new dishes at 1:10 to 1:40 dilutions. Cells were used up to 15 passages from the time of thawing.

Determining Cell Count

Cells were dissociated with trypsin-EDTA (Gibco) and resuspended in DMEM. 50 μL of this suspension was mixed with 200 μL of Trypan Blue (Gibco) and 750 μL of PBS to create a 1:20 dilution of cells. Cells were loaded onto a hematocytometer and viewed under a light microscope (NIKON Diaphot-TMD; Nikon Canada). The following formula was used to determine cell count:

Cell count(/mL)=no. of viable cells×dilution×2500

Transient Transfection of Cell Cultures

Transient transfections were performed at 75% confluency, as estimated under a light microscope (NIKON Diaphot-TMD; Nikon Canada), using Lipofectamine 2000 (Invitrogen). Transfections were performed according to the manufacturer's instructions. For a 35 mm cell culture dish, 3 μg of DNA and 7.5 μL of Lipofectamine (a 1:2.5 ratio of DNA to reagent) was diluted in 500 μL OptiMEM® I reduced serum medium (Gibco). Media was replaced no sooner than 16 hours post-transfection.

Determining Transfection Efficiency

Transfection efficiency was quantified for cell cultures transfected with a construct containing the eGFP cDNA. Cells were counterstained with Hoechst (Molecular Probes Inc.) to allow for simultaneous visualization of untransfected cells. Hoechst and eGFP fluorescence were observed using a NIKON Eclipse TE2000 inverted microscope and TE-FM Epi-Fluorescence attachment (Nikon Canada), and images taken for later analysis. Transfection efficiency was determined by the following formula:

Transfection efficiency(%)=no. of eGFP-expressing cells/no. of Hoechst stained cells×100.

Staining with Hoechst and Propidium Iodide

Hoechst 33342 was purchased as a 10 mg/mL solution in water (Molecular Probes Inc., Eugene, Oreg.). Propidium iodide (PI) was purchased as a powder and prepared by dissolving in PBS at 1 mg/mL. PI solutions were stored at 4° C. until use. Hoechst and PI were added directly to cell culture to 5 μg/mL and 10 μg/mL respectively. Cells were incubated at room temperature or at 37° C. for 10 minutes to allow for adequate uptake, and fluorescence observed using a NIKON Eclipse TE2000 inverted microscope and TE-FM Epi-Fluorescence attachment (Nikon Canada).

Frozen Storage of Cells

To freeze cells, cells were dissociated with trypsin-EDTA (Gibco) and resuspended in DMEM. Cells were pelleted by centrifugation at 1500 rpm for 5 minutes in a tabletop centrifuge (Sorvall® GLC-1, Sorvall, Newtown, Conn.), the supernatant aspirated, and cells resuspended in a freezing solution (DMEM supplemented with 20% FBS and 10% dimethyl sulfoxide (DMSO)). Cells were dispensed into 2 mL cryoovials (Sarstedt) at 106-107 cells/mL and placed in a "Mr. Frosty" freezing container (Nalgene) at −80° C. (Form a −86 C ULT freezer, Thermo Electron Corp.) for at least 2 hours. The contents of the container, when filled with isopropanol, experience a cooling rate of 1° C. per minute. Cells were transferred to a −140° C. liquid nitrogen freezer (Cryoplus 1, Form a Scientific) for long-term storage.

To thaw cells, the contents of the cryovial were rapidly warmed to 37° C. in a water bath (Precision® model 282, Thermo Electron Corp.) and added to pre-warmed DMEM (Gibco). Cells were pelleted by centrifugation at 1500 rpm for 5 minutes in a tabletop centrifuge (Sorvall® GLC-1, Sorvall), the supernatant aspirated, and cells resuspended in DMEM supplemented with 10% FBS (Gibco) and 1% antibiotic-antimycotic (Gibco).

Preparing Poly-D-Lysine Coated Plates

Poly-D-lysine (mw>300,000; Sigma-Aldrich) was purchased in its lyophilized powder form and stored at −20° C. until use. For 24-well plates, poly-D-lysine was diluted in water at 0.1 mg/mL and 250μ dispensed into each well. Plates were incubated at 37° C. in a humidified incubator for at least 4 hours, the solution aspirated, wells washed twice with water, and allowed to dry. Coated plates were stored at 4° C. for up to three months.

Calcium Uptake and Cell Death Assays

Calcium Imaging with Fluo-3

Fluo-3 was purchased from Molecular Probes Inc. in its acetoxymethyl (AM) ester form. A 5 mM fluo-3 AM stock was prepared in DMSO and stored at −20° C. for up to several days. Pluronic® F-127 was purchased as a 10% solution in water (Molecular Probes Inc.). On the day of the experiment, a loading solution containing 5 μM fluo-3 AM and 0.02% pluronic in a HEPES buffered salt solution (HBSS; 121 mM NaCl, 5 mM KCl, 20 mM D-glucose, 10 mM HEPES acid, 10 mM HEPES-Na salt, 3 mM NaHCO$_3$, 1 mM Na-pyruvate, and 1.8 mM CaCl2, pH adjusted to 7.4 with NaOH) was prepared by brief vortex followed by sonication (FS5; Fisher Scientific) for at least 2 minutes. Cells were washed with HBSS, loaded with fluo-3 AM by incubation at 37° C. for 30 minutes, and washed again to remove excess dye. Fluo-3 fluorescence was visualized using a NIKON Eclipse TE2000 inverted microscope and TE-FM Epi-Fluorescence attachment (Nikon Canada) or measured using a Fluoroskan Ascent FL microplate reader (λ excitation=485 nm, λ emission=527 nm) and accompanying Ascent software (Thermo Electron Corp.).

Calcium Uptake Assay

Untransfected cells or cells transfected with the TRPM7/pTracer or ΔPDZ/pTracer construct were plated onto 24-well plates, 24-hours post-transfection. Untransfected cells were plated at 0.75×10$^6$ cells/well and transfected cells at 1×10$^6$ cells/well. The plates were coated with poly-D-lysine to strengthen cell adhesion and to minimize cell loss during washes. Cells were loaded by incubation with 5 μM fluo-3 AM and 0.02% pluronic in HBSS at 37° C. for 30 minutes. Following loading, cells were washed with an aglycaemic HBSS containing, in mM: 20 N-methyl-D-glucamine (NMDG), 121 NaCl, 5 KCl, 10 HEPES acid, 10 HEPES-Na salt, 3 NaHCO$_3$, 1 Na-pyruvate, and 1.8 CaCl2, pH adjusted to 7.4 with HCl. Calcium uptake, as assessed by fluo-3 fluorescence, was measured in response to 0, 5, 10, 15, 20, or 25 mM sodium cyanide (NaCN; Mallinckrodt Baker Inc., Phillipsburg, N.J.) dissolved in aglycaemic HBSS. A 250 mM NaCN stock was prepared in water and stored at room temperature for up to 2 weeks. Measurements of fluo-3 fluorescence were taken over a 2 hour period at 10 minutes intervals at room temperature (22-25° C.). Calcium uptake assays were performed 48 hours post-transfection.

Cell Death Assay

Cell death, as assessed by PI uptake, was examined at the end of the 2 hour calcium uptake assay. Cells were stained with 10 μg/mL PI and PI fluorescence measured using the Fluoroskan microplate reader (λ excitation=590 nm, λ emission=630 nm) and accompanying Ascent software (Thermo Electron Corp.). To obtain a reading of maximal fluorescence (Fmax), 0.5% Triton X-100 was added to each well and allowed to incubate for 20 minutes. Cell death assays were performed 48 hours post-transfection.

Data Analysis

Data was entered into Excel (Microsoft, Seattle, Wash.) or SigmaPlot (SPSS Inc., Chicago, Ill.) for analysis. Pooled data are presented as the mean of at least 3 separate experiments±sem. Calcium uptake is expressed as a fraction of baseline uptake: ΔFt=(Ft−Fo)/Fo where Ft is the fluorescence at time t, and Fo is the fluorescence at baseline. Cell death is expressed as a percentage of total cell death: cell death (%)=Ft/Fmax×100 where Ft is the fluorescence at time t and Fmax is the maximal fluorescence obtained by permeabilization with Triton X-100. Concentration-response curves were fit by nonlinear regression with a 4 parameter logistic curve represented by the following equation: y=min+{(max−min)/[1+(x/EC50)n]} where y is the response at concentration x, min is the minimal response, max is the maximal response, EC50 is the concentration required for half-maximal response, and n is the Hill slope. Statistical analysis of data was carried out with a two-tailed Student's t test, or a one-way analysis of variance (ANOVA) followed by post hoc pairwise multiple comparisons testing using the Holm-Sidak method, where appropriate.

Microscopy

Fluorescent and Light Microscopy

Cell cultures were observed using a NIKON Eclipse TE2000 inverted microscope (Nikon Canada), and images taken with a Hamamatsu ORCA-ER digital camera and SimplePCI© software (Compix, Cranberry Township, Pa.). Fluorescence was observed using the TE-FM Epi-Fluorescence attachment (Nikon Canada).

Example 2

Assay for Blockage of Ion Channel Function

To further understand the structure function relationships between the TRPM7 inhibitors identified in the TRPM7-dependent HEK death assay, the activity of a subset of these inhibitors described herein were tested for their ability to inhibit TRPM7 currents in cell systems. Whole-cell patch clamp recordings were used essentially as described to test the TRPM7 inhibitors in HEK293 cells, H9c2 cardiomyocytes and cultured neurons. Inhibition of channel activity is not a requisite activity for a TRPM7 inhibitor, and indeed some of the inhibitors identified in the HEK293 TRPM7-dependent death assay increase survival but do not appear to block TRPM7 currents at the concentrations tested (Tables X and Y). However, blockage of the TRPM7 ion channel function is a clear demonstration of activity of a TRPM7 inhibitor. Table X shows the results of testing of these TRPM7 inhibitors in electrophysiology experiments at 5 uM. Those that provide >10% inhibition of TRPM7 channel activity in the HEK293 cell system were labeled with the concentration tested (generally 5 uM). Thus, the compounds in this table marked with such a value are able to block the activity gof the TRPM7 ion channel. FIGS. 2A-C provide an example of this for the TRPM7 inhibitor 399 (Structure 9). FIG. 2A shows a time course plot of the effects of 399 (5 uM) on TRPM7 like currents on HEK293 cells (in seconds). FIG. 2B demonstrates the IV curves of TRPM7 like currents recorded before, during and after 399 (5 uM). FIG. 2C shows the dose-response curve of 399 effects on TRPM7 like currents. Numbers in brackets indicate the number of independent tests, and the bars represent the SEM.

Figure 6:
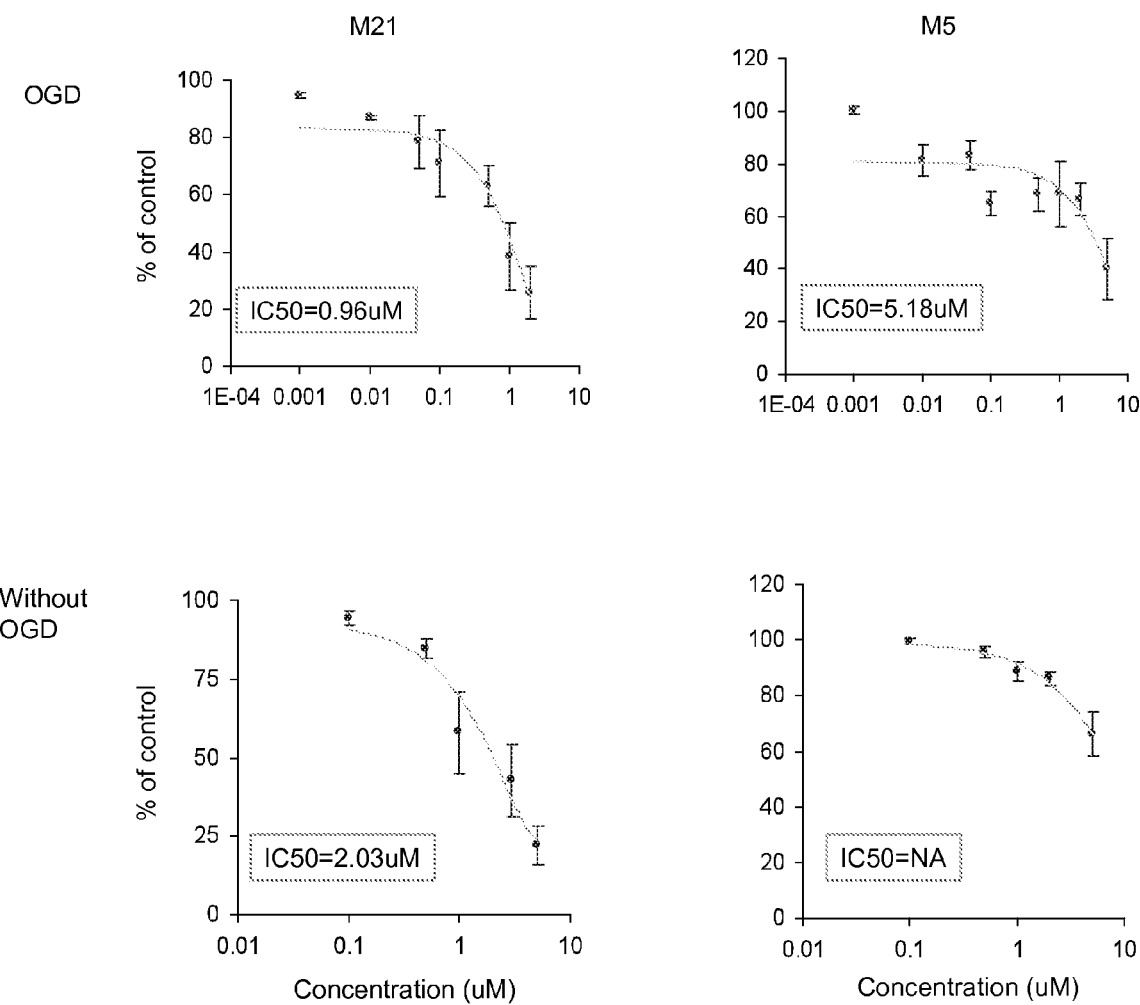
FIG. 6: TRPM7 Inhibitors block TRPM7 currents more effectively under conditions simulating Ischemic injury (oxygen-glucose depravation).

This assay can be varied to assess the effect of compounds on TRPM7 channel activity under ischemic conditions such as OGD. FIG. 6 demonstrates the use of such assays in the screening of TRPM7 inhibitors with M21 (left panels) and M5 (right panels). The top panels show the results of titration of TRPM7 inhibitors on TRPM7 currents under OGD conditions, and the bottom panels show the results under normal conditions. TRPM7 inhibitors appear to have a reduction of the IC50 values of approximately 50% in the OGD condition relative to the normal test conditions. As TRPM7 inhibitors have been demonstrated to be effective at reducing ischemic damage, the OGD assay may be a better indicator of efficacy. In addition, the assay is more sensitive and suggests an improved method for screening of TRPM7 inhibitors.

Methods:

Whole-cell currents were recorded using an Axopatch 1D or MultiClamp 700B amplifier and were digitized at 10 kHz and low-pass filtered at 2 kHz, at room temperature. pClamp10 software was used for data acquisition and analysis. Patch electrodes were pulled from Borosilicate glass and fire polished to a resistance of 2-4 MΩ. All drugs were administrated directly to cell bodies under recording through the fast exchange perfusion system.

For TRPM7-tet-on HEK293 Cells

The intracellular solution (ICS) contains (mM) 145 Cs-methanesulfonate, 8 NaCl, 1 MgCl2, 4.1 CaCl2, 10 EGTA, and 10 HEPES, 5 ATP, pH at 7.4, with 300-305 mOsm. The extracellular solution (ECS) contains (mM) 140 NaCl, 5 KCl, 2 CaCl2, 20 HEPES, and 10 glucose, pH at 7.4 and with 315-320 mOsm.

In Oxygen-Glucose Deprivation (OGD) tests, Nystatin perforated patch clamp was used, and cells were superfused with the ECS containing (mM): 140 NaCl, 5 KCl, 0.1 CaCl2, 0.1 MgCl2, 10 HEPES, and bubbled with N2, while control ECS with 1 MgCl2, 2 CaCl2 and 10 Glucose.

Voltage stimuli lasting 250 ms were delivered at 5-s intervals with voltage ramps ranging from −100 to +100 mV. The current values at −80 mV and +80 mV on I-V curve represent the measures of inward and outward current respectively.

For Neurons

Primary mixed cortical neurons were cultured from 16-18 days fetus of cd-1 mouse. 10-18 days after plating on the cover slip, cultures were transferred to the recording chamber with extracellular solution depending on the test of the ion channels For $Na^+$ and $K^+$ channels, the ECS contains (mM): 140 NaCl, 5.4 KCl, 2 CaCl2, 1 MgCl2, 25 HEPES and 10 Glucose, pH at 7.25-7.4, with 0.1 Nimodipine. The ICS contains (mM): 140 KCl, 1 CaCl2, 1 MgCl2, 2 ATP-Na2, 10 EGTA and 10 HEPES with pH at 7.3.

For $Ca^{2+}$ channel, the ECS contains (mM): 140 NaCl, 5 KCl, 3 CaCl2, 1 MgCl2, 10 HEPES and 10 Glucose, pH at 7.25-7.4, with 1 4-AP, 10 TEA and 0.5 TTX. The ICS contains (mM): 140 CsCl, 2 ATPNa2, 10 EGTA and 10 HEPES with pH at 7.3.

Under voltage clamp mode, the neurons were hold at −70 mV. Voltage commands from −80 mV to 60 mV at 10 mV step were applied for 200 msec, the $Na^+$ and $K^+$ current components were calculated as the maximum inward current at the initial 10 msec and the plateau level of the last 50 msec at different voltage commands respectively. While for $Ca^{2+}$, voltage commands from −80 mV to 10 mV at 10 mV step were applied for 80 msec, the maximum inward current at the initial 10 msec at different voltage commands were measured.

The AMPAR, NMDAR and GABAR currents were evoked by briefly applying AMPA (20-30 mM×1-2 sec), NMDA (30-100 mM×2-4 sec) and GABA (1-10 mM×0.5-1 sec), respectively, via a fast step perfusion system.

Example 3

Assay for Treatment of Cancer

Cell Proliferation Studies

Cells were grown to 70% confluency, trypsinized, counted, and seeded in 96-well flat-bottom plates at a final concentration of $2.5 \times 10^3$-$5.0 \times 10^3$ cells/well in growth media containing 5% FBS (Day 0). Other well sizes and cell densities were used successfully as well. Cells were allowed to incubate in growth media for 24 hours to allow for maximum adhesion. Treatment with the test agent began on Day 1 and continued for 72 hours either with or without retreatment. At the 72 hour time point, viable cell numbers are quantified by the CellTiter-Glo® cell viability assay as described above, or using standard MTT, SRB or BrDU assays. Experiments were repeated at least twice with the same concentrations to determine growth inhibitory activity. Results from the dose response of these studies were used to calculate an $IC_{50}$ value (concentration that effectively inhibits cell growth by 50 percent of control) for each agent. In an alternative format, this assay was used to screen potential TRPM7 inhibitory compounds at a fixed concentration, usually 5 or 10 uM. Alternatively, lower or higher concentrations were used. Table 1 shows the results of such experiments, where compounds were tested at 10 uM in the cell proliferation assay using a number of different cancer cell lines. A '+' sign indicates that more than 40% inhibition was observed. NIH 3T3 cells were used as a control cell line to demonstrate that the compounds would reduce proliferation of cancerous cells preferentially. Although inhibitors 399 and 509 show inhibition of NIH 3T3 cells as well as cancer cell lines, they reduced inhibition of the cancer cell lines preferentially, with titrations demonstrating that effective concentrations for reducing proliferation of cancer cells can be 20× lower than for non-cancerous cell lines. Thus, for the compounds in Table 1, all are potential anti-cancer agents. Some, like 399 and 509, are more general and may be effective against a wide range of cancers. Others, like 2785, are more specific and may be effective against a subset of cancers.

TABLE 1

| Structure | HeLa | MCF7 | MCF10A | NIH3T3 | B16F10 | Y79 | DMS53 | WI-38 |
|---|---|---|---|---|---|---|---|---|
| 9 | + | + | + | + | + | + | + | + |
| 51 | + | + |  | + | + | + | + | + |
| 53 | + |  | + |  | + | + |  |  |
| 59 | + | + | + |  | + | + | + |  |
| 60 | + | + | + |  | + | + | + | + |
| 62 | + | + | + |  | + | + |  |  |
| 69 | + | + | + |  | + | + | + | + |
| 99 | + |  |  |  | + | + |  |  |
| 101 | + |  |  |  |  |  |  |  |
| 107 | + |  |  |  |  |  |  |  |
| 115 | + | + | + |  | + | + | + | + |
| 118 | + | + | + |  |  | + | + | + |

Data Collection—For the cell proliferation studies, data from each experiment was collected and expressed as % Cell Growth using the following calculation:

$$\% \text{ Cell Growth} = (f_{test}/f_{vehicle}) \times 100$$

Where $f_{test}$ is the luminescent signal of the tested sample, and $f_{vehicle}$ is the luminescence of the vehicle in which the drug is dissolved (or appropriate measure for the other viability/proliferation measures). Dose response graphs and $IC_{50}$ values were generated using standard software using the following variable slope equation:

$$Y = \frac{(\text{Top} - \text{Bottom})}{(1 + 10^{((\log IC50 - X) \cdot \text{HillSlope})})}$$

Where X is the logarithm of concentration and Y is the response. Y starts at the Bottom and goes to Top with a sigmoid shape.

Conclusion

Inhibition of TRPM7 with small molecule inhibitors reduce the proliferation of a wide range of cancers at non-toxic concentrations, and thus are effective anti-cancer agents for cancers arising from many different mechanisms. Similar to the role of TRPM7 in ischemia, the data suggest that TRPM7 plays a fundamental role in cancer cell proliferation, and that inhibition of TRPM7 provides an effective treatment for a wide range of cancers including all of those demonstrated herein.

Example 4

TRPM7 Inhibitors in Treatment or Protection from Neurotrauma

Inhibitors of TRPM7 were tested for their ability to provide neuroprotection to rat brains subjected to concussive brain trauma using a rodent model of fluid percussion injury (FPI). FPI was performed as described in the literature using 350-370 g male Sprague Dawley rats (Charles River, St. Constant, Quebec, Canada). In brief, 24 h before injury, the animal was anesthetized using 2% halothane and 2:1 nitrous oxide:oxygen. A 4.8 mm craniotomy was made with its center between the bregma and lambda and between the sagittal suture and right temporal ridge. A modified Leur-loc fitting was attached over the craniotomy and cemented in place using Acron MC/R dental acrylic (GC America, Alsip, Ill.). The Leur-loc was filled with saline, and a small piece of gelfoam was inserted. The incision was sutured, and the animal was returned to its cage overnight if not used same day. The following day, the incision was reopened, cleaned, and the gelfoam was removed. The animal was attached to the fluid percussion injury device (Custom Design and Fabrication, Richmond, Va.) and was administered a 2 to 6 atm injury. Injury severity was recorded using an oscilloscope attached to a transducer, and by sectioning the brains and staining with 2,3,5-Triphenyltetrazolium chloride staining (TTC). Immediately after injury, the Leur-loc setup was removed en bloc, the wound was cleaned, and the incision was resutured. The animal was then returned to its cage. One or 1 h hours after fluid percussion injury, animals were reanesthetized as above and decapitated. Whole brains were extracted and chilled at_20° C. for 10 min. Coronal brain sections were made and incubated in 2% 2,3,5-triphenyltetrazolium chloride (TTC) in saline solution for 30 min at 37° C. (Joshi et al., 2004).

Figure 3:
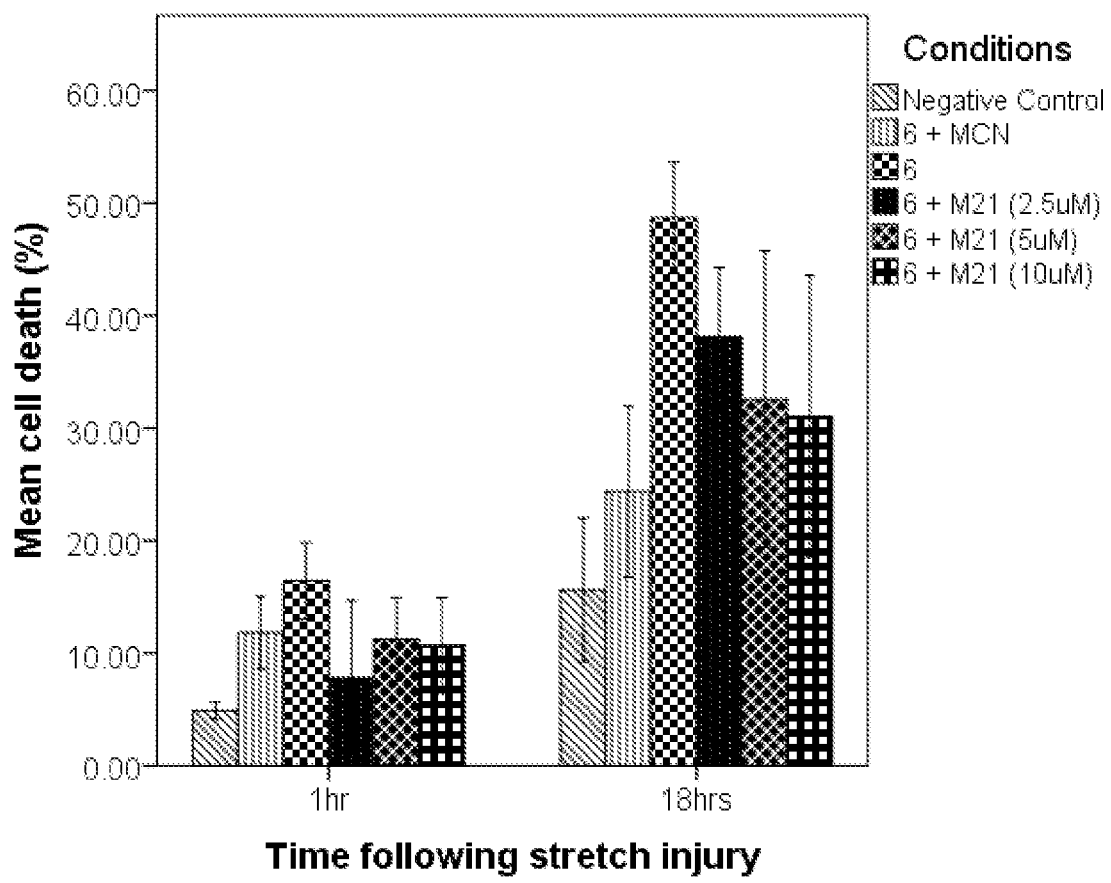
FIG. 3: M21 can protect neurons from cell death due to stretch injuries

FIG. 1 shows an example of the extent of injuries at 2-6 atm and the effect of treatment of such injuries with varying concentrations of TRPM7 inhibitors. In the example, M21 applied prior to the injury or 1 hour after showed significant protection of the rat brains from fluid percussion-induced neuronal damage. In light of these data, other TRPM7 inhibitors are expected to work similarly, and can be administered as either a protective agent (before injury) or treatment (after injury). Likewise, TRPM7 inhibitors are also expected to provide neuroprotection to other types of brain injuries. FIG. 3 shows an example of the effect of TRPM7 inhibitors on the sublethal neuronal stretch injury model. This model is described in Arundine et al, (J. Neurosci, 2004:8106-23). TRPM7 inhibitors such as M21 were applied 1 hour after stretch injury and cells were assessed for survival by PI fluorescence 24 hours after the injury. Increasing concentrations of the TRPM7 inhibitor M21 showed increased protection from cell death relative to untreated cultures. The columns labeled 6+MCN indicates that a control mixture of MK-801, CNQX and nimodipine was administered prior to injury in this model. This model can be used to demonstrate the efficacy of TRPM7 compounds in neurotrauma, and is consistent with the results of the fluid percussion injury model. Thus, this assay can be predictive of in vivo efficacy.

FIGS. 4A, B demonstrates the Rotarod performance of rats subjected to lateral FPI in the presence or absence of TRPM7 inhibitors. Panel A shows the mean latency on the Rotarod, with higher values indicating better performance. Compared to the FPI+Vehicle, animals treated with the TRPM7 inhibitor M21 showed near wild type levels of performance even on the first day post injury, with M21 animals being able to maintain balance on the Rotarod twice the time of injured animals treated with vehicle alone. In FIG. 4B, we see that M21 treated animals show distance traveled and activity post FPI comparable to uninjured animals. Thus, M21 and TRPM7 inhibitors are effective treatments to reduce the damaging effects of neurotrauma, including concussions.

FPI treated animals were also tested in the Morris water maze, which is a test of spatial learning and memory. FIG. 5A shows that animals subjected to FPI on average take more than twice as long to identify the platform as normal animals. Animals given M21 one hour after FPI showed remarkable performance with latencies to reach the platform similar to uninjured animals by day 2. FIG. 5B shows the performance of individual rodents in the assay, demonstrating that this performance is consistent across the injured animals.

Conclusion: TRPM7 inhibitors are effective treatments for neurotrauma (i.e., traumatic injury to the CNS) as measured by several different assays, improving both the survival of neurons as well as the physiomotor and learning/memory deficits associated with traumatic brain injury.

Example 5

Screening Additional M5, M6 or M21-Related Compounds

Table X and FIGS. 7-51 show screening data for several additional compounds that are variants of M5, M6 or M21. The synthesis of compounds of Table X and FIGS. 7-51 is shown in Appendices A-C. The compounds shown in FIGS. 7-51 can be related to the appropriate row of Table X by the compound number shown in the figures and in the first column of Table X. The compounds in Table X other than M5, M6 and M21 themselves, are believed to be novel. The Table provides a number identifying the compound, its structurer, molecular weight and its cluster (i.e., whether the compound resembles M5, M6 or M21). The three columns relations to PI uptake describe the results of screening the compounds in the type of assay from Example 1. In all three column, the lower the number, the more potent the compound in protecting against cell death. The next column shows the effect of a compound on TRPM7 ion channel current using the type of assay described in Example 2 Inhibition of the current indicates a compound acts directly on the TRPM7 ion channel. If a value of 5 uM is shown, the compound significantly inhibits the ion channel at that concentration. The last two columns show an effect on proliferation of Weri retinoblastoma or HeLa cervical cancer cells. Inhibition of proliferation is a measure of anti-neoplastic activity. Compounds not significantly active in any of the assays are not included in the table. If no data is shown, no test was performed.

Several of the compounds were tested for stability in rat microsomes and solubility in aqueous solution. Stability was classified as high, medium or low if the half-life was greater than 30 min, 5-30 minutes or less than five minutes respectively. Solubility was classified as high, medium or low if solubility was greater than 500 micromolar, 100-500 micromolar or less than 100 micromolar respectively. Compounds 56 and 135 had high stability and compound 80 had medium stability. Compounds 10, 135, 69, and 73 had medium solubility.

Table Y shows similar screening data for several commercially available compounds related to M5, M6 or M21. Most compounds were not tested for effects on TRPM7 ion channel or cancer proliferation. Compound 6 showed 33% inhibition at 10 uM and 9% inhibition at 5 uM on Weri cells. Compound 9 showed 42% inhibition at 10 uM and 18% inhibition at 5 uM on Weri cells. Compound 15 inhibited ion channel function at 5 uM.

* * *

All of the compositions and methods disclosed and claimed herein can be made and executed without undue experimentation in light of the present disclosure. While the compositions and methods of this invention have been described in terms of preferred embodiments, variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All citations including literature, patent documents, accession numbers and the like are incorporated by reference in their entirety for all purposes to the same extent as so individually denoted. If more than one sequence is associated with an accession number at different times, the sequence associated with the accession number as of Dec. 11, 2009 is meant. Unless otherwise apparent from the context any step, embodiment, or feature of the invention can be used in combination with any other.

Reference List

Aarts et al., (2003) Cell 115, 863-877.
Aarts et al., (2002) Science 298, 846-850.
Aarts & Tymianski (2005a). Neuroscientist. 11, 116-123.
Aarts & Tymianski (2005b) Pflugers Arch.
Alvarez et al. (2006) J. Neurosci. 26, 7820-7825.
Bennett et al. (1996) Cold Spring Harbor Symposia on Quantitative Biology 61, 373-384.
Block (1999) Prog. Neurobiol. 58, 279-295.
Bonavita et al. (2003) FEBS Lett. 536, 85-91.
Brideau et al., (2003) J. Biomol. Screen. 8, 634-647.
Bridge et al., (2003). Nat. Genet. 34, 263-264.
Cheng et al., (2006). J. Neurosci. 26, 3713-3720.
Coaxum et al. (2007) Am. J. Physiol Heart Circ. Physiol 292, H2220-H2226.
Corish and Tyler-Smith (1999) Protein Eng 12, 1035-1040.
Davis et al. (1997) Lancet 349, 32.
Du et al. (1996) J. Cereb. Blood Flow Metab 16, 195-201.
Ekht et al. (1999) Circ. Res. 85, e70-e77.
Elbashir et al. (2001) Nature 411, 494-498.
Fanselow (1980) Pavlov. J. Biol. Sci. 15, 177-182.
Fiorillo et al. (2006) Cell Mol. Life. Sci. 63, 3061-3071.
Gavrieli et al. (1992). J Cell Biol 119, 493-501.
Hanano et al. (2004) J. Pharmacol. Sci 95, 403-419.
Harteneck et al. (2000) Trends Neurosci. 23, 159-166.
Hausenloy and Scorrano (2007) Clin. Pharmacol. Ther. 82, 370-373.
Hescheler et al. (1991) Circ. Res. 69, 1476-1486.
Jiang et al. (2008) Brain Res. Bull. 76, 124-130.
Jiang, Li, and Yue (2005) J. Gen. Physiol 126, 137-150.
Kimes and Brandt (1976) Exp. Cell Res. 98, 367-381.
Kirino, T (2000) Neuropathology. 20 Suppl, S95-S97.
Kumar et al. (2001). J. Neurochem. 77, 1418-1421.
Lawlor et al. (2007) Mol. Neurodegener. 2, 11.
Lees et al. (2000) Lancet 355, 1949-1954.
Levrand et al. (2006) Free Radic. Biol. Med. 41, 886-895.
Lin et al. (2004) J. Am. Coll. Nutr. 23, 556S-560S.
Lipinski et al. (2001) Adv. Drug Deliv. Rev. 46, 3-26.
Lipton (1999). Physiol Rev. 79, 1431-1568.
Lisman et al. (2002) Nat. Rev. Neurosci. 3, 175-190.
Lo et al. (2003) Nat. Rev. Neurosci. 4, 399-415.
Lo et al. (2005) Stroke 36, 189-192.
Mastakov et al. (2001). Mol. Ther. 3, 225-232.
Monteilh-Zoller et al. (2003). J. Gen. Physiol 121, 49-60.
Montell et al. (2002) Cell 108, 595-598.
Morris et al. (1999) J. Neurosurg. 91, 737-743.
Morris et al. (1984) J. Neurosci. Methods 11, 47-60.
Mullen et al. (1992) Development 116, 201-211.
Nadler et al. (2001) Nature 411, 590-595.
Paxinos and Watson (1998). The Rat Brain in Stereotaxic Coordinates. Academic Press).
Petito et al. (1987) Neurology 37, 1281-1286.
Pulsinelli and Brierly (1979). Stroke 10, 267-272.
Pulsinelli et al. (1982). Ann Neurol 11, 491-498.
Rod and Auer (1992). Stroke 23, 725-732.
Rothman and Olney (1986). Ann Neurol 19, 105-111.
Runnels et al. (2001). Science 291, 1043-1047.
Runnels et al. (2002). Nat. Cell Biol. 4, 329-336.
Sakamoto et al. (1998) Biochem. Biophys. Res. Commun. 251, 576-579.
Sattler (1998) J Neurochem 71, 2349-2364.
Schmitz et al. (2005) J. Biol. Chem. 280, 37763-37771.
Schmitz et al. (2003). Cell 114, 191-200.
Schwarze et al. (1999) Science 285, 1569-1572.
Silver and Erecinska (1990) J Gen Physiol 95, 837-866.
Sledz et al. (2003) Nat. Cell Biol. 5, 834-839.
Su et al. (2006) J. Biol. Chem. 281, 11260-11270.
Sun et al. (2006) J. Neurophysiol. 95, 2590-2601.
Tian et al. (2007) Neurosci. Lett. 419, 93-98.
Volpe et al. (1985) Neurology 35, 1793-1797.
Volpe et al. (1984) Stroke 15, 558-562.
Wei et al. (2007) Proc. Natl. Acad. Sci. U.S.A. 104, 16323-16328.
Whitlock et al. (2006) Science 313, 1093-1097.
Zordoky and El-Kadi (2007) J. Pharmacol. Toxicol. Methods 56, 317-322.

TABLE X

| Sr. No | MW | Vial Barcode | Notebook No. | Cluster | Purity (%) | Quantity (mg) | Dispatch Date | Normalized ratio of PI uptake (5 μM) | Normalized ratio of PI uptake (10 μM) | IC50 (μM)PI uptake | TRPM7 current |
|---|---|---|---|---|---|---|---|---|---|---|---|
| 1 | 327.83 | 10021391 | ER0119/032/01 | M5/M6 | 97.9 | 24.39 | 25 Feb. 2011 | 0.545 | 0.216 | 9.8 | |
| 2 | 341.85 | 10021392 | ER0119/032/02 | M5/M6 | 95.66 | 25.31 | 25 Feb. 2011 | 0.179 | 0.018 | 3.27 | |
| 3 | 357.85 | 10021393 | ER0119/032/03 | M5/M6 | 96 | 22.05 | 25 Feb. 2011 | 0.695 | 0.276 | 5.66 | |
| 6 | 324.80 | 10021396 | ER0119/046/01 | M5/M6 | 95.15 | 23.3 | 25 Feb. 2011 | 0.770 | 0.760 | | 5 μM |
| 7 | 359.85 | 10021397 | ER0119/048/02 | M5/M6 | 95.57 | 24.17 | 25 Feb. 2011 | 0.274 | 0.067 | 4.05 | |
| 9 | 327.83 | 10021399 | ER0119/062/01 | M5/M6 | 96 | 22.35 | 25 Feb. 2011 | 0.060 | 0.035 | 1.19 | 5 μM, IC50 |
| 10 | 357.85 | 10021400 | ER0119/062/02 | M5/M6 | 96.2 | 22.89 | 25 Feb. 2011 | 0.011 | 0.000 | 0.05 | |
| 20 | 359.87 | 10021380 | ER0119-070-002 | M5/M6 | 97 | 21.2 | 11 Mar. 2011 | 0.019 | 0.000 | 0.08 | |
| 21 | 329.84 | 10021381 | ER0119-070-001 | M5/M6 | 100 | 21.3 | 11 Mar. 2011 | 0.016 | 0.003 | 1 | |
| 26 | 300.74 | EOAI3356087 | EV0947-022-003 | M21 | 99 | 56.1 | 9 Mar. 2011 | 0.410 | 0.041 | 5.59 | |
| 28 | 353.17 | EOAI3356089 | EV0947-028-003 | M21 | 99 | 25.8 | 9 Mar. 2011 | 0.314 | 0.002 | 4.03 | 5 μM |
| 32 | 362.27 | 10021575 | ER0121-090-001 | M5/M6 | 100 | 26.0 | 25 Mar. 2011 | 0.267 | 0.049 | 3.69 | |
| 35 | 329.84 | 10021788 | ER0122-016-001 | M5/M6 | 95 | 27.2 | 25 Mar. 2011 | 0.530 | 0.330 | 4.57 | |
| 38 | 331.83 | 10021791 | ER0122-058-001 | M5/M6 | 99 | 25.4 | 25 Mar. 2011 | 0.286 | 0.098 | 4.09 | |
| 40 | 373.89 | 10021156 | ER0122-048-002 | M5/M6 | 96 | 16.1 | 25 Mar. 2011 | 0.042 | 0.000 | 1.77 | |
| 41 | 343.87 | 10021794 | ER0122-048-001 | M5/M6 | 97 | 21.1 | 25 Mar. 2011 | 0.344 | 0.027 | 4.34 | |
| 42 | 315.79 | 10021795 | ER0121-048-001 | M5/M6 | 97 | 26.8 | 25 Mar. 2011 | 0.304 | 0.010 | 3.99 | |
| 43 | 317.80 | 10021796 | ER0122-030-001 | M5/M6 | 96 | 18.1 | 25 Mar. 2011 | 0.060 | 0.020 | 2.54 | |
| 44 | 331.83 | 10021797 | ER0122-040-001 | M5/M6 | 96 | 26.8 | 25 Mar. 2011 | 0.336 | 0.070 | 4.25 | |
| 45 | 325.4 | 10023502 | ER0124-048-001 | M5/M6 | 100 | 24.5 | 08 Apr. 2011 | 0.399 | 0.072 | 4.66 | |
| 46 | 409.85 | 10023503 | ER0122-070-001 | M5/M6 | 100 | 22.3 | 08 Apr. 2011 | 0.149 | 0.137 | 1.88 | |
| 47 | 337.84 | 10023504 | ER0122-064-002 | M5/M6 | 87 | 24.9 | 08 Apr. 2011 | 0.297 | 0.121 | 3.59 | |
| 51 | 302.78 | 10023509 | ER0124-024-002 | M5/M6 | 100 | 26.8 | 08 Apr. 2011 | 0.305 | 0.063 | 4 | |
| 52 | 422.93 | 10023501 | ER0124-054-002 | M5/M6 | 93 | 17.4 | 08 Apr. 2011 | 0.079 | 0.022 | 1.29 | |
| 53 | 311.83 | 10023510 | ER0122-094-001 | M5/M6 | 98 | 22.9 | 08 Apr. 2011 | 0.011 | 0.003 | 1.83 | 5 μM |
| 54 | 313.84 | 10023500 | ER0124-042-001 | M5/M6 | 97 | 15.6 | 08 Apr. 2011 | 0.024 | 0.029 | 1.5 | |
| 55 | 327.87 | 10023512 | ER0124-044-001 | M5/M6 | 100 | 25.3 | 08 Apr. 2011 | 0.147 | 0.059 | 2.14 | |
| 56 | 309.36 | 10023471 | ER0124-014-004 | M21 | 98 | 36.6 | 08 Apr. 2011 | 0.255 | 0.240 | 0.43 | |
| 57 | 406.09 | 10024121 | ER0124-030-001 | M5/M6 | 100 | 25.6 | 21 Apr. 2011 | 0.110 | 0.039 | 1.71 | |
| 59 | 370.09 | 10024123 | ER0124-076-001 | M5/M6 | 94 | 25.9 | 21 Apr. 2011 | 0.195 | 0.375 | 1.25 | |
| 60 | 371.07 | 10024124 | ER0124-050-003 | M5/M6 | 97 | 26.8 | 21 Apr. 2011 | 0.294 | 0.110 | 4.03 | |
| 61 | 355.08 | 10024125 | ER0124-050-002 | M5/M6 | 100 | 27.3 | 21 Apr. 2011 | 0.235 | 0.400 | 2.02 | |
| 62 | 371.07 | 10024126 | ER0124-050-001 | M5/M6 | 100 | 25.8 | 21 Apr. 2011 | 0.116 | 0.051 | 2.83 | |
| 63 | 387.07 | 10024127 | ER0124-090-001 | M5/M6 | 100 | 19.7 | 21 Apr. 2011 | 0.042 | 0.024 | 0.62 | |
| 64 | 340.97 | 10024128 | ER0124-094-001 | M5/M6 | 97 | 26.8 | 21 Apr. 2011 | 0.154 | 0.080 | 2.87 | |
| 67 | 387.07 | 10024131 | ER0124-080-003 | M5/M6 | 100 | 25.9 | 21 Apr. 2011 | 0.054 | 0.019 | 0.37 | |
| 69 | 371.07 | 10024133 | ER0124-080-002 | M5/M6 | 100 | 22.5 | 21 Apr. 2011 | 0.042 | 0.028 | 0.34 | |

TABLE X-continued

| Sr. No | MW | Vial Barcode | Notebook No. | Cluster | Purity (%) | Quantity (mg) | Dispatch Date | Normalized ratio of PI uptake (5 μM) | Normalized ratio of PI uptake (10 μM) | IC50 (μM)PI uptake | TRPM7 current |
|---|---|---|---|---|---|---|---|---|---|---|---|
| 70 | 387.07 | 10024134 | ER0124-080-001 | M5/M6 | 100 | 15.9 | 21 Apr. 2011 | 0.035 | 0.013 | 0.47 | |
| 71 | 389.09 | 10024135 | ER0124-098-001 | M5/M6 | 100 | 28.2 | 21 Apr. 2011 | 0.005 | 0.003 | 0.42 | |
| 72 | 427.06 | 10024136 | ER0124-098-002 | M5/M6 | 95 | 26.6 | 21 Apr. 2011 | 0.000 | 0.000 | 0.39 | |
| 73 | 373.09 | 10024137 | ER0124-098-003 | M5/M6 | 100 | 26.4 | 21 Apr. 2011 | 0.000 | 0.000 | 0.18 | |
| 77 | 316.05 | 10023911 | ER0124-058-002 | M21 | 100 | 26.0 | 21 Apr. 2011 | 0.071 | 0.003 | 1.99 | |
| 78 | 344.08 | 10023902 | ER0124-088-002 | M21 | 95 | 27.7 | 21 Apr. 2011 | 0.088 | 0.190 | 0.77 | |
| 80 | 334.04 | 10024110 | ER0124-060-003 | M21 | 95 | 22.3 | 21 Apr. 2011 | 0.721 | 0.102 | | |
| 83 | 384.11 | 10024928 | ER0128-016-001 | M5/M6 | 96 | 27.0 | 6 May 2011 | 0.234 | 0.043 | 3.44 | |
| 87 | 359.05 | 10024932 | ER0128-032-001 | M5/M6 | 96 | 16.0 | 6 May 2011 | 0.273 | 0.097 | 3.29 | |
| 88 | 359.05 | 10024933 | ER0128-032-002 | M5/M6 | 100 | 12.0 | 6 May 2011 | 0.321 | 0.064 | 4.52 | |
| 89 | 389.09 | 10024934 | ER0124-098-004 | M5/M6 | 98 | 25.0 | 6 May 2011 | 0.008 | 0.012 | 0.32 | |
| 90 | 377.07 | 10024001 | ER0128-054-001 | M5/M6 | 100 | 12.0 | 6 May 2011 | 0.009 | 0.000 | 0.49 | |
| 92 | 371.13 | 10024935 | ER0128-042-001 | M21 | 97 | 17.0 | 6 May 2011 | 0.072 | 0.037 | 0.96 | |
| 93 | 343.10 | 10024936 | ER0128-018-001 | M21 | 93 | 12.0 | 6 May 2011 | 0.071 | 0.041 | 0.21 | |
| 94 | 343.10 | 10024937 | ER0128-026-001 | M21 | 92 | 24.0 | 6 May 2011 | 0.073 | 0.042 | 0.65 | |
| 96 | 347.88 | 10022780 | ER0128-080-001 | M5/M6 | 100 | 23.6 | 27 May 2011 | 0 | 0.056 | 1.55 | 5 μM |
| 97 | 341.85 | 10022781 | ER0134-030-001 | M5/M6 | 100 | 26 | 27 May 2011 | 0 | 0.084 | 1.24 | 5 μM |
| 98 | 406.93 | 10022782 | ER0134-028-002 | M5/M6 | 100 | 27.1 | 27 May 2011 | 0.36 | 0.067 | 2.53 | |
| 99 | 420.95 | 10022783 | ER0134-028-003 | M5/M6 | 98 | 26.26 | 27 May 2011 | 0 | 0.1 | 0.84 | |
| 101 | 422.93 | 10022785 | ER0134-028-006 | M5/M6 | 100 | 26.39 | 27 May 2011 | 0.573 | 0.228 | 5.73 | |
| 102 | 436.95 | 10022786 | ER0134-028-007 | M5/M6 | 100 | 28.41 | 27 May 2011 | 0.206 | 0.059 | 1.61 | |
| 103 | 455.98 | 10022787 | ER0134-028-008 | M5/M6 | 100 | 24.8 | 27 May 2011 | 0.444 | 0.312 | 0.81 | |
| 104 | 456.99 | 10022788 | ER0134-028-009 | M5/M6 | 100 | 26.88 | 27 May 2011 | 0.307 | 0.094 | 0.98 | |
| 105 | 472.99 | 10022789 | ER0134-028-010 | M5/M6 | 100 | 25.99 | 27 May 2011 | 0.07 | 0.17 | 0.86 | |
| 106 | 406.93 | 10022923 | ER0128-074-001 | M5/M6 | 100 | 20.28 | 27 May 2011 | 0 | 0.054 | 1.2 | |
| 107 | 422.93 | 10022924 | ER0128-074-002 | M5/M6 | 100 | 23.54 | 27 May 2011 | 0.08 | 0.1 | 2.37 | |
| 108 | 355.84 | 10022925 | ER0128-046-001 | M5/M6 | 100 | 22.52 | 27 May 2011 | 0.038 | 0.11 | 1.09 | |
| 110 | 327.83 | 10022791 | ER0134-024-001 | M5/M6 | 100 | 31.22 | 27 May 2011 | 0.037 | 0.06 | 1.38 | |
| 112 | 315.79 | 10022793 | ER0134-024-003 | M5/M6 | 100 | 25.72 | 27 May 2011 | 0.666 | 0.244 | | |
| 113 | 327.83 | 10022794 | ER0134-024-004 | M5/M6 | 100 | 24.3 | 27 May 2011 | 0.36 | 0.07 | 3.21 | 5 μM |
| 114 | 332.25 | 10022795 | ER0134-024-005 | M5/M6 | 100 | 28.65 | 27 May 2011 | 0.065 | 0.1 | 2.26 | |
| 115 | 341.85 | 10022796 | ER0134-016-001 | M5/M6 | 100 | 24.44 | 27 May 2011 | 0.042 | 0.13 | 0.36 | |
| 116 | 346.27 | 10022797 | ER0134-016-002 | M5/M6 | 93 | 9.37 | 27 May 2011 | 0.788 | 0.358 | 4.75 | |
| 117 | 329.82 | 10022798 | ER0134-016-003 | M5/M6 | 100 | 9.91 | 27 May 2011 | 0.02 | 0.07 | 1.67 | 5 μM |
| 118 | 341.85 | 10022799 | ER0134-016-004 | M5/M6 | 100 | 7.32 | 27 May 2011 | 0.019 | 0.047 | 1.31 | 5 μM |
| 120 | 417.91 | 10022802 | ER0134-048-001 | M5/M6 | 87 | 13.51 | 27 May 2011 | 0.079 | 0.066 | 2.55 | 5 μM |
| 121 | 329.84 | 10022805 | ER0134-052-001 | M5/M6 | 100 | 23.09 | 27 May 2011 | 0.053 | 0.036 | 1.4 | 5 μM |
| 123 | 317.81 | 10022807 | ER0134-052-003 | M5/M6 | 100 | 19.69 | 27 May 2011 | 0.356 | 0.128 | 4.18 | 5 μM |
| 124 | 329.84 | 10022808 | ER0134-052-004 | M5/M6 | 100 | 16 | 27 May 2011 | 0 | 0.06 | 1.13 | |
| 125 | 334.26 | 10022809 | ER0134-052-005 | M5/M6 | 100 | 14.43 | 27 May 2011 | 0.363 | 0.122 | 4.69 | |
| 126 | 419.92 | 10022810 | ER0134-056-001 | M5/M6 | 85 | 5.46 | 27 May 2011 | 0.012 | 0.059 | 1.03 | |

TABLE X-continued

| Sr. No | MW | Vial Barcode | Notebook No. | Cluster | Purity (%) | Quantity (mg) | Dispatch Date | Normalized ratio of PI uptake (5 μM) | Normalized ratio of PI uptake (10 μM) | IC50 (μM)PI uptake | TRPM7 current |
|---|---|---|---|---|---|---|---|---|---|---|---|
| 127 | 331.84 | 10022811 | ER0134-054-003 | M5/M6 | 94 | 18.71 | 27 May 2011 | 0.038 | 0.044 | 0.93 | |
| 128 | 343.87 | 10022812 | ER0134-054-004 | M5/M6 | 100 | 11.45 | 27 May 2011 | 0.01 | 0.06 | 0.43 | |
| 129 | 387.92 | 10022813 | ER0134-066-001 | M5/M6 | 100 | 24.37 | 27 May 2011 | 0.05 | 0.07 | 2.23 | |
| 130 | 378.25 | 10022814 | ER0128-090-001 | M21 | 90 | 14.77 | 27 May 2011 | 0.1 | 0.06 | 0.93 | |
| 131 | 351.18 | 10022815 | ER0128-098-001 | M21 | 98 | 18.25 | 27 May 2011 | 0.29 | 0.03 | 3.42 | 5 μM |
| 132 | 406.30 | 10022816 | ER0128-092-001 | M21 | 91 | 9.57 | 27 May 2011 | 0.73 | 0.1 | 4.46 | |
| 133 | 333.74 | 10022818 | ER0134-032-001 | M21 | 85 | 8.68 | 27 May 2011 | 0.367 | 0.123 | 3.31 | |
| 134 | 343.80 | 10022819 | ER0134-032-002 | M21 | 91 | 8.8 | 27 May 2011 | 0.564 | 0.305 | | |
| 136 | 378.25 | 10022821 | ER0134-050-001 | M21 | 89 | 18.34 | 27 May 2011 | 0.534 | 0.238 | 18.45 | |
| 137 | 350.20 | 10022822 | ER0134-050-002 | M21 | 97 | 21.44 | 27 May 2011 | 0.575 | 0.296 | 8.5 | |
| 138 | 327.35 | 10022824 | ER0134-058-001 | M21 | 93 | 23.37 | 27 May 2011 | 0.034 | 0.026 | 0.47 | |
| 140 | 315.75 | 10022826 | ER0134-060-001 | M21 | 92 | 21.96 | 27 May 2011 | 0.487 | 0.062 | 11.1 | |
| M21 | 335.18 | | | M21 | | | | | | 4.97 | 5 μM |

TABLE Y

| Structure | Molecular Weight | ID and NO | Clusters | Normalized ratio of PI uptake (5 μM) | Normalized ratio of PI uptake (10 μM) | IC50 (μM) PI uptake |
|---|---|---|---|---|---|---|
| (structure #1) | 282.2907 | STOCK1N-70089 #1 | M21 | 0.181 | 0.005 | 3.16 |
| (structure #2) | 300.736 | STOCK6S-31467 #2 | M21 | 0.472 | 0.1 | 12.59 |
| (structure #3) | 323.3856 | STOCK1N-36829 #3 | M21 | 0.262 | 0.102 | 4.72 |

TABLE Y-continued

| Structure | Molecular Weight | ID and NO | Clusters | Normalized ratio of PI uptake (5 μM) | Normalized ratio of PI uptake (10 μM) | IC50 (μM) PI uptake |
|---|---|---|---|---|---|---|
| 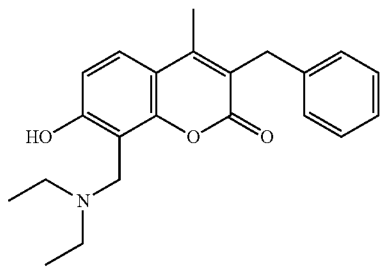 [SMILES: CCN(CC)Cc1c(O)ccc2c(C)c(Cc3ccccc3)c(=O)oc12] | 351.4388 | STOCK4S-10213 #1 | M21 | 0.398 | 0.242 | 4.3 |
| 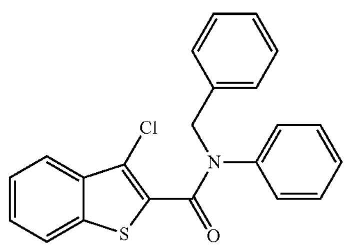 [SMILES: O=C(c1sc2ccccc2c1Cl)N(Cc1ccccc1)c1ccccc1] | 377.887 | MCC1879 #5 | M5&M6 | 0.108 | 0.062 | 1.77 |
| 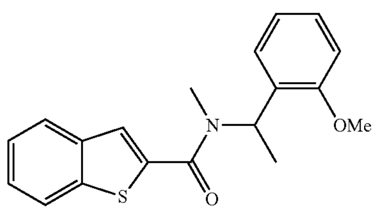 [SMILES: COc1ccccc1C(C)N(C)C(=O)c1cc2ccccc2s1] | 325.425 | T6681713 #6 | M5&M6 | 0.328 | 0.059 | 5.48 |
| 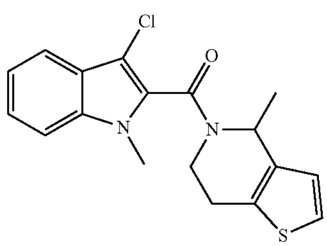 [SMILES: CC1c2ccsc2CCN1C(=O)c1c(Cl)c2ccccc2n1C] | 344.858 | T6857127 #7 | M5&M6 | 0 | 0 | 0.8 |
| 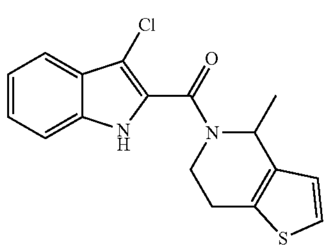 [SMILES: CC1c2ccsc2CCN1C(=O)c1[nH]c2ccccc2c1Cl] | 330.832 | T6899791 #8 | M5&M6 | 0 | 0 | 0.7 |
| 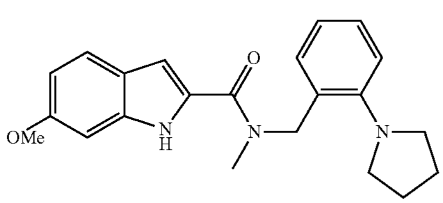 [SMILES: COc1ccc2cc(C(=O)N(C)Cc3ccccc3N3CCCC3)[nH]c2c1] | 363.453 | T6899266 #9 | M5&M6 | 0.029 | 0 | 2.32 |

TABLE Y-continued

| Structure | Molecular Weight | ID and NO | Clusters | Normalized ratio of PI uptake (5 μM) | Normalized ratio of PI uptake (10 μM) | IC50 (μM) PI uptake |
|---|---|---|---|---|---|---|
| 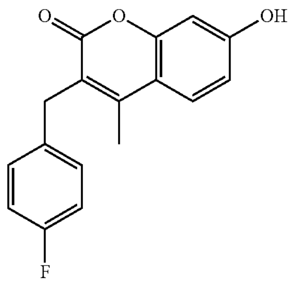 [SMILES: Cc1c(Cc2ccc(F)cc2)c(=O)oc2cc(O)ccc12] | 284.2817 | RJF01910SC #10 | M21 | 0.465 | 0.261 | 4.15 |
| 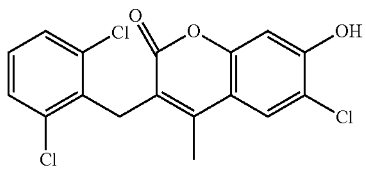 [SMILES: Cc1c(Cc2c(Cl)cccc2Cl)c(=O)oc2cc(O)c(Cl)cc12] | 369.626 | RJF00028SC #11 | M21 | 0.233 | 0.136 | 3.16 |
| 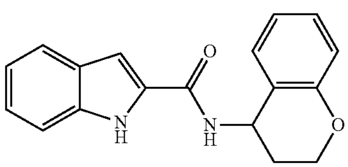 [SMILES: O=C(NC1CCOc2ccccc21)c1cc2ccccc2[nH]1] | 292.332 | T6749380 #12 | M5&M6 | 0.043 | 0.029 | 2.8 |
| 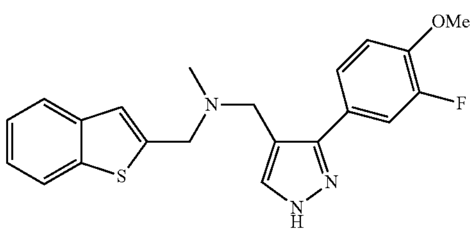 [SMILES: COc1ccc(-c2n[nH]cc2CN(C)Cc2cc3ccccc3s2)cc1F] | 381.466 | Ambcb42783454 #13 | M5&M7 | 0.498 | 0.266 | 4.7 |
| 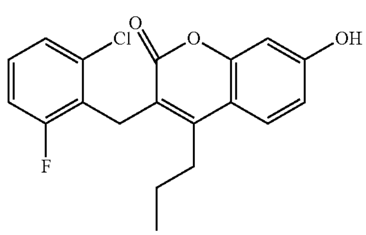 [SMILES: CCCc1c(Cc2c(F)cccc2Cl)c(=O)oc2cc(O)ccc12] | 346.78 | RJF01538SC #14 | M21 | 0.16 | 0.057 | 2.78 |

Appendix A. Synthesis of M5-Related Compounds

Preparation of Substituted Benzothiophene Derivatives M5-Series

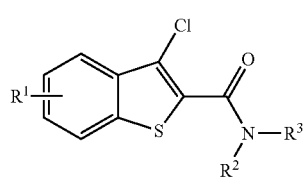

1. Synthetic_Route

The general synthetic route of this template is summarized in Scheme 1.

Scheme 1

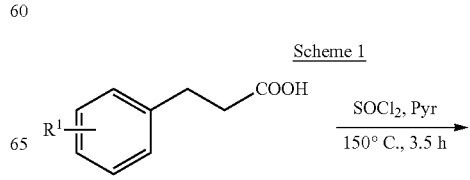

-continued

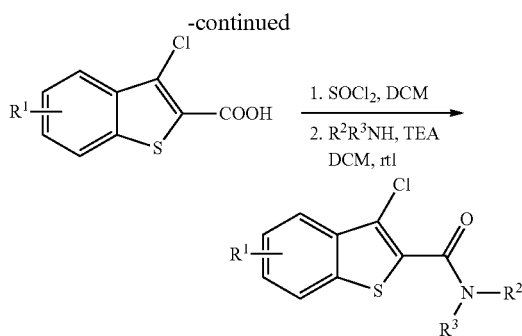

2.1.1 Synthetic Protocol
2.2.1 Preparation of Substituted Benzothiophene Derivative

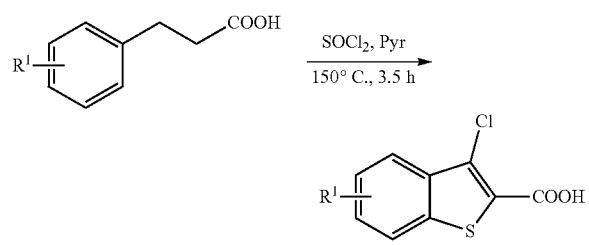

Condition—Acid (1 eq), SOCl$_2$ (4.5 eq), pyridine (0.1 eq), 3.5 hr

Procedure—

Thionyl chloride (5 eq.) was added dropwise to a round-bottom flask containing a mixture of hydrocinnamic acid (1 eq.) and pyridine (0.1 eq.) heated to 150° C. TLC after 3 h showed complete consumption of starting material. The reaction mixture was cooled to it and water (10 vol), 35% HCl (1 vol.), and THF (15 vol) were added and the mixture heated at 60° C. for 30 minutes. After 30 minutes, the THF was removed in vacuo and the obtained precipitate was filtered, dissolved in a 3:1 water:ethanol mixture (20 vol) and heated at 90° C. for 1 hr. After 1 h, the solution was cooled to it and allowed to stir overnight. The separated solid was filtered and recrystallized from toluene to get the corresponding benzothiophene-2-carboxylic acid. The results for various substituted chlorobenzothiophene carboxylic acids are given in Table 1.

TABLE 1

| Sr. No | Benzothiophene Acid | Purity % | % Yield |
|---|---|---|---|
| 1 | 3-chloro-1-benzothiophene-2-carboxylic acid | 95 | 35 |
| 2 | 3-chloro-6-methyl-1-benzothiophene-2-carboxylic acid | 74 | 57 |
| 3 | 3-chloro-6-fluoro-1-benzothiophene-2-carboxylic acid | 92 | 69 |
| 4 | 3-chloro-6-(trifluoromethyl)-1-benzothiophene-2-carboxylic acid | 98 | 19 |
| 5 | 3-chloro-5-methoxy-1-benzothiophene-2-carboxylic acid | 95 | 77 |
| 6 | 3-chloro-4-methyl-1-benzothiophene-2-carboxylic acid | 98 | 30 |
| 7 | 3-chloro-6-methoxy-1-benzothiophene-2-carboxylic acid | 90 | 48 |
| 8 | 3-chloro-4-fluoro-1-benzothiophene-2-carboxylic acid | 100 | 11 |
| 9 | 3-chloro-5-fluoro-1-benzothiophene-2-carboxylic acid | 95 | 54 |
| 10 | 3-chloro-5,6-dimethoxy-1-benzothiophene-2-carboxylic acid | 40 | 46 |

1.2.2 Preparation of Amides
1.2.3 Preparation of Amides

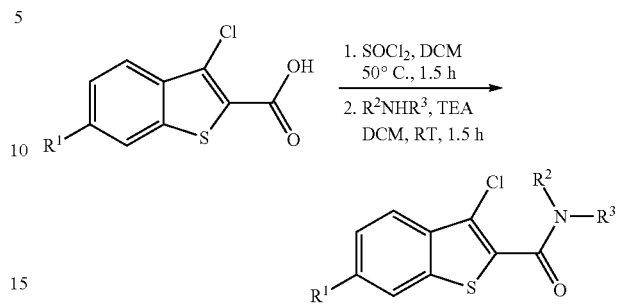

Thionyl chloride (5 eq.) was slowly added to a solution of acid (1 eq.) in dichloroethane (4 vol). The reaction was maintained at it for 5-6 hours. The reaction was monitored by quenching with methanol and looking at the methyl ester by LCMS. After completion of the reaction, solvent and thionyl chloride were removed in vacuo. The acid chloride was taken to the next step without further purifications. To a solution of amine (0.9 equiv.) and triethylamine (2 eq.) in dichloroethane (10 vol) was added a solution of the acid chloride (1 eq.) in dichloroethane (5 vol). The reaction was allowed to shake at room temperature. After completion of reaction (as monitored by HPLCMS) the reaction mixture was diluted with dichloroethane (3 mL), washed with water (2×5 vol), brine (1×5 vol), dried over anhydrous sodium sulfate and concentrated in vacuo to get the desired product. Yields of amides is given in Tables 2a-2b TABLE 2a

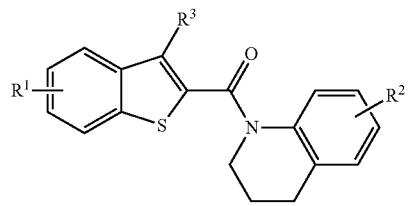

| Entry | Comp ID | R$^1$ | R$^2$ | R$^3$ | LCMS % | Yield % |
|---|---|---|---|---|---|---|
| 1 | 10021392 | H | 6-Me | Cl | 96 | 90 |
| 2 | 10023503 | 6-CF$_3$ | 6-Me | Cl | 100 | 75 |
| 3 | 10024125 | 4-Me | 6-Me | Cl | 100 | 89 |
| 4 | 10024126 | 5-OMe | 6-Me | Cl | 100 | 85 |
| 5 | 10024932 | 4-F | 6-Me | Cl | 96 | 60 |
| 6 | 10021575 | H | 6-Cl | Cl | 100 | 76 |
| 7 | 10024933 | 5-F | 6-Me | Cl | 100 | 75 |
| 8 | 10021391 | H | H | Cl | 98 | 94 |
| 9 | 10023502 | H | 6-Me | F | 100 | 45 |
| 10 | 10021397 | 6-F | 6-Me | Cl | 96 | 83 |
| 11 | 10024124 | 6-OMe | 6-Me | Cl | 97 | 98 |
| 12 | 10021568 | H | 6-F | Cl | 98 | 70 |
| 13 | 10021398 | H | 6-Me | Me | 98 | 48 |
| 14 | 10021382 | 6-Me | 6-Me | Cl | 96 | 87 |
| 15 | 10021563 | H | 6-OMe | H | 100 | 81 |
| 16 | 10021562 | H | 6-Me | H | 100 | 75 |
| 17 | 10021393 | H | 6-0Me | Cl | 96 | 83 |
| 18 | 10021576 | H | 6-Cl | H | 100 | 78 |
| 19 | 10021569 | H | 6-F | H | 100 | 75 |
| 20 | 10021395 | H | H | H | 95.8 | 91 |

Additional Amide Analogs:—

TABLE 2b

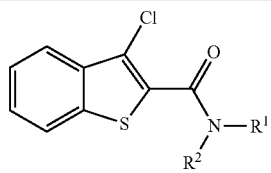

| Entry | Comp ID | $R^1R^2$ = | LCMS % | Yield % |
|---|---|---|---|---|
| 1 | 10024929 | morpholine | 100 | 40 |
| 2 | 10024930 | pyrrolidine | 100 | 72 |
| 3 | 10024931 | piperidine | 100 | 69 |
| 4 | 10022781 | 1,2,3,4-tetrahydronaphthalen-1-amine | 100 | 45 |
| 5 | 10024130 | 3,4-dihydro-2H-1-benzopyran-4-amine | 90 | 35 |
| 6 | 10022780 | 4-methyl-4H,5H,6H,7H-thieno[3,2-c]pyridine | 100 | 47 |
| 7 | 10024123 | [2-(pyrrolidin-1-yl)phenyl]methanamine | 94 | 35 |

2.2.2c Preparation of Amides (Acyclic):—

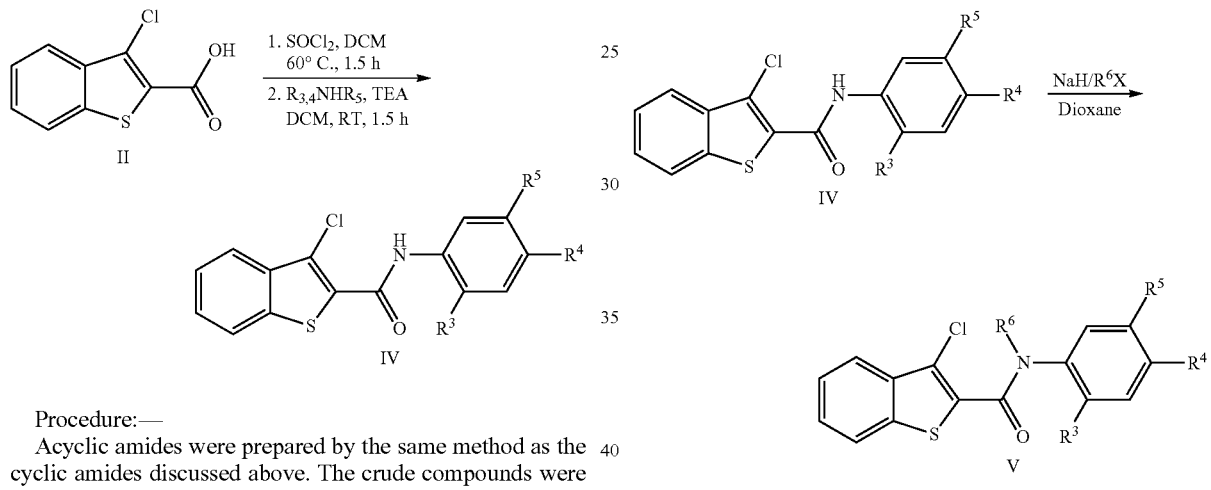

Procedure:—

Acyclic amides were prepared by the same method as the cyclic amides discussed above. The crude compounds were purified using flash silica gel column chromatography to get the pure products. The results for all acyclic amide products are given in Table 3

TABLE 3

| Entry | Comp ID | $R^3$ | $R^4$ | $R^5$ | LCMS (%) | Yield (%) |
|---|---|---|---|---|---|---|
| 1 | 10021565 | Me | H | OMe | 97 | 75 |
| 2 | 10021564 | Me | Me | H | 99 | 76 |
| 3 | 10021566 | H | Me | H | 97 | 85 |
| 4 | 10021394 | H | H | H | 98 | 98 |

2.2.3 Preparation N-Alkylated Derivatives

Procedure:—

To a stirred solution of amide in dioxane at room temperature was added sodium hydride and stirred 15 min at room temperature. Methyl iodide was added dropwise to the stirred solution and heated to 55° C. for 2 hrs. The TLC shows completion of reaction. The reaction mixture quenched with water and extracted with ethyl acetate. The ethyl acetate was dried over sodium sulphate and concentrated to gave the crude product, which was purified by flash silica gel column chromatography. The results for all amide products are given in Table 4.

TABLE 4

| Entry | Comp ID | $R^3$ | $R^4$ | $R^5$ | $R^6$ | LCMS (%) | Yield (%) |
|---|---|---|---|---|---|---|---|
| 1 | 10024121 | Me | Me | H | 2-Picolyl | 100 | 20 |
| 2 | 10023501 | Me | H | OMe | 2-Picolyl | 93 | 20 |
| 3 | 10021788 | Me | Me | H | Me | 95 | 55 |
| 1 | 10021789 | Me | H | OMe | Me | 98 | 50 |
| 4 | 10021343 | H | Me | H | Me | 100 | 65 |
| 5 | 10021339 | H | H | H | Me | 98 | 70 |
| 6 | 10022924 | Me | H | OMe | 3-Picolyl | 100 | 45 |
| 7 | 10022785 | Me | H | OMe | 4-Picolyl | 100 | 46 |

TABLE 4-continued

| Entry | Comp ID | R³ | R⁴ | R⁵ | R⁶ | LCMS (%) | Yield (%) |
|---|---|---|---|---|---|---|---|
| 8 | 10022786 | Me | H | OMe | 6-Me,2-Picolyl | 100 | 56 |
| 9 | 10022787 | Me | H | OMe | 2-Acetyl thiophene | 100 | 42 |
| 10 | 10022789 | Me | H | OMe | 2-Me-quinoline | 100 | 83 |
| 11 | 10022923 | Me | Me | H | 3-Picolyl | 100 | 47 |
| 12 | 10022782 | Me | Me | H | 4-Picolyl | 100 | 44 |
| 13 | 10022783 | Me | Me | H | 6-Me,2-Picolyl | 98 | 39 |
| 14 | 10022784 | Me | Me | H | 2-Acetyl thiophene | 100 | 45 |
| 15 | 10022788 | Me | Me | H | 2-Me-quinoline | 100 | 77 |
| 16 | 10024928 | N—Me-(2-(pyrrolidin-1-yl)phenyl)methanamine | | | | 96 | 50 |

2.2.4 Reduction[i]:

[i]Patent; glaxo group limited; Bueno-Calderon, Jose Maria; Fernandez-Molina, Jorge; Leon-Diaz, Maria Luisa; Mallo-Rubio, Araceli; Manzano-Chinchon, M Pilar; WO2010/81904; (2010); (A1)

2.2.5 Preparation of 3-Fluoro-2-Benzothiophene Carboxylic Acid[ii]

[ii]Patent; Bruton, Gordon; Faller, Andrew; Orlek, Barry Sidey; Rana, Kishore Kalidas; Walker, Graham; US2003/199571; (2003); (A1) English

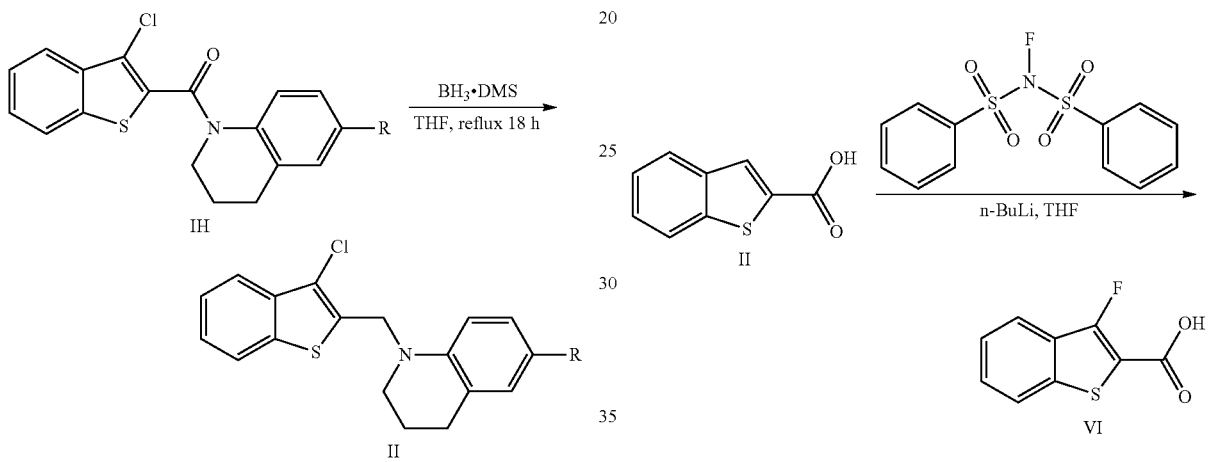

Procedure:—

A mixture of I (1 eq.) and borane-dimethylsulfide (3 eq.) in tetrahydrofuran (10 vol) was refluxed until TLC showed complete consumption of starting material (>16 h). Water (10 vol) was added to the reaction and it was extracted with ethyl acetate (2×25 vol). The combined organic layers were washed with saturated brine (1×20 vol), dried over anhydrous sodium sulfate and concentrated in vacuo to get the crude product II. Crude product was purified using flash silica gel column chromatography. The results for all amine products are given in Table 5.

Procedure:—

Acid II (1 eq.) was dissolved in dry tetrahydrofuran (10 vol) in a dry nitrogen-purged flask and the solution was cooled to −78° C. (CO₂/Acetone). n-Butyl lithium (2.2 eq. of a 1.6M solution in hexanes) was slowly added to the reaction and it was allowed to stir at −78° C. for 1 hour. A solution of N-fluorobenzenesulfonimide (1.2 eq.) in tetrahydrofuran (10 vol) was then added to the reaction mixture and it was allowed to come to room temperature. On completion of the reaction (HPLC-MS and TLC), the reaction mixture was diluted with diethyl ether (15 vol) and quenched with 1N HCl. The organic layer was washed with water (2×15 vol), saturated brine (1×15 vol), dried over anhydrous sodium sulfate and concentrated in vacuo to get the crude product VI (Yield 40%). The crude product was taken to the next step without further purification.

2.2.6 Preparation of Amides

TABLE 5

| Entry | Comp ID | R | LCMS (%) | Yield (%) |
|---|---|---|---|---|
| 1 | 10021790 | Me | 98 | 81 |
| 2 | 10021791 | F | 99 | 65 |
| 3 | 10021792 | Ome | 95 | 83 |

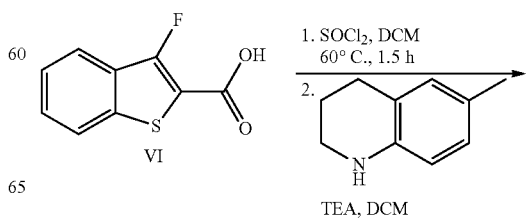

-continued

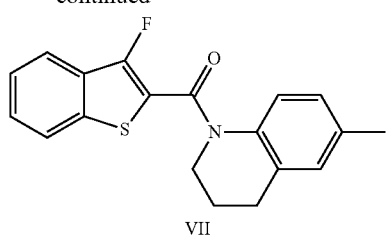

VII

Procedure:—

Acyclic amides were prepared by the same method as the cyclic amides discussed above. The crude compounds were purified using flash silica gel column chromatography to get the pure product (Yield 42%)

Preparation of Sulfonamides Derivatives (M5-Series)

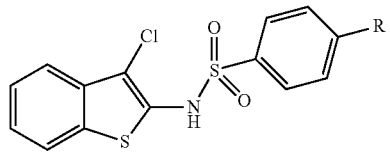

1. Synthetic_Route

The general synthetic route is summarized in Scheme 1.

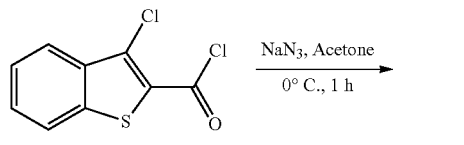

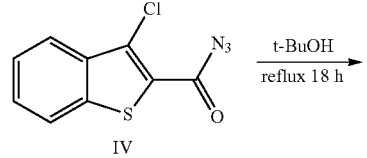

IV

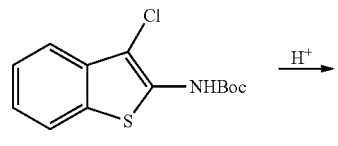

V

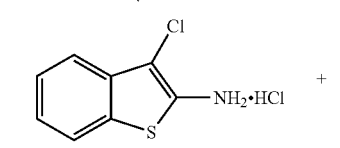

VI

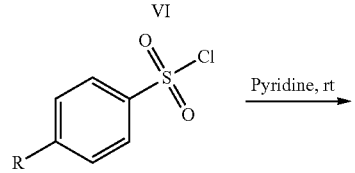

Pyridine, rt

-continued

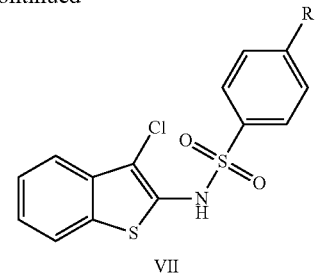

VII

Synthetic Protocol 3.2.2—Preparation of 1-{[(3-chloro-1-benzothiophen-2-yl)carbonyl]imino}diazenium (IV)

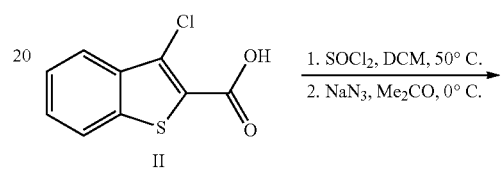

II

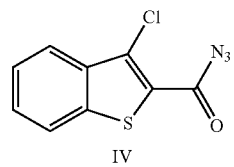

IV

Procedure:— the benzothiophene acid was converted to the acid chloride as described. The crude acid chloride was (1 eq.) was then suspended acetone (10 vol) and the solution cooled to OC. Sodium azide (1.1 eq.) was added and the reaction stirred until TLC showed complete disappearance of starting material. The reaction mass was poured onto ice and extracted with diethyl ether (4×25 vol). The combined organic layers were dried over anhydrous sodium sulfate and concentrated in vacuo (Note: The solvent was removed under mild vacuum and room temperature to avoid the risk of explosion) to get the acyl azide IV which was used in the next step without purification (Yield ~quantitative)

3.2.3—Preparation of tert-butyl N-(3-chloro-1-benzothiophen-2-yl)carbamate (V)

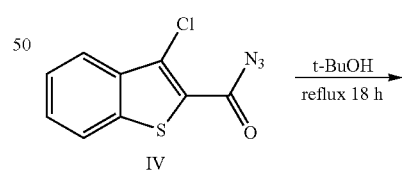

IV

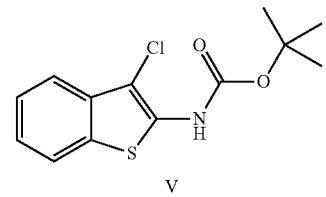

V

Procedure:

The acyl azide IV (1 eq.) was taken in tert-butanol (10 vol), reaction mixture was heated to reflux temperature for 18 hours. After the completion of reaction (Checked by TLC), reaction mass was evaporated to dryness and the crude product was triturated with diethyl ether to get pure product V (Yield 80%).

3.2.4—Preparation of 3-chloro-1-benzothiophen-2-amine hydrochloride salt (VI)—

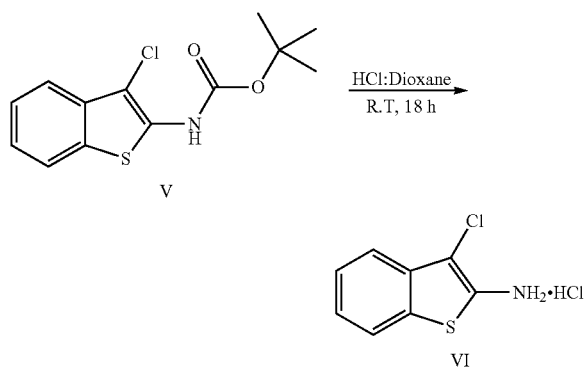

Procedure—

The BOC-protected amine V (1 eq.) was dissolved in 4N HCl in dioxane (20 vol) and stirred at ambient temperature for 6 hours. The suspension was diluted with diethyl ether, the solid obtained was filtered, washed with diethyl ether and dried under vacuo to get desired product (Yield:—100%).

3.2.5—Preparation of Sulfonamides—

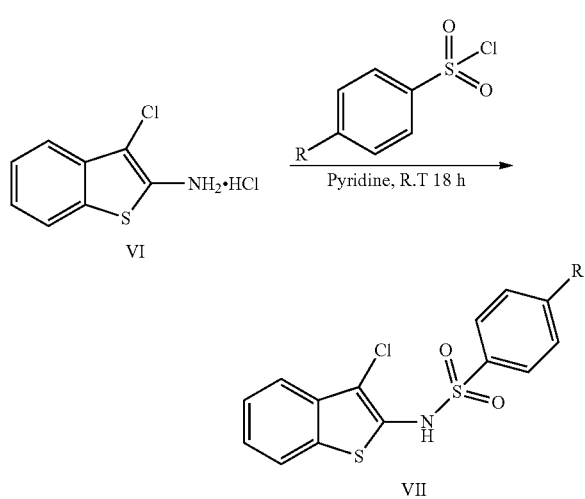

Procedure:—

A solution of the substituted aryl sulphonyl chloride (1 eq.) in dichloromethane was slowly added to a solution of the amine hydrochloride salt VI (1 eq.) in pyridine (10 vol) held at 0° C. The reaction was allowed to come to room temperature and stirred until TLC showed complete disappearance of starting material. The reaction mixture was concentrated in vacuo and acidified with 2N HCl (pH<2). The mixture was extracted with ethyl acetate (4×25 vol) and the organic layer was washed with water (2×25 vol), saturated brine (1×25 vol), dried over anhydrous sodium sulfate and the solvent removed in vacuo to get the crude product VII. The results for the sulfonamide products are given in Table 6

TABLE 6

| Sr. No | Comp. ID | R | LCMS | Yield % |
|---|---|---|---|---|
| 1 | 10023504 | Me | 87 | 12 |
| 2 | 10023505 | OMe | 100 | 11 |
| 3 | 10024128 | F | 97 | 10 |

Preparation of Urea Derivatives

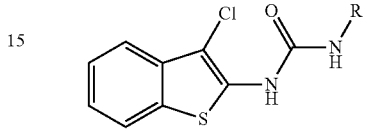

4.2.1 Synthetic_Route

The general synthetic route is summarized in following Scheme—

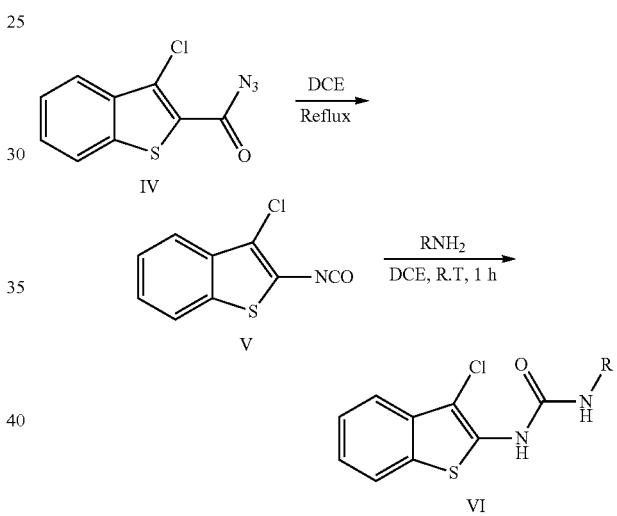

Procedure:—

A solution of IV (1 eq) in dichloroethane (10 vol) was refluxed for 1 hour. The reaction mixture was cooled to 0° C., and a solution of the amine (1 eq) in dichloroethane (1 vol) was added to it. The reaction mixture was stirred at room temperature until TLC showed complete reaction. Water (10 vol) was added to the reaction and it was extracted with dichloroethane (2×10 vol). The organic layer was washed with saturated brine (1×10 vol), dried over anhydrous sodium sulfate and concentrated in vacuo to get the crude product which was purified by flash silica gel column chromatography. The results for all urea products are given in Table 7

TABLE 7

| Sr. No. | Comp ID | Amine | Purity (%) | Yield (%) |
|---|---|---|---|---|
| 1 | 10023507 | 6-Methyl-1,2,3,4-tetrahydroquinoline | 96 | 82 |
| 2 | 10022790 | 1-Amino tetralin | 100 | 60 |

Preparation of Thienopyridine Derivative:—
5.2.1 Synthetic_Route—

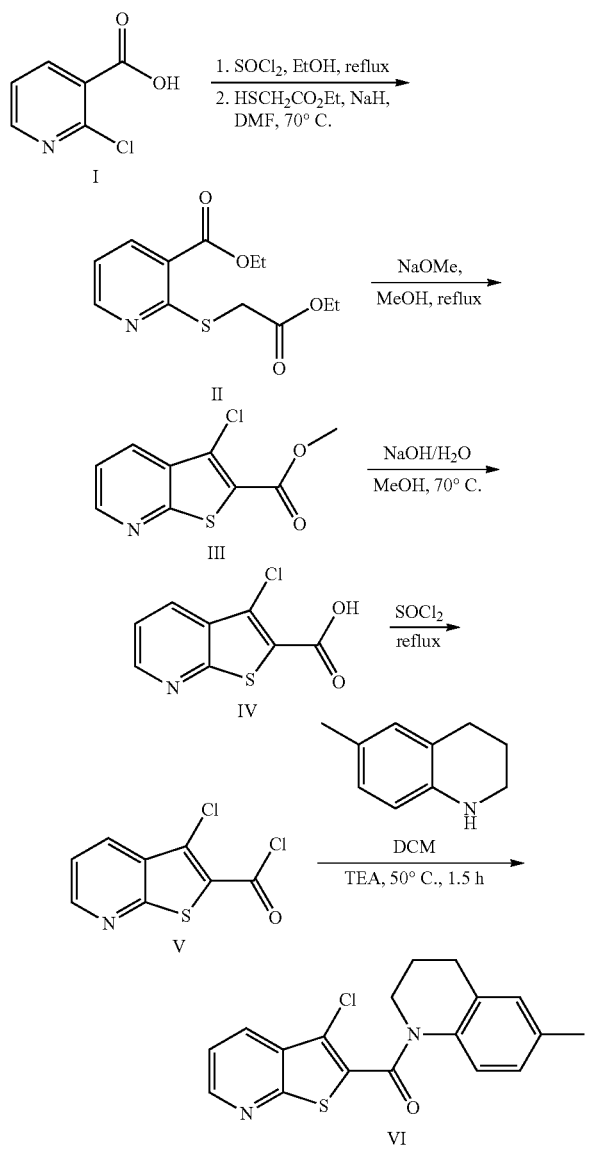

5.2.2 Esterification
Procedure:—
To a mixture of 2-chloropyridine-3-carboxylic acid (1 eq.) and $SOCl_2$ (5 eq.) in benzene were heated at 100° C. for 3 hours. After 3 hours so (vent was removed in vacuo. Then added to ethanol (5 vol) dropwise to reaction mixture and further heated at 1 hour under reflux temperature. The solvent was then removed in vacuo, dissolved the product in toluene (10 vol), the solution was dried over sodium sulphate and concentrate to get oil II. The crude product was taken for the next step without further purifications (Yield 96%). A round bottom flask charged with NaH (60 percent dispersion in mineral oil, 1.1 eq.) in dimethylformamide (10 vol) then ethyl thioglycolate (1 eq.) was added drop wise as a solution in dimethylformamide (5 vol). After hydrogen evolution had ceased, 2-chloro nicotinic acid ethyl ester (1 eq.) was added drop wise as a solution in dimethylformamide (5 vol). The reaction was heated at 65° C. for 90 min. On completion of reaction (TLC), the reaction was cooled to room temperature and diluted with water (10 vol). The mixture was extracted with diethyl ether (2×25 vol) and the organic phase washed with water (2×20 vol) followed by saturated brine (10 vol), dried over anhydrous sodium sulphate, filtered, and evaporated in vacuo to get pure product II. (Yield:—64%)

5.2.4 Cyclisation
Procedure:—
A solution of compound II (1 eq.) and sodium methoxide (5 eq.) in methanol (20 vol) was heated to reflux for 30 min. On completion of reaction (TLC), the mixture was cooled to room temperature, diluted with water (10 vol) and acidified using 1N HCl (pH~3). A white solid was precipitate out which was filtered and washed with water (30 vol), dried to get pure product V (Yield:—65%).

5.2.5 Ester Hydrolysis
Procedure:—
To a solution of comp V (1 eq.) in methanol (10 vol) and 2N NaOH (4 eq.) in water was heated at 70° C. for 4 hours. On completion of reaction (TLC), the solvent was removed in vacuo and the reaction acidified with acetic acid (pH~5). The aqueous layer was extracted with ethyl acetate (2×15 vol), dried over anhydrous sodium sulfate and concentrated in vacuo to get pure product IV (Yield:—83%).

5.2.6-7 Coupling
Procedure:—
To a solution of amine (0.5 eq.) and triethylamine (3 eq.) in dichloromethane (5 vol) was added acid chloride V (1 eq.) dissolved in of dichloromethane (15 vol). The reaction was shaken overnight at room temperature. On completion of the reaction (HPLC-MS and TLC), it was diluted with dichloromethane (10 vol) and washed with 1N HCl (1×10 vol), saturated sodium bicarbonate (1×10 vol) and water (2×15 vol). The organic layer was dried over anhydrous sodium sulfate and concentrated in vacuo to give a crude product VI. The crude product was purified by flash silica gel column chromatography (Yield 11%).

Preparation of Indole Derivative:
6.2.1 Synthetic_Route:—

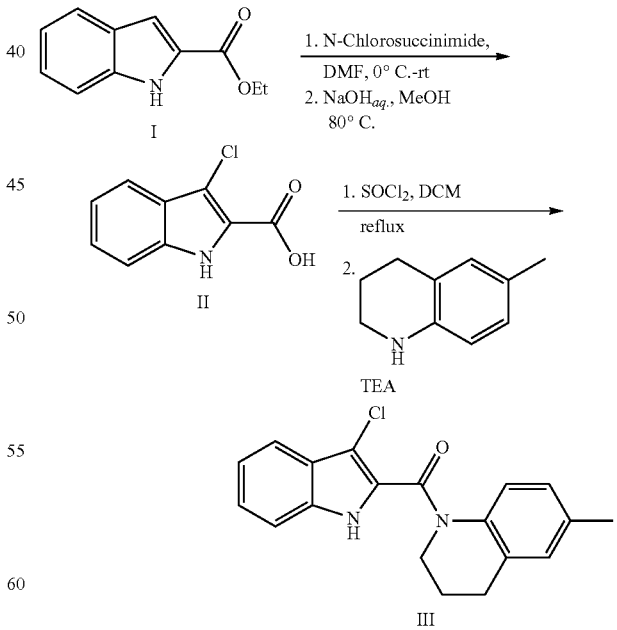

6.2.3 Chlorination[iii]:—
[iii]Bioorganic & Medicinal Chemistry 16 (2008) 3587-3595
Procedure:—
To a stirred solution of I (1 eq.) in dimethylformamide (10 vol) was added a solution of N-chlorosuccinimide (1.1 eq.) in dimethylformamide (10 vol) at 0° C. The reaction was stirred for 18 hours at room temperature. On completion of reaction (HPLC-MS and TLC) the reaction mixture was poured into ice water and the resulting precipitate was collected by filtration, washed with water (20 vol) and dried in vacuo to get the chloro ester as a white solid (Yield 91.8%). A solution of comp of the chloro ester (1 eq) in methanol (10 vol) and aqueous 4N NaOH (4 eq.) was refluxed for 4 hours. On completion of reaction (HPLC-MS, TLC), the solvent was removed in vacuo and the reaction was acidified with acetic acid (pH~5), The aqueous layer was extracted with ethyl acetate (2×15 vol), dried over anhydrous sodium sulphate and concentrated in vacuo to get II as a white solid (Yield 86%).

6.2.5 Coupling:—

Procedure:—

The acid chlorides were made as described previously. To a solution of amine (1 eq.) in dichloromethane (10 vol) and triethylamine (3 eq.) was added the acid chloride (1 eq.) dissolved in dichloromethane (15 vol). The reaction was stirred at room temperature for 1 hour. On completion of the reaction (HPLC-MS and TLC), it was diluted with dichloromethane (10 vol) and washed with 1N HCl (10 vol), saturated sodium bicarbonate (10 vol) and water (15 vol). The organic layer was dried over sodium sulfate and concentrated in vacuo to give a crude product III. The crude product was triturated with pentane to afford the product as a white solid. (Yield 72%)

Preparation of Keto Derivatives—

8.2.1 Synthetic Route:—

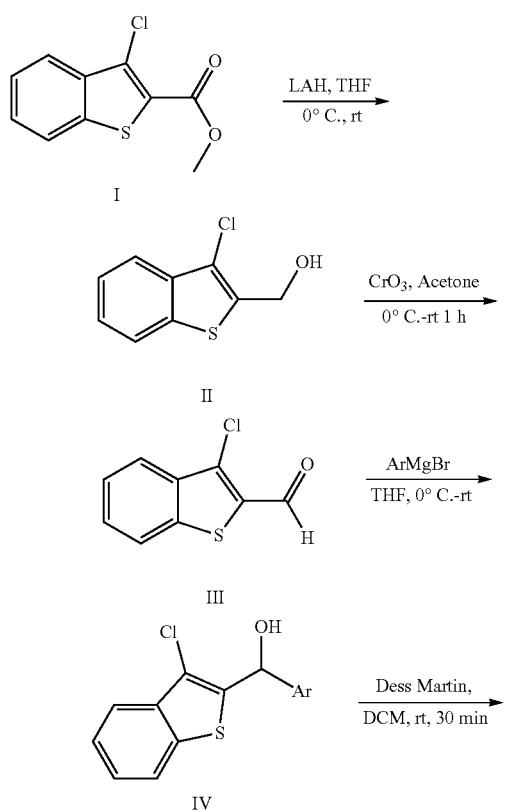

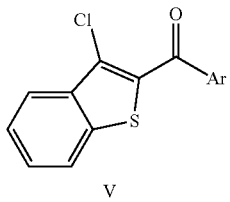

V 7.2.3 Preparation of Alcohol II—

Lithium aluminum hydride (4 eq.) was suspended in THF (10 vol) at 0° C. and a solution of II (1 eq.) in tetrahydrofuran (10 vol) was slowly added to this. The mixture was heated slowly to reflux for 4 hours. On completion of reaction (HPLC-MS and TLC), the reaction mixture was cooled to room temperature and added dropwise to a saturated solution of Rochelle's salt in $H_2O$ with stirring. The bi-phasic mixture was stirred rapidly at room temperature for 1 hour. The layers were separated and the aqueous layer was extracted with ethyl acetate (5×10 vol) until TLC of the aqueous layer showed no evidence of the title compound II. The combined organic layers were dried over anhydrous sodium sulfate and concentrated in vacuo to furnish the crude product III (Yield:—65%) which was used in the next step without purification.

7.2.4 Preparation of Aldehyde III—

The alcohol II (1 eq.) was dissolved in acetone (10 vol), and $CrO_3$ (1.5 eq.) was added to it at ° C. The reaction mixture was stirred at room temperature for 1 hour. On completion of reaction (HPLC-MS and TLC), the reaction mixture was filtered through Celite®, washed with acetone (20 vol) and concentrated in vacuo to get desired product III (Yield:—70%) which was used in the next step without purification.

7.2.5 Preparation of Alcohol IV

Compound III (1 eq.) was dissolved in tetrahydrofuran (10 vol) and cooled to 0° C. The Grignard reagent was added to this slowly and the mixture was allowed to stir at 0° C. for 2 hours. On completion of the reaction (HPLC-MS and TLC), it was quenched with ice-cold water (10 vol), and the reaction was concentrated in vacuo. The crude residue was acidified using acetic acid (pH~5) and the aqueous layer was extracted with ethyl acetate (2×20 vol), dried over anhydrous sodium sulfate and concentrated to get pure product IV. The results for all alcohol products are given in Table 8.

TABLE 8

| Entry | Ar | Purity (%) | Yield (%) |
|---|---|---|---|
| 1 | Ph | 90 | 50 |
| 2 | 4-OMe—Ph | 80 | 52 |

7.2.6 Preparation of Ketone V

The alcohol IV (1 eq) was dissolved in dichloromethane (10 vol) and Dess Martin reagent (1 eq.) was added to it slowly over 10 minutes. The reaction mixture was stirred at room temperature for 30 min. On completion of the reaction (HPLC-MS and TLC), the reaction mixture was concentrated and the crude residue was purified by flash silica gel column chromatography to get pure product V. The results for all keto products are given in Table 9.

TABLE 9

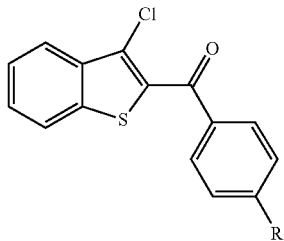

| Entry | Comp ID | R | Purity (%) | Yield (%) |
|---|---|---|---|---|
| 1 | 10023508 | H | 100 | 38 |
| 2 | 10023509 | OMe | 100 | 30 |

10024928: 3-chloro-N-methyl-N-{[2-(pyrrolidin-1-yl)phenyl]methyl}-1-benzothiophene-2-carboxamide

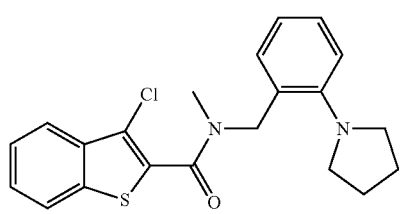 [SMILES: CN(Cc1ccccc1N1CCCC1)C(=O)c1sc2ccccc2c1Cl]

$^1$H NMR (300 MHz, CDCl$_3$): δ ppm 0.82-0.95 (m, 1 H), 1.1-1.5 (s, 3 H), 1.85-2.03 (d, 3 H), 2.88-3.07 (m, 4 H), 3.16 (s, 2 H), 4.66 (s, 1 H), 4.90 (s, 1 H), 6.95-7.03 (m, 2 H), 7.21-7.48 (m, 3 H), 7.46-7.48 (m, 2 H), 7.75-7.87 (m, 2 H); LCMS m/z=384, 386 [M+H][M+H]$^+$.

10024929: 4-[(3-chloro-1-benzothiophen-2-yl)carbonyl]morpholine

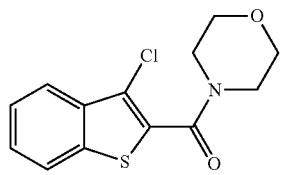 [SMILES: O=C(c1sc2ccccc2c1Cl)N1CCOCC1]

$^1$H NMR (300 MHz, CDCl$_3$): δ ppm 3.54-3.76 (s, 8 H), 7.44-7.53 (m, 2 H), 7.81-7.87 (m, 2 H); LCMS m/z=381, 383 [M+H]$^+$.

10024930: 1-[(3-chloro-1-benzothiophen-2-yl)carbonyl]pyrrolidine

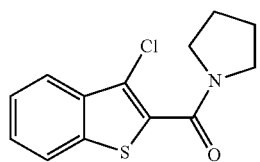 [SMILES: O=C(c1sc2ccccc2c1Cl)N1CCCC1]

$^1$H NMR (300 MHz, CDCl$_3$): δ ppm 1.92-2.03 (m, 4 H), 3.47-3.51 (m, 2 H), 3.67-3.72 (m, 2 H), 7.26-7.52 (m, 2 H), 7.80-7.87 (m, 2 H); LCMS m/z=265, 267 [M+H]$^+$.

10024931: 1-[(3-chloro-1-benzothiophen-2-yl)carbonyl]piperidine

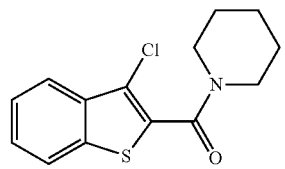 [SMILES: O=C(c1sc2ccccc2c1Cl)N1CCCCC1]

$^1$H NMR (300 MHz, CDCl$_3$): δ ppm 1.59-1.69 (m, 7 H), 3.43-3.76 (d, 4 H), 7.26-7.51 (m, 2 H), 7.80-7.86 (m, 2 H); LCMS m/z=279, 281 [M+H]$^+$.

10022780: 5-[(3-chloro-1-benzothiophen-2-yl)carbonyl]-4-methyl-4H,5H,6H,7H-thieno[3,2-C]pyridine

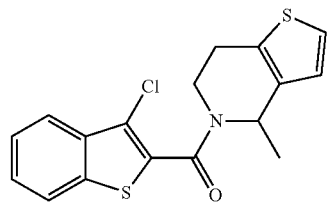 [SMILES: CC1c2ccsc2CCN1C(=O)c1sc2ccccc2c1Cl]

$^1$H NMR (300 MHz, CDCl$_3$): δ ppm 1.509-1.597 (t, 4 H), 2.7-2.8 (m, 1 H), 3.0-3.2 (m, 1 H), 3.4-3.5 (m, 1 H), 3.94-3.97 (d, 1 H), 6.65-6.85 (d, 1 H), 7.1-7.2 (d, 1.H), 7.4-7.5 (m 1.H), 7.80-7.88 (m, 2.H); LCMS m/z=348, 350 [M+H]$^+$.

10022781: 3-chloro-N-(1,2,3,4-tetrahydronaphthalen-1-yl)-1-benzothiophene-2-carboxamide

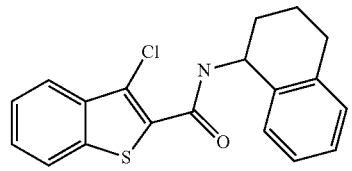 [SMILES: O=C(NC1CCCc2ccccc21)c1sc2ccccc2c1Cl]

$^1$H NMR (300 MHz, CDCl$_3$): δ ppm 1.9-2.0 (m, 3 H), 2.1-2.2 (m, 1 H), 2.8-2.9 (m, 2H), 5.41-5.48 (q, 1 H), 7.1-7.2 (m, 3 H), 7.3-7.5 (m, 4 H), 7.83-7.86 (m, 2 H), LCMS m/z=342, 344 [M+H]$^+$.

10022782: 3-chloro-N-(2,4-dimethyl phenyl)-N-(pyridine-ylmethyl)-1-benzothiophene-2-carboxamide

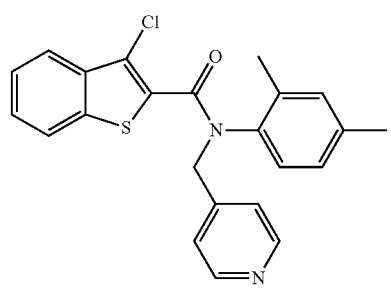 [SMILES: Cc1ccc(N(Cc2ccncc2)C(=O)c2sc3ccccc3c2Cl)c(C)c1]

¹H NMR (300 MHz, CDCl₃): δ ppm 2.01-2.04 (s, 3 H), 2.1-2.2 (s, 3 H), 4.41-4.46 (d, 1 H), 5.46-5.51 (d, 1 H), 6.7-6.8 (m, 2 H), 6.9 (s, 1 H), 7.2-7.4 (m, 4 H), 7.5-7.6 (d, 1 H), 7.7-7.8 (d, 1 H), 8.56-8.58 (d, 2 H); LCMS m/z=407.0, 409.0, 410.0 [M+H]⁺.

10022783: 3-chloro-N-(2,4-dimethyl phenyl)-N[(6-methylpyridin-2-yl)methyl]-1-benzothiophene-2-carboxamide

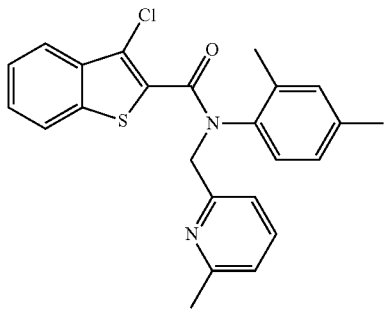 [SMILES: Cc1ccc(N(Cc2cccc(C)n2)C(=O)c2sc3ccccc3c2Cl)c(C)c1]

¹H NMR (300 MHz, CDCl₃): δ ppm 2.1-2.2 (s, 6 H), 2.4 (s, 3 H), 4.51-4.56 (d, 1 H), 5.62-5.67 (d, 1 H), 6.74-6.77 (d, 1 H), 6.9 (s, 1 H), 7.0-7.2 (m, 2.H), 7.3-7.4 (m, 3.H), 7.5-7.6 (m, 2.H), 7.7-7.8 (d, 1.H); LCMS m/z=421, 423, 424 [M+H]⁺.

10022784: 3-chloro-N-(2,4-dimethyl phenyl)-N[2-oxo-2-(thiophene-2-yl)ethyl]-1-benzothiophene-2-carboxamide

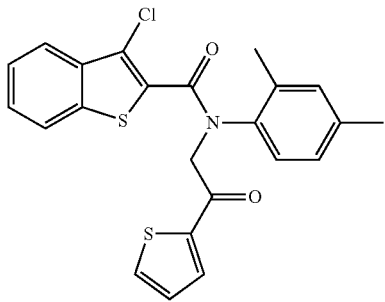 [SMILES: Cc1ccc(N(CC(=O)c2cccs2)C(=O)c2sc3ccccc3c2Cl)c(C)c1]

¹H NMR (300 MHz, CDCl₃): δ ppm 2.2 (s, 3 H), 2.3 (s, 3 H), 4.4-4.5 (d, 1 H), 5.6-5.7 (d, 1 H), 6.86-6.89 (d, 1 H), 6.9 (s, 1 H), 7.14-7.17 (m, 1 H), 7.3-7.4 (m, 3 H), 7.5-7.6 (m, 2 H), 7.80-7.84 (m, 2 H); LCMS m/z=440, 442 [M+H]⁺.

10022785: 3-chloro-N-(5-methoxy-2-methylphenyl)-N-(pyridine-4-yl methyl)-1-benzothiophene-2-carboxamide

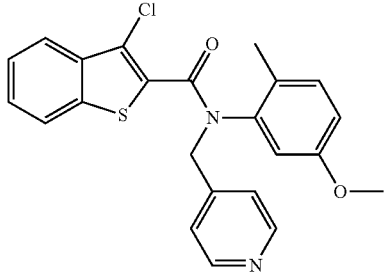 [SMILES: COc1ccc(C)c(N(Cc2ccncc2)C(=O)c2sc3ccccc3c2Cl)c1]

¹H NMR (300 MHz, CDCl₃): δ ppm 2.1 (s, 3 H), 3.5 (s, 3 H), 4.4-4.5 (d, 1 H), 5.4-5.5 (d, 1 H), 6.48-6.49 (d, 1 H), 6.6-6.7 (d, 1 H), 7.0-7.03 (d, 1 H), 7.2-7.4 (m, 4 H), 7.6-7.63 (d, 1 H), 7.7-7.8 (d, 1 H), 8.57-8.59 (d, 2 H); LCMS m/z=423, 426 [M+H]⁺.

10022786: 3-chloro-N-(5-methoxy-2-methylphenyl)-N-[(6-methylpyridin-2-yl)methyl]-1-benzothiophene-2-carboxamide

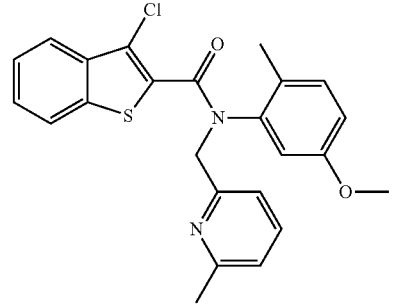 [SMILES: COc1ccc(C)c(N(Cc2cccc(C)n2)C(=O)c2sc3ccccc3c2Cl)c1]

¹H NMR (300 MHz, CDCl₃): δ ppm 2.0 (s, 3 H), 2.5 (s, 3 H), 3.6 (s, 3 H), 4.52-4.57 (d, 1 H), 5.63-5.68 (d, 1 H), 6.6-6.68 (m, 1 H), 6.7 (s, 1 H), 6.98-7.00 (m, 2 H), 7.3-7.4 (m, 3 H), 7.5-7.6 (m, 2 H), 7.7-7.8 (m, 1 H); LCMS m/z=437, 439, 440 [M+H]⁺.

10022787: 3-chloro-N-(5-methoxy-2-methylphenyl)-N-[2-oxo-2-(thiophene-2-yl)ethyl]-1-benzothiophene-2-carboxamide

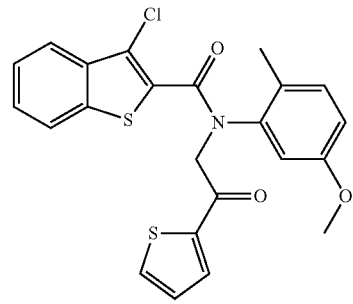 [SMILES: COc1ccc(C)c(N(CC(=O)c2cccs2)C(=O)c2sc3ccccc3c2Cl)c1]

¹H NMR (300 MHz, CDCl₃): δ ppm 2.3 (s, 3 H), 3.6 (s, 3 H), 4.4-4.5 (d, 1 H), 5.7-5.76 (d, 1 H), 6.69-6/(m, 1 H), 7.03-7.07 (d, 1 H), 7.14-7.18 (m, 2 H), 7.3-7.4 (m, 2 H), 7.62-7.64 (m, 1 H), 7.68-7.70 (m, 1 H), 7.82-7.85 (m, 2 H); LCMS m/z=455.9, 456.9[M+H]⁺.

10022788: 3-chloro-N-(2,4-dimethylphenyl)-N-(quinolin-2-ylmethyl)-1-benzothiophene-2-carboxamide

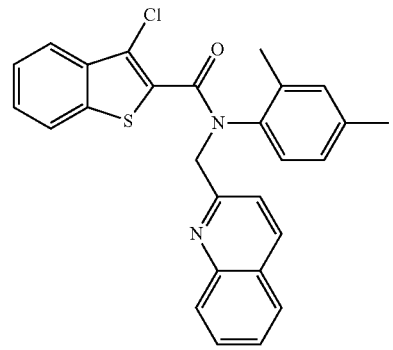 [SMILES: Cc1ccc(N(Cc2ccc3ccccc3n2)C(=O)c2sc3ccccc3c2Cl)c(C)c1]

¹H NMR (300 MHz, CDCl₃): δ ppm 2.0 (s, 3 H), 2.2 (s, 3 H), 4.70-4.75 (d, 1 H), 5.8-5.9 (d, 1 H), 6.69-6.7 (d, 1 H), 6.91 (s, 1 H), 7.0-7.03 (d, 1 H), 7.3-7.4 (m, 2 H), 7.49-7.52 (m, 1

H), 7.6-7.7 (m, 2 H), 7.7-7.8 (m, 3 H), 7.9-8.0 (d, 1 H), 8.1-8.2 (d, 1 H); LCMS m/z=457, 459 [M+H]⁺.

10022789: 3-chloro-N-(2,4-dimethylphenyl)-N-(quinolin-2-ylmethyl)-1-benzothiophene-2-carboxamide

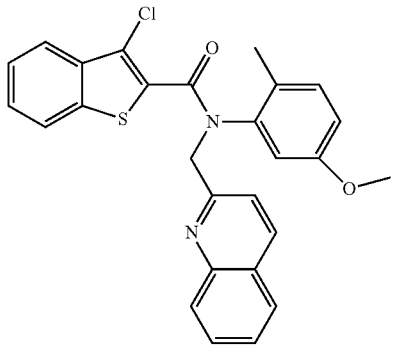 [SMILES: COc1ccc(C)c(N(Cc2ccc3ccccc3n2)C(=O)c2sc3ccccc3c2Cl)c1]

¹H NMR (300 MHz, CDCl₃): δ ppm 2.2 (s, 3 H), 3.5 (s, 3 H), 4.72-4.77 (d, 1 H), 5.8-5.9 (d, 1 H), 6.62-6.66 (m, 1 H), 6.85-6.86 (m, 1 H), 6.98-7.01 (d, 1 H), 7.3-7.4 (m, 2 H), 7.50-7.53 (m, 1 H), 7.6-7.8 (m, 5H), 8.01-8.03 (d, 1 H), 8.1-8.2 (d, 1H) LCMS m/z=473, 475 [M+H]⁺.

10022923: 3-chloro-N-(2,4-dimethylphenyl)-N-(pyridine-3-ylmethyl)-1-benzothiophene-2-carboxamide

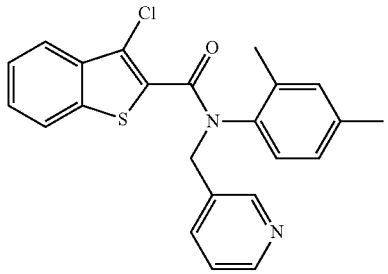 [SMILES: Cc1ccc(N(Cc2cccnc2)C(=O)c2sc3ccccc3c2Cl)c(C)c1]

¹H NMR (300 MHz, CDCl₃): δppm 2.1 (s, 3 H), 2.2 (s, 3 H), 4.54-4.59 (d, 1 H), 5.39-5.4 (d, 1 H), 6.7-6.8 (m, 2 H), 6.9 (s, 1 H), 7.22-7.4 (m, 4 H), 7.5-7.6 (d, 1 H), 7.7-7.8 (m, 2 H), 8.4-8.5 (m, 2 H); LCMS m/z=407, 409 [M+H]⁺.

10022924: 3-chloro-N-(2,4-dimethylphenyl)-N-(pyridine-3-ylmethyl)-1-benzothiophene-2-carboxamide

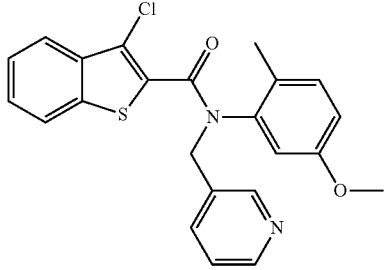 [SMILES: COc1ccc(C)c(N(Cc2cccnc2)C(=O)c2sc3ccccc3c2Cl)c1]

¹H NMR (300 MHz, CDCl₃): δ ppm 2.0 (s, 3 H), 3.5 (s, 3 H), 4.5-4.6 (d, 1 H), 5.40-5.45 (d, 1 H), 6.43-6.44 (d, 1 H), 6.6-6.7 (d, 1 H), 6.9-7.0 (d, 1 H), 7.2-7.4 (m, 3 H), 7.5-7.6 (d, 1 H), 7.7-7.8 (m, 2 H), 8.4-8.5 (m, 2 H): LCMS m/z=423, 425 [M+H]⁺.

10024932: 1-[(3-chloro-4-fluoro-1-benzothiophen-2-yl)carbonyl]-6-methyl-1,2,3,4-tetrahydroquinoline

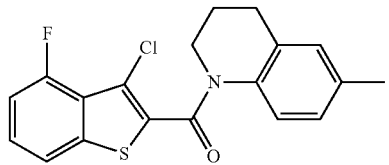 [SMILES: Cc1ccc2c(c1)CCCN2C(=O)c1sc2cccc(F)c2c1Cl]

¹H NMR (300 MHz, CDCl₃): δ ppm 0.82-0.88 (m, 1 H), 1.25 (s, 3 H), 2.03-2.12 (m, 2 H), 2.24 (s, 3 H), 2.80-2.84 (t, 2 H), 3.90-3.95 (t, 2 H), 6.70-6.85 (s, 1 H), 6.97 (s, 1 H), 7.01-7.04 (s, 1 H), 7.07 (s, 1 H), 7.31-7.38 (m, 1 H), 7.53-7.55 (m, 1 H); LCMS m/z=359, 361 [M+H]⁺.

10024933: 1-[(3-chloro-5-fluoro-1-benzothiophen-2-yl)carbonyl]-6-methyl-1,2,3,4-tetrahydroquinoline

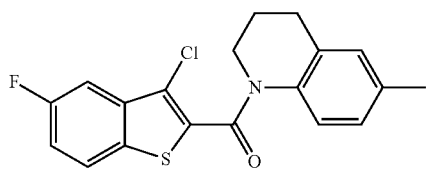 [SMILES: Cc1ccc2c(c1)CCCN2C(=O)c1sc2ccc(F)cc2c1Cl]

¹H NMR (300 MHz, CDCl₃): δ ppm 2.03-2.12 (m, 2 H), 2.2 (s, 3 H), 2.80-2.85 (m, 2 H), 3.91-3.95 (m, 2 H), 6.67-6.70 (m, 1 H), 6.97 (s, 1 H), 7.17 (s, 1 H), 7.17-7.29 (m, 1 H), 7.37-7.40 (m, 1 H), 7.70-7.74 (m, 1 H); LCMS m/z=359, 361 [M+H]⁺.

10024121: 3-chloro-N-(2,4-dimethylphenyl)-N-(pyridin-2-ylmethyl)-1-benzothiophene-2-carboxamide

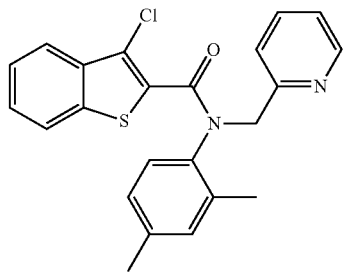 [SMILES: Cc1ccc(N(Cc2ccccn2)C(=O)c2sc3ccccc3c2Cl)c(C)c1]

¹H NMR (300 MHz, CDCl₃): δ ppm 2.18-2.27 (d, 6.H), 4.60-4.65 (d, 1 H), 5.62-5.66 (d, 1 H), 6.75-6.77 (m, 1 H), 6.91-6.95 (m, 2 H), 7.17-7.21 (m, 1 H), 7.37-7.41 (m, 2 H), 7.59-7.60 (m, 1 H), 7.62-7.81 (m, 3 H), 8.48 (d, 1 H); LCMS m/z=406, 408 [M+H]⁺.

10024122: 1-[(1H-indol-2-yl)carbonyl]-6-methyl-1,2,3,4-tetrahydroquinoline

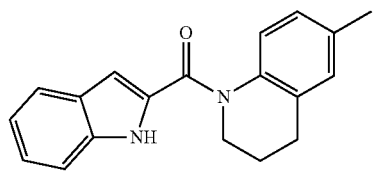 [SMILES: Cc1ccc2c(c1)CCCN2C(=O)c1cc2ccccc2[nH]1]

¹H NMR (400 MHz, CDCl₃): δ ppm 2.00-2.09 (m, 2.H), 2.34 (s, 3.H), 2.76-2.80 (t, 2.H), 3.97-1.02 (t, 2.H), 4.77-4.78 (s, 2.H), 6.23 (s, 1 H), 6.84-6.87 (m, 1 H), 7.04-7.10 (m, 3.H), 7.13-7.27 (m, 2 H), 7.38-7.41 (s, 1 H), 7.47-7.50 (m, 1 H), 9.12 (s, 1 H); LCMS m/z=290 [M+H]⁺.

10024123: 3-chloro-N-{[2-(pyrrolidin-1-yl)phenyl]methyl}-1-benzothiophene-2-carboxamide

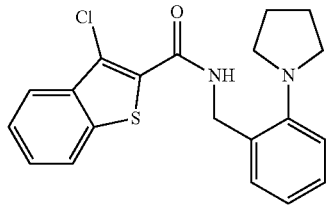 [SMILES: O=C(NCc1ccccc1N1CCCC1)c1sc2ccccc2c1Cl]

¹H NMR (300 MHz, CDCl₃): δ ppm 1.96-2.00 (m, 4 H), 3.21-3.25 (m, 4 H), 4.7-4.8 (d, 2 H), 6.94-6.99 (m, 1 H), 7.06-7.09 (d, 1 H), 7.23-7.33 (m, 1 H), 7.46-7.51 (m, 2 H), 7.82-7.86 (m, 2 H), 8.1 (s, 1 H); LCMS m/z=370, 372 [M+H]⁺.

10024124: 1-[(3-chloro-6-methoxy-1-benzothiophen-2-yl)carbonyl]-6-methyl-1,2,3,4-tetrahydroquinoline

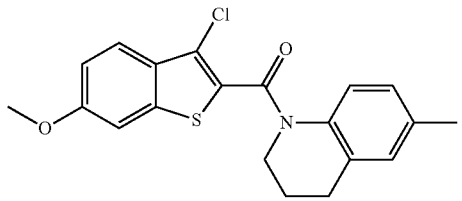

¹H NMR (300 MHz, CDCl₃): δ ppm 2.02-2.11 (m, 2 H), 2.2 (s, 3 H), 2.7-2.8 (t, 2 H), 3.87-3.94 (m, 5 H), 6.67-6.70 (m, 1 H), 6.82-6.84 (s, 1 H), 7.00-7.01 (s, 1 H), 7.03-7.04 (d, 1 H), 7.21-7.25 (d, 1 H), 7.5-7.6 (d, 2 H); LCMS m/z=371, 373 [M+H]⁺.

10024125: 1-[(3-chloro-4-methyl-1-benzothiophen-2-yl)carbonyl]-6-methyl-1,2,3,4-tetrahydroquinoline

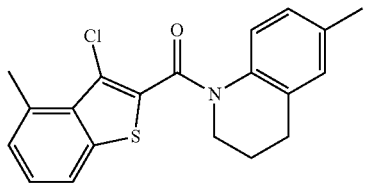 [SMILES: Cc1ccc2c(c1)CCCN2C(=O)c1sc2cccc(C)c2c1Cl]

¹H NMR (300 MHz, CDCl₃): δ ppm 2.02-2.10 (m, 2 H), 2.24 (s, 3 H), 2.77-2.83 (m, 5 H), 3.89-3.93 (t, 2 H), 6.72-6.74 (d, 1 H), 6.90-6.96 (s, 1 H), 7.10-7.13 (d, 1 H), 7.23-7.28 (m, 1 H), 7.58-7.61 (d, 1 H); LCMS m/z=355, 357 [M+H]⁺.

10024126: 1-[(3-chloro-5-methoxy-1-benzothiophen-2-yl)carbonyl]-6-methyl-1,2,3,4-tetrahydroquinoline

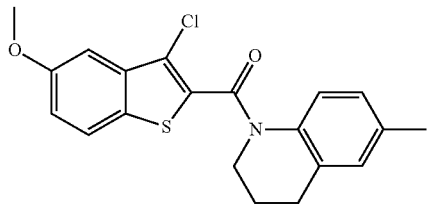 [SMILES: COc1ccc2sc(C(=O)N3CCCc4cc(C)ccc43)c(Cl)c2c1]

¹H NMR (300 MHz, CDCl₃): δ ppm 2.05-2.09 (m, 2 H), 2.24 (s, 3 H), 2.80-2.84 (t, 2 H), 3.86-3.91 (s, 2 H), 3.93-3.95 (m, 2 H), 6.68-6.70 (d, 1 H), 6.84-6.96 (s, 1 H), 7.05-7.06 (s, 1 H), 7.08-7.12 (m, 1 H), 7.26 (m, 1 H), 7.62-7.65 (d, 1 H); LCMS m/z=371, 373 [M+H]⁺.

10024127: 2-[(3-chloro-1-benzothiophen-2-yl)carbonyl]-6,7-dimethoxy-1,2,3,4-tetrahydroisoquinoline

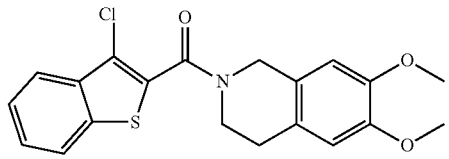 [SMILES: COc1cc2c(cc1OC)CN(C(=O)c1sc3ccccc3c1Cl)CC2]

¹H NMR (300 MHz, CDCl₃): δ ppm 1.37-1.42 (m, 1 H), 2.86 (m, 2 H), 3.07-3.14 (br, 1 H), 3.72-3.86 (m, 7 H), 4.03 (s, 1 H), 4.61 (s, 1 H), 4.88 (s, 1 H), 6.63 (br, 1 H), 7.46-7.54 (m, 2 H), 7.83-7.90 (m, 2 H); LCMS m/z=387, 389 [M+H]⁺.

10024128: N-(3-chloro-1-benzothiophen-2-yl)-4-fluorobenzene-1-sulfonamide

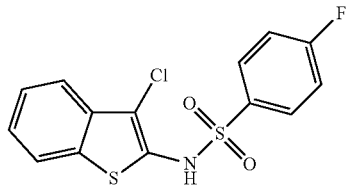 [SMILES: O=S(=O)(Nc1sc2ccccc2c1Cl)c1ccc(F)cc1]

¹H NMR (300 MHz, CDCl₃): δ ppm 1.23-1.28 (m, 1 H), 6.97 (s, 1 H), 7.10-7.41 (m, 2H), 7.44 (m, 2 H), 7.60-7.61 (m, 1 H), 7.63 7.86 (m, 1 H), 7.87-7.88 (m, 1 H); LCMS m/z=340, 342 [M+H]⁺.

10024129: N-(3-chloro-1-benzothiophen-2-yl)-2-cyanobenzamide

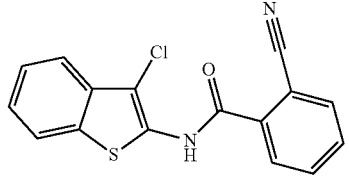 [SMILES: N#Cc1ccccc1C(=O)Nc1sc2ccccc2c1Cl]

¹H NMR (300 MHz, CDCl₃): δ ppm 7.52-7.73 (br, 2 H), 7.76-7.81 (m, 4 H), 7.83-7.90 (m, 1 H), 7.92-8.23 (d, 1 H); LCMS m/z=312, 314 [M+H]⁺.

10024130: 3-chloro-N-(3,4-dihydro-2H-1-benzopyran-4-yl)-1-benzothiophene-2-carboxamide

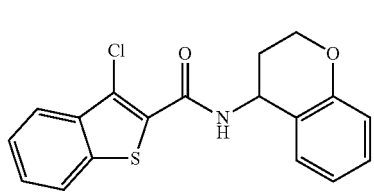 [SMILES: O=C(NC1CCOc2ccccc21)c1sc2ccccc2c1Cl]

¹H NMR (300 MHz, CDCl₃): δ ppm 1.25 (m, 1 H), 1.96-2.04 (m, 2 H), 2.17 (br, 1 H), 3.21-3.25 (m, 2 H), 4.07-4.10 (m, 2 H), 4.70 (s, 1 H), 6.70-6.89 (m, 5 H), 6.91 (s, 1 H), 6.95-6.97 (m, 3 H), 7.64-7.75 (m, 1 H); LCMS m/z=343, 345 [M+H]⁺.

10023502: 1-[(3-fluoro-1-benzothiophen-2-yl)carbonyl]-6-methyl-1,2,3,4-tetrahydroquinoline

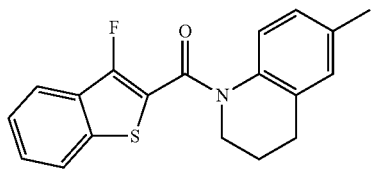

$^1$H NMR (400 MHz, CDCl$_3$): δ ppm 2.04-2.07 (m, 2 H), 2.26 (s, 3 H), 2.79-2.83 (t, 2 H), 3.91-3.95 (t, 2 H), 6.74 (m, 1 H), 6.90-6.92 (s, 1 H), 7.00 (s, 1 H), 7.26-7.44 (m, 2 H), 7.60-7.62 (d, 1 H), 7.74 (d, 1 H); LCMS m/z=325 [M+H]$^+$.

10023503: 1-{[3-chloro-6-(trifluoromethyl)-1-benzothiophen-2-yl]carbonyl}-6-methyl-1,2,3,4-tetrahydroquinoline

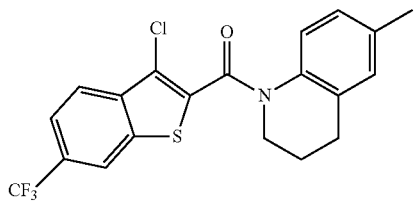 [SMILES: Cc1ccc2c(c1)CCCN2C(=O)c1sc2cc(C(F)(F)F)ccc2c1Cl]

$^1$H NMR (400 MHz, CDCl$_3$): δ ppm 2.07-2.15 (m, 2 H), 2.23 (s, 3 H), 2.81-2.85 (t, 2 H), 3.93-3.96 (t, 2 H), 6.67-6.77 (br, 1 H), 6.98 (s, 1 H), 7.64-7.66 (d, 1 H), 7.82-7.84 (d, 1 H), 8.08 (s, 1 H); LCMS m/z=409, 411 [M+H]$^+$.

10023504: N-(3-chloro-1-benzothiophen-2-yl)-4-methylbenzene-1-sulfonamide

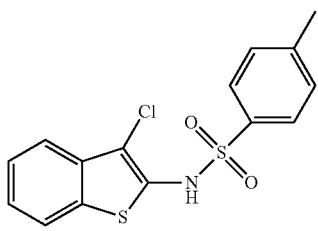 [SMILES: Cc1ccc(S(=O)(=O)Nc2sc3ccccc3c2Cl)cc1]

$^1$H NMR (400 MHz, CDCl$_3$): δ ppm 1.25 (s, 6 H), 2.39 (s, 3 H), 6.96 (s, 1 H), 7.24-7.26 (m, 5 H), 7.35-7.40 (m, 2 H), 7.59-7.61 (d, 1 H), 7.69 (d, 1 H), 7.71-7.76 (m, 2 H); LCMS m/z=337, 339 [M+H]$^+$.

10023505: N-(3-chloro-1-benzothiophen-2-yl)-4-methoxybenzene-1-sulfonamide

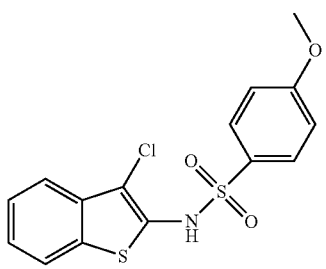 [SMILES: COc1ccc(S(=O)(=O)Nc2sc3ccccc3c2Cl)cc1]

$^1$H NMR (400 MHz, CDCl$_3$): δ ppm 3.83 (s, 3 H), 6.90-6.96 (d, 3 H), 7.35-7.40 (m, 2 H), 7.59-7.61 (d, 1 H), 7.69-7.71 (d, 1 H), 7.80-7.81 (d, 1 H); LCMS m/z=353, 355 [M+H]$^+$.

10023507: N-(3-chloro-1-benzothiophen-2-yl)-6-methyl-1,2,3,4-tetrahydroquinoline-1-carboxamide

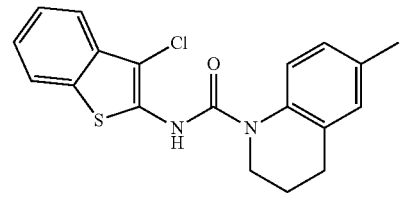 [SMILES: Cc1ccc2c(c1)CCCN2C(=O)Nc1sc2ccccc2c1Cl]

$^1$H NMR (400 MHz, CDCl$_3$): δ ppm 1.99-2.03 (m, 2 H), 2.37 (s, 3 H), 2.76-2.79 (t, 2 H), 3.86-3.89 (t, 2 H), 7.08 (s, 1 H), 7.11-7.12 (d, 1 H), 7.14-7.28 (m, 3 H), 7.35-7.39 (m, 2 H), 7.58-7.71 (d, 1 H), 7.73 (d, 1 H), 8.17 (s, 1 H); LCMS m/z=356, 358 [M+H]$^+$.

10023508: (3-chloro-1-benzothiophen-2-yl)(phenyl)methanone

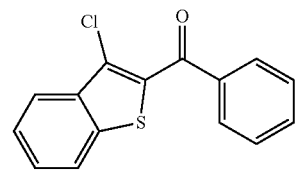 [SMILES: O=C(c1ccccc1)c1sc2ccccc2c1Cl]

$^1$H NMR (400 MHz, CDCl$_3$): δ ppm 0.84 (br, 1 H), 1.25-1.56 (m, 2 H), 7.50-7.55 (m, 4 H), 7.61-7.63 (m, 1 H), 7.85-7.96 (m, 3 H), 7.97-7.98 (m, 1 H); LCMS m/z=272, 274 [M+H]$^+$.

10023509: (3-chloro-1-benzothiophen-2-yl)(4-methoxyphenyl)methanone

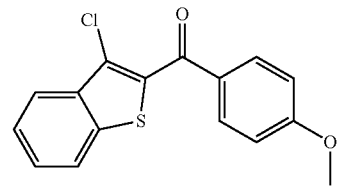 [SMILES: COc1ccc(C(=O)c2sc3ccccc3c2Cl)cc1]

$^1$H NMR (400 MHz, CDCl$_3$): δ ppm 3.90 (s, 3 H), 6.88-6.99 (d, 2 H), 7.53-7.54 (d, 2 H), 7.85-7.87 (d, 1 H), 7.92-7.97 (m, 3 H); LCMS m/z=302, 304 [M+H]$^+$.

10023501: 3-chloro-N-(5-methoxy-2-methylphenyl)-N-(pyridin-2-ylmethyl)-1-benzothiophene-2-carboxamide

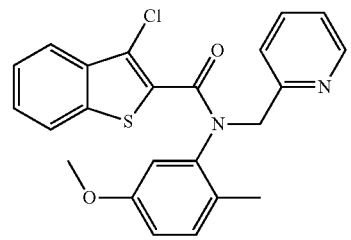 [SMILES: COc1ccc(C)c(N(Cc2ccccn2)C(=O)c2sc3ccccc3c2Cl)c1]

$^1$H NMR (400 MHz, CDCl$_3$): δ ppm 2.18 (s, 3 H), 3.59 (s, 3 H), 4.62-4.65 (d, 1 H), 5.63-5.67 (d, 1 H), 6.65-6.69 (m, 2

H), 6.98-7.00 (d, 2 H), 7.20-7.26 (m, 1 H), 7.36-7.40 (m, 2 H), 7.60-7.65 (m, 2 H), 7.67-7.72 (m, 1 H), 7.79-8.51 (m, 1 H), 8.52 (s, 1 H); LCMS m/z=422, 424 [M+H]⁺.

10021575: 6-chloro-1-[(3-chloro-1-benzothiophen-2-yl)carbonyl]-1,2,3,4-tetrahydroquinoline

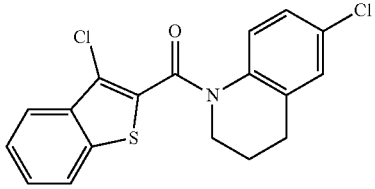 [SMILES: O=C(c1sc2ccccc2c1Cl)N1CCCc2cc(Cl)ccc21]

¹H NMR (400 MHz, CDCl₃): δ ppm 2.05-2.12 (t, 2 H), 2.83-2.87 (t, 2 H), 3.92-3.95 (t, 2 H), 6.85-6.87 (m, 2 H), 7.15-7.26 (s, 1 H), 7.44-7.47 (m, 2 H), 7.73-7.81 (m, 2 H). LCMS m/z=362, 364 [M+H]⁺.

10021576: 1-[(1-benzothiophen-2-yl)carbonyl]-6-chloro-1,2,3,4-tetrahydroquinoline

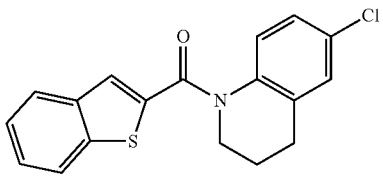 [SMILES: O=C(c1cc2ccccc2s1)N1CCCc2cc(Cl)ccc21]

¹H NMR (400 MHz, CDCl₃): δ ppm 2.03-2.10 (m, 2 H), 2.81-2.85 (t, 2 H), 3.93-3.97 (t, 2 H), 6.92-6.94 (d, 1 H), 6.95-6.98 (d, 1 H), 7.00 (s, 1 H), 7.34-7.40 (m, 3 H), 7.70-7.72 (d, 1 H), 7.77-7.80 (d, 1 H); LCMS m/z=327, 329 [M+H]⁺.

10021787: 1-({3-chlorothieno[2,3-b]pyridin-2-yl}carbonyl)-6-methyl-1,2,3,4-tetrahydroquinoline

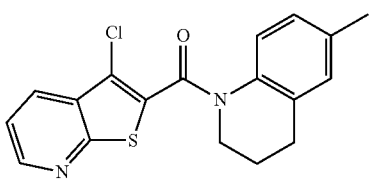 [SMILES: Cc1ccc2c(c1)CCCN2C(=O)c1sc2ncccc2c1Cl]

¹H NMR (400 MHz, CDCl₃): δ ppm 2.07-2.10 (m, 2 H), 2.23-2.31 (s, 3 H), 2.81-2.84 (t, 2 H), 3.93-3.96 (t, 2 H), 6.67-6.69 (br, 1 H), 6.97 (s, 1 H), 7.36-7.39 (m, 1 H), 7.97-8.00 (d, 1 H), 8.63-8.65 (s, 1 H); LCMS m/z=342, 344 [M+H]⁺.

10021788: 3-chloro-N-(2,4-dimethylphenyl)-N-methyl-1-benzothiophene-2-carboxamide

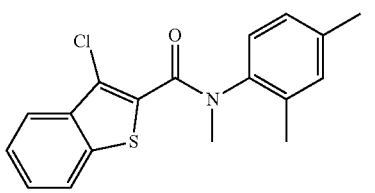

¹H NMR (400 MHz, CDCl₃): δ ppm 2.23 (s, 3 H), 2.29 (s, 3 H), 3.33-3.38 (s, 3 H), 6.86-6.88 (d, 1 H), 6.96 (s, 1 H), 7.04-7.06 (d, 1 H), 7.34-7.39 (m, 2 H), 7.77-7.79 (d, 2 H), 7.86-7.88 (d, 1 H); LCMS m/z=329, 331 [M+H]⁺.

10021789: 3-chloro-N-(5-methoxy-2-methylphenyl)-N-methyl-1-benzothiophene-2-carboxamide

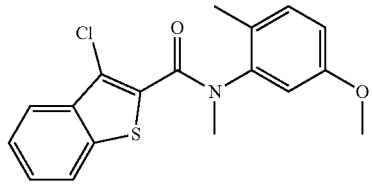 [SMILES: COc1ccc(C)c(N(C)C(=O)c2sc3ccccc3c2Cl)c1]

¹H NMR (400 MHz, CDCl₃): δ ppm 2.26-2.32 (s, 3 H), 3.34-3.40 (s, 3 H), 3.74 (s, 3 H), 6.69-6.71 (m, 2 H), 7.04-7.06 (d, 1 H), 7.35-7.41 (m, 2 H), 7.51-7.79 (d, 1 H), 7.85-7.90 (d, 1 H); LCMS m/z=345, 347 [M+H]⁺.

10021790: 1-[(3-chloro-1-benzothiophen-2-yl)methyl]-6-methyl-1,2,3,4-tetrahydroquinoline

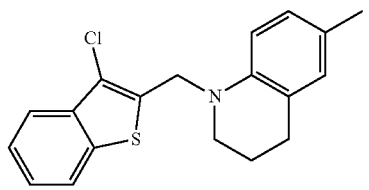 [SMILES: Cc1ccc2c(c1)CCCN2Cc1sc2ccccc2c1Cl]

¹H NMR (400 MHz, CDCl₃): δ ppm 1.98-2.04 (m, 2 H), 2.20 (s, 3 H), 2.75-2.78 (t, 2 H), 3.36-3.38 (t, 2 H), 4.70 (s, 2 H), 6.57-6.59 (d, 2 H), 6.82-6.84 (m, 2 H), 7.25 (s, 1 H), 7.30-7.34 (m, 2 H), 7.39-7.43 (m, 1 H), 7.67-7.69 (d, 1 H), 7.76-7.78 (d, 1 H); LCMS m/z=327, 329 [M+H]⁺.

10021791: 1-[(3-chloro-1-benzothiophen-2-yl)methyl]-6-fluoro-1,2,3,4-tetrahydroquinoline

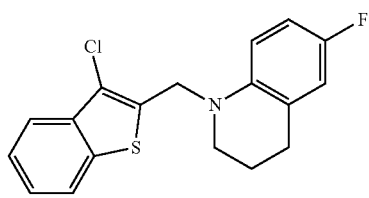 [SMILES: Fc1ccc2c(c1)CCCN2Cc1sc2ccccc2c1Cl]

¹H NMR (400 MHz, CDCl₃): δ ppm 2.00-2.02 (m, 2 H), 2.76-2.79 (t, 2 H), 3.36-3.38 (t, 2 H), 4.69 (s, 2 H), 6.54-6.58 (m, 1 H), 6.70-6.73 (m, 2 H), 7.33-7.36 (m, 1 H), 7.40-7.42 (m, 1 H), 7.68-7.77 (d, 1 H), 7.78-7.79 (d, 1 H); LCMS m/z=331, 333 [M+H]⁺.

10021792: 1-[(3-chloro-1-benzothiophen-2-yl)methyl]-6-methoxy-1,2,3,4-tetrahydroquinoline

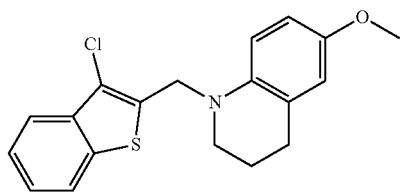 [SMILES: COc1ccc2c(c1)CCCN2Cc1sc2ccccc2c1Cl]

¹H NMR (400 MHz, CDCl₃): δ ppm 2.00-2.02 (m, 2 H), 2.77-2.80 (t, 2 H), 3.32-3.35 (t, 2 H), 3.72 (s, 3 H), 4.68 (s, 2

H), 6.61-6.62 (s, 3 H), 7.31-7.35 (m, 1 H), 7.40-7.43 (m, 1 H), 7.68-7.70 (d, 1 H), 7.76-7.78 (d, 1 H); LCMS m/z=343, 345 [M+H]⁺.

10021562: 1-[(1-benzothiophen-2-yl)carbonyl]-6-methyl-1,2,3,4-tetrahydroquinoline

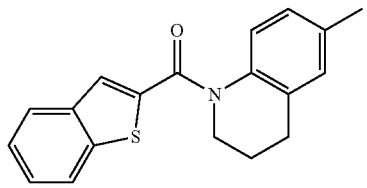 [SMILES: Cc1ccc2c(c1)CCCN2C(=O)c1cc2ccccc2s1]

¹H NMR (400 MHz, CDCl₃): δ ppm 2.04-2.07 (m, 2 H), 2.29 (s, 3 H), 2.79-2.82 (t, 2 H), 3.92-3.96 (t, 2 H), 6.75-6.77 (d, 1 H), 6.89-6.91 (d, 1 H), 7.02-7.03 (s, 1 H), 7.31-7.36 (m, 3 H), 7.67-7.69 (d, 1 H), 7.76-7.78 (d, 1 H); LCMS m/z=307 [M+H]⁺.

10021563: 1-[(1-benzothiophen-2-yl)carbonyl]-6-methoxy-1,2,3,4-tetrahydroquinoline

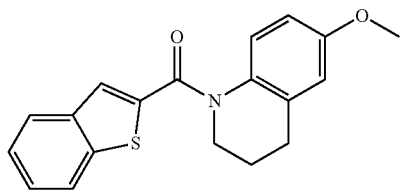 [SMILES: COc1ccc2c(c1)CCCN2C(=O)c1cc2ccccc2s1]

¹H NMR (400 MHz, CDCl₃): δ ppm 2.04-2.07 (m, 2 H), 2.79-2.83 (t, 2 H), 3.77 (s, 3 H), 3.92-3.96 (t, 2 H), 6.54 (d, 1 H), 6.76 (s, 1 H), 6.93-6.96 (d, 1 H), 7.31-7.36 (m, 3 H), 7.67-7.75 (d, 1 H), 7.77 (d, 1 H); LCMS m/z=323 [M+H]⁺.

10021564: 3-chloro-N-(2,4-dimethylphenyl)-1-benzothiophene-2-carboxamide

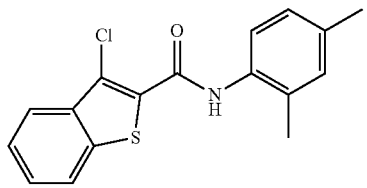 [SMILES: Cc1ccc(NC(=O)c2sc3ccccc3c2Cl)c(C)c1]

¹H NMR (400 MHz, CDCl₃): δ ppm 2.33-2.39 (d, 6 H), 7.07-7.09 (m, 2 H), 7.51-7.53 (d, 2 H), 7.86-7.88 (m, 2 H), 7.90-8.01 (d, 1 H), 8.76 (s, 1 H); LCMS m/z=315, 317 [M+H]⁺.

10021565: 3-chloro-N-(5-methoxy-2-methylphenyl)-1-benzothiophene-2-carboxamide

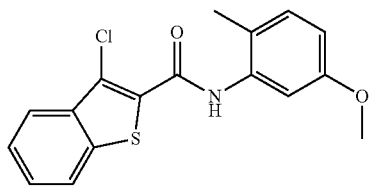 [SMILES: COc1ccc(C)c(NC(=O)c2sc3ccccc3c2Cl)c1]

¹H NMR (400 MHz, CDCl₃): δ ppm 2.29-2.37 (s, 3 H), 3.84 (s, 3 H), 6.67-6.70 (d, 1 H), 7.12-7.14 (d, 1 H), 7.52-7.54 (m, 2 H), 7.87-7.94 (m, 2 H), 7.97 (s, 1 H), 8.87 (s, 1 H); LCMS m/z=331, 333 [M+H]⁺.

10021566: 3-chloro-N-(4-methylphenyl)-1-benzothiophene-2-carboxamide

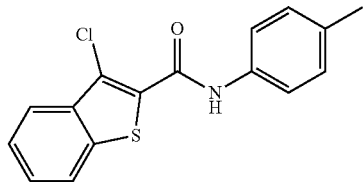 [SMILES: Cc1ccc(NC(=O)c2sc3ccccc3c2Cl)cc1]

¹H NMR (400 MHz, CDCl₃): δ ppm 2.36 (s, 3 H), 7.19-7.26 (d, 2 H), 7.51-7.58 (m, 4 H), 7.86-7.93 (m, 2 H), 8.87 (s, 1 H); LCMS m/z=301, 303 [M+H]⁺.

10021343: 3-chloro-N-methyl-N-(4-methylphenyl)-1-benzothiophene-2-carboxamide

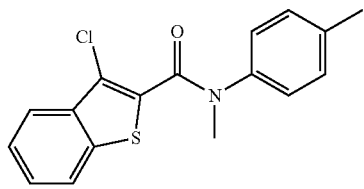 [SMILES: Cc1ccc(N(C)C(=O)c2sc3ccccc3c2Cl)cc1]

¹H NMR (400 MHz, CDCl₃): δ ppm 2.25 (s, 3 H), 3.49 (s, 3 H), 7.02-7.10 (m, 4 H), 7.36-7.39 (m, 2 H), 7.66-7.74 (m, 2 H); LCMS m/z=315, 317 [M+H]⁺.

10021568: 1-[(3-chloro-1-benzothiophen-2-yl)carbonyl]-6-fluoro-1,2,3,4-tetrahydroquinoline

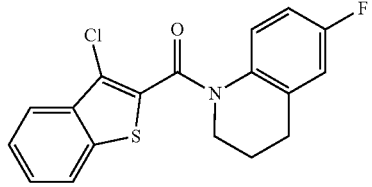 [SMILES: O=C(c1sc2ccccc2c1Cl)N1CCCc2cc(F)ccc21]

¹H NMR (400 MHz, CDCl₃): δ ppm 2.07-2.10 (m, 2 H), 2.85-2.88 (t, 2 H), 3.92-3.95 (t, 2 H), 6.58-6.63 (br, 1 H), 6.86-6.89 (m, 1 H), 7.44-7.46 (m, 2 H), 7.73-7.79 (m, 1 H), 7.80-7.81 (m, 1 H); LCMS m/z=345, 347 [M+H]⁺.

10021569: 1-[(1-benzothiophen-2-yl)carbonyl]-6-fluoro-1,2,3,4-tetrahydroquinoline

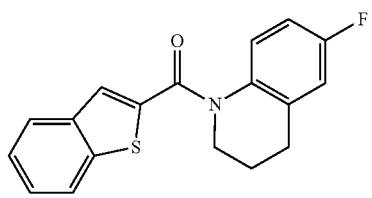 [SMILES: O=C(c1cc2ccccc2s1)N1CCCc2cc(F)ccc21]

¹H NMR (400 MHz, CDCl₃): δ ppm 2.03-2.10 (m, 2 H), 2.82-2.85 (t, 2 H), 3.94-3.97 (t, 2 H), 6.67-6.70 (m, 1 H), 6.71-6.94 (m, 1 H), 6.95-7.03 (m, 1 H), 7.32-7.69 (m, 3 H), 7.71-7.77 (d, 2 H), 7.79 (d, 1 H); LCMS m/z=311 [M+H]+.

10021339: 3-chloro-N-methyl-N-phenyl-1-benzothiophene-2-carboxamide

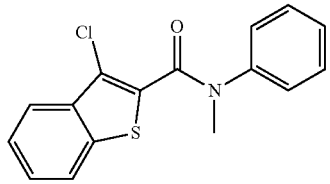 [SMILES: CN(C(=O)c1sc2ccccc2c1Cl)c1ccccc1]

¹H NMR (400 MHz, CDCl₃): δ ppm 3.52 (s, 3 H), 7.16-7.26 (m, 7 H), 7.36-7.39 (m, 2 H), 7.66-7.74 (m, 2 H); LCMS m/z=301, 303 [M+H]+.

10021382: 1-[(3-chloro-6-methyl-1-benzothiophen-2-yl)carbonyl]-6-methyl-1,2,3,4-tetrahydroquinoline

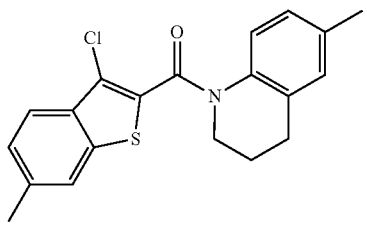 [SMILES: Cc1ccc2c(c1)CCCN2C(=O)c1sc2cc(C)ccc2c1Cl]

¹H NMR (400 MHz, CDCl₃): δ ppm 2.02-2.10 (m, 2 H), 2.23 (s, 3 H), 2.48 (s, 3 H), 2.76-2.83 (m, 2 H), 3.91-3.94 (m, 2 H), 6.66-6.69 (m, 1 H), 6.84 (br, 1 H), 6.95-7.01 (s, 1 H), 7.22-7.26 (m, 1 H), 7.51-7.61 (m, 2 H); LCMS m/z=355, 357 [M+H]+.

10021391: 1-[(3-chloro-1-benzothiophen-2-yl)carbonyl]-1,2,3,4-tetrahydroquinoline

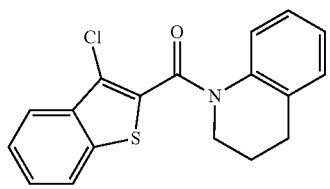 [SMILES: O=C(c1sc2ccccc2c1Cl)N1CCCc2ccccc21]

¹H NMR (400 MHz, CDCl₃): δ ppm 2.08-2.11 (m, 2 H), 2.86-2.89 (t, 2 H), 3.94-3.98 (t, 2 H), 6.86-7.04 (m, 3 H), 7.15-7.17 (m, 1 H), 7.42-7.44 (m, 2 H), 7.71-7.78 (m, 1 H), 7.79-7.80 (m, 1 H); LCMS m/z=327, 329 [M+H]+.

10021392: 1-[(3-chloro-1-benzothiophen-2-yl)carbonyl]-6-methyl-1,2,3,4-tetrahydroquinoline

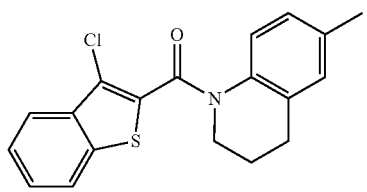 [SMILES: Cc1ccc2c(c1)CCCN2C(=O)c1sc2ccccc2c1Cl]

¹H NMR (400 MHz, CDCl₃): δ ppm 2.06-2.09 (m, 2 H), 2.23 (s, 3 H), 2.81-2.84 (t, 2 H), 3.92-3.95 (t, 2 H), 6.67-6.69 (br, 1 H), 6.83-6.86 (br, 1 H), 6.96 (s, 1 H), 7.72-7.74 (d, 2 H), 7.77-7.80 (m, 2 H); LCMS m/z=341, 343 [M+H]+.

10021393: 1-[(3-chloro-1-benzothiophen-2-yl)carbonyl]-6-methoxy-1,2,3,4-tetrahydroquinoline

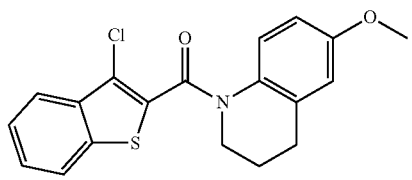 [SMILES: COc1ccc2c(c1)CCCN2C(=O)c1sc2ccccc2c1Cl]

¹H NMR (400 MHz, CDCl₃): δ ppm 206-2.09 (t, 2 H), 2.82-2.86 (t, 2 H), 3.72 (s, 3 H), 3.91-3.95 (t, 2 H), 6.44 (br, 1 H), 6.69 (s, 1 H), 7.42-7.44 (d, 2 H), 7.72-7.79 m, 2H); LCMS m/z=357, 359 [M+H]+.

10021394: 3-chloro-N-phenyl-1-benzothiophene-2-carboxamide

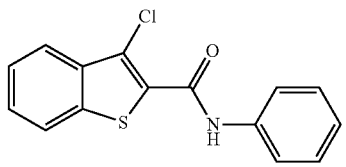 [SMILES: O=C(Nc1ccccc1)c1sc2ccccc2c1Cl]

¹H NMR (400 MHz, CDCl₃): δ ppm 7.18-7.21 (m, 1 H), 7.38-7.40 (m, 2 H), 7.42-7.54 (m, 2 H), 7.68-7.86 (m, 2 H), 7.88-7.93 (m, 2 H), 8.92 (s, 1 H); LCMS m/z=287, 289 [M+H]+.

10021395: 1[(1-benzothiophen-2-yl)carbonyl]-1,2,3,4-tetrahydroquinoline

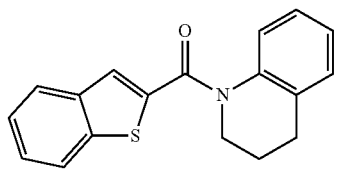 [SMILES: O=C(c1cc2ccccc2s1)N1CCCc2ccccc21]

¹H NMR (400 MHz, CDCl₃): δ ppm 2.06-2.09 (m, 2 H), 2.83-2.87 (t, 2 H), 3.95-3.98 (t, 2 H), 6.94-6.97 (m, 1 H), 7.01-708 (m, 1 H), 7.09-7.11 (m, 1 H), 7.21-7.26 (m, 1 H), 7.28-7.36 (m, 3 H), 7.66-7.76 (d, 1 H), 7.78 (d, 1 H); LCMS m/z=293 [M+H]+.

10021396: 1-[(3-chloro-1H-indol-2-yl)carbonyl]-6-methyl-1,2,3,4-tetrahydroquinoline

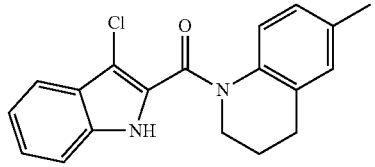 [SMILES: Cc1ccc2c(c1)CCCN2C(=O)c1[nH]c2ccccc2c1Cl]

¹H NMR (400 MHz, CDCl₃): δ ppm 2.04-2.08 (m, 2 H), 2.26 (s, 3 H), 2.82-2.86 (t, 2 H), 3.95-3.98 (t, 2 H), 6.72-6.74 (m, 1 H), 6.79-6.81 (m, 1 H), 6.98 (s, 1 H), 7.14-7.18 (m, 1 H), 7.28-7.32 (m, 1 H), 7.36-7.52 (d, 1 H), 7.53 (d, 1 H), 8.83 (s, 1 H); LCMS m/z=324, 326 [M+H]⁺.

10021397: 1-[(3-chloro-6-fluoro-1-benzothiophen-2-yl)carbonyl]-6-methyl-1,2,3,4-tetrahydroquinoline

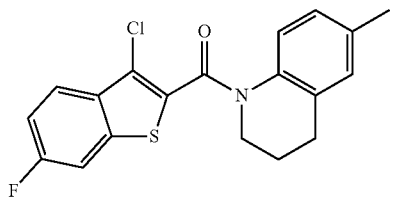 [SMILES: Cc1ccc2c(c1)CCCN2C(=O)c1sc2cc(F)ccc2c1Cl]

¹H NMR (400 MHz, CDCl₃): δ ppm 2.06-2.09 (m, 2 H), 2.24 (s, 3 H), 2.80-2.84 (t, 2 H), 3.91-3.95 (t, 2 H), 6.68-6.70 (m, 1 H), 6.80 (br, 1 H), 6.97 (s, 1 H), 7.15-7.20 (m, 1 H), 7.45-7.48 (d, 1H), 7.66-7.69 (m, 1H); LCMS m/z=359, 361 [M+H]⁺.

10021398: 6-methyl-1-[(3-methyl-1-benzothiophen-2-yl)carbonyl]-1,2,3,4-tetrahydroquinoline

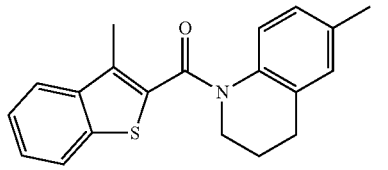 [SMILES: Cc1ccc2c(c1)CCCN2C(=O)c1sc2ccccc2c1C]

¹H NMR (400 MHz, CDCl₃): δ ppm 2.03-2.07 (m, 2 H), 2.13 (s, 3 H), 2.23 (s, 3 H), 2.79-2.82 (m, 2 H), 3.91-3.94 (t, 2 H), 6.66-6.68 (m, 1 H), 6.80-6.82 (m, 1 H), 6.96 (s, 1 H), 7.35-7.37 (m, 2 H), 7.60-7.63 (m, 1 H), 7.76-7.78 (m, 1 H); LCMS m/z=321 [M+H]⁺.

10022790: 3-(3-chloro-1-benzothiophen-2-yl)-1-(1,2,3,4-tetrahydronaphthalen-1-yl)urea

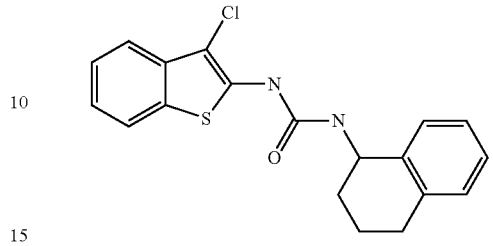

¹H NMR (300 MHz, CDCl₃): δ ppm 1.83-1.89 (m, 3 H), 2.06-2.10 (m, 1 H), 2.75-2.80 (m, 2 H), 5.11-5.13 (m, 1 H), 5.23-5.26 (m, 1 H), 7.07-7.12 (m, 3 H), 7.16-7.19 (m, 1 H), 7.35-7.41 (m, 2 H), 7.59-7.62 (d, 1 H), 7.69-7.72 (d, 1 H) LCMS m/z 357, 359 [M+H]⁺.

Appendix B: Preparation of Substituted Benzothiophene Derivatives (M6-Series)

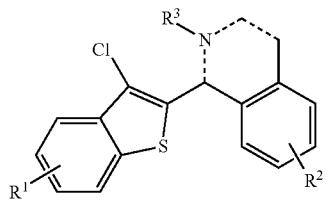

1. Synthetic Route

The general synthetic route of this template is summarized in Scheme 1

Scheme 1

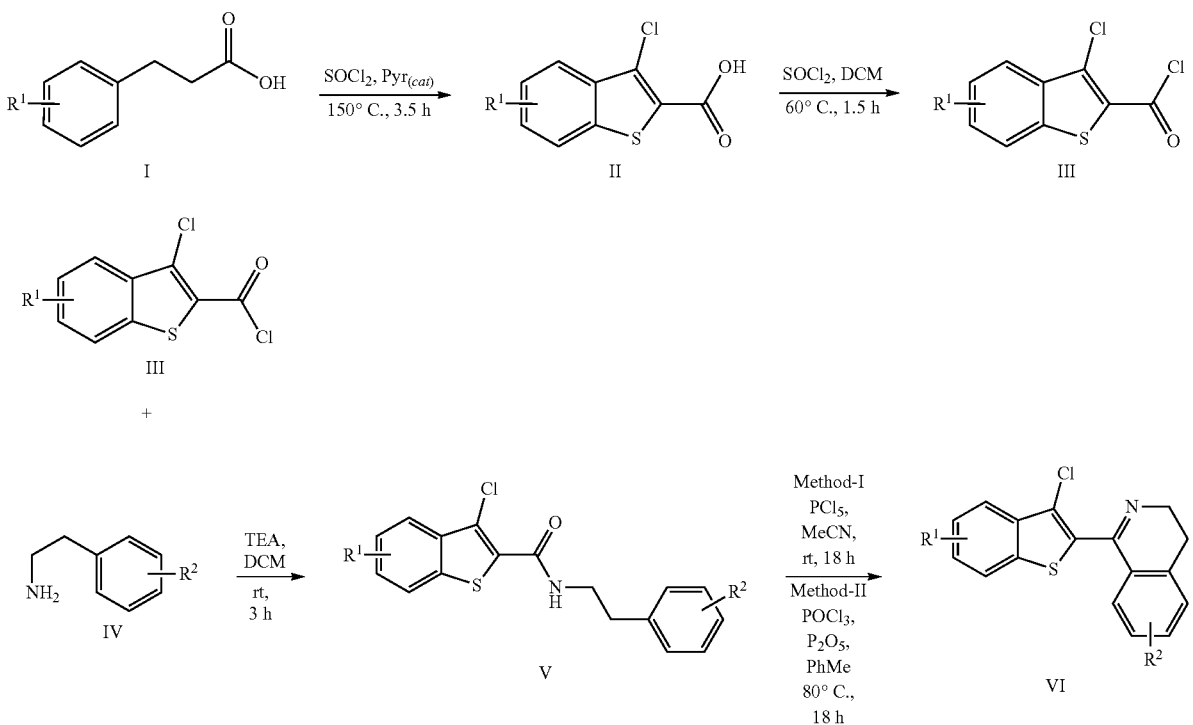

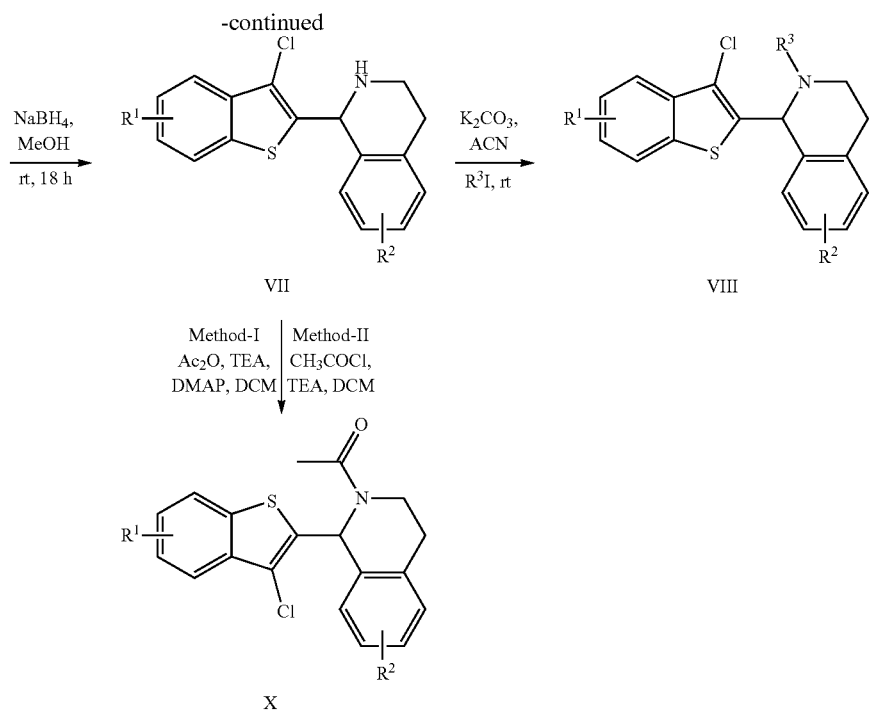

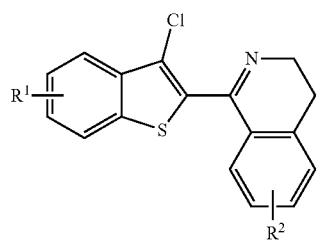

VI

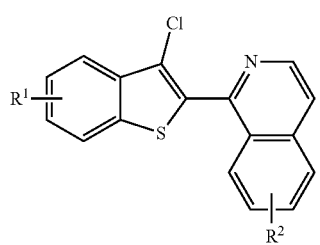

IX

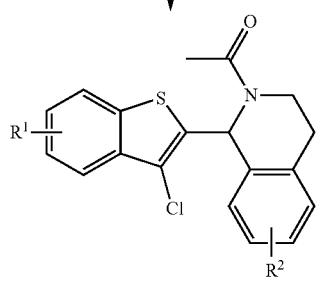

X

2.1.1 Synthetic Protocol
2.2.1 Preparation of Substituted Benzothiophene Derivative

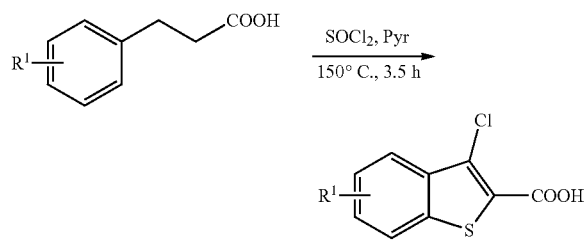

Condition—Acid (1 eq), SOCl$_2$ (4.5 eq), Pyridine (0.1 eq), 150° C., 3.5 hr

Procedure—

Thionyl chloride (4.5 eq.) was added dropwise to a round-bottom flask containing a mixture of hydro-cinnamic acid (1 eq.) and pyridine (0.1 eq.) heated to 150° C. TLC after 3 hours showed complete consumption of starting material. The reaction mixture was cooled to rt and water (6 vol), 35% HCl (0.6 vol), and THF (10 vol) were added and the mixture heated at 60° C. for 30 minutes. After 30 minutes, the THF was removed in vacuo and the obtained precipitate was filtered, dissolved in a 3:1 water:ethanol mixture (20 vol) and heated at 90° C. for 1 hour. After 1 hour, the solution was cooled to rt and allowed to stir overnight. The separated solid was filtered and recrystallized from toluene to get (Yield:—35%) chlorobenzothiophene-2-carboxylic acid.

TABLE 1

| Sr. No | Benzothiophene Acid | Purity (%) | Yield (%) |
|---|---|---|---|
| 1 | 3-chloro-1-benzothiophene-2-carboxylic acid | 95 | 35 |
| 2 | 3-chloro-6-methyl-1-benzothiophene-2-carboxylic acid | 74 | 57 |
| 3 | 3-chloro-6-fluoro-1-benzothiophene-2-carboxylic acid | 92 | 69 |

TABLE 1-continued

| Sr. No | Benzothiophene Acid | Purity (%) | Yield (%) |
|---|---|---|---|
| 4 | 3-chloro-6-(trifluoromethyl)-1-benzothiophene-2-carboxylic acid | 98 | 19 |
| 5 | 3-chloro-5-methoxy-1-benzothiophene-2-carboxylic acid | 95 | 77 |
| 6 | 3-chloro-4-methyl-1-benzothiophene-2-carboxylic acid | 98 | 30 |
| 7 | 3-chloro-6-methoxy-1-benzothiophene-2-carboxylic acid | 90 | 48 |
| 8 | 3-chloro-4-fluoro-1-benzothiophene-2-carboxylic acid | 100 | 11 |
| 9 | 3-chloro-5-fluoro-1-benzothiophene-2-carboxylic acid | 95 | 54 |
| 10 | 3-chloro-5,6-dimethoxy-1-benzothiophene-2-carboxylic acid | 40 | 46 |

2.2.2a
2b Synthesis of Amides

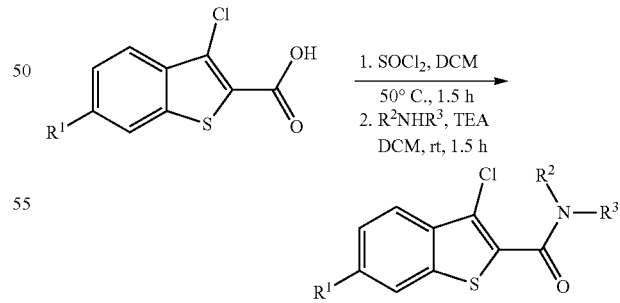

Thionyl chloride (5 eq.) was slowly added to a solution of acid (1 eq.) in dichloroethane (10 vol) in a dried, nitrogen-purged round-bottom flask fitted with a stirbar. The reaction was maintained at 50-60° C. for 5-6 hours. The reaction was monitored by quenching with methanol and looking at the methyl ester by LCMS. After completion of the reaction, solvent and thionyl chloride were removed in vacuo. The acid chloride was taken to the next step without further purifications. To a solution of the phenethylamine (0.9 eq.) and triethylamine (2 eq.) in dichloroethane (10 vol) was added a solution of the acid chloride (1 eq.) in dichloroethane (15 vol). The reaction was allowed to shake at room temperature. After completion of reaction (as monitored by HPLCMS) the reaction mixture was diluted with dichloroethane (30 vol), washed with water (40 vol×2 times), brine (20 vol), dried over anh. sodium sulfate and concentrated in vacuo to get the desired product.

1.2.2 Synthesis of Imine:—

Method 1

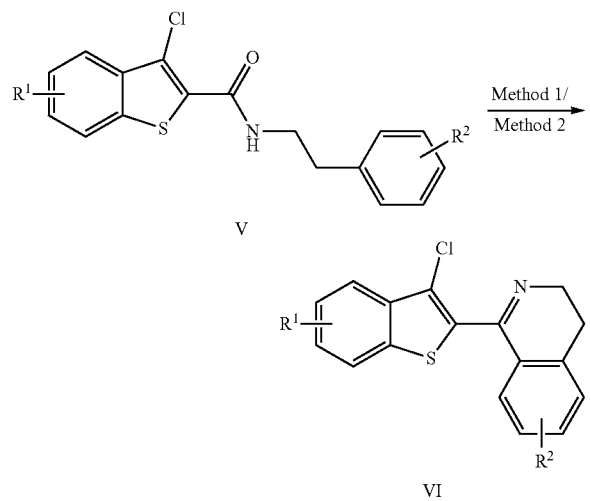

Phosphorus pentachloride (3 eq.) was added to a solution of the amide (1 eq.) in acetonitrile (20 vol) at room temperature. The reaction mixture was stirred for 18 hours at room temperature. On completion of the reaction (HPLC-MS and TLC) the reaction was basified to pH>12 with aq. NaOH and extracted with ethyl acetate (25 vol×2 times). The combined organic layers were washed with water (15 vol×2 times), saturated brine (15 vol), dried over anhydrous sodium sulfate and concentrated in vacuo to get the crude product VI. The crude product was then purified by flash chromatography to get the purified products in yields of 40-45%.

Method 2

Phosphorus oxychloride (5 eq.) and $P_2O_5$ (5 eq) was added to a solution of the amide (1 eq) in acetonitrile (20 vol) at room temperature. The reaction mixture was stirred for 18 hours at room temperature. On completion of the reaction (HPLC-MS and TLC) the reaction was basified to pH>12 with aq. NaOH and extracted with ethyl acetate (25 vol×2 times). The combined organic layers were washed with water (15 vol×2 times), saturated brine (15 vol), dried over anhydrous sodium sulfate and concentrated in vacuo to get the crude product VI. The crude product was then purified by flash chromatography to get the purified products in yields of 40-45%. Yield of compounds is given in Table 2.

TABLE 2

| Entry | Comp ID | $R^1$ | $R^2$ | $R^3$ | $R^4$ | Method | Purity (%) | Yield (%) |
|---|---|---|---|---|---|---|---|---|
| 1 | 10021400 | H | H | OMe | OMe | 1 | 96.2 | 87 |
| 2 | 10024133 | 4-Me | H | OMe | OMe | 2 | 100 | 60 |
| 3 | 10024131 | 6-OMe | H | OMe | OMe | 2 | 100 | 60 |
| 4 | 10024134 | 5-OMe | H | OMe | OMe | 2 | 100 | 60 |
| 5 | 10023510 | H | H | Me | H | 2 | 98 | 90 |
| 6 | 10021795 | H | H | F | H | 2 | 97 | 93 |
| 7 | 10021399 | H | H | OMe | H | 1 | 96 | 90 |
| 8 | 10024132 | 6-$CF_3$ | H | OMe | OMe | 2 | 100 | 60 |
| 9 | 10022796 | 4-Me | OMe | H | H | 2 | 100 | 60 |
| 10 | 10022797 | 4-Me | H | H | Cl | 2 | 93 | 60 |
| 11 | 10022798 | 4-Me | F | H | H | 2 | 100 | 71 |
| 12 | 10022799 | 4-Me | H | H | OMe | 2 | 100 | 60 |
| 13 | 10022801 | 6-OMe | OMe | H | H | 2 | 93 | 60 |
| 14 | 10022802 | 5,6-OMe | H | OMe | OMe | 2 | 87 | 60 |
| 15 | 10022791 | H | OMe | H | H | 2 | 100 | 80 |
| 16 | 10022792 | H | H | H | Cl | 2 | 100 | 80 |
| 17 | 10022793 | H | F | H | H | 2 | 100 | 78 |
| 18 | 10022794 | H | H | H | OMe | 2 | 100 | 80 |
| 19 | 10022795 | H | Cl | H | H | 2 | 100 | 80 |

1.2.3 Reduction of Imine:—

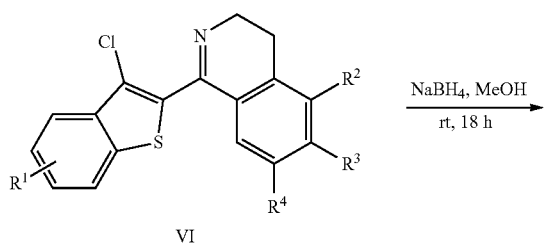

To a solution of the imine (1 eq.) in methanol (20 vol) was added NaBH₄ (1 eq.) at room temperature. The On completion of the reaction (HPLC-MS and TLC), water (10 vol) was added to the reaction and the methanol was removed in vacuo. The aqueous layer was extracted with ethyl acetate (2×20 vol) and the organic layer was washed with water (2×10 vol), saturated brine (10 vol), dried over anhydrous sodium sulfate and concentrated in vacuo to get the desired product VII. The crude product was triturated with pentane to get pure product VII (Yield 70-80%). The results for all amine compounds are given in Table 3.

TABLE 3

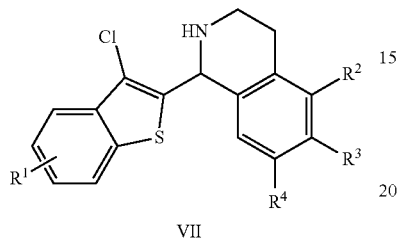

| Entry | Comp ID | $R^1$ | $R^2$ | $R^3$ | $R^4$ | Purity (%) | Yield (%) |
|---|---|---|---|---|---|---|---|
| 1 | 10021380 | H | H | OMe | OMe | 97 | 80 |
| 2 | 10024137 | 4-Me | H | OMe | OMe | 100 | 80 |
| 3 | 10024934 | 5-OMe | H | OMe | OMe | 98 | 75 |
| 4 | 10024136 | 6-CF₃ | H | OMe | OMe | 95 | 70 |
| 5 | 10024135 | 6-OMe | H | OMe | OMe | 100 | 81 |
| 6 | 10024001 | 4-F | H | OMe | OMe | 100 | 65 |
| 7 | 10021381 | H | H | OMe | H | 100 | 78 |
| 8 | 10023500 | H | H | Me | H | 97 | 83 |
| 9 | 10021796 | H | H | F | H | 96 | 80 |
| 10 | 10022805 | H | OMe | H | H | 100 | 72 |
| 11 | 10022806 | H | H | H | Cl | 100 | 80 |
| 12 | 10022807 | H | F | H | H | 100 | 81 |
| 13 | 10022808 | H | H | H | OMe | 100 | 70 |
| 14 | 10022809 | H | Cl | H | H | 100 | 80 |
| 15 | 10022811 | 4-Me | F | H | H | 94 | 85 |
| 16 | 10022812 | 4-Me | H | H | OMe | 100 | 82 |
| 17 | 10022810 | 5,6-OMe | H | OMe | OMe | 85 | 80 |

1.2.4 N-alkylation of 1,2,3,4-tetrahydroisoquinoline

Alkyl iodide (1 eq.) was added dropwise to a solution of the 1,2,3,4-tetrahydroisoquinoline (1 eq.) and anhydrous potassium carbonate (3 eq.) in dry acetonitrile (20 vol). The reaction was stirred at room temperature until TLC showed complete consumption of starting amine (2-18 hours). Water (20 vol) was added to the reaction and it was extracted with ethyl acetate (15 vol×3 times). The organic lay-er was washed with water (10 vol×2 times), saturated brine (10 vol), dried over anhydrous sodium sulfate and the solvent removed in vacuo to get the crude product VIII. The crude compound was purified by flash column chromatography.

1.2.5 N-acylation

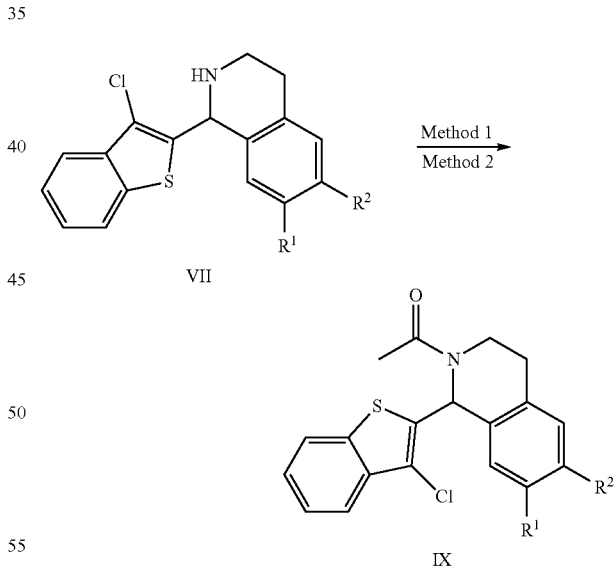

Method 1

Acetic anhydride (1.5 eq.) was added slowly to a stirred solution of amine VII (1 eq.), triethylamine ((3 eq.) and N,N-dimethylaminopyridine (0.1 eq.) in dichloromethane (10 vol) at room temperature. On completion of the reaction (HPLC-MS and TLC), water (10 vol) was added to the reaction and it was extracted with DCM (20 vol×2 times). The organic layer was washed with water (10 vol×2 times), saturated brine (10 vol), dried over anhydrous sodium sulfate and concentrated in vacuo to get the desired product IX.

Method 2

Acetyl chloride (1 eq.) was added slowly to a stirred solution of amine VII (1 eq.), triethylamine (3 eq.) and N,N-dimethylaminopyridine (0.1 eq.) in dichloromethane (10 vol) at room temperature. On completion of the reaction (HPLC-MS and TLC), an additional amount of dichloromethane (10 vol) was added to the reaction and it was washed with dil. HCl 1N (10 vol×2 times), saturated $NaHCO_3$ (10 vol) and water (10 vol). The organic layer was dried over anhydrous sodium sulfate and concentrated in vacuo to give the crude product. The crude compound was purified by flash silica gel chromatography. The results for all substituted N-alkylated and N-acylated compounds are given in Table 4.

TABLE 4

| Entry | Comp ID | $R^1$ | $R^2$ | $R^3$ | Method | Purity (%) | Yield (%) |
|---|---|---|---|---|---|---|---|
| 1 | 10021156 | OMe | OMe | Me | | 96 | 49 |
| 2 | 10021794 | H | OMe | Me | | 97 | 80 |
| 3 | 10021797 | H | F | Me | | 96 | 57 |
| 4 | 10022813 | OMe | OMe | Et | | 100 | 82 |
| 5 | 10023512 | H | Me | Me | | 100 | 80 |
| 6 | 10024140 | OMe | OMe | Ac | 1 | 95 | 74 |
| 7 | 10024141 | H | F | Ac | 2 | 100 | 80 |
| 8 | 10024142 | H | Me | Ac | 2 | 97 | 88 |

1.2.6 Aromatization of Imine—

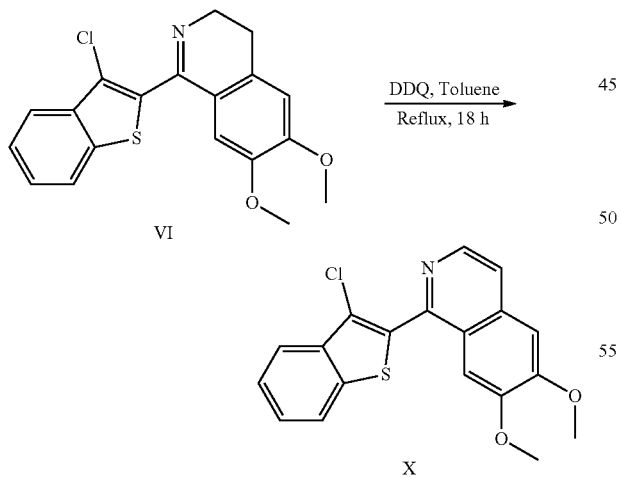

Procedure—

To a solution of imine VI (1 eq.) in toluene (10 vol), was added 2,5-dichloro-3,6-dicyano-1,4-benzoquinone (DDQ) (5 eq.) under stirring. The resulting solution was refluxed for 18 hours. On completion of the reaction (HPLC-MS and TLC), the mass was allowed to come to room temperature and filtered. The crude solid was washed with toluene and purified by recrystallization from ethanol to get X (40%).

10021400: 1-(3-chloro-1-benzothiophen-2-yl)-6,7-dimethoxy-3,4-dihydroisoquinoline

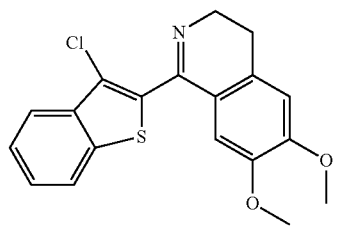 [SMILES: COc1cc2c(cc1OC)C(c1sc3ccccc3c1Cl)=NCC2]

$^1$H NMR (400 MHz, $CDCl_3$): δ ppm 2.76-2.80 (t, 2 H), 3.75 (s, 3 H), 3.88-3.92 (m, 2 H), 3.96 (s, 3 H), 6.78 (s, 1 H), 6.88 (s, 1 H), 7.47-7.50 (m, 2 H), 7.85-7.89 (m, 2 H); LCMS m/z=357, 359 $[M+H]^+$.

10021795: 1-(3-chloro-1-benzothiophen-2-yl)-6-fluoro-3,4-dihydroisoquinoline

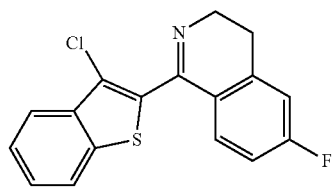 [SMILES: Fc1ccc2c(c1)CCN=C2c1sc2ccccc2c1Cl]

$^1$H NMR (400 MHz, $CDCl_3$): δ ppm 2.83-2.87 (t, 2 H), 3.91-3.95 (t, 2 H), 6.94-7.00 (m, 2 H), 7.30-7.34 (m, 1 H), 7.46-7.50 (m, 2 H), 7.84-7.88 (m, 2 H); LCMS m/z=315, 317 $[M+H]^+$.

10023510: 1-(3-chloro-1-benzothiophen-2-yl)-6-methyl-3,4-dihydroisoquinoline

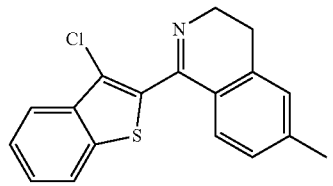 [SMILES: Cc1ccc2c(c1)CCN=C2c1sc2ccccc2c1Cl]

$^1$H NMR (400 MHz, $CDCl_3$): δ ppm 2.39 (s, 3 H), 2.80-2.83 (t, 2 H), 3.90-3.94 (m, 2 H), 7.05-7.09 (m, 2 H), 7.19-7.26 (m, 1 H), 7.45-7.49 (m, 2 H), 7.83-7.88 (m, 2 H); LCMS m/z=311, 313 $[M+H]^+$.

10021399: 6-methoxy-1-(3-methyl-1-benzothiophen-2-yl)-3,4-dihydroisoquinoline

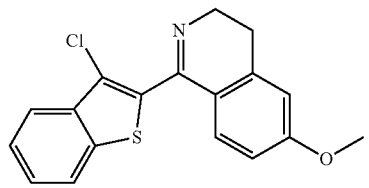 [SMILES: COc1ccc2c(c1)CCN=C2c1sc2ccccc2c1Cl]

¹H NMR (400 MHz, CDCl₃): δ ppm 2.81-2.85 (t, 2 H), 3.54 (s, 3 H), 3.86-3.93 (m, 2 H), 6.74-6.80 (m, 2 H), 7.25-7.44 (m, 2 H), 7.44-7.50 (m, 2 H), 7.84-7.88 (m, 2 H); LCMS m/z=307, 309 [M+H]⁺.

10022794: 1-(3-chloro-1-benzothiophen-2-yl)-7-methoxy-3,4-dihydroisoquinoline

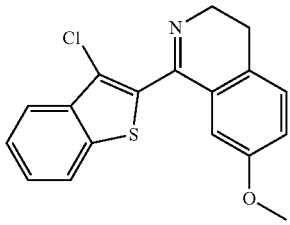

¹H NMR (300 MHz, CDCl₃): δ ppm 2.76-2.80 (t, 2 H), 3.72 (s, 3 H), 3.90-3.95 (q, 2 H), 6.88 (s, 1 H), 6.95-6.99 (d, 1 H), 7.46-7.50 (m, 2 H), 7.84-7.89 (m, 2 H); LCMS m/z 328, 330, 331 [M+H]⁺.

10022791: 1-(3-chloro-1-benzothiophen-2-yl)-5-methoxy-3,4-dihydroisoquinoline

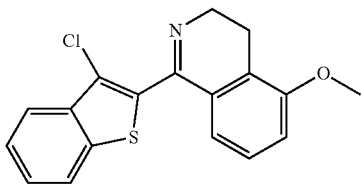 [SMILES: COc1cccc2c1CCN=C2c1sc2ccccc2c1Cl]

¹H NMR (300 MHz, CDCl₃): δ ppm 1.25 (s, 2 H), 2.81-2.86 (t, 2 H), 3.91 (s, 3 H), 6.93-6.5 (d, 1 H), 6.99-7.00 (d, 1 H), 7.21-7.24 (d, 1 H), 7.42-7.5 (m, 2 H), 7.83-7.88 (m, 2 H); LCMS m/z 328, 330, 331 [M+H]⁺

10022792: 7-chloro-1-(3-chloro-1-benzothiophen-2-yl)-3,4-dihydroisoquinoline

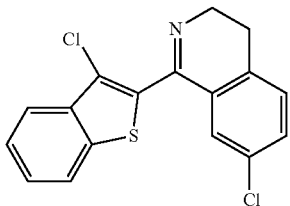 [SMILES: Clc1ccc2c(c1)C(c1sc3ccccc3c1Cl)=NCC2]

¹H NMR (300 MHz, CDCl₃): δ ppm 2.79-2.84 (m, 2 H), 3.92-3.97 (m, 2 H), 7.21-7.25 (m, 1 H), 7.30 (s, 1 H), 7.39-7.40 (d, 1 H), 7.48-7.54 (m, 2 H), 7.85-7.91 (m, 2 H); LCMS m/z 331, 335 [M+H]⁺

10022795: 5-chloro-1-(3-chloro-1-benzothiophen-2-yl)-3,4-dihydroisoquinoline

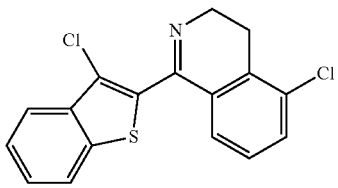 [SMILES: Clc1cccc2c1CCN=C2c1sc2ccccc2c1Cl]

¹H NMR (300 MHz, CDCl₃): δ ppm 2.94-2.99 (t, 2 H), 3.94-3.99 (m, 2 H), 7.18-7.24 (m, 3 H), 7.45-7.52 (m, 3 H), 7.84-7.90 (m, 2 H); LCMS m/z 331, 335 [M+H]⁺.

10022793: 1-(3-chloro-1-benzothiophen-2-yl)-5-fluoro-3,4-dihydroisoquinoline

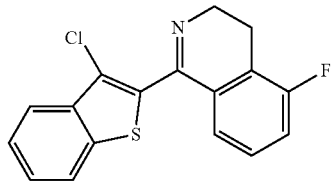 [SMILES: Fc1cccc2c1CCN=C2c1sc2ccccc2c1Cl]

¹H NMR (300 MHz, CDCl₃): δ ppm 2.86-2.91 (m, 2 H), 3.93-3.98 (m, 2 H), 7.12-7.27 (m, 3 H), 7.45-7.52 (m, 2 H), 7.84-7.89 (m, 2 H); LCMS m/z 316, 318, 319 [M+H]⁺

10024133: 1-(3-chloro-4-methyl-1-benzothiophen-2-yl)-6,7-dimethoxy-3,4-dihydroisoquinoline

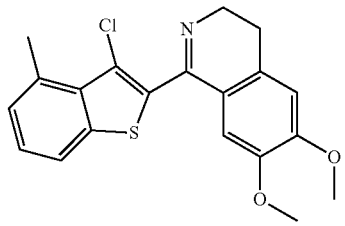 [SMILES: COc1cc2c(cc1OC)C(c1sc3cccc(C)c3c1Cl)=NCC2]

¹H NMR (300 MHz, CDCl₃): δ ppm 2.76-2.81 (t, 2 H), 2.88 (s, 3 H), 3.74 (s, 3 H), 3.88-3.93 (m, 2 H), 3.95 (s, 3 H), 6.77 (s, 1 H), 6.83 (s, 1 H), 7.16-7.19 (d, 1 H), 7.26-7.32 (m, 1 H), 7.68-7.70 (d, 1 H); LCMS m/z=371, 373 [M+H]⁺.

10024131: 1-(3-chloro-6-methoxy-1-benzothiophen-2-yl)-6,7-dimethoxy-3,4-dihydroisoquinoline

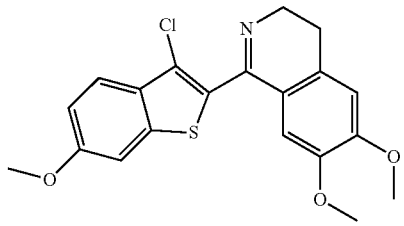

¹H NMR (300 MHz, CDCl₃): δ ppm 2.73-2.78 (t, 2 H), 3.76 (s, 3 H), 3.85-3.95 (m, 8 H), 6.77 (s, 1 H), 6.91 (s, 1 H), 7.08-7.11 (d, 1 H), 7.26-7.30 (s, 1 H), 7.73-7.76 (d, 1 H); LCMS [M+H]⁺ 387.06, (100%).
LCMS m/z=387, 389 [M+H]⁺.

10024134: 1-(3-chloro-5-methoxy-1-benzothiophen-2-yl)-6,7-dimethoxy-3,4-dihydroisoquinoline

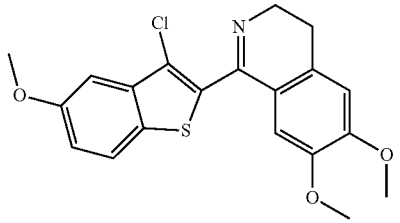

¹H NMR (300 MHz, CDCl₃): δ ppm 2.75-2.80 (t, 2 H), 3.73-3.75 (s, 3 H), 3.87-4.02 (m, 8 H), 6.78 (s, 1 H), 6.88 (s, 1 H), 7.09-7.13 (d, 1 H), 7.26-7.29 (s, 1 H), 7.70-7.73 (d, 1 H); LCMS m/z=387, 389 [M+H], [M+H]⁺.

10024132: 1-(3-chloro-6-methyl-1-benzothiophen-2-yl)-6,7-dimethoxy-3,4-dihydroisoquinoline

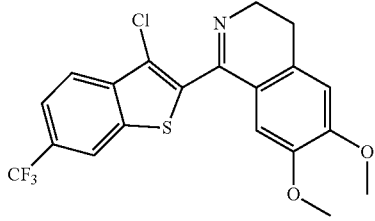 [SMILES: COc1cc2c(cc1OC)C(c1sc3cc(C(F)(F)F)ccc3c1Cl)=NCC2]

¹H NMR (300 MHz, CDCl₃): δ ppm 2.76-2.81 (t, 2 H), 3.74 (s, 3 H), 3.89-3.96 (m, 5 H), 6.79-6.82 (d, 2 H), 7.70-7.73 (d, 1 H), 7.98-8.00 (d, 2 H), 8.16 (s, 1 H); LCMS m/z=425, 427 [M+H]⁺.

10022802: 1-(3-chloro-5,6-dimethoxy-1-benzothiophen-2-yl)-6,7-dimethoxy-3,4-dihydroisoquinoline

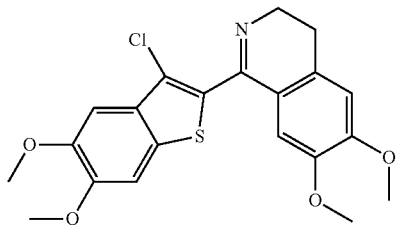

¹H NMR (300 MHz, CDCl₃): δ ppm 2.80-2.85 (m, 2 H), 3.85-4.03 (m, 14 H), 6.85 (s, 1 H), 7.30-7.34 (s, 1 H), 7.84 (s, 1 H); LCMS m/z 418, 420 [M+H]⁺

10022796: 1-(3-chloro-4-methyl-1-benzothiophen-2-yl)-5-methoxy-3,4-dihydroisoquinoline

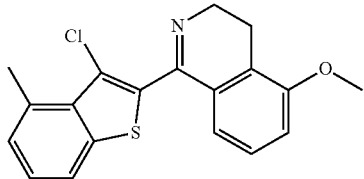 [SMILES: COc1cccc2c1CCN=C2c1sc2cccc(C)c2c1Cl]

¹H NMR (300 MHz, CDCl₃): δ ppm 2.81-3.03 (m, 5 H), 3.89 (s, 5 H), 6.89-6.92 (d, 1 H), 6.98-7.01 (d, 1 H), 7.15-7.31 (m, 3 H), 7.66-7.68 (d, 1 H); LCMS m/z 342, 344 [M+H]⁺

10022799: 1-(3-chloro-4-methyl-1-benzothiophen-2-yl)-7-methoxy-3,4-dihydroisoquinoline

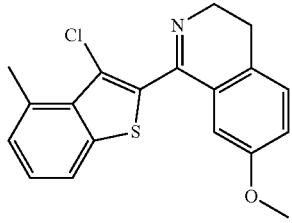 [SMILES: COc1ccc2c(c1)C(c1sc3cccc(C)c3c1Cl)=NCC2]

¹H NMR (300 MHz, CDCl₃): δ ppm 2.76-2.81 (t, 2 H), 2.88 (s, 3 H), 3.91-3.96 (t, 2 H), 6.83-6.84 (s, 1 H), 6.94-6.98 (m, 1 H), 7.16-7.20 (m, 2 H), 7.29-7.32 (d, 1 H), 7.66-7.79 (d, 1 H); LCMS m/z 342, 345 [M+H]⁺

10022798: 1-(3-chloro-4-methyl-1-benzothiophen-2-yl)-5-fluoro-3,4-dihydroisoquinoline

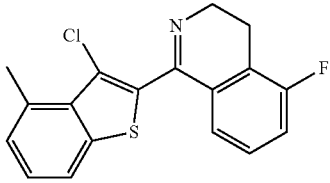 [SMILES: Cc1cccc2sc(C3=NCCc4c(F)cccc43)c(Cl)c12]

¹H NMR (300 MHz, CDCl₃): δ ppm 2.87-2.91 (m, 5 H), 3.93-3.99 (t, 2 H), 7.08-7.32 (m, 5 H), 7.67-7.69 (d, 1 H); LCMS m/z 3330, 332 [M+H]⁺

10022801: 1-(3-chloro-6-methoxy-1-benzothiophen-2-yl)-5-methoxy-3,4-dihydroisoquinoline

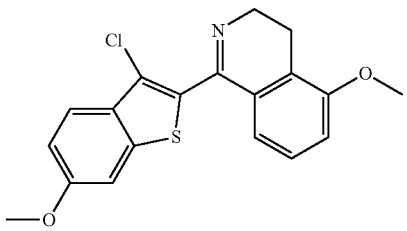

¹H NMR (300 MHz, CDCl₃): δ ppm 0.83-0.88 (t, 2 H), 2.79-2.84 (t, 2 H), 3.75-3.86 (m, 6 H), 6.91-7.07 (m, 2 H), 7.10 (d, 1 H), 7.10-7.22 (t, 1 H), 7.28-7.61 (m, 1 H), 7.71-7.74 (d, 1 H); LCMS m/z 358, 361 [M+H]⁺

10022797: 7-chloro-1-(3-chloro-4-methyl-1-benzothiophen-2-yl)-3,4-dihydroisoquinoline

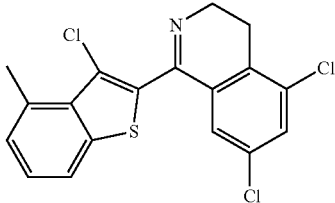 [SMILES: Cc1cccc2sc(C3=NCCc4c(Cl)cc(Cl)cc43)c(Cl)c12]

¹H NMR (300 MHz, CDCl₃): δ ppm 2.80-2.89 (m, 5 H), 3.92-3.97 (m, 1 H), 7.18-7.39 (m, 4 H), 7.68-7.70 (d, 1 H); LCMS m/z 345, 348 [M+H]⁺

10021380: 1-(3-chloro-1-benzothiophen-2-yl)-6,7-dimethoxy-1,2,3,4-tetrahydroisoquinoline

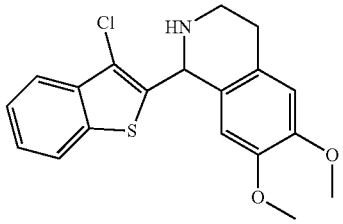 [SMILES: COc1cc2c(cc1OC)C(c1sc3ccccc3c1Cl)NCC2]

¹H NMR (400 MHz, CDCl₃): δ ppm 2.77-2.81 (m, 1 H), 2.94-2.98 (m, 1 H), 3.08-3.12 (m, 1 H), 3.32-3.35 (m, 1 H), 3.49 (s, 1 H), 3.68 (s, 3 H), 3.87 (s, 3 H), 5.72 (s, 1 H), 6.48 (s, 1 H), 6.64 (s, 1 H), 7.36-7.39 (m, 1 H), 7.43-7.45 (m, 1 H), 7.70-7.84 (d, 1 H), 7.86 (d, 1 H); LCMS m/z=359, 361 (M+H)⁺.

10021796: 1-(3-chloro-1-benzothiophen-2-yl)-6-fluoro-1,2,3,4-tetrahydroisoquinoline

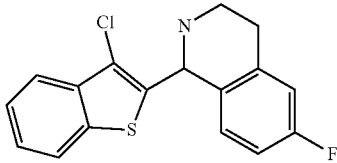 [SMILES: Fc1ccc2c(c1)CCNC2c1sc2ccccc2c1Cl]

¹H NMR (400 MHz, CDCl₃): δ ppm 2.83-2.87 (m, 1 H), 3.05-3.15 (m, 2 H), 3.34-3.38 (m, 1 H), 5.74 (s, 1 H), 6.76-6.78 (m, 1, 1 H), 6.79-6.86 (m, 1 H), 6.87-6.92 (m, 1 H), 7.37-7.39 (m, 1 H), 7.43-7.47 (m, 1 H), 7.70-7.72 (d, 1 H), 7.73-7.86 (d, 1 H); LCMS m/z=317, 319 [M+H]⁺.

10023500: 1-(3-chloro-1-benzothiophen-2-yl)-6-methyl-1,2,3,4-tetrahydroisoquinoline

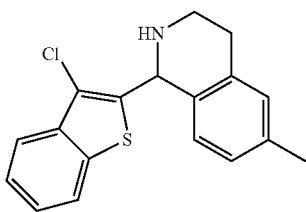 [SMILES: Cc1ccc2c(c1)CCNC2c1sc2ccccc2c1Cl]

¹H NMR (400 MHz, CDCl₃): δ ppm 2.30 (s, 3 H), 2.80-2.84 (m, 1 H), 3.04-3.06 (m, 1 H), 3.14-3.15 (m, 1 H), 3.35-3.38 (m, 1 H), 5.76 (s, 1 H), 6.83-6.90 (m, 1 H), 6.98 (s, 1 H), 7.33-7.37 (m, 1 H), 7.42-7.46 (m, 1 H), 7.68-7.69 (m, 1 H), 7.70-7.83 (d, 1 H), 7.85 (d, 1H); LCMS m/z=312, 314 [M+H]⁺.

10021381: 1-(3-chloro-1-benzothiophen-2-yl)-6-methoxy-1,2,3,4-tetrahydroisoquinoline

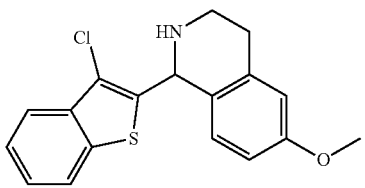 [SMILES: COc1ccc2c(c1)CCNC2c1sc2ccccc2c1Cl]

¹H NMR (400 MHz, CDCl₃): δ ppm 2.82-2.86 (m, 1 H), 3.03-3.05 (m, 2 H), 3.13-3.17 (m, 1 H), 3.33-3.37 (m, 1 H), 3.78 (s, 3 H), 5.73 (s, 1 H), 6.63-6.69 (m, 2 H), 6.87-6.89 (d, 1 H), 7.33-7.38 (m, 1 H), 7.42-7.46 (m, 1 H), 7.69-7.71 (d, 1 H), 7.83-7.85 (d, 1 H); LCMS m/z=329, 331 [M+H]⁺.

10022808: 1-(3-chloro-1-benzothiophen-2-yl)-7-methoxy-1,2,3,4-tetrahydroisoquinoline

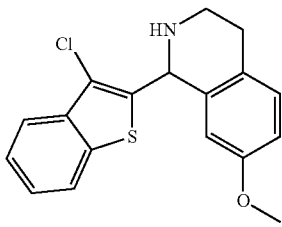 [SMILES: COc1ccc2c(c1)C(c1sc3ccccc3c1Cl)NCC2]

¹H NMR (300 MHz, CDCl₃): δ ppm 2.77-2.84 (m, 1 H), 3.00-3.03 (m, 1 H), 3.02-3.05 (m, 1 H), 3.33-3.40 (m, 1 H), 3.66 (s, 3 H), 5.76 (s, 1 H), 6.50-6.51 (s, 1 H), 6.74-6.78 (d, 1 H), 7.07-7.10 (m, 1 H), 7.36-7.42 (t, 1 H), 7.45-7.47 (t, 1 H), 7.69-7.72 (d, 1 H), 7.83-7.86 (d, 1 H); LCMS m/z 330, 332 [M+H]⁺

10022805: 1-(3-chloro-1-benzothiophen-2-yl)-5-methoxy-1,2,3,4-tetrahydroisoquinoline

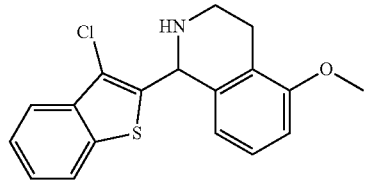 [SMILES: COc1cccc2c1CCNC2c1sc2ccccc2c1Cl]

¹H NMR (300 MHz, CDCl₃): δ ppm 2.83-2.86 (m, 2 H) 3.0-3.1 (m, 1 H) 3.34-3.4 (m, 1 H), 3.8 (s, 3 H), 5.76 (s, 1 H) 6.56-6.59 (d, 1 H), 6.71-6.74 (d, 1 H), 7.02-7.08 (t, 1 H), 7.32-7.38 (q, 1 H), 7.41-7.46 (q, 1 H), 7.68-7.71 (d, 1 H), 7.83-7.85 (d, 1 H); LCMS; LCMS m/z 330, 332 [M+H]⁺

10022806: 7-chloro-1-(3-chloro-1-benzothiophen-2-yl)-1,2,3,4-tetrahydroisoquinoline

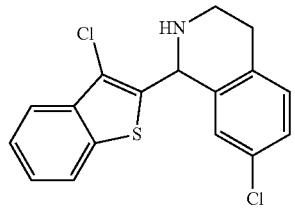 [SMILES: Clc1ccc2c(c1)C(c1sc3ccccc3c1Cl)NCC2]

¹H NMR (300 MHz, CDCl₃): δ ppm 2.77-2.85 (m, 1 H), 2.98-3.0 (m, 2 H), 3.3-3.41 (m, 1 H), 5.74 (s, 1 H), 6.93 (s, 1 H), 7.10-7.16 (m, 2H), 7.41-7.49 (m, 2 H), 7.71-7.74 (d, 1 H), 7.85-7.87 (d, 1 H); LCMS; LCMS m/z 331, 335 [M+H]⁺

10022809: 5-chloro-1-(3-chloro-1-benzothiophen-2-yl)-1,2,3,4-tetrahydroisoquinoline

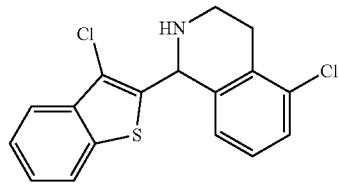 [SMILES: Clc1cccc2c1CCNC2c1sc2ccccc2c1Cl]

¹H NMR (300 MHz, CDCl₃): δ ppm 2.35 (s, 1 H), 2.89-3.05 (m, 2 H), 3.13-3.21 (m, 1 H), 3.39-3.46 (m, 1 H), 5.76 (s, 1 H), 6.86-6.89 (d, 1 H), 6.00-7.05 (t, 1 H), 7.26-7.28 (d, 1 H), 7.35-7.37 (m, 1 H), 7.40-7.48 (m, 1 H), 7.70-7.73 (d, 1 H), 7.84-7.86 (d, 1 H) LCMS m/z 333, 337 [M+H]⁺.

10022807: 1-(3-chloro-1-benzothiophen-2-yl)-5-fluoro-1,2,3,4-tetrahydroisoquinoline

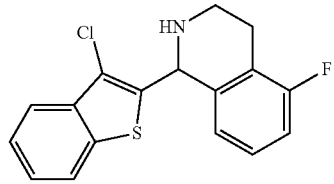 [SMILES: Fc1cccc2c1CCNC2c1sc2ccccc2c1Cl]

¹H NMR (300 MHz, CDCl₃): δ ppm 2.85-2.94 (m, 2 H), 3.10-3.19 (m, 1 H), 3.37-3.44 (m, 1 H), 5.77 (s, 1 H), 6.74-6.77 (d, 1 H), 6.88-6.94 (t, 1 H), 7.01-7.08 (q, 1 H), 7.35-7.39 (t, 1 H), 7.40-7.48 (t, 1 H), 7.70-7.73 (d, 1 H), 7.84-7.86 (d, 1 H); LCMS; LCMS m/z 318, 320 [M+H]⁺

10024137: 1-(3-chloro-4-methyl-1-benzothiophen-2-yl)-6,7-dimethoxy-1,2,3,4-tetrahydroisoquinoline

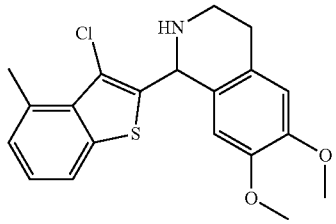 [SMILES: COc1cc2c(cc1OC)C(c1sc3cccc(C)c3c1Cl)NCC2]

$^1$H NMR (300 MHz, CDCl$_3$): δ ppm 2.78-2.96 (m, 1 H), 3.06 (m, 4 H), 3.28-3.36 (m, 1 H), 3.70 (s, 3 H), 3.88 (s, 3 H), 5.70 (s, 1 H), 6.49 (s, 1 H), 6.64 (s, 1 H), 7.11-7.20 (m, 1 H), 7.22-7.26 (s, 1 H), 7.51-7.54 (d, 1 H); LCMS m/z=373, 375 [M+H]$^+$.

10024135: 1-(3-chloro-6-methoxy-1-benzothiophen-2-yl)-6,7-dimethoxy-3,4-dihydroisoquinoline

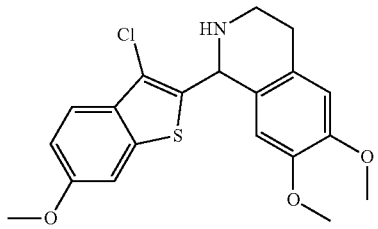

$^1$H NMR (300 MHz, CDCl$_3$): δ ppm 2.03 (br, 1 H), 2.75-2.96 (m, 1 H), 2.99-3.08 (m, 1 H), 3.11-3.12 (m, 1 H), 3.13-3.36 (m, 1 H), 3.68 (s, 3 H), 3.85-3.87 (d, 6 H), 5.66 (s, 1 H), 6.48 (s, 1 H), 6.63 (s, 1 H), 7.04-7.07 (d, 1 H), 7.16-7.26 (s, 1 H), 7.69-7.72 (d, 1 H); LCMS m/z=389, 391 [M+H], [M+H]$^+$.

10024934: 1-(3-chloro-5-methoxy-1-benzothiophen-2-yl)-6,7-dimethoxy-1,2,3,4-tetrahydroisoquinoline

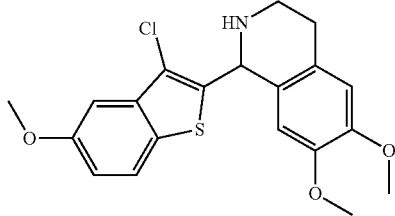

$^1$H NMR (300 MHz, CDCl$_3$): δ ppm 2.7-2.94 (m, 1 H), 2.92-2.94 (m, 1 H), 3.08-3.14 (m, 1 H), 3.29-3.3 (m, 1 H), 3.35 (s, 3 H), 3.87-3.93 (d, 6 H), 5.69 (s, 1 H), 6.49 (s, 1 H), 6.63 (s, 1 H), 6.99-7.02 (d, 1 H), 7.55-7.58 (d, 1 H); LCMS m/z=391, 393 [M+H]$^+$.

10024001: 1-(3-chloro-4-fluoro-1-benzothiophen-2-yl)-6,7-dimethoxy-1,2,3,4-tetrahydroisoquinoline

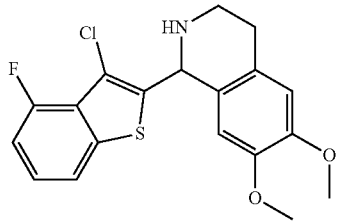

$^1$H NMR (300 MHz, CDCl$_3$): δ ppm 1.25 (s, 3 H), 2.7-2.83 (m, 1 H), 2.91-2.95 (m, 1 H), 3.08-3.15 (m, 1 H), 3.28-3.35 (m, 1 H), 3.71 (s, 3 H), 3.87 (s, 3 H), 5.69 (s, 1 H), 6.50 (s, 1 H), 6.64 (s, 1 H), 7.02-7.09 (m, 1 H), 7.24-7.31 (m, 4 H), 7.45-7.47 (d, 1 H); LCMS m/z=377, 379 [M+H]$^+$.

10024136: 1-(3-chloro-6-methyl-1-benzothiophen-2-yl)-6,7-dimethoxy-1,2,3,4-tetrahydroisoquinoline

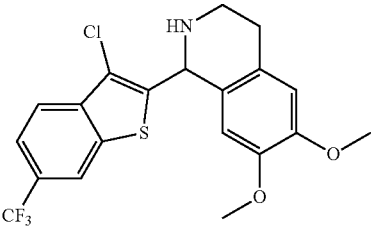 [SMILES: COc1cc2c(cc1OC)C(c1sc3cc(C(F)(F)F)ccc3c1Cl)NCC2]

$^1$H NMR (300 MHz, CDCl$_3$): δ ppm 2.04-2.09 (br, 2 H), 2.77-2.84 (m, 1 H), 2.95-2.97 (m, 1 H), 3.08-3.12 (m, 1 H), 3.14-3.35 (m, 1 H), 3.68 (s, 3 H), 3.88 (s, 3 H), 5.30 (s, 1 H), 5.73 (s, 1, 1 H), 6.46 (s, 1 H), 6.79-6.82 (s, 1 H), 7.66-7.69 (d, 1 H), 7.93-7.95 (d, 1 H), 7.99 (m, 1 H); LCMS m/z=427, 429 [M+H]$^+$.

10022810: 1-(3-chloro-5,6-dimethoxy-1-benzothiophen-2-yl)-6,7-dimethoxy-1,2,3,4-tetrahydroisoquinoline

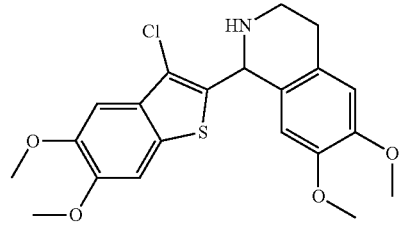

$^1$H NMR (300 MHz, CDCl$_3$): δ ppm 2.19-2.24 (m, 1 H), 2.74-2.88 (m, 2 H), 3.06-3.19 (m, 1 H), 3.75 (s, 3 H), 3.85-3.91 (m, 10 H), 6.56 (s, 1 H), 6.64 (s, 1 H), 7.14 (s, 2 H); LCMS m/z 420 [M+H]$^+$ 10021156: 1-(3-chloro-1-benzothiophen-2-yl)-6,7-dimethoxy-2-methyl-1,2,3,4-tetrahydroisoquinoline

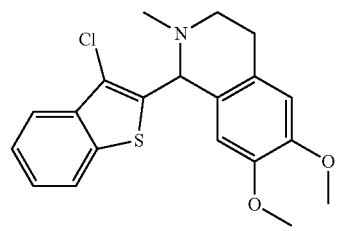 [SMILES: COc1cc2c(cc1OC)C(c1sc3ccccc3c1Cl)N(C)CC2]

$^1$H NMR (400 MHz, CDCl$_3$): δ ppm 2.40 (s, 3 H), 2.69-2.76 (m, 2 H), 3.13-3.17 (m, 2 H), 3.63 (s, 3 H), 3.82-3.85 (s, 3 H), 5.05 (s, 1 H), 6.44 (s, 1 H), 6.61 (s, 1 H), 7.36-7.50 (m, 1 H), 7.70-7.72 (m, 1 H), 7.84 (d, 1 H), 7.86 (d, 1 H); LCMS m/z=373, 375 [M+H]$^+$.

10022813: 1-(3-chloro-1-benzothiophen-2-yl)-2-ethyl-6,7-dimethoxy-1,2,3,4-tetrahydroisoquinoline

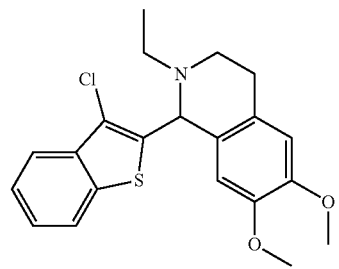 [SMILES: CCN1CCc2cc(OC)c(OC)cc2C1c1sc2ccccc2c1Cl]

¹H NMR (300 MHz, CDCl₃): δ ppm 1.10 (t, 3 H), 2.48-2.77 (m, 4 H), 3.03 (m, 1 H), 3.24 (m, 1 H), 3.64 (s, 3 H), 3.84 (s, 3 H), 5.29 (s, 1 H), 6.52 (s, 1 H), 6.60 (s, 1 H), 7.37 (dt, 1 H), 7.41 (dt, 1 H), 7.68 (dd, 1 H), 7.82 (dd, 1 H). LCMS m/z=387.9, 388, 391 [M+H]⁺.

10021797: 1-(3-chloro-1-benzothiophen-2-yl)-6-fluoro-2-methyl-1,2,3,4-tetrahydroisoquinoline

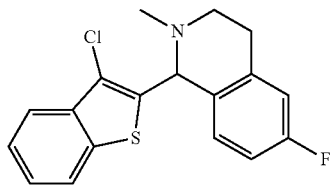 [SMILES: CN1CCc2cc(F)ccc2C1c1sc2ccccc2c1Cl]

¹H NMR (400 MHz, CDCl₃): δ ppm 2.39 (s, 3 H), 2.66-2.72 (m, 1 H), 2.76-2.82 (m, 1 H), 3.16-3.22 (m, 2 H), 5.05 (s, 1 H), 6.71-6.73 (m, 1 H), 6.75-6.86 (m, 2 H), 7.25-7.39 (m, 1 H), 7.43-7.45 (m, 1 H), 7.70-7.84 (d, 1 H), 7.86 (d, 1 H); LCMS m/z=331, 333 [M+H]⁺.

10023512: 1-(3-chloro-1-benzothiophen-2-yl)-2,6-dimethyl-1,2,3,4-tetrahydroisoquinoline

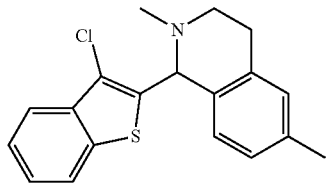 [SMILES: Cc1ccc2c(c1)CCN(C)C2c1sc2ccccc2c1Cl]

¹H NMR (400 MHz, CDCl₃): δ ppm 2.27 (s, 3 H), 2.39 (s, 3 H), 2.66-2.80 (m, 2 H), 3.16-3.24 (m, 2 H), 5.05 (s, 1 H), 6.77-6.79 (d, 1 H), 6.84-6.86 (d, 1 H), 6.95 (s, 1 H), 7.42-7.46 (m, 1 H), 7.68-7.83 (m, 1 H), 7.84-7.85 (d, 1 H), 7.86 (d, 1 H); LCMS m/z=327, 329 [M+H]⁺.

10021794: 1-(3-chloro-1-benzothiophen-2-yl)-6-methoxy-2-methyl-1,2,3,4-tetrahydroisoquinoline

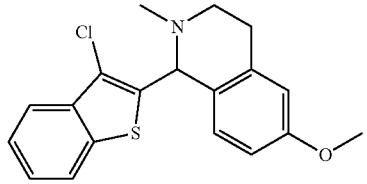 [SMILES: COc1ccc2c(c1)CCN(C)C2c1sc2ccccc2c1Cl]

¹H NMR (400 MHz, CDCl₃): δ ppm 2.39 (s, 3 H), 2.66-2.72 (m, 1 H), 2.76-2.80 (m, 1 H), 3.18-3.25 (m, 2 H), 3.75 (s, 3 H), 5.03 (s, 1 H), 6.59-6.61 (d, 1 H), 6.62 (s, 1 H), 6.65-6.82 (d, 1 H), 7.35-7.44 (m, 1 H), 7.69-7.83 (m, 1 H), 7.84 (d, 1 H), 7.85 (d, 1 H); LCMS m/z=343, 346 [M+H]⁺.

10024140: 1-[1-(3-chloro-1-benzothiophen-2-yl)-6,7-dimethoxy-1,2,3,4-tetrahydroisoquinolin-2-yl]ethan-1-one

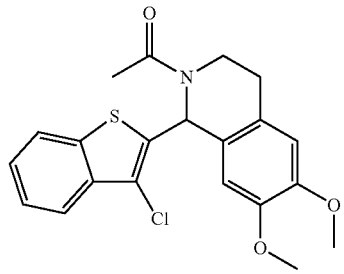 [SMILES: COc1cc2c(cc1OC)C(c1sc3ccccc3c1Cl)N(C(C)=O)CC2]

¹H NMR (300 MHz, CDCl₃): δ ppm 2.19-2.30 (d, 3 H), 2.80-2.95 (m, 2 H), 3.36-3.47 (m, 1 H), 3.75-3.87 (m, 8 H), 6.64-6.69 (m, 2 H), 7.26-7.45 (m, 2 H), 7.65-7.70 (m, 1 H), 7.82-7.84 (m, 1 H); LCMS m/z=401, 403 [M+H]⁺.

10024141: 1-[1-(3-chloro-1-benzothiophen-2-yl)-6-fluoro-1,2,3,4-tetrahydroisoquinolin-2-yl]ethan-1-one

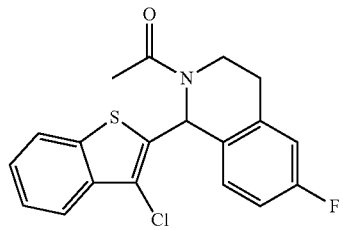 [SMILES: CC(=O)N1CCc2cc(F)ccc2C1c1sc2ccccc2c1Cl]

¹H NMR (300 MHz, CDCl₃): δ ppm 2.19-2.29 (m, 3 H), 2.94-3.04 (br, 2 H), 3.81-3.94 (m, 1 H), 6.89-6.92 (br, 2 H), 7.15-7.26 (m, 1 H), 7.40-7.48 (m, 2 H), 7.65-7.72 (m, 1 H), 7.81-7.87 (m, 1 H); LCMS m/z=359, 361 [M+H]⁺.

10024142: 1-[1-(3-chloro-1-benzothiophen-2-yl)-6-methyl-1,2,3,4-tetrahydroisoquinolin-2-yl]ethan-1-one

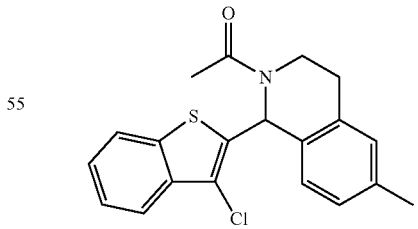

¹H NMR (300 MHz, CDCl₃): δ ppm 0.85-090 (m, 1 H), 1.21-1.31 (m, 2 H), 2.15-2.31 (m, 6 H), 2.85-3.01 (m, 2 H), 3.37-3.47 (m, 1 H), 3.81-3.88 (m, 1 H), 4.69-4.74 (m, 1 H), 6.97-7.07 (br, 2 H), 7.09-7.26 (m, 1 H), 7.33-7.47 (m, 2 H), 7.63-7.70 (m, 1 H), 7.81-7.86 (m, 1 H); LCMS m/z=355, 357 [M+H]⁺.

10022925: 1-(3-chloro-1-benzothiophen-2-yl)-6,7-dimethoxyisoquinoline

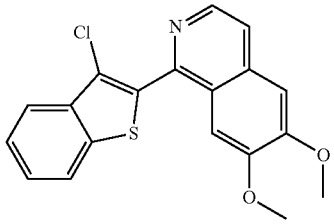 [SMILES: COc1cc2ccnc(-c3sc4ccccc4c3Cl)c2cc1OC]

$^1$H NMR (300 MHz, CDCl$_3$): δ ppm 3.8 (s, 3 H), 4 (s, 3 H) 7.16 (s, 1 H) 7.23 (s, 1 H), 7.5-7.54 (m, 2 H), 7.60-7.62 (d, 1 H), 7.9-7.97 (m, 2 H), 8.53 (d, 1 H); LCMS m/z 356, 358, 359 [M+H]$^+$.

10022811: 1-(3-chloro-4-methyl-1-benzothiophen-2-yl)-5-fluoro-1,2,3,4-tetrahydroisoquinoline

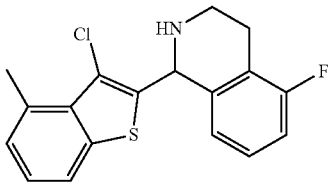 [SMILES: Cc1cccc2sc(C3NCCc4c(F)cccc43)c(Cl)c12]

$^1$H NMR (300 MHz, CDCl$_3$): δ ppm 2.35 (s, 1 H), 2.88-2.95 (m, 2 H), 3.09-3.18 (m, 1 H), 3.34-3.42 (m, 1 H), 5.75 (s, 1 H), 6.76-6.79 (d, 1 H), 6.88-6.93 (t, 1 H), 7.04-7.09 (m, 1 H), 7.12-7.18 (m, 1 H), 7.14-7.20 (m, 1 H), 7.52-7.55 (d, 1 H); LCMS m/z 332, 334 [M+H]$^+$ Appendix C. Synthesis of M21-Related Compounds Preparation of Substituted Coumarins and Quinolone Derivatives

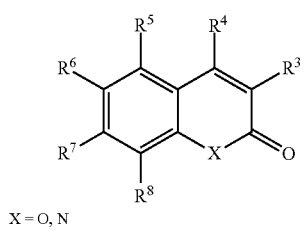

X = O, N

1. Summary

The template involves synthesis of substituted Coumarins and Quinolone.

2. Synthetic Route

The general synthetic route of this template is summarized in Scheme 1.

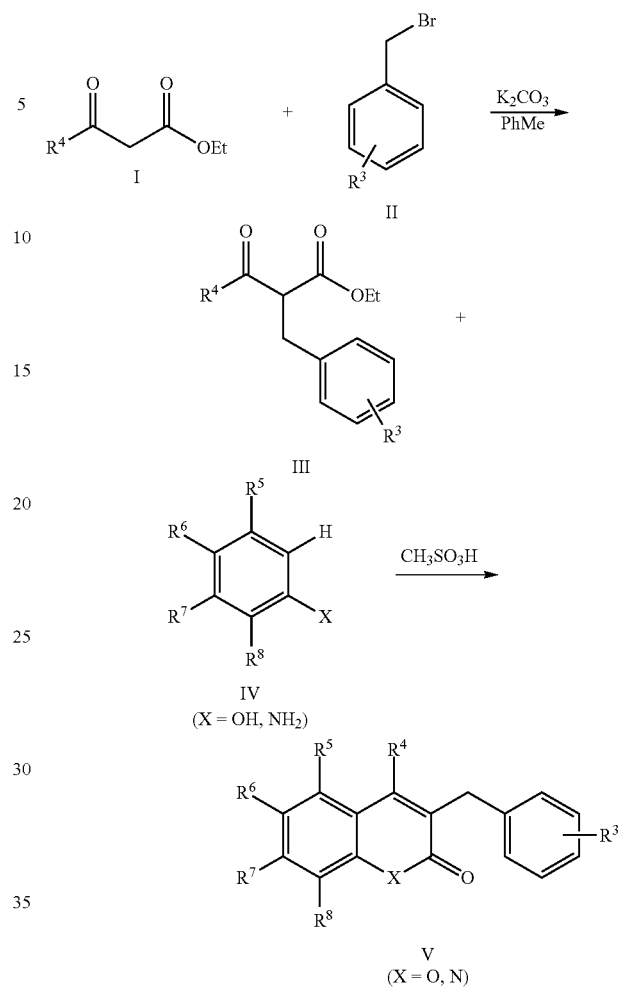

2.2.1 Synthesis of 2-substituted-β-ketoesters

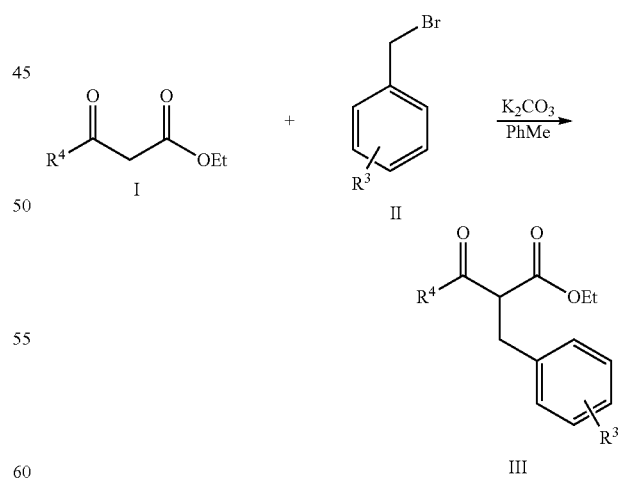

Procedure:

Substituted benzyl bromide II (1 eq) was added to a solution of the respective β-ketoester 1 (1 eq) and potassium carbonate (1.1 eq) in toluene (15 vols) at room temperature, the mixture was heated to reflux until TLC showed complete consumption of the starting materials. The reaction mass concentrated in vacuo, water (15 vols) was added to the reaction mass and extracted with dichloromethane (25 vol×2 times). Combined organic layer was washed with water (20 vol×2 times), saturated brine (20 vol), dried over $Na_2SO_4$ and concentrated in vacuo to get the crude product III was purified by flash chromatography using 230-400 mesh silica (Yield: 25-60%). Details of alkylated keto ester was given in below Table 1

TABLE 1

| Entry | $R^3$ | $R^4$ | Purity (%)* | Yield (%) |
|---|---|---|---|---|
| 1 | 2,6-Cl | Et | >90 | 27 |
| 2 | 2-Cl, 6-F | Et | >90 | 32 |
| 3 | 3-Cl | Et | >90 | 22 |
| 4 | 3,4-Cl | Et | >90 | 36 |
| 5 | 4-F | Et | >90 | 33 |
| 6 | 3-Cl | n-Pr | >90 | 48 |
| 7 | 3,4-Cl | n-Pr | >90 | 25 |

*Purity by $^1$H NMR 2.2.2 Synthesis of Substituted Chromen-2-Ones (X=O)

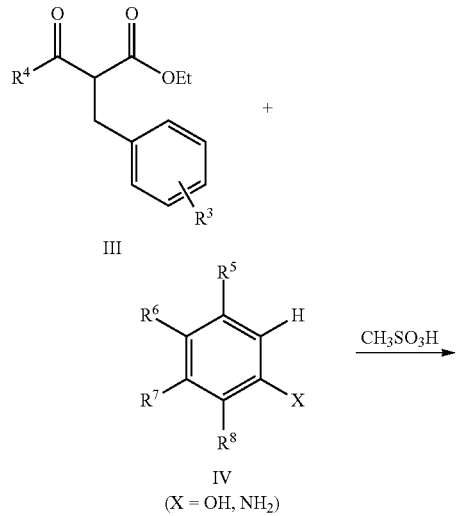

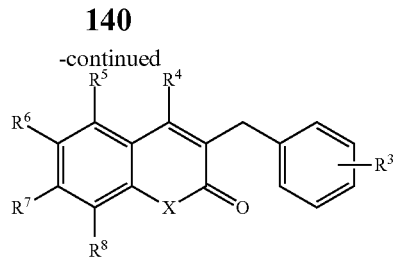

Procedure::

A solution of IV (1 eq) and keto ester III (3 eq) was heated at 85° C. in methanesulfonic acid (5 vol) until TLC showed complete consumption of the starting materials. The reaction mixture was cooled to room temperature and water (5 vol) was added to it. The reaction was basified to pH>10 with aqueous 20% NaOH solution and extracted with ethyl acetate (3×20 vol). The aqueous layer was then acidified using 2N HCl and extracted with ethyl acetate (3×25 vol). The combined organic layers were washed with water (2×20 vol), saturated brine (1×20 vol), dried over anhydrous sodium sulfate and concentrated in vacuo to get the desired product V.

2.2.3 Synthesis of Quinolones (X=N)

Procedure::

Substituted aniline IV (1 eq) was added portionwise to the keto ester III (3 eq.) preheated to 160° C. under nitrogen. The reaction was allowed to stir until TLC showed complete disappearance of starting aniline. The reaction was cooled to and diluted with a 1:1 mixture of heptanes and diethyl ether. The resultant solid was filtered and dried to get the crude product which was used in the next step without further purification. This product was added to methanesulfonic acid (5 vol) preheated to 85° C. The reaction was allowed to stir at that temperature (15-60 mins) until TLC showed complete disappearance of starting material. The reaction mixture was cooled to room temperature and ice water (15 vol) was added to it. The resultant solid was filtered, washed with aq. Sodium bicarbonate and water and dried to get the pure V. Details of compounds are given in Table 2.

TABLE 2

| Entry | Comp ID | X | $R^3$ | $R^4$ | $R^5$ | $R^6$ | $R^7$ | Purity LCMS | Yield % |
|---|---|---|---|---|---|---|---|---|---|
| 1 | 10024936 | N | 4-Cl | Me | OMe | H | OMe | 93 | 42 |
| 2 | 10023471 | N | H | Me | OMe | H | OMe | 98 | 25 |
| 3 | 10024937 | N | 3-Cl | Me | OMe | H | OMe | 92 | 37 |
| 4 | 10024935 | N | 3-Cl | Propyl | OMe | H | OMe | 97 | 28 |
| 5 | 10023911 | O | 3-Cl | Me | OH | H | OH | 100 | 45 |
| 6 | EOAl3356087 | O | 3-Cl | Me | H | H | OH | 99 | 52 |
| 7 | EOAl3356089 | O | 3,4-Cl | Me | H | F | OH | 99 | 56 |
| 8 | 10024938 | N | 2-F,6-Cl | Me | OMe | H | OMe | 95 | 37 |
| 9 | 10024110 | O | 2-F,6-Cl | Me | OH | H | OH | 95 | 32 |
| 10 | EOAl3356085 | O | H | Me | H | H | OH | 100 | 48 |
| 11 | 10023909 | O | 2,6-Cl | Me | OH | H | OH | 96 | 36 |
| 12 | EOAl3356086 | O | 4-Cl | Me | H | H | OH | 99 | 38 |
| 13 | EOAl3356091 | O | 3,4-Cl | Me | H | H | MeOEt | 97 | 54 |
| 14 | EOAl3356088 | O | 3,4-Cl | Me | H | Me | OH | 100 | 62 |
| 15 | EOAl3356084 | O | 3,4-Cl | Me | H | H | OH | 100 | 59 |
| 16 | 10022814 | N | 3,4-Cl | Me | OMe | H | OMe | 90 | 26 |
| 17 | 10022816 | N | 3,4-Cl | Propyl | OMe | H | OMe | 91 | 42 |
| 18 | 10022815 | O | 3,4-Cl | Me | OH | H | OH | 98 | 28 |
| 19 | 10022824 | N | 4-F | Me | OMe | H | OMe | 93 | 39 |
| 20 | EOAl3356092 | O | 2,6-Cl | Me | H | H | EtNMe$_2$ | 100 | 55 |

Additional Compound:

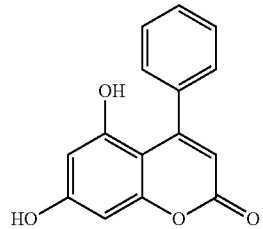 [SMILES: O=c1cc(-c2ccccc2)c2c(O)cc(O)cc2o1]

| Entry | Comp ID | Purity LCMS | Yield % |
|---|---|---|---|
| 1 | 10024109 | 89 | 25 |

2.2.4 O-Methylation of Coumarins:

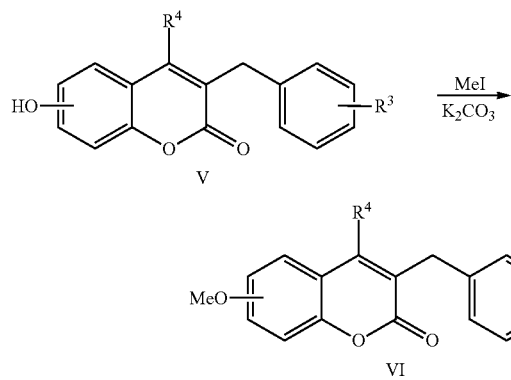

Procedure:

Methyl iodide (10 eq.) was added to a solution of hydroxycoumarin (1 eq) and potassium carbonate (2 eq.) in acetonitrile at room temperature. The reaction was allowed to stir at room temperature until TLC showed complete disappearance of starting material (overnight). The reaction mass was filtered and the filtrate was concentrated in vacuo to get the crude residue. Water (10 vol) was added to this and it was extracted with dichloromethane (2×25 vol). The combined organic layers were washed with water (2×20 vol), saturated brine (1×20 vol), dried over anhydrous sodium sulfate and concentrated in vacuo to get crude product which was purified by flash column chromatography. Details of O-methylated compounds are given in Table 3.

TABLE 3

| Entry | Comp ID | X | $R^3$ | $R^4$ | $R^5$ | $R^6$ | $R^7$ | Purity LCMS | Yield |
|---|---|---|---|---|---|---|---|---|---|
| 1 | 10023902 | O | 3-Cl | Me | OMe | H | OMe | 95 | 52 |
| 2 | 10024923 | O | 2,6-Cl | Me | OMe | H | OMe | 88 | 32 |
| 3 | 10023910 | O | 2-F, 6-Cl | Me | OMe | H | OMe | 96 | 37 |
| 4 | EOAl3356090 | O | 3,4-Cl | Me | H | H | OMe | 100 | 42 |

2.2.5 Demethylation:

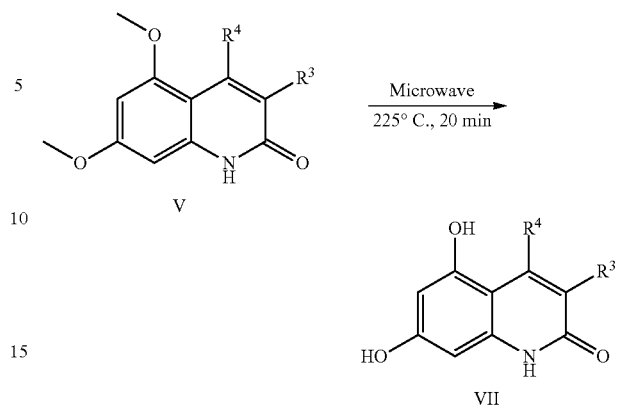

Procedure:

Substituted quinoline (1 eq.) and pyridinium hydrochloride (5×w/w) was taken up in a microwave tube. The reaction mixture was irradiated at 225° C. for 20 min. Water (10 vol) was added to the reaction mass and it was extracted with ethyl acetate (2×25 vol). The organic layer was washed with saturated brine (1×25 vol), dried over anhydrous sodium sulfate and concentrated in vacuo to get pure VII. Details of demethylated compounds were given in below Table-4.

TABLE 4

| Entry | Comp ID | $R^3$ | $R^4$ | Purity LCMS | Yield % |
|---|---|---|---|---|---|
| 1 | 10022819 | 3-Cl | Propyl | 91 | 27 |
| 2 | 10022818 | 2-Cl, 6-F | Me | 85 | 42 |
| 3 | 10022820 | H | Me | 98 | 55 |
| 4 | 10022821 | 3,4-Cl | Propyl | 89 | 29 |
| 5 | 10022825 | 4-F | Me | 96 | 59 |
| 6 | 10022826 | 3-Cl | Me | 92 | 35 |
| 7 | 10022822 | 2,6 Cl | Me | 97 | 52 |

2.2.6 Dimethylation (Grignard)

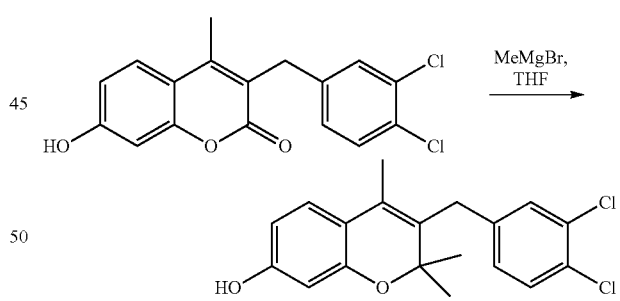

Procedure:

Methyl magnesium bromide (1 mL, 4.5 eq. of a 3M solution in diethyl ether diluted with 5 mL of anhydrous diethyl ether) was added to a refluxing solution of 3-[(3,4-dichloro phenyl)methyl]-7-hydroxy-4-methyl-2H-chromen-2-one (80 mg, 0.23 mmol, 1 eq.) in tetrahydrofuran (5 mL) over 20 min and the reaction was refluxed under nitrogen for 2 h. After completion of reaction (by TLC), the reaction was cooled to room temperature and quenched with an excess of cold 1N HCl. The mixture was extracted with ethyl acetate (2×20 mL), washed with saturated brine (1×10 mL), dried over anhydrous sodium sulfate and concentrated in vacuo. The crude compound was purified by flash silica gel column chromatography to get 27 mg (31%) of desired product.

¹H NMR Data

EOAI3356084:
3-benzyl-7-methoxy-4-methyl-2H-chromen-2-one

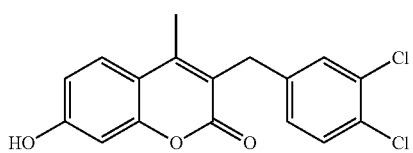 [SMILES: Cc1c(Cc2ccc(Cl)c(Cl)c2)c(=O)oc2cc(O)ccc12]

¹H NMR (500 MHz, DMSO-$d_6$) δ ppm 10.52 (br. s, 1 H), 7.65 (d, J=8.8 Hz, 1 H), 7.52 (d, J=8.2 Hz, 1 H), 7.49 (d, J=2.0 Hz, 1 H), 7.20 (dd, J=8.3, 2.0 Hz, 1 H), 6.81 (d, J=8.7, 2.4 Hz, 1 H), 6.70 (d, J=2.4 Hz 1 H), 3.92 (s, 2 H), 2.40 (s, 3 H); LCMS m/z=335, 337, 339 [M+H]$^+$.

EOAI3356085:
3-benzyl-7-hydroxy-4-methyl-2H-chromen-2-one

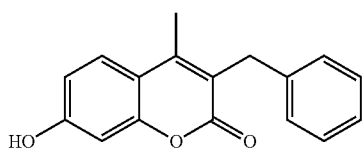 [SMILES: Cc1c(Cc2ccccc2)c(=O)oc2cc(O)ccc12]

¹H NMR (500 MHz, DMSO-$d_6$) δ ppm 10.48 (br. S, 1 H), 7.64 (d, J=8.8 Hz, 1 H), 7.23-7.30 (m, 2 H), 7.14-7.23 (m, 3 H), 6.80 (dd, J=8.8, 2.4 Hz, 1 H), 6.70 (d, J=2.4 Hz, 1 H), 3.92 (s, 2 H), 2.39 (s, 3 H); LCMS m/z=267, [M+H]$^+$.

EOAI3356086: 3-[(4-chlorophenyl)methyl]-7-hydroxy-4-methyl-2H-chromen-2-one

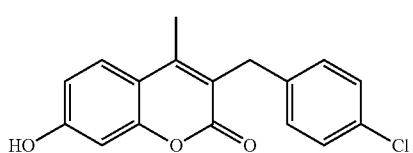 [SMILES: Cc1c(Cc2ccc(Cl)cc2)c(=O)oc2cc(O)ccc12]

¹H NMR (500 MHz, DMSO-$d_6$) δ ppm 10.48 (br. S, 1 H), 7.64 (d, J=8.7 Hz, 1 H), 7.29-7.35 (m, 2 H), 7.21-7.27 (m, 2 H), 6.80 (dd, J=8.7, 2.3 Hz, 1 H), 6.70 (d, J=2.4 Hz, 1 H), 3.91 (s, 2 H), 2.39 (s, 3 H); LCMS m/z=301, 303, [M+H]$^+$.

EOAI3356087: 3-[(3-chlorophenyl)methyl]-7-hydroxy-4-methyl-2H-chromen-2-one

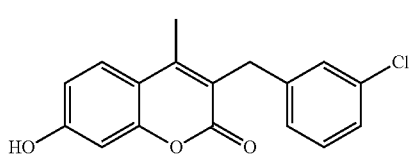 [SMILES: Cc1c(Cc2cccc(Cl)c2)c(=O)oc2cc(O)ccc12]

¹H NMR (500 MHz, DMSO-$d_6$) δ ppm 10.48 (br. S, 1 H), 7.65 (d, J=8.7 Hz, 1 H), 7.21-7.35 (m, 3 H), 7.18 (d, J=7.4 Hz, 1 H), 6.81 (d, J=8.7 Hz, 1 H), 6.71 (br. S, 1 H), 3.93 (s, 2 H), 2.40 (s, 3 H); LCMS m/z=301, 303, ([M+H]$^+$.

EOAI3356090:
3-benzyl-7-methoxy-4-methyl-2H-chromen-2-one

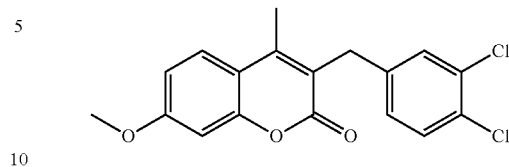

¹H NMR (500 MHz, DMSO-$d_6$) δ ppm 11.04 (s, 1 H), 7.60-7.70 (m, 1 H), 7.45-7.56 (m, 2 H), 7.16-7.25 (m, 1 H), 6.90 (s, 1 H), 3.93 (s, 2 H), 2.39 (s, 3 H); LCMS m/z=349, 351, 353, [M+H]$^+$.

EOAI3356091: 3-[(3,4-dichlorophenyl)methyl]-7-(2-methoxyethoxy)-4-methyl-2H-chromen-2-one

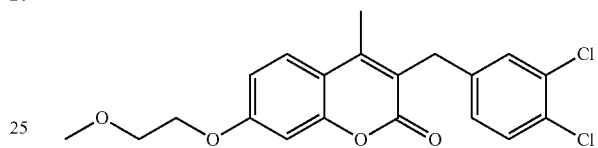

¹H NMR (500 MHz, DMSO-$d_6$) δ ppm 7.74 (d, J=8.7 Hz, 1 H), 7.43-7.60 (m, 2 H), 7.21 (d, J=8.5 Hz, 1 H), 6.92-7.07 (m, 2 H), 4.12-4.28 (m, 2 H), 3.95 (s, 2 H), 3.61-3.75 (m, 2 H), 3.31 (br. S, 3 H), 2.44 (s, 3 H); LCMS m/z=393, 395, 397, [M+H]$^+$

EOAI3356092:
3-benzyl-7-methoxy-4-methyl-2H-chromen-2-one

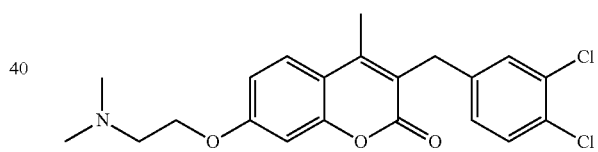

¹H NMR (500 MHz, DMSO-$d_6$) δ ppm 7.74 (d, J=9.0 Hz, 1 H), 7.53 (d, J=8.4 Hz, 1 H), 7.51 (d, J=1.9 Hz, 1 H), 7.22 (dd, J=8.3, 2.0 Hz, 1 H), 7.01 (d, J=2.5 Hz, 1 H), 6.98 (dd, J=8.8, 2.5 Hz, 1 H), 4.16 (t, J=5.7 Hz, 2 H), 3.95 (s, 2 H), 2.64 (t, J=5.7 Hz, 2 H), 2.44 (s, 3 H), 2.22 (s, 6 H); LCMS m/z=406, 408, 410, [M+H]$^+$.

10022815: 3-[(3,4-dichlorophenyl)methyl]-5,7-dihydroxy-4-methyl-2H-chromen-2-one

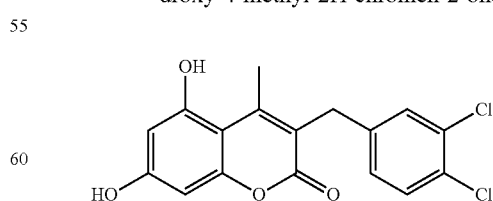

¹H NMR (300 MHz, DMSO-$d_6$) δ ppm 3.83 (s, 3 H), 5.64 (s, 2 H), 6.16 (d, 1 H), 6.27 (d, 1 H), 7.14 (dd, 1 H), 7.44 (s, 1 H), 7.49 (dd, 1 H), 10.27 (s, 1 H), 10.55 (s, 1 H); LCMS m/z=349.0, 350, 351 [M+H]$^+$.

10022814: 3-[(3,4-dichlorophenyl)methyl]-5,7-dimethoxy-4-methyl-1,2-dihydroquinolin-2-one

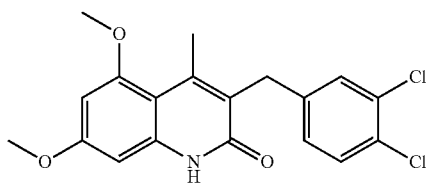 [SMILES: COc1cc(OC)c2c(C)c(Cc3ccc(Cl)c(Cl)c3)c(=O)[nH]c2c1]

$^{1}$H NMR (300 MHz, DMSO-d$_6$) δ ppm 1.22 (s, 3 H), 3.77-3.88 (s, 6 H), 3.97 (s, 2 H), 6.31 (d, 1 H), 6.45 (d, 1 H), 7.12 (dd, 1 H), 7.40 (dd, 1 H), 7.47 (dd, 1 H), 11.60 (s, 1 H); LCMS m/z=387.9, 378, 379.9, 381 [M+H]$^+$.

10023911: 3-[(3-chlorophenyl)methyl]-5,7-dihydroxy-4-methyl-2H-chromen-2-one

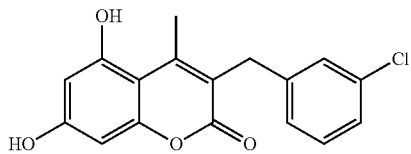 [SMILES: Cc1c(Cc2cccc(Cl)c2)c(=O)oc2cc(O)cc(O)c12]

$^{1}$H NMR (400 MHz, DMSO-d$_6$): δ ppm 2.48-2.52 (s, 3 H), 3.8 (s, 2 H), 6.16-6.27 (d, 2 H), 7.12 (s, 1 H), 7.21-7.31 (m, 3 H), 10.24 (s, 1 H), 10.51 (s, 1 H) LCMS m/z=316, 3, 318. [M+H]$^+$.

10023902: 3-[(3-chlorophenyl)methyl]-5,7-dimethoxy-4-methyl-2H-chromen-2-one

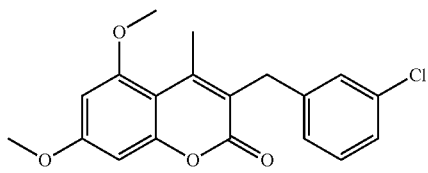

$^{1}$H NMR (300 MHz, CDCl$_3$): δ ppm 2.55 (s, 3 H), 3.84 (s, 6 H), 4.00 (s, 2 H), 6.30-6.31 (s, 1 H), 6.45 (d, 1 H), 7.14-7.19 (m, 4 H), 7.26 (s, 1 H); LCMS); LCMS m/z=344, 3, 346 [M+H]$^+$.

10023909: 3-[(2,6-dichlorophenyl)methyl]-5,7-dihydroxy-4-methyl-2H-chromen-2-one

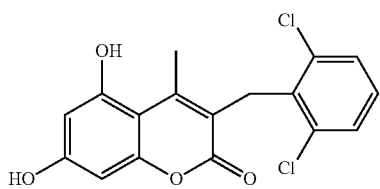 [SMILES: Cc1c(Cc2c(Cl)cccc2Cl)c(=O)oc2cc(O)cc(O)c12]

$^{1}$H NMR (400 MHz, DMSO-d$_6$): δ ppm 2.41 (s, 3 H), 2.48-2.53 (m, 1 H) 4.1 (s, 2 H), 6.12 (s, 1 H), 6.23-6.27 (s, 1 H), 7.21-7.26 (m, 1 H), 7.39-7.41 (m, 2 H), 10.2 (s, 1 H), 10.48 (s, 1 H); LCMS m/z=350, 3, 352, 3, 354 [M+H]$^+$.

10024923: 3-[(2-chloro-6-fluorophenyl)methyl]-5,7-dimethoxy-4-methyl-2H-chromen-2-one

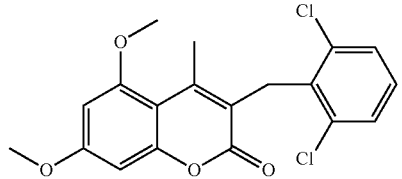

$^{1}$H NMR (300 MHz, CDCl$_3$): δ ppm 2.39-2.41 (s, 2 H), 3.75-3.89 (m, 6 H), 4.3 (s, 2 H), 6.27-6.28 (s, 1 H), 6.42-6.43 (s, 1 H), 7.05-7.10 (m, 1 H), 7.26-7.28 (s, 2 H), LCMS m/z=378, 380, 382 (M+H)$^+$.

10024110: 3-[(2-chloro-6-fluorophenyl)methyl]-5,7-dihydroxy-4-methyl-2H-chromen-2-one

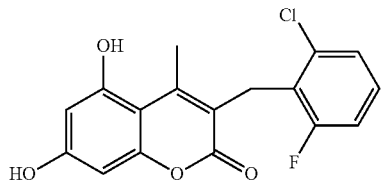 [SMILES: Cc1c(Cc2c(F)cccc2Cl)c(=O)oc2cc(O)cc(O)c12]

$^{1}$H NMR (400 MHz, DMSO-d$_6$): δ ppm 2.46-2.49 (m, 3 H), 4.00 (s, 2 H), 6.13 (s, 1 H), 6.24 (s, 1 H), 7.08-7.15 (m, 1 H), 7.22-7.28 (m, 2 H), 10.2 (s, 1 H), 10.48 (s, 1 H); LCMS m/z=334, 3, 336 [M+H]$^+$.

10023910: 3-[(2-chloro-6-fluorophenyl)methyl]-5,7-dimethoxy-4-methyl-2H-chromen-2-one

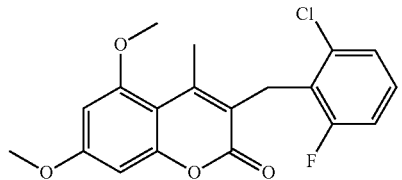

$^{1}$H NMR (400 MHz, CDCl$_3$): δ ppm 2.46 (s, 3 H), 3.81-3.90 (d, 6 H), 4.19 (s, 2 H), 6.27-6.28 (s, 1 H), 6.43-6.44 (s, 1 H), 6.88-6.94 (m, 2 H); LCMS m/z=362, 3, 364 [M+H]$^+$.

EOAI3356088: 3-[(3,4-dichlorophenyl)methyl]-7-hydroxy-4,6-dimethyl-2H-chromen-2-one

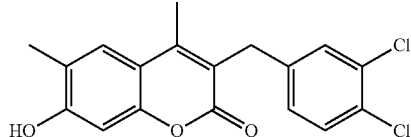 [SMILES: Cc1cc2c(C)c(Cc3ccc(Cl)c(Cl)c3)c(=O)oc2cc1O]

$^{1}$H NMR (500 MHz, DMSO-d$_6$) δ ppm 10.48 (s, 1 H), 7.33-7.75 (m, 3 H), 7.19 (d, J=7.6 Hz, 1 H), 6.62-6.82 (m, 1 H), 3.92 (br. s, 2 H), 2.40 (s, 3 H), 2.18 (s, 3 H); LCMS m/z=349, 351, 353, [M+H][M+H]$^+$.

EOAI3356089: 3-[(3,4-dichlorophenyl)methyl]-6-fluoro-7-hydroxy-4-methyl-2H-chromen-2-one

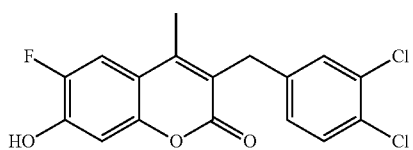 [SMILES: Cc1c(Cc2ccc(Cl)c(Cl)c2)c(=O)oc2cc(O)c(F)cc12]

$^1$H NMR (500 MHz, DMSO-$d_6$) δ ppm 10.48 (s, 1 H), 7.33-7.75 (m, 3 H), 7.19 (d, J=7.6 Hz, 1 H), 6.62-6.82 (m, 1 H), 3.92 (br. S, 2 H), 2.40 (s, 3 H), 2.18 (s, 3 H); LCMS m/z=353, 355, 357, [M+H][M+H]$^+$.

10022820: 3-benzyl-5,7-dihydroxy-4-methyl-1,2-dihydroquinolin-2-one

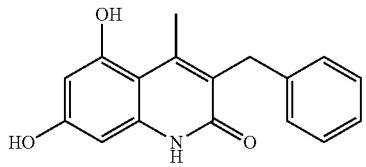 [SMILES: Cc1c(Cc2ccccc2)c(=O)[nH]c2cc(O)cc(O)c12]

$^1$H NMR (300 MHz, DMSO-$d_6$) δ ppm 3.32 (s, 3 H), 3.93 (s, 2 H), 6.08 (s, 1 H), 6.17 (s, 1 H), 7.11-7.24 (m, 5 H), 9.73 (s, 1 H), 9.98 (s, 1 H), 11.29 (s, 1 H); LCMS m/z=280, 2801.1 [M+H]$^+$ 10023471: 3-benzyl-5,7-dimethoxy-4-methyl-1,2-dihydroquinolin-2-one

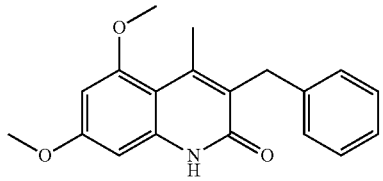 [SMILES: COc1cc(OC)c2c(C)c(Cc3ccccc3)c(=O)[nH]c2c1]

$^1$H NMR (300 MHz, CDCl$_3$): δ ppm 2.47-2.49 (s, 3 H), 3.77-3.80 (s, 6 H), 3.97 (s, 2 H), 6.29-6.30 (s, 1 H), 6.45 (s, 1 H), 7.10-7.24 (m, 5 H), 11.55 (s, 1H); LCMS [M+H]$^+$ 309.14, (98%); LCMS m/z=309 [M+H]$^+$.

10022826: 3-[(3-chlorophenyl)methyl]-5,7-dihydroxy-4-methyl-1,2-dihydroquinolin-2-one

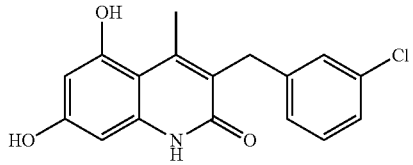 [SMILES: Cc1c(Cc2cccc(Cl)c2)c(=O)[nH]c2cc(O)cc(O)c12]

$^1$H NMR (300 MHz, DMSO-$d_6$) δ ppm 3.29 (s, 3 H), 3.93 (s, 2 H), 6.09 (s, 1H), 6.17 (s, 1 H), 7.10 (m, 4 H), 9.76 (s, 1 H), 10.03 (s, 1 H), 11.33 (s, 1 H); LCMS m/z=316, 318.0[M+H]$^+$.

10024937: 3-[(3-chlorophenyl)methyl]-5,7-dimethoxy-4-methyl-1,2-dihydroquinolin-2-one

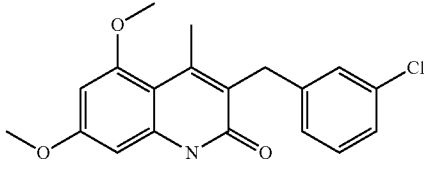 [SMILES: COc1cc(OC)c2c(C)c(Cc3cccc(Cl)c3)c(=O)[nH]c2c1]

$^1$H NMR (300 MHz, CDCl$_3$): δ ppm 2.59-2.63 (s, 3 H), 3.77-3.84 (d, 6 H), 4.1 (s, 2 H), 6.23 (s, 1 H), 6.27 (s, 1 H), 6.91-7.16 (s, 3 H), 7.18-7.26 (s, 1 H), 10.65 (s, 1 H); LCMS m/z=z=343, 345 [M+H]$^+$.

10024936: 3-[(2-chloro-6-fluorophenyl)methyl]-5,7-dimethoxy-4-methyl-2H-chromen-2-one

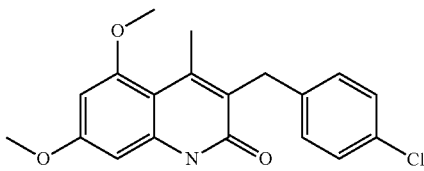 [SMILES: COc1cc(OC)c2c(C)c(Cc3ccc(Cl)cc3)c(=O)[nH]c2c1]

$^1$H NMR (300 MHz, CDCl$_3$): δ ppm 2.56-2.62 (m, 3 H), 3.77-3.82 (s, 6 H), 4.08-4.14 (s, 2 H), 6.2 (s, 1 H), 6.35-6.36 (s, 1 H), 7.14-7.20 (s, 4 H), 10.82 (s, 1 H); LCMS m/z=z=343, 345 [M+H]$^+$.

10022819: 3-[(3-chlorophenyl)methyl]-5,7-dihydroxy-4-propyl-1,2-dihydroquinolin-2-one

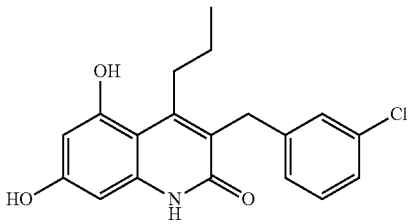 [SMILES: CCCc1c(Cc2cccc(Cl)c2)c(=O)[nH]c2cc(O)cc(O)c12]

$^1$H NMR (300 MHz, CDCl$_3$) δ ppm 0.92 (t, 3 H), 1.42 (m, 2 H), 2.99 (m, 2 H), 4.04 (s, 2 H), 6.27 (dd, 2 H), 7.10 (m, 4 H), 9.20 (br s, 1 H), 9.41 (br s, 1 H), 10.52 (br s, 1 H); LCMS m/z=342, 344 [M+H]$^+$ 10024935: 3-[(2-chloro-6-fluorophenyl)methyl]-5,7-dimethoxy-4-methyl-2H-chromen-2-one

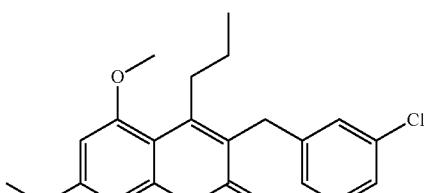

$^1$H NMR (300 MHz, CDCl$_3$): δ ppm 0.95-1.007 (t, 3 H), 1.25-1.56 (m, 2 H), 2.98-3.03 (t, 2 H), 3.76 (s, 3 H) 3.86 (s, 3 H), 4.10 (s, 2 H), 6.24-6.29 (d, 2 H) 6.9-7.16 (s, 3 H), 7.18-7.60 (m, 1 H), 10.8 (s, 1 H), LCMS m/z=371, 373 (M+H)$^+$.

10022821: 3-[(3,4-dichlorophenyl)methyl]-5,7-dihydroxy-4-propyl-1,2-dihydroquinolin-2-one

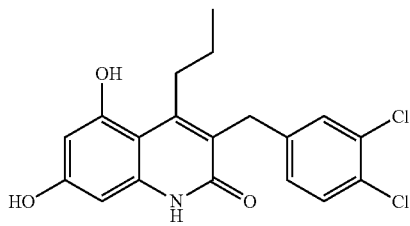 [SMILES: CCCc1c(Cc2ccc(Cl)c(Cl)c2)c(=O)[nH]c2cc(O)cc(O)c12]

¹H NMR (300 MHz, DMSO-d₆) δ ppm 1.18 (t, 3 H), 1.32 (m, 2 H), 2.93 (m, 2 H), 3.91 (s, 2 H), 6.02 (s, 1 H), 6.10 (s, 1 H), 7.05 (dd, 1 H), 7.08 (d, 1 H), 7.16 ((dd, 1 H), 9.78 (s, 1 H), 10.0 (s, 1 H), 11.3 (s, 1 H); LCMS m/z=378.0, 381.0 [M+H]⁺.

10022816: 3-[(3,4-dichlorophenyl)methyl]-5,7-dimethoxy-4-propyl-1,2-dihydroquinolin-2-one

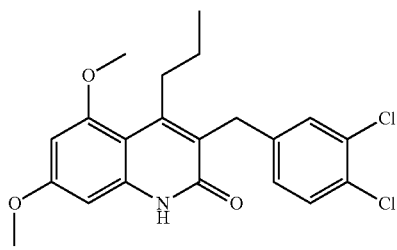 [SMILES: CCCc1c(Cc2ccc(Cl)c(Cl)c2)c(=O)[nH]c2cc(OC)cc(OC)c12]

¹H NMR (300 MHz, CDCl₃) δ ppm 0.97 (t, 3 H), 1.46 (m, 2 H), 2.97 (m, 2 H), 3.73 (s, 3 H), 3.81 (s, 3 H), 4.01 (s, 2 H), 6.26 (d, 1 H), 6.31 (d, 1 H), 7.07 (dd, 1 H), 7.27 (s, 1 H), 7.33 (s, 1 H), 11.20 (br s, 1 H); LCMS m/z=406, 409 [M+H]⁺.

10022825: 3-[(4-fluorophenyl)methyl]-5,7-dihydroxy-4-methyl-1,2-dihydroquinolin-2-one

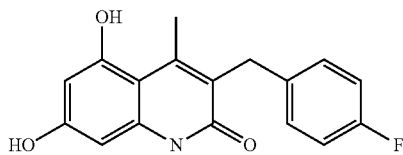 [SMILES: Cc1c(Cc2ccc(F)cc2)c(=O)[nH]c2cc(O)cc(O)c12]

¹H NMR (300 MHz, DMSO-d₆) δ ppm 3.31 (s, 3 H), 3.90 (s, 2 H), 6.08 ((s, 1 H), 6.16 (s, 1 H), 7.00 (dt, 2 H), 7.16 (dt, 2 H), 9.73 (s, 1 H), 9.99 (s, 1 H), 11.30 (s, 1 H); LCMS m/z=298, 299.0[M+H]⁺.

10022824: 3-[(4-fluorophenyl)methyl]-5,7-dimethoxy-4-methyl-1,2-dihydroquinolin-2-one

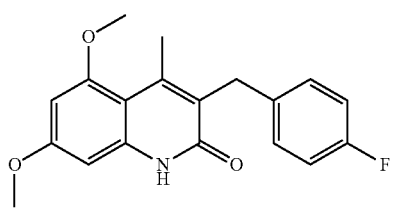 [SMILES: COc1cc(OC)c2c(C)c(Cc3ccc(F)cc3)c(=O)[nH]c2c1]

¹H NMR (300 MHz, CDCl₃) δ ppm 2.56 (s, 3 H), 3.83 (s, 6 H), 4.07 (s, 2 H), 6.21 (d, 1 H), 6.46 (d, 1 H), 6.90 (dt, 2 H), 7.16 (dt, 2 H), 11.4 (s, 1 H); LCMS m/z=328, 329.1[M+H]⁺.

10022818: 3-[(2-chloro-6-fluorophenyl)methyl]-5,7-dihydroxy-4-methyl-1,2-dihydroquinolin-2-one

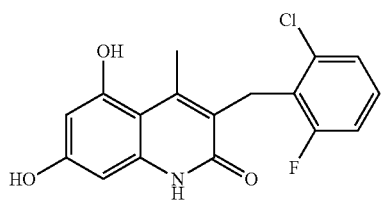

¹H NMR (300 MHz, DMSO-d₆) δ ppm 2.35 (s, 3 H), 4.08 (s, 2 H), 6.08 (s, 1 H), 6.27 (s, 1 H), 7.07 (m, 1 H), 7.22 (dd, 2 H), 9.71 (s, 1 H), 9.96 (s, 1 H), 11.19 (s, 1H); LCMS m/z=334, 336 [M+H]⁺.

10024938: 3-[(2-chloro-6-fluorophenyl)methyl]-5,7-dimethoxy-4-methyl-1,2-dihydroquinolin-2-one

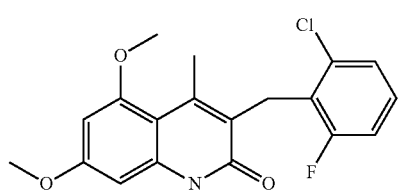 [SMILES: COc1cc(OC)c2c(C)c(Cc3c(F)cccc3Cl)c(=O)[nH]c2c1]

¹H NMR (300 MHz, CDCl₃): δ ppm 2.5 (s, 3 H), 3.8 (s, 3 H), 3.85 (s, 3 H), 4.3 (s, 2 H), 6.20-6.21 (s, 1 H), 6.27-6.28 (s, 1 H), 6.85-6.91 (m, 1 H), 7.06-7.11 (m, 3 H), 10.44 (s, 1 H); LCMS m/z=361, 363 [M+H]⁺.

10022822: 3-[(2,6-dichlorophenyl)methyl]-5,7-dihydroxy-4-methyl-1,2-dihydroquinolin-2-one

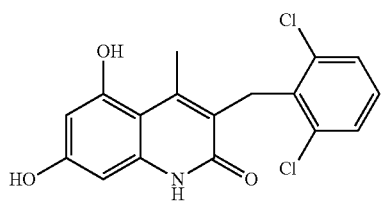 [SMILES: Cc1c(Cc2c(Cl)cccc2Cl)c(=O)[nH]c2cc(O)cc(O)c12]

¹H NMR (300 MHz, DMSO-d₆) δ ppm 2.29 (s, 3 H), 4.22 (s, 2 H), 6.05 (d, 1 H), 6.15 (d, 1 H), 7.21 (dd, 1 H), 7.39 (dd, 2 H), 9.71 (s, 1 H), 9.95 (s, 1 H), 11.15 (s, 1 H); LCMS m/z=348, 350, 352 [M+H]⁺

10024109:
5,7-dihydroxy-4-phenyl-2H-chromen-2-one

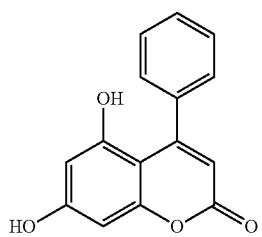

¹H NMR (400 MHz, DMSO-d₆): δ ppm 5.73 (s, 1 H), 6.13-6.14 (s, 1 H), 6.24-6.25 (s, 1 H), 7.26-7.37 (m, 6 H), 10.11 (s, 1 H), 10.39 (s, 1 H); LCMS m/z=254 [M+H]⁺.

10022827: 3-[(3,4-dichlorophenyl)methyl]-2,2,4-trimethyl-2H-chromen-7-ol

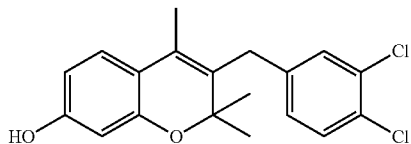 [SMILES: CC1=C(Cc2ccc(Cl)c(Cl)c2)C(C)(C)Oc2cc(O)ccc21]

$^1$H NMR (300 MHz, DMSO-$d_6$) δ ppm 0.94 (s, 3 H), 1.16 (s, 3 H), 1.64 (s, 3 H), 3.57 (q, 2 H), 4.1 (s, 1 H), 6.14 (dd, 1 H), 6.25 (dd, 1 H), 6.62 (dd, 1 H), 7.32 (dd, 1 H), 7.47 (dd, 1 H), 7.60 (s, 1 H), 9.05 (s, 1 H), 9.11 (s, 1 H); LCMS); LCMS m/z=349.2, 351 [M+H]$^+$

What is claimed is:

1. A compound of Formula IIa or a pharmaceutically acceptable salt thereof, the compound having the following structure:

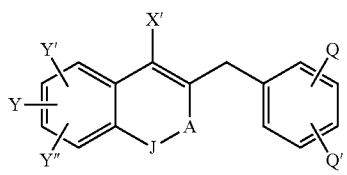

IIa wherein,
Y and Y' are each independently selected from the group consisting of hydroxyl and $C_1$-$C_6$ alkoxy,
Y" is selected from the group consisting of hydrogen, hydroxyl and $C_1$-$C_6$ alkoxy,
X' is $C_1$-$C_6$ alkyl,
A is —(C=O)—,
Q and Q' are each independently halogen, and
J is O or NH.

2. The compound of claim 1, wherein J is O.
3. The compound of claim 1, wherein X' is pentyl, butyl, propyl, ethyl or methyl.
4. The compound of claim 3, wherein X' is n-propyl.
5. The compound of claim 4, wherein Y is methoxy or ethoxy, and Y' is other than hydrogen.
6. The compound of claim 4, wherein Y is hydroxy, and Y' is other than hydrogen.
7. The compound of claim 1, wherein Y" is hydrogen.
8. The compound of claim 1, wherein said halogen for Q and Q' in each instance is independently fluoro or chloro.
9. The compound of claim 1, wherein J is N—H.
10. The compound of claim 1, having one of the following structures:

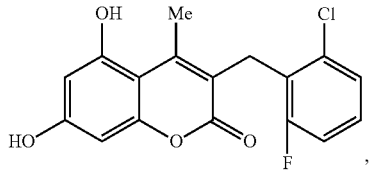

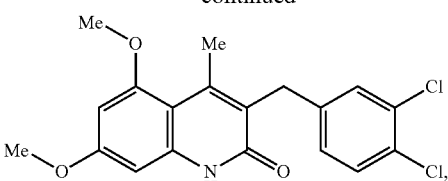

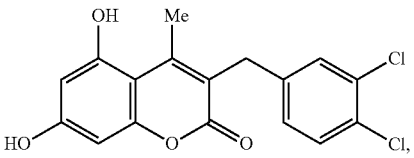

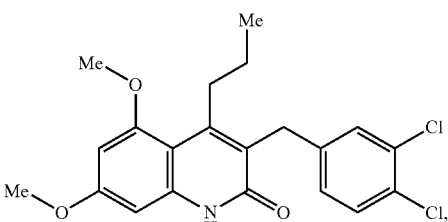

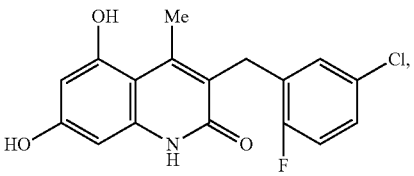

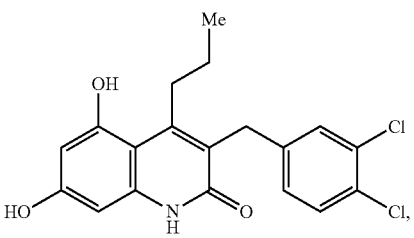

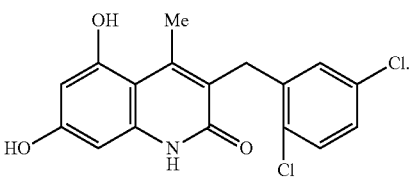

11. A pharmaceutical composition comprising a compound or pharmaceutically acceptable salt thereof of claim 1 and a carrier suitable for human administration.

12. The pharmaceutical composition of claim 1, formulated as a pill or capsule.

* * * * *

UNITED STATES PATENT AND TRADEMARK OFFICE
CERTIFICATE OF CORRECTION

PATENT NO.         : 9,334,256 B2                              Page 1 of 1
APPLICATION NO.    : 14/125928
DATED              : May 10, 2016
INVENTOR(S)        : Xiujun Sun et al.

It is certified that error appears in the above-identified patent and that said Letters Patent is hereby corrected as shown below:

In the Claims

In claim 1, at column 151, line 31, delete the text

"Y and Y' are each independently selected from the group consisting of hydroxyl and $C_1$-$C_6$ alkoxy, Y" is selected from the group consisting of hydrogen, hydroxyl and $C_1$-$C_6$ alkoxy,"

replace it with the text

-- Y is selected from the group consisting of hydroxyl and C1-C6 alkoxy,

Y' and Y" are each independently selected from the group consisting of hydrogen, hydroxyl and C1-C6 alkoxy wherein Y' is other than hydrogen, --.

Signed and Sealed this
Fifth Day of July, 2016

Michelle K. Lee
*Director of the United States Patent and Trademark Office*